(12) United States Patent
Ferrari et al.

(10) Patent No.: US 7,157,454 B2
(45) Date of Patent: Jan. 2, 2007

(54) DERIVATIVES OF N-(ARYLSULFONYL)BETA-AMINOACIDS COMPRISING A SUBSTITUTED AMINOMETHYL GROUP, THE PREPARATION METHOD THEREOF AND THE PHARMACEUTICAL COMPOSITIONS CONTAINING SAME

(75) Inventors: Bernard Ferrari, Les Matelles (FR); Jean Gougat, Grabels (FR); Yvette Muneaux, Les Matelles (FR); Pierre Perreaut, Saint-Clement-de-Riviere (FR); Lionel Sarran, Mauguio (FR)

(73) Assignee: Sanofi-Aventis, Paris (FR)

( * ) Notice: Subject to any disclaimer, the term of this patent is extended or adjusted under 35 U.S.C. 154(b) by 389 days.

(21) Appl. No.: 10/472,674

(22) PCT Filed: Mar. 27, 2002

(86) PCT No.: PCT/FR02/01059

§ 371 (c)(1),
(2), (4) Date: Sep. 18, 2003

(87) PCT Pub. No.: WO02/076964

PCT Pub. Date: Oct. 3, 2002

(65) Prior Publication Data

US 2004/0116353 A1    Jun. 17, 2004

(30) Foreign Application Priority Data

Mar. 28, 2001    (FR) .................................. 01 04315

(51) Int. Cl.
| | |
|---|---|
| *C07D 295/18* | (2006.01) |
| *C07D 211/34* | (2006.01) |
| *C07D 307/81* | (2006.01) |
| *C07D 405/12* | (2006.01) |
| *C07C 237/30* | (2006.01) |
| *C07C 311/19* | (2006.01) |
| *A61K 31/40* | (2006.01) |

(52) U.S. Cl. .............................. 514/235.5; 514/252.13; 514/278; 514/307; 514/321; 514/364; 514/423; 514/452; 514/602; 514/604; 544/60; 544/141; 544/159; 544/372; 546/16; 546/114; 546/146; 546/196; 546/283.7; 546/199; 546/202; 546/208; 546/309; 546/329; 546/330; 548/180; 548/200; 548/247; 548/364.4; 548/454; 548/525; 548/540; 549/55; 549/77; 549/366; 549/439; 549/443; 549/496; 562/427; 562/430; 564/84; 564/86

(58) Field of Classification Search ................. 544/60, 544/141, 159, 372; 546/16, 114, 146, 196, 546/283.7, 199, 202, 208, 309, 329, 330; 548/126, 166, 180, 200, 247, 364.4, 454, 548/525, 540; 549/55, 77, 366, 439, 443, 549/496; 562/427, 430; 564/84, 86; 514/235.5, 514/252.13, 278, 307, 321, 364, 423, 452, 514/602, 604
See application file for complete search history.

(56) References Cited

U.S. PATENT DOCUMENTS

| | | | |
|---|---|---|---|
| 5,506,258 A | 4/1996 | Christophe et al. | 514/423 |
| 5,714,497 A | 2/1998 | Christophe et al. | 514/307 |
| 5,968,951 A | 10/1999 | Dodey et al. | 514/311 |
| 6,015,812 A | 1/2000 | Ferrari et al. | 514/235.8 |

FOREIGN PATENT DOCUMENTS

| | | |
|---|---|---|
| EP | 0614911 | 9/1994 |
| WO | WO 96/40639 | 12/1996 |
| WO | WO 97/25315 | 7/1997 |

OTHER PUBLICATIONS

Altamura et al., Regulatory Peptides, 80, 13-26, 1999.*
Chemical Abstract No. 2002:642428 (2002).

* cited by examiner

*Primary Examiner*—Fiona T. Powers
(74) *Attorney, Agent, or Firm*—Kelly L. Bender

(57) ABSTRACT

The invention relates to compounds of formula:

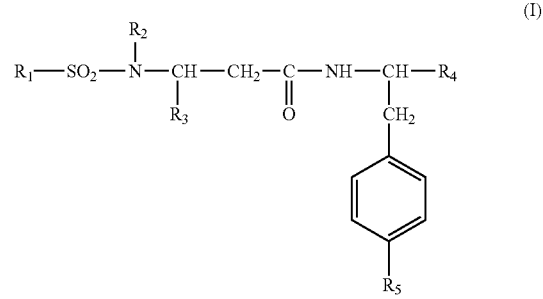

(I)

These compounds show affinity for the bradykinin receptors with selectivity towards the $B_1$ receptors; they may be used for the preparation of medicinal products intended for treating or preventing inflammation pathologies and persistent or chronic inflammatory diseases.

50 Claims, No Drawings

DERIVATIVES OF N-(ARYLSULFONYL)BETA-AMINOACIDS COMPRISING A SUBSTITUTED AMINOMETHYL GROUP, THE PREPARATION METHOD THEREOF AND THE PHARMACEUTICAL COMPOSITIONS CONTAINING SAME

The present invention relates to novel N-(arylsulphonyl) beta-amino acid derivatives comprising a substituted aminomethyl group, to their preparation and to pharmaceutical compositions containing them.

These compositions have affinity for the bradykinin (BK) receptors. Bradykinin is a nonapeptide belonging, like kallidin, to the kinin class and shows physiological activity in the cardiovascular field and as a mediator in inflammation and pain. Several bradykinin receptors are distinguished: the $B_1$ and $B_2$ receptors (D. Regoli et al., Pharmacol. Rev., 1980, 32, 1–46). More specifically, the $B_2$ receptors are the receptors for bradykinin and kallidin: they are predominant and are especially found in most tissues; the $B_1$ receptors are the receptors specific for [des-Arg$^9$] bradykinin and [des-Arg$^{10}$] kallidin: they are induced during inflammation processes.

Bradykinin receptors have been cloned for various species, especially for the human species: $B_1$ receptor: J. G. Menke et al., J. Biol. Chem., 1994, 269 (34), 21583–21586; $B_2$ receptor: J. F. Hess, Biochem. Biophys. Res. Commun., 1992, 184, 260–268.

Patent application WO 97/25315 describes compounds of formula:

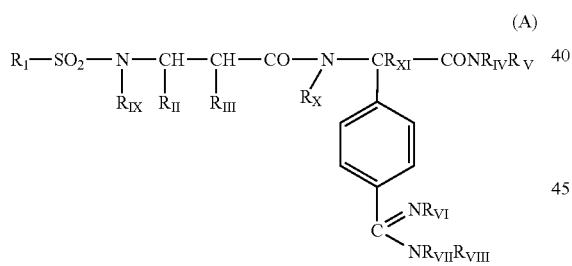

(A)

in which:
$R_I$, $R_{II}$, $R_{III}$, $R_{IV}$, $R_V$, $R_{VI}$, $R_{VII}$, $R_{VIII}$, $R_{IX}$, $R_X$ and $R_{XI}$ have different values. These compounds show affinity for the bradykinin receptors.

Novel compounds have now been found, which show affinity for the bradykinin receptors with selectivity towards the bradykinin $B_1$ receptors, which are bradykinin $B_1$ receptor antagonists and which show advantages as regards their absorption.

These compounds may be used for the preparation of medicinal products that are useful for treating or preventing any pathology in which bradykinin and the $B_1$ receptors are involved, especially inflammation pathologies and persistent or chronic inflammatory diseases.

Thus, according to one of its aspects, the subject of the present invention is compounds of formula:

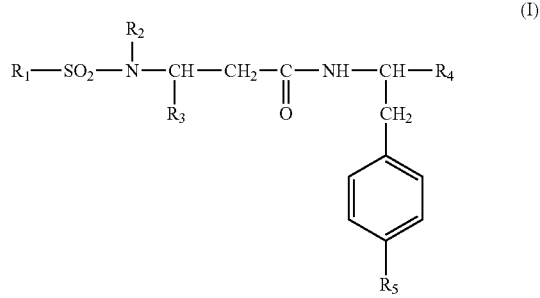

(I)

in which:
$R_1$ represents a phenylvinyl group; a phenyl group which is unsubstituted or substituted one or more times with $R_6$, which may be identical or different; a naphthyl group which is unsubstituted or substituted one or more times with $R_6$, which may be identical or different; a tetrahydronaphthyl group; a naphtho[2,3-d][1,3]dioxol-6-yl group; a heterocyclic radical chosen from quinolyl, isoquinolyl, 1-benzofur-2-yl, 2,1,3-benzoxadiazol-4-yl, 2,1,3-benzothiadiazol-4-yl, 1,3-benzothiazol-2-yl, 1-benzothiophen-2-yl, 1H-pyrazol-4-yl, thien-2-yl, 5-isoxazolthien-2-yl, benzothien-2-yl, thieno[3,2-c]pyrid-2-yl; the said heterocyclic radicals being unsubstituted or substituted one or more times with $R_6$, which may be identical or different;

$R_2$ represents hydrogen or a $(C_1-C_4)$alkyl group and $R_3$ represents a phenyl group which is unsubstituted or substituted one or more times with $R_7$, which may be identical or different; a heterocyclic radical chosen from benzo[1,3]dioxol-5-yl, 2,1,3-benzothiadiazol-5-yl, 2,1,3-benzoxadiazol-5-yl, benzothiophen-5-yl, 2,3-dihydrobenzo[1,4]dioxin-6-yl, benzofuryl, dihydrobenzofuryl, 1,3-thiazol-2-yl, furyl and thienyl, the said heterocyclic radical being unsubstituted or substituted one or more times with a halogen atom or with a $(C_1-C_4)$alkyl group;

or alternatively $R_2$ represents a phenyl group which is unsubstituted or substituted one or more times with $R_6$, which may be identical or different; a heterocyclic radical chosen from benzo[1,3]dioxol-5-yl, pyridyl and indanyl, and $R_3$ represents hydrogen;

$R_4$ represents a group —CONR$_8$R$_9$; a group —CSNR$_8$R$_9$; a group —COR$_{13}$; a phenyl group which is unsubstituted or substituted one or more times with $R_{10}$; a heterocyclic radical chosen from pyridyl, imidazolyl, furyl, benzimidazolyl, benzothiazol-2-yl and benzo[1,3]dioxol-5-yl, the said radicals being unsubstituted or substituted with one or more methyl groups or halogen atoms;

$R_5$ represents a group —CH$_2$NR$_{11}$R$_{12}$ or CH$_2$N(O) R$_{11}$R$_{12}$;

$R_6$ represents a halogen atom; a $(C_1-C_4)$alkyl group; a trifluoromethyl group; a $(C_1-C_4)$alkoxy group; a 2-fluoroethoxy group; a trifluoromethoxy, methylenedioxy or difluoromethylenedioxy group;

$R_7$ represents a halogen atom; a $(C_1-C_4)$alkyl group; a phenyl group; a trifluoromethyl group; a $(C_1-C_4)$ alkoxy group; a benzyloxy group; a trifluoromethoxy group;

$R_8$ and $R_9$ each independently represent hydrogen; a $(C_1-C_4)$alkyl group; a $(C_3-C_7)$cycloalkyl group; a $(C_3-C_7)$cycloalkyl$(C_1-C_4)$alkyl group; an ω-$(C_1-C_4)$ dialkylamino$(C_2-C_4)$alkyl group;

or alternatively $R_8$ and $R_9$, together with the nitrogen atom to which they are attached, constitute a heterocyclic radical chosen from pyrrolidinyl, morpholin-4-yl, thiomorpholin-4-yl, azepin-1-yl, piperidyl which is unsubstituted or substituted with one or more halogen atoms or one or more $(C_1-C_4)$alkyl or $(C_1-C_4)$alkoxy or trifluoromethyl groups, 3,4-dihydropiperid-1-yl, cyclohexyl-spiro-4-piperid-1-yl, and piperazinyl which is unsubstituted or substituted with one or more $(C_1-C_4)$ alkyl groups;

$R_{10}$ represents a halogen atom; a $(C_1-C_4)$alkyl group; a hydroxy group; a $(C_1-C_6)$alkoxy group; $R_{10}$ can also represent a group —$CH_2NR_{11}R_{12}$ when $R_5$ represents a group —$CH_2NR_{11}R_{12}$, the said groups then being identical;

$R_{11}$ and $R_{12}$ each independently represent hydrogen; a $(C_1-C_6)$alkyl group; a $(C_2-C_4)$alkenyl group; a $(C_3-C_7)$cycloalkyl group; a $(C_3-C_7)$cycloalkyl$(C_1-C_4)$ alkyl group; an ω-hydroxy$(C_2-C_4)$alkylene group; an ω-methoxy$(C_2-C_4)$alkylene group; ω-trifluoromethyl $(C_2-C_4)$alkylene group; an ω-halo$(C_2-C_4)$alkylene group, or alternatively $R_{11}$ and $R_{12}$, together with the nitrogen atom to which they are attached, constitute a monocyclic, bicyclic or heterocyclic radical chosen from azetidinyl, pyrrolidinyl, morpholin-4-yl, thiomorpholin-4-yl, piperid-1-yl, piperazin-1-yl, 1,2,3,6-tetrahydropyrid-1-yl, 2,3,4,5-tetrahydropyridinium, decahydroquinolyl, decahydroisoquinolyl, tetrahydroisoquinolyl, octahydro-1H-isoindolyl, $(C_4-C_6)$cycloalkyl-spiro-piperidyl, 3-azabicyclo[3.1.0]hexyl and 7-azabicyclo[2.2.1]heptan-7-yl, which may be unsubstituted or substituted one or more times with a halogen atom or a $(C_1-C_4)$alkyl, hydroxyl, $(C_1-C_4)$alkoxy, trifluoromethyl, difluoromethylene or phenyl group;

$R_{13}$ represents a phenyl, thiazol-2-yl or pyridyl group;

and also the salts thereof with mineral or organic acids and/or the solvates thereof or the hydrates thereof.

The term "halogen" means a fluorine, chlorine, bromine or iodine atom.

The terms "alkyl", "alkylene" and "alkoxy", respectively, mean a linear or branched alkyl radical, a linear or branched alkylene radical or a linear or branched alkoxy radical, respectively.

The compounds of formula (I) comprise at least one asymmetric carbon atom, and the pure enantiomers or diastereoisomers and also mixtures thereof in all proportions are subjects of the invention.

Preferably, a subject of the present invention is compounds of formula:

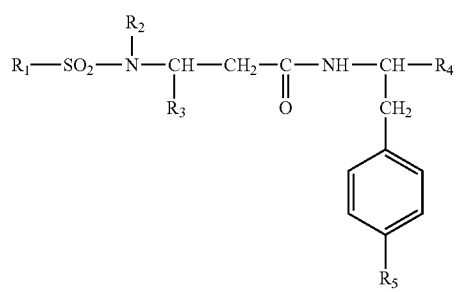

(I)

in which:

$R_1$ represents a phenylvinyl group; a phenyl group which is unsubstituted or substituted one or more times with $R_6$, which may be identical or different; a naphthyl group which is unsubstituted or substituted one or more times with $R_6$, which may be identical or different; a tetrahydronaphthyl group; a heterocyclic radical chosen from quinolyl, 1-benzofur-2-yl, 2,1,3-benzoxadiazol-4-yl, 2,1,3-benzothiadiazol-4-yl, 1,3-benzothiazol-2-yl, 1-benzothiophen-2-yl, 1H-pyrazol-4-yl, thien-2-yl, 5-isoxazolethien-2-yl, benzothien-2-yl, thieno[3,2-c]pyrid-2-yl; naphtho[2,3-d][1,3]dioxol-6-yl; the said heterocyclic radicals being unsubstituted or substituted one or more times with $R_6$, which may be identical or different;

$R_2$ represents hydrogen or a $(C_1-C_4)$alkyl group and $R_3$ represents a phenyl group which is unsubstituted or substituted one or more times with $R_7$, which may be identical or different; a heterocyclic radical chosen from benzo[1,3]dioxol-5-yl which is unsubstituted or substituted in the -2 position with two fluorine atoms; 2,1,3-benzothiadiazol-5-yl; 2,3-dihydrobenzo[1,4]dioxin-6-yl; 1,3-thiazol-2-yl; 1-benzofur-2-yl; 1-benzofur-5-yl; furyl; thien-2-yl; thien-3-yl;

or $R_2$ represents a phenyl group which is unsubstituted or substituted one or more times with $R_6$, which may be identical or different; a heterocyclic radical chosen from benzo[1,3]dioxol-5-yl; pyridyl; indanyl; and $R_3$ represents hydrogen;

$R_4$ represents a group —$CONR_8R_9$; a phenyl group which is unsubstituted or substituted one or more times with $R_{10}$; a heterocyclic radical chosen from pyridyl, imidazolyl, furyl, benzimidazolyl, benzothiazol-2-yl and benzo[1,3]dioxol-5-yl, the said radicals being unsubstituted or substituted with a methyl;

$R_5$ represents a group —$CH_2NR_{11}R_{12}$;

$R_6$ represents a halogen atom; a $(C_1-C_4)$alkyl group; a trifluoromethyl group; a $(C_1-C_4)$alkoxy group; a 2-fluoroethoxy group; a trifluoromethoxy, methylenedioxy or difluoromethylenedioxy group;

$R_7$ represents a halogen atom; a $(C_1-C_4)$alkyl group; a trifluoromethyl group; a $(C_1-C_4)$alkoxy group; a benzyloxy group; a trifluoromethoxy group;

$R_8$ and $R_9$ each independently represent hydrogen; a $(C_1-C_4)$alkyl group; a $(C_3-C_7)$cycloalkyl group; a $(C_3-C_7)$cycloalkyl$(C_1-C_4)$alkyl group; an ω-$(C_1-C_4)$ dialkylamino$(C_2-C_4)$alkyl group;

or $R_8$ and $R_9$, together with the nitrogen atom to which they are attached, constitute a heterocyclic radical chosen from pyrrolidinyl, piperidyl, morpholin-4-yl, thiomorpholin-4-yl, piperazin-1-yl, 4-methylpiperazin-1-yl, 4-methylpiperid-1-yl, 2-methylpiperid-1-yl, 4,4-dimethylpiperid-1-yl, 4,4-difluoropiperid-1-yl, 4-trifluoromethylpiperid-1-yl, 3,4-dihydropiperid-1-yl, azepin-1-yl and cyclohexyl-spiro-4-piperid-1-yl;

$R_{10}$ represents a halogen atom; a $(C_1-C_4)$alkyl group; a hydroxyl group; a $(C_1-C_6)$alkoxy group; $R_{10}$ can also represent a group —$CH_2NR_{11}R_{12}$ when $R_5$ represents a group —$CH_2NR_{11}R_{12}$, the said groups then being identical;

$R_{11}$ and $R_{12}$ each independently represent hydrogen; a $(C_1-C_6)$alkyl group; a $(C_2-C_4)$alkenyl group; a $(C_3-C_7)$cycloalkyl group; a $(C_3-C_7)$cycloalkyl$(C_1-C_4)$ alkyl group; an ω-hydroxy$(C_2-C_4)$alkylene group; an ω-methoxy$(C_2-C_4)$alkylene group; an ω-trifluoromethyl$(C_2-C_4)$alkylene group; an ω-halo$(C_2-C_4)$alkylene group;

or $R_{11}$ and $R_{12}$, together with the nitrogen atom to which they are attached, constitute a monocyclic, bicyclic or heterocyclic radical chosen from azetidinyl, pyrrolidinyl, morpholin-4-yl, thiomorpholin-4-yl, piperid-1-yl, piperazin-1-yl, 1,2,3,6-tetrahydropyrid-1-yl, decahydroquinolyl, decahydroisoquinolyl, octahydro-1H-isoindolyl, ($C_4$–$C_6$)cycloalkyl-spiro-piperidyl and 3-azabicyclo[3.1.0]hexyl, which may be unsubstituted or substituted one or more times with a halogen atom or a ($C_1$–$C_4$)alkyl, hydroxyl, ($C_1$–$C_4$)alkoxy, trifluoromethyl, difluoromethylene or phenyl group;

and also the salts thereof with mineral or organic acids and/or solvates thereof or hydrates thereof.

Furthermore, certain values of the substituents are preferred. Thus, the compounds of formula (I) that are preferred are those in which at least one of the substituents has a value specified below:

a—$R_1$ represents a 2,4-dichloro-3-methylphenyl, naphthyl, 6-methoxynaphth-2-yl, 3-methylbenzothiophen-2-yl, 3-methyl-5-chlorobenzothiophen-2-yl, 3-methyl-5-methoxybenzothiophen-2-yl, 3-methyl-6-methoxybenzothiophen-2-yl or 3-methyl-1-benzofur-2-yl group; $R_2$, $R_3$, $R_4$ and $R_5$ are as defined for a compound of formula (I);

b—$R_2$ represents hydrogen and preferably $R_3$ represents a benzo[1,3]dioxol-5-yl or phenyl group which is unsubstituted or substituted with a halogen; $R_1$, $R_4$ and $R_5$ are as defined for a compound of formula (I);

c—$R_4$ represents a group —$CONR_8R_9$ and preferably —$NR_8R_9$ represents a di($C_1$–$C_4$)alkylamino radical, most particularly an N-methylisopropyl radical; a pyrrolidinyl or piperidyl group which is unsubstituted or substituted one or two times with a methyl or a halogen; $R_1$, $R_2$, $R_3$ and $R_5$ are as defined for a compound of formula (I);

d—$R_5$ represents a group —$CH_2NR_{11}R_{12}$ in which —$NR_{11}R_{12}$ represents an ethylisobutylamino, ethylisopropylamino, ethyl-tert-butylamino, diisopropylamino, cyclopentylmethylamino or cyclopentylethylamino radical or a piperidyl radical which is unsubstituted or substituted one or more times with a methyl or a halogen; $R_1$, $R_2$, $R_3$ and $R_4$ are as defined for a compound of formula (I).

Thus, preferably, the present invention relates to compounds of formula:

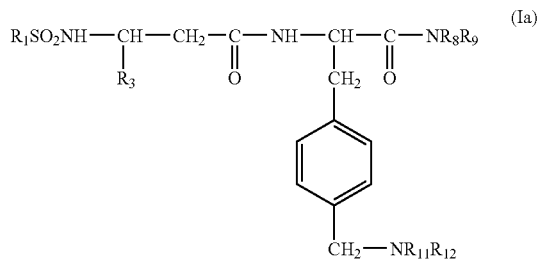

(Ia)

in which:
$R_1$ represents a 2,4-dichloro-3-methylphenyl, naphthyl, 6-methoxynaphth-2-yl, 3-methylbenzothiophen-2-yl, 3-methyl-5-chlorobenzothiophen-2-yl, 3-methyl-5-methoxybenzothiophen-2-yl, 3-methyl-6-methoxybenzothiophen-2-yl or 3-methyl-1-benzofur-2-yl group;

$R_3$ represents a benzo[1,3]dioxol-5-yl or phenyl group which is unsubstituted or substituted with a halogen;

$R_8$ and $R_9$, together with the nitrogen atom to which they are attached, constitute a di($C_1$–$C_4$)alkylamino, pyrrolidinyl or piperidyl radical which is unsubstituted or substituted one or two times with a methyl or a halogen;

$R_{11}$ and $R_{12}$, together with the nitrogen atom to which they are attached, constitute an ethylisobutylamino, ethylisopropylamino, ethyl-tert-butylamino, diisopropylamino, cyclopentylmethylamino or cyclopentylethylamino radical or a piperidyl radical which is unsubstituted or substituted one or more times with a methyl or a halogen;

and also the salts thereof with mineral or organic acids and/or solvates thereof or hydrates thereof.

The compounds of formula (Ia) having the (R,R) configuration are particularly preferred.

Most particularly, a subject of the present invention is a compound chosen from:
(R,R) 2-((3-(1,3-benzodioxol-5-yl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide;
(R,R) 2-((3-(1,3-benzodioxol-5-yl)-3-((2-naphthylsulphonyl)amino)propanoyl)amino)-3-(4-((cyclopentyl(ethyl)amino)methyl)phenyl)-N-isopropyl-N-methylpropanamide;
(R,R) 3-(4-((2,6-cis-dimethyl-1-piperidyl)methyl)phenyl)-2-((3-(((6-methoxy-2-naphthyl)sulphonyl)amino)-3-phenylpropanoyl)amino)-N-isopropyl-N-methyl propanamide;
(R,R) 2-((3-(1,3-benzodioxol-5-yl)-3-(((6-methoxy-2-naphthyl)sulphonyl)amino)propanoyl)amino)-3-(4-((tert-butyl(ethyl)amino)methyl)phenyl)-N-isopropyl-N-methylpropanamide;
(R,R) 2-((3-(1,3-benzodioxol-5-yl)-3-(((3-methyl-1-benzothiophen-2-yl)sulphonyl)amino)propanoyl)amino)-3-(4-((2,6-cis-dimethyl-1-piperidyl)methyl)phenyl)-N-isopropyl-N-methylpropanamide;
(R,R) 3-(4-((2,6-cis-dimethyl-1-piperidyl)methyl)phenyl)-2-((3-(((5-methoxy-3-methyl-1-benzothiophen-2-yl)sulphonyl)amino)-3-phenylpropanoyl)amino)-N-isopropyl-N-methylpropanamide;
(R,R) N-(4-((2,6-cis-dimethyl-1-piperidyl)methyl)benzyl)-3-(((6-methoxy-2-naphthyl)sulphonyl)amino)-3-phenyl-N-(1-piperidylcarbonyl)propanamide;
(R,R) 2-((3-(4-chlorophenyl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide;
(R,R) 3-(4-((2,6-cis-dimethyl-1-piperidyl)methyl)phenyl)-2-((3-(((6-methoxy-2-naphthyl)sulphonyl)amino)-3-phenylpropanoyl)amino)-N,N-diethylpropanamide;
(R,R) 2-((3-(3-fluorophenyl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide;
(R,R) 2-((3-(1,3-benzodioxol-5-yl)-3-(((3-methyl-1-benzofur-2-yl)sulphonyl)amino)propanoyl)amino)-3-(4-((2,6-cis-dimethyl-1-piperidyl)methyl)phenyl)-N-isopropyl-N-methylpropanamide;
(R,R) 2-((3-(1,3-benzodioxol-5-yl)-3-((2-naphthylsulphonyl)amino)propanoyl)amino)-3-(3-((tert-butyl(ethyl)amino)methyl)phenyl)-N-isopropyl-N-methylpropanamide;
(R,R) 3-(4-(7-azabicyclo[2.2.1]hept-7-ylmethyl)phenyl)-2-((3-(1,3-benzodioxol-5-yl)-3-(((6-methoxynaphthyl)sulphonyl)amino)propanoyl)amino)-N-isopropyl-N-methyl propanamide;

and also the salts thereof with mineral or organic acids and/or solvates thereof or hydrates thereof.

According to another of its aspects, the present invention relates to a process for preparing the compounds of formula (I), salts thereof and/or solvates thereof or hydrates thereof, characterized in that:

an acid or a functional derivative of this acid of formula:

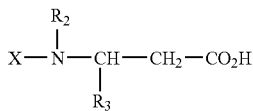
(II)

in which $R_2$ and $R_3$ are as defined for a compound of formula (I), X represents either hydrogen or a group $R_1$—$SO_2$— in which $R_1$ is as defined for a compound of formula (I), or an N-protecting group, is reacted with a compound of formula:

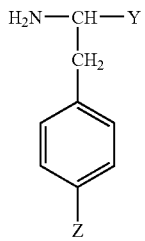
(III)

in which Y represents either $R_4$ as defined for a compound of formula (I), or a $(C_1–C_4)$alkoxycarbonyl, and Z represents either $R_5$ as defined for a compound of formula (I), or a —CN group, on the condition that, when Y represents $R_4$ which represents a phenyl substituted with a group —$CH_2NR_{11}R_{12}$, Z represents $R_5$ which represents a group —$CH_2NR_{11}R_{12}$, $R_{11}$ and $R_{12}$ being as defined for a compound of formula (I);

and when X=$R_1SO_2$—, Y=$R_4$ and Z=$R_5$, the expected compound of formula (I) is obtained;

or when X≠$R_1SO_2$ and/or Y≠$R_4$ and/or Z≠$R_5$, that is to say when at least one of the X, Y and Z groups represents, respectively, X=H or an N-protecting group, Y=$(C_1–C_4)$alkoxycarbonyl, Z=—CN, the compound thus obtained of formula:

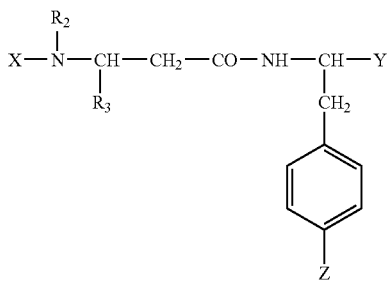
(IV)

is subjected to one or more of the following steps:

when X represents an N-protecting group, this group is removed and the compound thus obtained of formula:

(V)

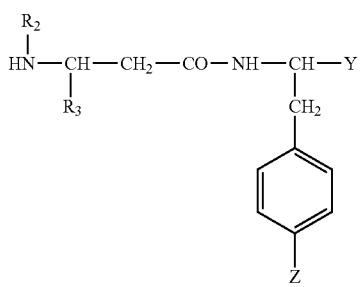

is reacted with a sulphonyl halide of formula:

$R_1SO_2$-Hal     (VI)

in which Hal represents a halogen;

when Y represents a $(C_1–C_4)$alkoxycarbonyl, it is hydrolyzed and the acid thus obtained or a functional derivative of this acid of formula:

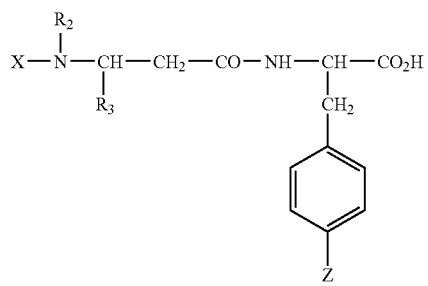
(VII)

is reacted with a compound of formula:

$HNR_8R_9$     (VIII);

in which $R_8$ and $R_9$ are as defined for a compound of formula (I);

when Z represents a —CN group, this group is converted into $R_5$.

Optionally, the compound thus obtained is converted into one of the salts thereof with mineral or organic acids.

In the course of any of the steps of the process for preparing the compounds of formula (I) or of the intermediate compounds thereof of formula (II), (III), (IV), (V) or (VII), it may be necessary and/or desirable to protect the reactive or sensitive functional groups, such as the amine, hydroxyl or carboxyl groups, present on any of the molecules concerned. This protection may be carried out using the conventional protecting groups, such as those described in *Protective Groups in Organic Chemistry*, J. F. W. McOmie, Ed. Plenum Press, 1973 and in *Protective Groups in Organic Synthesis*, T. W. Greene and P. G. M. Wutts, published by John Wiley and Sons, 1991. The removal of the protecting groups may be carried out in a suitable subsequent step using the methods known to those skilled in the art, which do not affect the rest of the molecule concerned.

The N-protecting groups possibly used are the standard N-protecting groups that are well known to those skilled in the art, such as, for example, the tert-butoxycarbonyl, fluorenylmethoxycarbonyl, benzyl, trityl or benzyloxycarbonyl group.

The compounds of formula (I) or the compounds of formula (IV) may be prepared in the form of a mixture of isomers or in optically pure form. To obtain optically pure compounds, it is possible either to separate the isomers by known methods of organic chemistry, or to use optically pure compounds of formulae (II) and (III) as starting materials and then to perform, where appropriate, non-racemizing synthetic methods that are known per se.

In step a) of the process, the compounds of formula (I) or the compounds of formula (IV) are prepared using the standard methods of peptide chemistry, for example those described in *The Peptides* Ed. E. Gross and J. Meienhofer, Academic Press, 1979, 1, 65–104. Known methods make it possible to carry out peptide couplings without racemization of the carbon atoms of each constituent amino acid; furthermore, the β-substituted β-alanines for which the chiral carbon was not adjacent to the carboxyl group are renowned for not undergoing racemization (Ann. Rev. Biochem., 1986, 55, 855–878). Moreover, patent application EP 236 163 describes processes for conserving the chirality of each amino acid.

Thus, in step a) of the process according to the invention, the functional derivative of the acid (II) that may be used is a functional derivative that reacts with amines, such as an anhydride, a mixed anhydride, an acid chloride or an activated ester such as the 2,5-dioxopyrrolidin-1-yl ester, the p-nitrophenyl ester or the benzotriazol-1-yl ester.

When the 2,5-dioxopyrrolidin-1-yl ester of the acid (II) is used, the reaction with the amine (III) is carried out in a solvent such as N,N-dimethylformamide, in the presence of a base such as triethylamine or N-N-diisopropylthylamine, at a temperature of between 0° C. and room temperature.

When an acid chloride is used, the reaction is carried out in a solvent such as dichloromethane, in the presence of a base such as triethylamine, N-methylmorpholine or N,N-diisopropylthylamine, at a temperature of between −60° C. and room temperature.

When a mixed anhydride of the acid (II) is used, this anhydride is generated in situ by reacting a $(C_1-C_4)$alkyl chloroformate with the acid of formula (II) in a solvent such as dichloromethane, in the presence of a base such as triethylamine, at a temperature of between −70° C. and 50° C., and it is reacted with the amine of formula (III), in a solvent such as dichloromethane, in the presence of a base such as triethylamine and at a temperature of between 0° C. and room temperature.

When the acid of formula (II) itself is used, the process is performed in the presence of a coupling agent used in peptide chemistry, such as 1,3-dicyclohexylcarbodiimide or benzotriazol-1-yloxytris(dimethylamino)phosphonium hexafluorophosphate or benzotriazol-1-yl-N,N,N',N'-tetramethyluronium tetrafluoroborate in the presence of a base such as triethylamine, N,N-diisopropylethylamine or N-ethylmorpholine, in a solvent such as dichloromethane, acetonitrile or N,N-dimethylformamide, or a mixture of these solvents, at a temperature of between 0° C. and room temperature.

Either a compound of formula (I) is thus obtained directly, or a compound of formula (IV) is thus obtained in which at least one of the groups X, Y and Z represents, respectively: X=N-protecting group, Y=$(C_1-C_4)$alkoxycarbonyl, Z=—CN, which is converted in one or more reactions, by standard methods well known to those skilled in the art, into a compound of formula (I). It is understood that, when several reactions are needed to convert a compound of formula (IV) into a compound of formula (I), the order of these reactions is determined so as not to affect the other substituents of the molecule concerned.

When, in the compound of formula (IV), X represents an N-protecting group, this group is removed according to the methods known to those skilled in the art. For example, when X represents a tert-butoxycarbonyl group, it is removed by the action of an acid such as hydrochloric acid or trifluoroacetic acid, for example, in a solvent such as methanol, ethyl ether, dioxane, tetrahydrofuran or dichloromethane, at a temperature of between 0° C. and room temperature. Next, the amine of formula (V) thus obtained is reacted with a sulphonyl halide of formula (VI) (preferably a chloride), in the presence of a base such as an alkali metal hydroxide (for example sodium hydroxide or potassium hydroxide) or an organic base (for example triethylamine, diisopropylethylamine or N-methylmorpholine), in a solvent such as dioxane, dichloromethane or acetonitrile, in the presence or absence of an activator such as dimethylaminopyridine (DMAP); the reaction may also be carried out in pyridine in the presence or absence of DMAP. The reaction is carried out at a temperature of between 0° C. and room temperature.

Either a compound of formula (I) is obtained, or a compound of formula (IV) is obtained in which $X=R_1SO_2—$.

When, in the compound of formula (IV), Y represents a $(C_1-C_4)$alkoxycarbonyl, it is hydrolyzed in acidic or basic medium according to the methods known to those skilled in the art. Next, the acid of formula (VII) thus obtained is reacted with a compound of formula (VIII) under the conditions described previously for the use of a compound of formula (II). Either a compound of formula (I) is obtained, or a compound of formula (IV) is obtained in which $R_4=—CONR_8R_9$.

When, in the compound of formula (IV), Z represents a cyano group, this group is converted into a group $R_5$ according to the standard methods that are well known to those skilled in the art.

For example, reduction of the —CN group gives either a compound of formula (I) or a compound of formula (IV), in which $R_5=—CH_2NH_2$. This reduction may be carried out using hydrogen, in the presence of a catalyst such as Raney® nickel, in a solvent such as methanol, toluene, dioxane or a mixture of these solvents, mixed with aqueous ammonia, at a temperature of between room temperature and 50° C.

The —CN group can be converted into a group $R_5=—CH_2NR_{11}R_{12}$ according to Scheme 1 below.

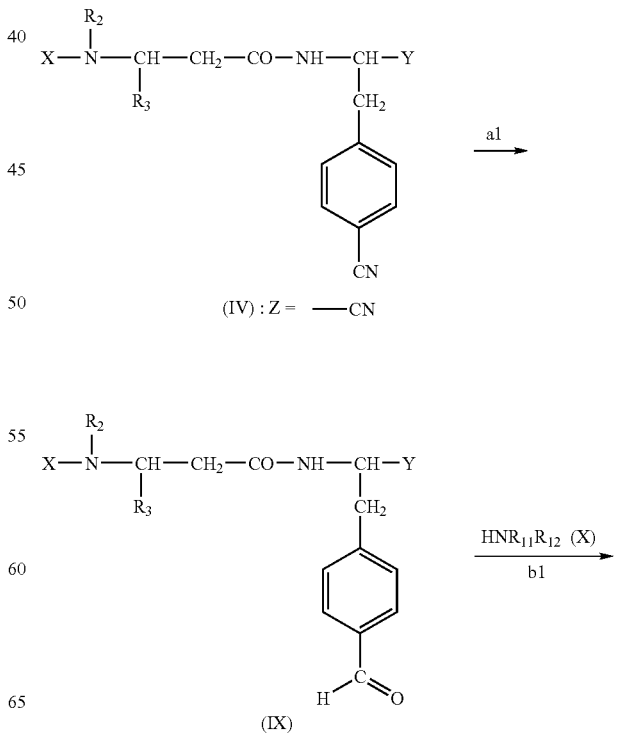

-continued

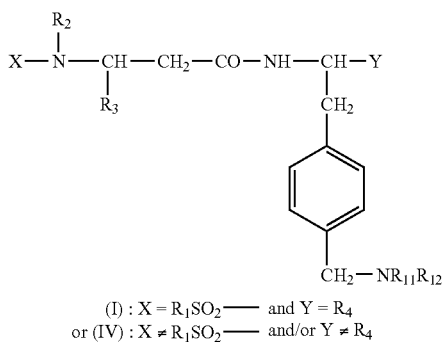

(I) : X = R₁SO₂— and Y = R₄
or (IV) : X ≠ R₁SO₂— and/or Y ≠ R₄

In step a1 of Scheme 1, the reduction of the nitrile derivative of formula (IV) to an aldehyde of formula (IX) is carried out according to the methods known to those skilled in the art such as, for example, the method described in Synth. Commun., 1990, 20(3), 459–467. The method described in Farmaco, Ed. Sci., 1988, 43(7/8), 597–612 may also be used, on the condition that, in the compound of formula (IV), X is other than an N-protecting group that is labile in acidic medium.

Next, in step b1, a compound of formula (X) is reacted with the aldehyde of formula (IX) in the presence or absence of an acid such as acetic acid, in a solvent such as methanol, dichloromethane or 1,2-dichloroethane, to form in situ an intermediate imine which is chemically reduced using, for example, sodium cyanoborohydride, sodium triacetoxyborohydride or sodium borohydride.

The —CN group can also be converted into a group $R_5$ according to Scheme 2 below.

SCHEME 2

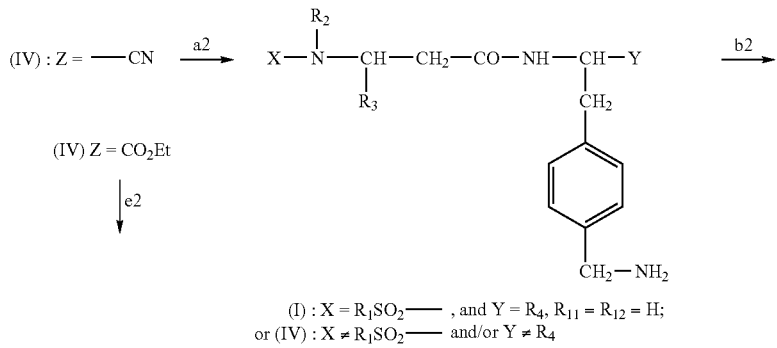

(IV) : Z = —CN  →a2

(IV) Z = CO₂Et

↓e2

(I) : X = R₁SO₂—, and Y = R₄, R₁₁ = R₁₂ = H;
or (IV) : X ≠ R₁SO₂— and/or Y ≠ R₄

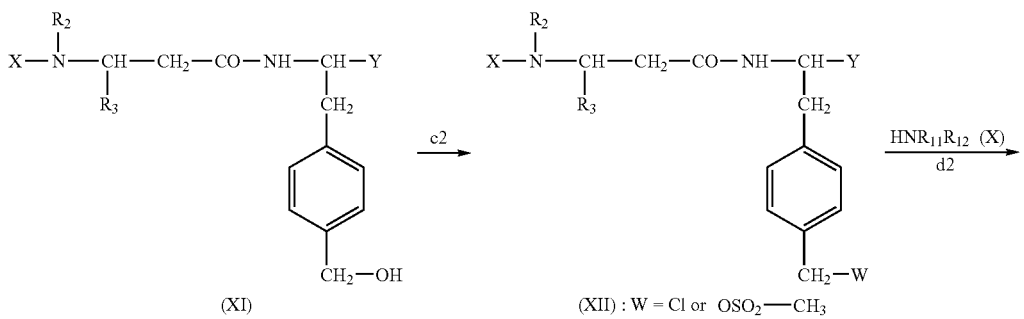

(XI)       (XII) : W = Cl or OSO₂—CH₃

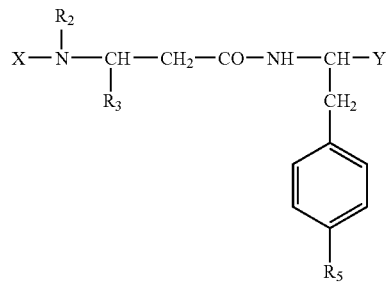

(I) : X = R₁SO₂— and Y = R₄
or (IV) : X ≠ R₁SO₂— and/or Y ≠ R₄

In step a2 of Scheme 2, the cyano group is reduced according to the methods described previously.

Next, in step b2, the amine thus obtained is converted into an alcohol of formula (XI) according to the methods known to those skilled in the art, for example by the action of sodium nitrite in aqueous medium, in a solvent such as dioxane and at a temperature of between room temperature and 110° C.

In step c2, the alcohol of formula (XI) is treated with methanesulphonyl chloride, in the presence of a base such as triethylamine, in a solvent such as dichloromethane and at a temperature of between 0° C. and the reflux point of the solvent. A compound of formula (XII) is thus obtained in which W=Cl or O—SO$_2$CH$_3$ depending on the operating conditions used.

In step d2, when a compound of formula (XII) in which W=Cl is used, the reaction is carried out with the compound of formula (X) in the presence of a base such as sodium hydride, in a solvent such as tetrahydrofuran, N,N-dimethylformamide, acetonitrile, toluene or 2-propanol and at a temperature of between room temperature and 100° C. When a compound of formula (XII) in which W=O—SO$_2$CH$_3$ is used, the reaction is carried out with a compound of formula (X) in the presence or absence of a base such as the triethylamine, in a solvent such as ethanol, N,N-dimethylformamide, acetonitrile or dichloromethane and at a temperature of between 0° C. and 100° C.

In step e2, the ester is reduced with a reducing agent such as NaBH$_4$ or LiAlH$_4$, for example.

A compound according to the invention of formula (I) in which R$_5$ represents a group —CH$_2$—N(O)—R$_{11}$R$_{12}$ is obtained from the analogous compound of formula (I) in which R$_5$ represents a group —CH$_2$—NR$_{11}$R$_{12}$, the other substituents being identical, and the reaction is carried out by the action of an oxidizing agent such as meta-chloroperbenzoic acid.

The compounds of formula (I) according to the invention are finally obtained.

The compounds of formula (I) thus obtained are isolated in the form of free base or in the form of salt, according to the standard techniques.

When the compounds of formula (I) are obtained in the form of free base, the salification is carried out by treatment with the chosen acid in an organic solvent. Treatment of the free base, dissolved, for example, in an ether such as diethyl ether or in an alcohol such as 2-propanol or methanol or in acetone or in dichloromethane or in ethyl acetate or in acetonitrile with a solution of the chosen acid in one of the abovementioned solvents, gives the corresponding salt, which is isolated according to the standard techniques.

Thus, the hydrochloride, the hydrobromide, the sulphate, the hydrogen sulphate, the dihydrogen phosphate, the methanesulphonate, the oxalate, the maleate, the succinate, the fumarate, the 2-naphthalenesulphonate, the benzenesulphonate or the para-toluenesulphonate, for example, is prepared.

At the end of the reaction, the compounds of formula (I) may be isolated in the form of one of the salts thereof, for example the chlorohydride; in this case, if it is necessary, the free base may be prepared by neutralizing the said salt with a mineral or organic base, such as sodium hydroxide or triethylamine or with an alkali metal carbonate or bicarbonate, such as sodium or potassium carbonate or bicarbonate.

The compounds of formula (VI) are known or prepared according to known methods. For example, 2,4-dichloro-3-methylbenzenesulphonyl chloride is prepared according to the process described in J. Am. Chem. Soc., 1940, 62, 511–512. 2-Quinolinesulphonyl chloride and 5,6,7,8-tetrahydronaphthalene-2-sulphonyl chloride are prepared according to the process described in WO 97/25315. 6-Methoxynaphthalene-2-sulphonyl chloride is prepared according to J. Org. Chem., 1992, 57, 2631–2641. 3-Methylbenzothienyl-2-sulphonyl chloride is prepared according to J. Het. Chem., 1988, 25, 639–641.

The compounds of formula (VIII) are known or prepared according to known methods.

The compounds of formula (X) are known or prepared according to known methods.

The compounds of formula (II), in which R$_2$ represents hydrogen or a (C$_1$–C$_4$)alkyl in racemic form or in the form of pure enantiomers, are known (Table 1) or prepared according to known methods such as those described in WO 97/25315.

TABLE I $$X-NH-CH-CH_2CO_2H$$
$$\phantom{X-NH-}|$$
$$\phantom{X-NH-}R_3$$
(II)

| X | R$_3$ | References |
|---|---|---|
| H | 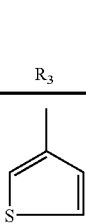 | Eur. J. Med. Chem. Chim. Therap., 1992, 27 (9), 961–965 |
| Boc | 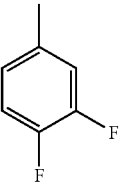 | J. Med. Chem., 1997, 40 (26), 4308–4318 |
| H | 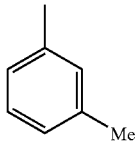 | Bull. Soc. Chim. Fr., 1987, 6, 1079–1083 |
| H | 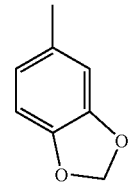 | Biorg. Med. Chem. 1994, 2 (9), 881 |
| H | 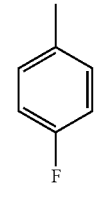 | Eur. J. Med. Chem. Chim. Therap., 1992, 27 (9), 961–965 |
| H | 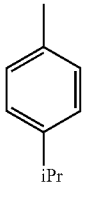 | Bull. Soc. Chim. Fr., 1987 6, 1079–1083 |

TABLE I-continued $$X-NH-CH(R_3)-CH_2CO_2H \quad (II)$$

| X | R₃ | References |
|---|---|---|
| H | 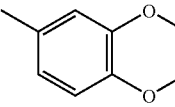 (methyl-benzodioxane) | Tetrahedron Lett., 1991, 32 (44), 6327–6328 |
| H | 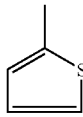 (methylthiophene) | Zh. Obshch. Khim., 1958, 28, 213–215 |
| H | 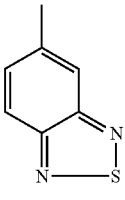 (methyl-benzothiadiazole) | Chem. Heterocycl. Compd., (Engl. Transl.) 1969, 5, 453–456 |
| H | 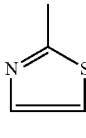 (methylthiazole) | J. American. Chem. Soc., 1957, 79, 4524–4527 |
| H | 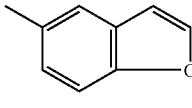 (methylbenzofuran) | Tetrahedron Lett., 2000, 41 (31), 5803–5806 |
| H | 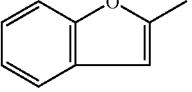 (benzofuran) | WO 97/08145 |
| H | 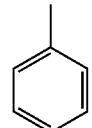 (4-CF₃-tolyl) | WO 98/40055 |
| H | 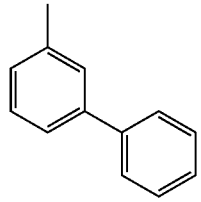 (methylbiphenyl) | WO 97/08145 |
| H | 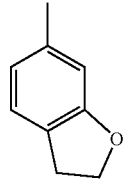 (methyl-dihydrobenzofuran) | Tetrahedron Lett. 2000, 41, 5803–5806 |

The compounds of formula (II) in which $R_3$ represents hydrogen may be prepared by known methods. It is possible, for example, to use the process described in Scheme 3 below in which R' represents a $(C_1-C_4)$alkyl and Pr represents an N-protecting group, for example a tert-butoxycarbonyl or fluorenylmethoxycarbonyl group.

SCHEME 3

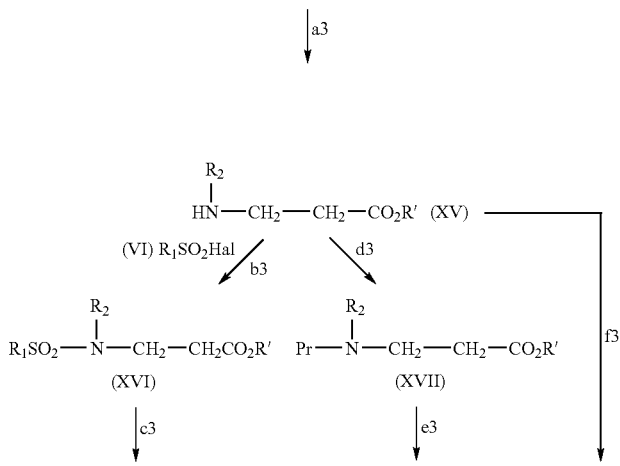

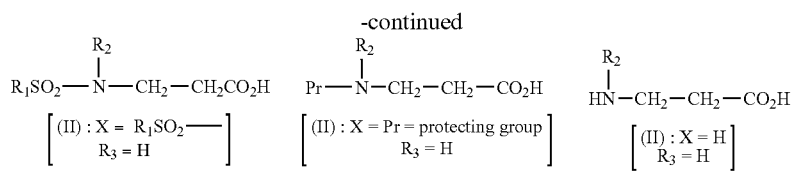

In step a3 of Scheme 3, a compound of formula (XIII) is reacted with an acrylic acid ester of formula (XIV) to give a compound of formula (XV). The reaction is carried out in the presence of an acid such as acetic acid and at the reflux temperature of the reaction mixture.

In step b3, compound (XV) is reacted with a sulphonyl halide of formula (VI), in the presence of a base such as sodium hydroxide, potassium hydroxide or 4-dimethylaminopyridine, in a solvent such as dioxane or pyridine, and at a temperature of between room temperature and 60° C.

In step c3, the ester of formula (XVI) thus obtained is hydrolyzed, according to the methods known to those skilled in the art, to give the expected compound of formula (II) in which $X=R_1SO_2-$.

Alternatively, in step d3, the amino-ester of formula (XV) is protected according to the methods known to those skilled in the art, for example with a tert-butoxycarbonyl or fluorenylmethoxycarbonyl group.

In step e3, the ester of formula (XVII) thus obtained is hydrolyzed according to the known methods, to give the compound of formula (II) in which X represents a protecting group.

Alternatively, according to step f3, the ester of formula (XV) is hydrolyzed in acidic or basic medium to give a compound of formula (II).

The compounds of formula (III) in which Y represents a $(C_1-C_4)$alkoxycarbonyl or a group $R_4=CONR_8R_9$ and $Z=-CN$ are known or prepared according to known methods such as those described in WO 97/25315, EP 0 614 911 or EP 0 236 164.

The other compounds of formula (III) in which Y represents $R_4$ and $Z=-CN$ are prepared according to Scheme 4 below.

SCHEME 4

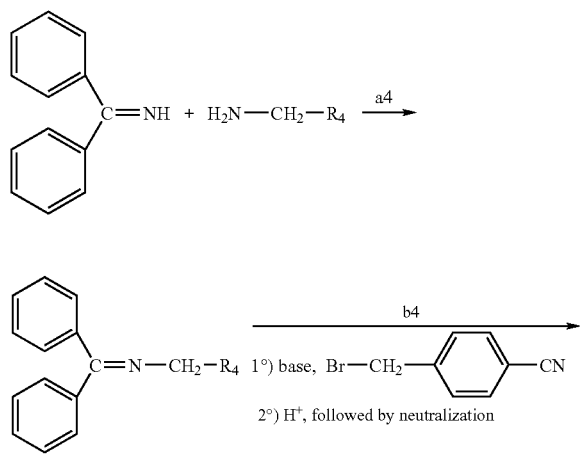

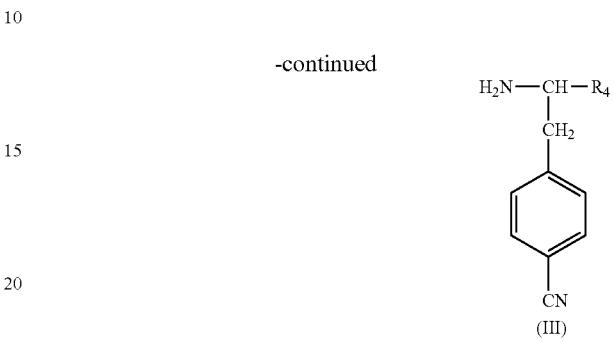

In step a4 of Scheme 4, the benzophenone imine is reacted with an amine of formula (XVIII) to give a compound of formula (XIX). The reaction is carried out in a solvent such as dichloromethane, chloroform or ethyl acetate, at a temperature of between room temperature and 50° C and in the presence or absence of a base such as triethylamine.

In step b4 the compound of formula (XIX) is treated with a strong base such as butyllithium, potassium tert-butoxide or lithium diisopropylamide to give a carbanion which is reacted with 4-(bromomethyl)benzonitrile.

The reaction is carried out in a solvent such as tetrahydrofuran, at a temperature of between −78° C. and room temperature. By treatment in acidic medium, the benzhydrylidene N-protecting group is removed to give an expected compound of formula (III).

Compounds of formula (XIX) may also be prepared according to the methods described in Bull. Soc. Chim. Fr., 1973, 2985, 2987, 2988, J. Am. Chem. Soc., 1982, 104 (3), 730 or Tetrahedron Lett., 1996, 1137.

The compounds of formula (XVIII) are known or prepared according to known methods. For example, compounds of formula (XVIII) may be prepared according to Scheme 5 below.

SCHEME 5

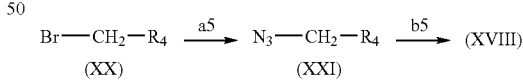

In step a5 of Scheme 5, a compound of formula (XX) is reacted with sodium azide to give a compound of formula (XXI). The reaction is carried out in a solvent such as dimethyl sulphoxide, at a temperature of between 0° C. and room temperature.

In step b5, the compound of formula (XXI) is reduced to a compound of formula (XVIII) according to the methods known to those skilled in the art.

The compounds of formula (XVIII) may also be prepared by reducing a nitrile of formula $R_4CN$, for example by the action of $LiAlH_4$.

The compounds of formula (III) in which Y represents a $(C_1-C_4)$alkoxycarbonyl and Z represents $R_5$ as defined for a compound of formula (I) are prepared according to Scheme 6 below in which R' represents a $(C_1-C_4)$alkyl.

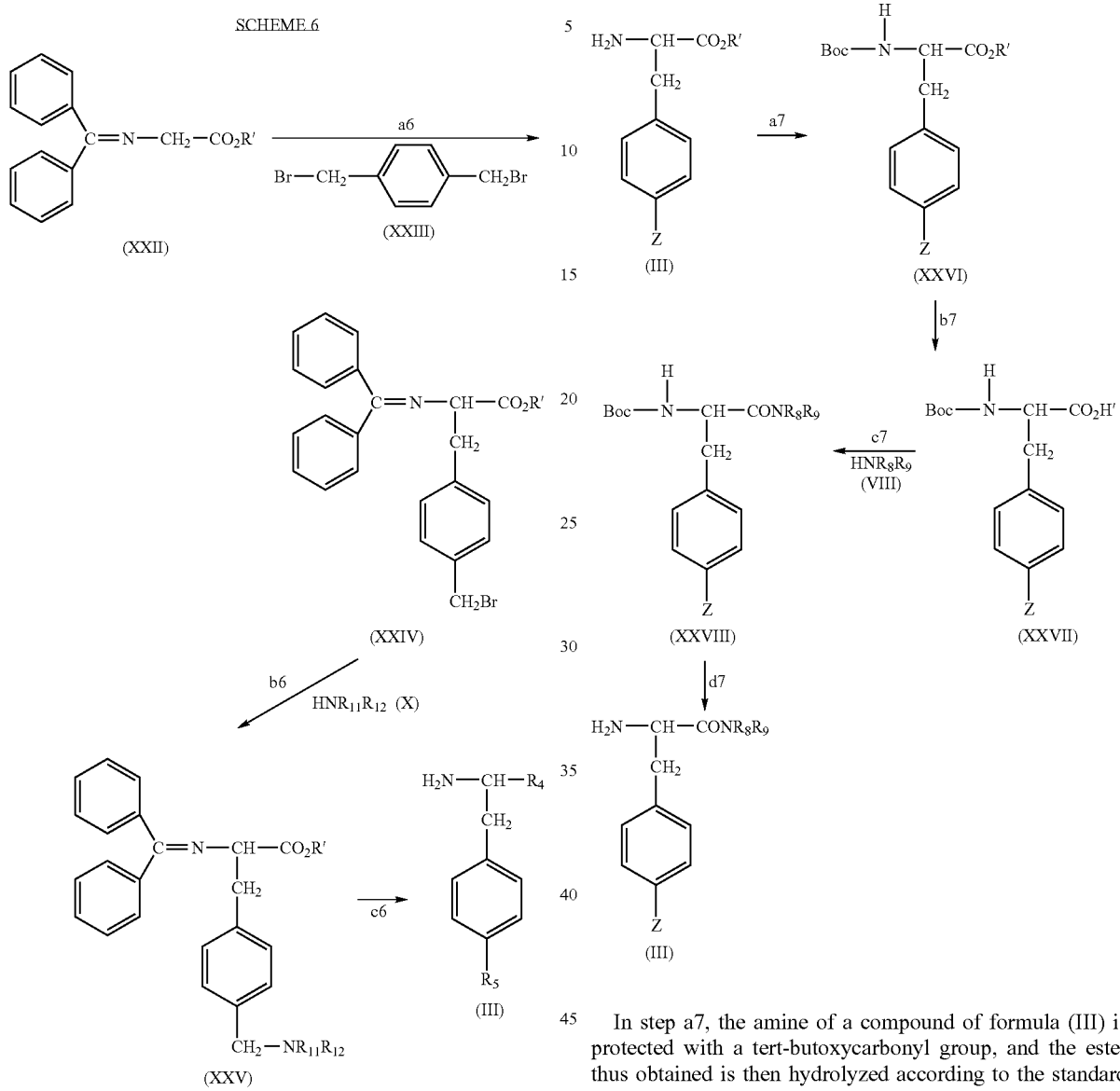

In step a6 of Scheme 6, a compound of formula (XXII) is reacted with α,α'-dibromo-p-xylene (XXIII) according to the method described in Tetrahedron Asymmetry, 1992, 3 (5), 637–650.

In step b6, the compound of formula (XXIV) thus obtained is reacted with a compound of formula (X) to give a compound of formula (XXV). The reaction is carried out in the presence of a base such as an alkali metal carbonate or bicarbonate (potassium carbonate, sodium carbonate or sodium bicarbonate), in a solvent such as N,N-dimethylformamide, acetonitrile, dichloromethane or toluene and at a temperature of between room temperature and 100° C.

In step c6, the N-protecting group is removed by the action of an acid such as, for example, hydrochloric acid.

The compounds of formula (III) in which Y represents $R_4$=$CONR_8R_9$ are also prepared according to Scheme 7 below in which R' represents a $(C_1-C_4)$alkyl.

In step a7, the amine of a compound of formula (III) is protected with a tert-butoxycarbonyl group, and the ester thus obtained is then hydrolyzed according to the standard methods (step b7); the acid of formula (XXVII) thus obtained is then reacted with a compound of formula (VIII) according to the methods described previously (step c7) and the compound (XXVIII) obtained is deprotected in acidic medium (step d7).

The compounds of formula (III) in which Y represents $R_4$ and Z represents $R_5$ as defined for a compound of formula (I) are prepared according to Scheme 8 below.

SCHEME 8

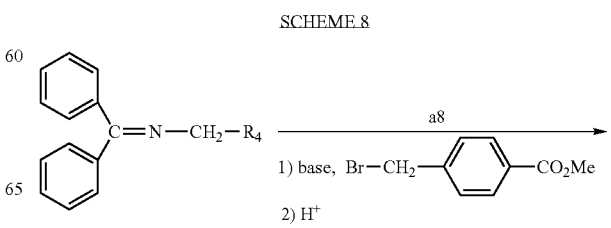

In step b8, the amine of formula (XXIX) is protected by reaction with di-tert-butyl dicarbonate.

In step c8, the ester of formula (XXX) thus obtained is reduced to an alcohol of formula (XXXI). The reduction is carried out in the presence of an reducing agent such as lithium aluminium hydride, sodium borohydride or diisobutylaluminium hydride, in a solvent such as tetrahydrofuran or toluene, at a temperature of between −78° C. and room temperature.

The alcohol of formula (XXXI) is reacted in step d8 with methanesulphonyl chloride, in the presence of a base such as triethylamine, in a solvent such as dichloromethane or tetrahydrofuran and at a temperature of between 0° C. and the reflux point of the solvent.

In step e8, the compound of formula (XXXII) thus obtained is reacted with a compound of formula (X), in the presence or absence of a base such as triethylamine, in a solvent such as ethanol, N,N-dimethylformamide, acetonitrile, toluene or dichloromethane and at a temperature of between 0° C. and 100° C.

In step f8, the N-protecting group of the compound of formula (XXXIII) thus obtained is removed by treatment in acidic medium.

The compounds of formula (III) in which Y represents either a $(C_1\text{–}C_4)$alkoxycarbonyl, or $R_4$ which represents a group —$CONR_8R_9$, a heterocyclic radical or a phenyl which is unsubstituted or substituted with a group other than a group —$CH_2NR_{11}R_{12}$, and Z represents $R_5$=—$CH_2NR_{11}R_{12}$, may also be prepared according to Scheme 9 below:

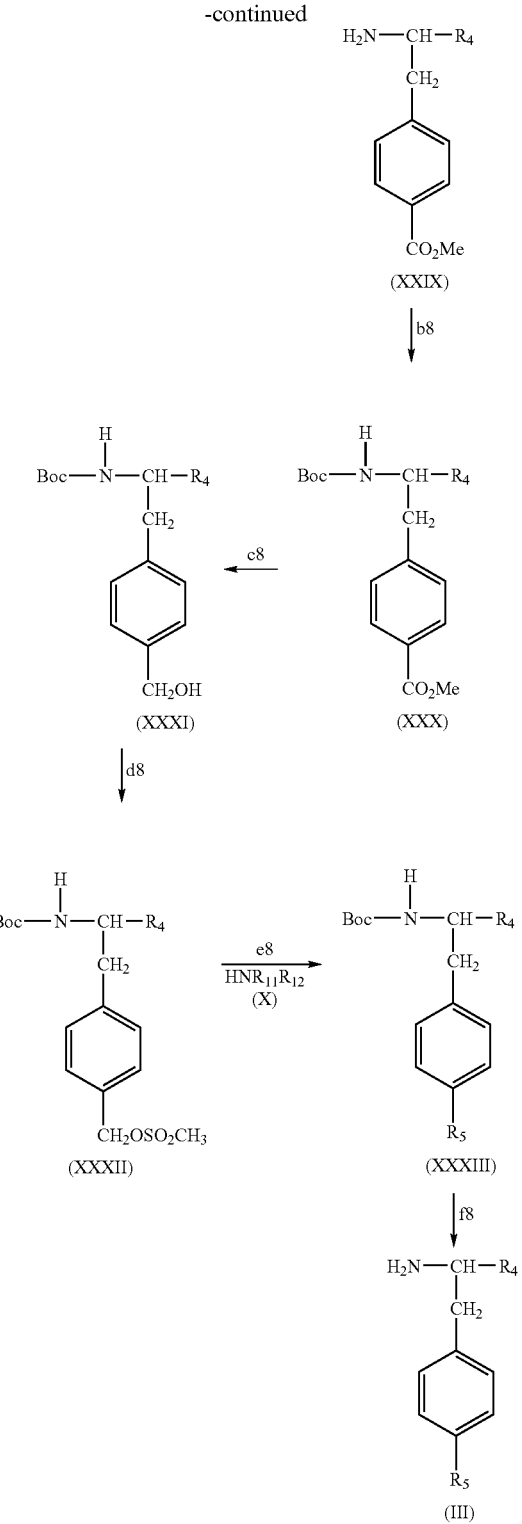

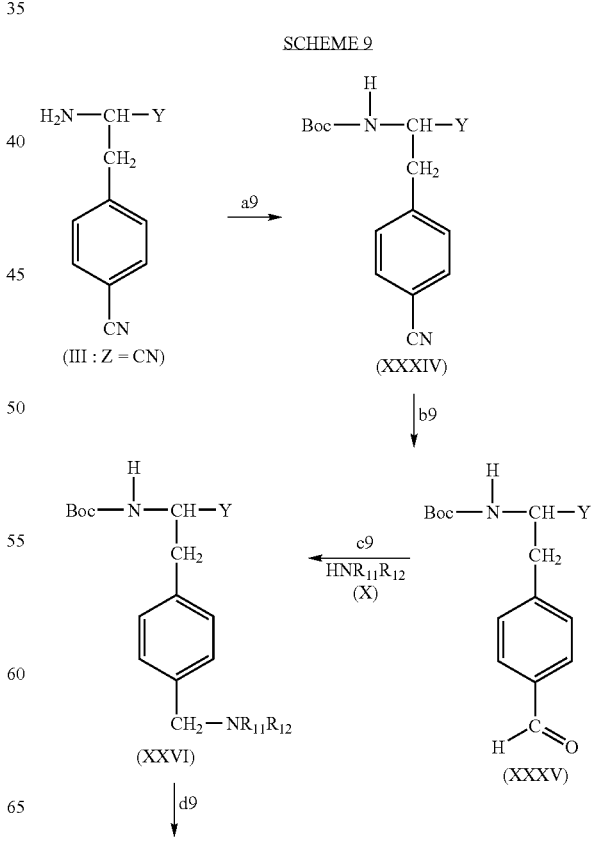

SCHEME 9

In step a8 of Scheme 8, the compound of formula (XIX) is reacted with methyl 4-(bromomethyl)benzoate in the presence of a base such as potassium tert-butoxide or lithium diisopropylamide in a solvent such as tetrahydrofuran at a temperature of between −78° C. and room temperature. By treatment in acidic medium, the benzhydrylidene protecting group is removed.

-continued

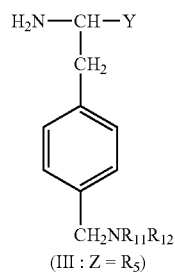

(III : Z = R5)

In step a9 of Scheme 9, the amine of a compound of formula (III) is protected according to the conventional methods.

In step b9, the nitrile of formula (XXXIV) is reduced to an aldehyde of formula (XXXV) according to the method described in Synth. Commun., 1990, 20 (3), 459–467.

Next, in step c9, a compound of formula (X) is reacted with the aldehyde of formula (XXXV) in the presence or absence of an acid such as acetic acid, in a solvent such as methanol, dichloromethane or 1,2-dichloroethane to form in situ an imine intermediate which is chemically reduced using, for example, sodium cyanoborohydride, sodium triacetoxyborohydride or sodium borohydride.

Finally, in step d9, the N-protecting group of the compound of formula (XXXVI) is removed by treatment in acidic medium.

The amines of formula (X) are known or prepared according to known methods described below:

TABLE II

| HNR11R12 | References |
|---|---|
|  | J. Pharm. Sci., 1963, 52, 1191 |
|  | J. Org. Chem., 1979, 44 (5), 771–7 |
|  | Chem. Pharm. Bull., 1993, 41 (11), 1971–1986 |
|  | Chem. Pharm. Bull., 1993, 41 (11), 1971–1986 |
|  | WO 98/22443 |

TABLE II-continued

| HNR11R12 | References |
|---|---|
|  | J. Org. Chem., 1970, 35 (11), 3663–3666 |
|  | Synth. Commun., 1999, 29 (10), 1747–1756 |
|  | J. Chem. Soc. Perkin Trans. 2, 1984, 737–744 |
|  | U.S. Pat. No. 2424063 |
|  | J. Org. Chem. USSR (Engl. Trans 1), 1992, 28 (3.1), 374–380 |
|  | Tetrahedron, 1999, 55 (31), 9439–9454 |
|  | J. Amer. Chem. Soc., 1955, 77, 4100–4102 |
|  | WO 95/22547 |
|  | WO 94/03437 |
|  | Chem. Ber., 1991, 791–801 |

A compound of formula (XXXV) may also be converted into a compound of formula (XXXVI) according to the following reaction scheme:

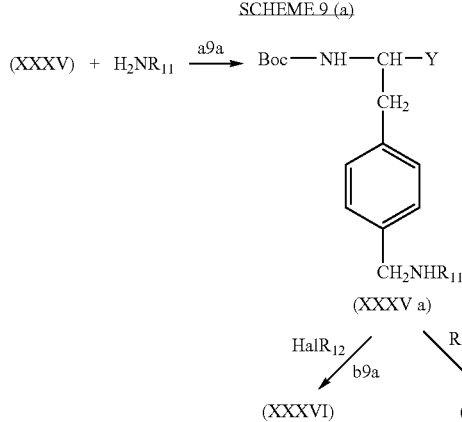

In step a9a, a reductive amination is carried out in the presence of a reducing agent such as NaHB(OAc)$_3$. Next, either an alkylation is performed with an alkyl halide, for example an iodide (step b9a), or a further reductive amination is performed by reacting a carbonyl derivative of formula R$_{12}$O (step c9a), R$_{12}$O representing a dialkyl ketone or an alkylaldehyde. Thus, for example, treating a compound (XXXVa), in which R$_{11}$ is cyclopropyl, with acetone gives a compound (XXXVI) in which R$_{11}$ is cyclopropyl and R$_{12}$ is isopropyl.

In the case where Y represents an alkoxycarbonyl group, a compound (III) in which Y represents a group CONR$_8$R$_9$ may be prepared according to Scheme 10 below:

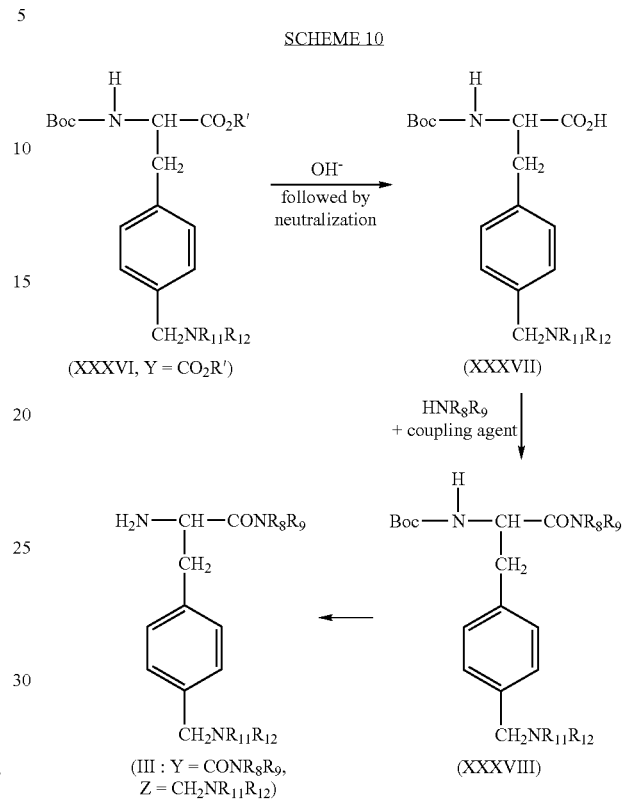

The compounds of formula (III) in which Y represents a phenyl substituted with a group —CH$_2$NR$_{11}$R$_{12}$ and Z represents R$_5$=—CH$_2$NR$_{11}$R$_{12}$ are prepared according to Scheme 11 below:

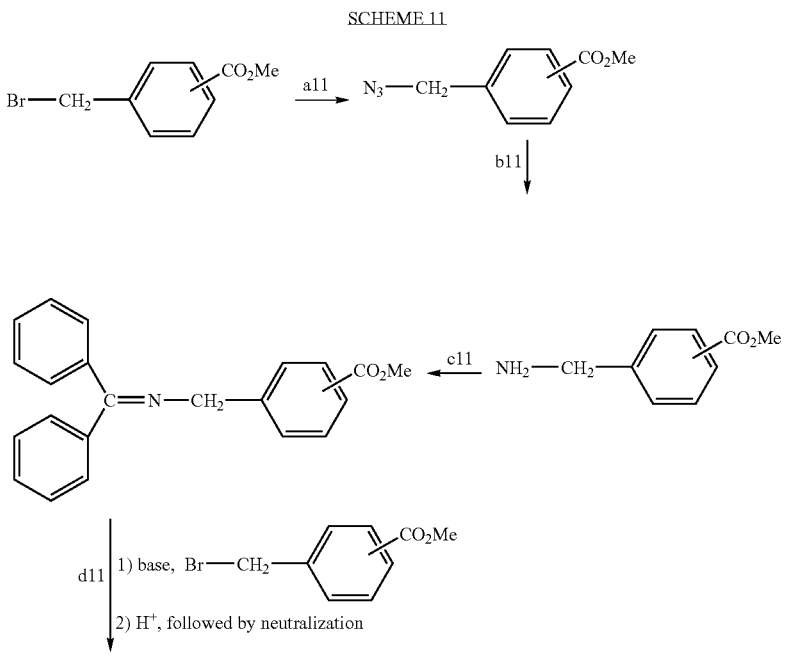

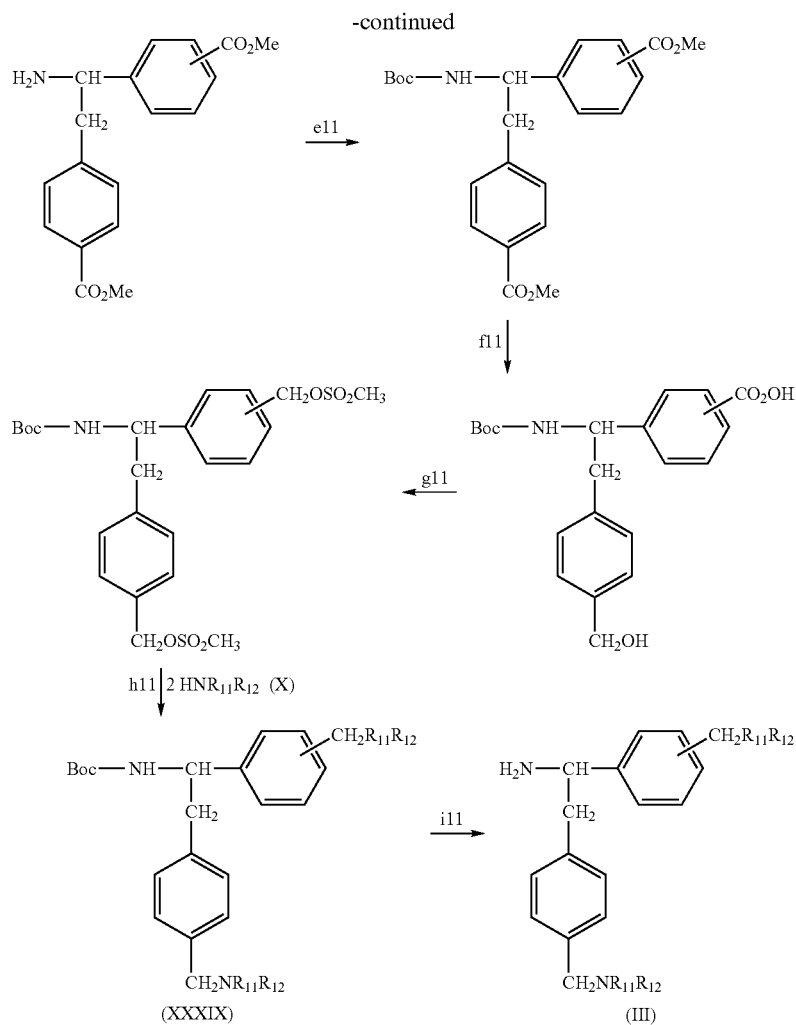
Steps a11 and b11 are carried out according to the methods described in Scheme 5.
Step c11 is carried out according to the process described in step a4 of Scheme 4.
Steps d11 to i11 are carried out according to the processes described in steps a8 to f8 of Scheme 8.
The compounds of formula (III) in which $R_4$ represents a group $COR_{13}$ may be prepared according to the scheme below.
SCHEME 12
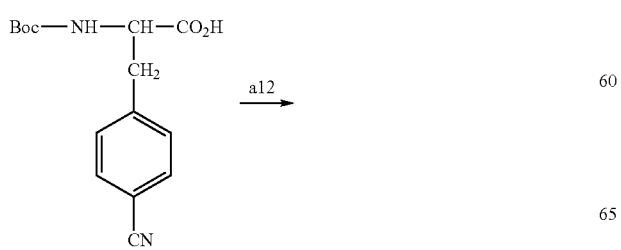
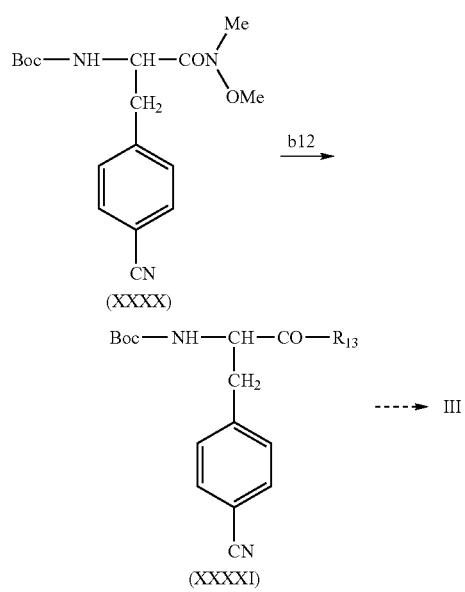

In step a12, N,O-dimethylhydroxylamine hydrochloride is reacted in the presence of a coupling agent, and in step b12, the lithiated derivative of the compound $R_{13}H$, prepared by the action of butyllithium on the compound $R_{13}H$, is added. The process is then performed according to steps b9, c9 and d9 of Scheme 9 to give a compound of formula (III) from the compound of formula (XXXXI).

The compounds of formula (III) in which $R_4$ represents a group $CSNR_8R_9$ are prepared by the action of Lawesson's reagent on an analogous compound of formula (III) in which $R_4$ represents a group $CONR_8R_9$ and the other substituents are identical (Tetrahedron, 1985, 41 (22), 5061–5087).

The optically pure compounds of formula (III) may be prepared by resolving the racemic mixtures by standard methods such as the method using optically active agents or enzymes. For example, when, in a compound of formula (III), Y represents a group —$CONR_8R_9$ or a $(C_1–C_4)$alkoxycarbonyl and Z=CN, the methods described in WO 97/25315 may be used; when, in a compound of formula (III), Y represents a pyridyl and Z=CN, the methods described in Tetrahedron, 1995, 51/46, 12731–12744 or in Synthesis, 1996, N° 8, 991–996 may be used.

Among the compounds of formulae (II) and (III), some are novel and constitute a further aspect of the invention.

The compounds of formula:

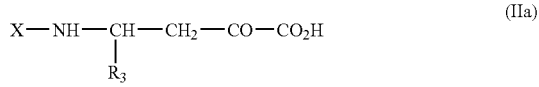

(IIa)

in which:
X represents hydrogen or an N-protecting group;
$R_3$ represents a heterocyclic radical chosen from: (2,2-difluoro)benzo[1,3]dioxol-5-yl, 3-isopropylphenyl, 3-trifluoromethoxyphenyl, 2,1,3-benzoxadiazol-5-yl, benzothiophen-5-yl, 1-benzofur-6-yl, 1-benzofur-4-yl, 1-benzofur-3-methyl-5-yl, 2,3-dihydrobenzofur-4-yl;

and also the salts thereof with mineral or organic acids, in racemic form or in the form of pure enantiomers;

are novel and constitute a further aspect of the present invention.

The compounds of formula:

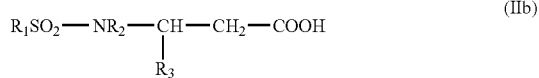

(IIb)

in which:
$R_1$ represents a phenylvinyl; a heterocycle chosen from quinolyl, 1-benzofur-2-yl, 2,1,3-benzoxadiazol-4-yl, 2,1,3-benzothiadiazol-4-yl, 1,3-benzothiazol-2-yl, 1-benzothiophen-2-yl, 1H-pyrazol-4-yl, thien-2-yl, 5-isoxazolthien-2-yl, benzothien-2-yl, thieno[3,2-c]pyrid-2-yl; naphtho[2,3-d][1,3]dioxol-6-yl; the said heterocycles being unsubstituted or substituted one or more times with $R_6$, which may be identical or different;
$R_2$ represents hydrogen or a $(C_1–C_4)$alkyl and $R_3$ represents a phenyl which is unsubstituted or substituted one or more times with $R_7$, which may be identical or different; a heterocyclic radical chosen from benzo[1,3]dioxol-5-yl which is unsubstituted or substituted in position -2 with two fluorine atoms; 2,1,3-benzothiadiazol-5-yl; 2,1,3-benzoxadiazol-5-yl; benzothiophen-5-yl; 2,3-dihydrobenzo[1,4]dioxin-6-yl; 1-benzofur-2-yl; 1-benzofur-5-yl; 1-benzofur-6-yl; 1-benzofur-4-yl; 1-benzofur-3-methyl-5-yl; 2,3-dihydrobenzofur-4-yl; 1,3-thiazol-2-yl; furyl; thien-2-yl; thien-3-yl;
or $R_2$ represents a phenyl which is unsubstituted or substituted one or more times with $R_6$, which may be identical or different; a benzo[1,3]dioxol-5-yl; a pyridyl; an indanyl; and $R_3$ represents hydrogen;
$R_6$ represents a halogen atom; a $(C_1–C_4)$alkyl group; a trifluoromethyl group; a $(C_1–C_4)$alkoxy group; a 2-fluoroethoxy group; a trifluoromethoxy, methylenedioxy or difluoromethylenedioxy group;
$R_7$ represents a halogen atom; a $(C_1–C_4)$alkyl group; a phenyl group; a trifluoromethyl group; a $(C_1–C_4)$ alkoxy group; a benzyloxy group; a trifluoromethoxy group;

and also the salts thereof with mineral or organic acids, in racemic form or in the form of pure enantiomers, are novel and form part of the invention.

The compounds of formula:

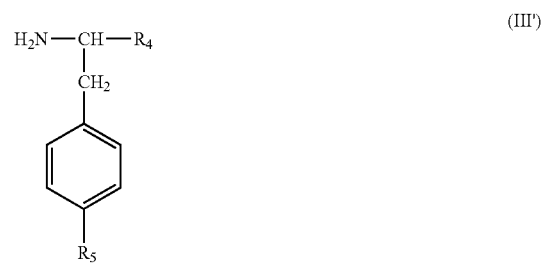

(III')

in which:
$R_4$ represents a group —$CONR_8R_9$; a group $CSNR_8R_9$; a group $COR_{13}$; a phenyl which is unsubstituted or substituted one or more times with $R_{10}$; a heterocyclic radical chosen from pyridyl, imidazolyl, furyl, benzimidazolyl, benzothiazol-2-yl and benzo[1,3]dioxol-5-yl, the said radicals being unsubstituted or substituted with a methyl;
$R_5$ represents a group —$CH_2NR_{11}R_{12}$ or —$CH_2N(O)R_{11}R_{12}$;
$R_8$ and $R_9$ each independently represent hydrogen; a $(C_1–C_4)$alkyl group; a $(C_3–C_7)$cycloalkyl group; a $(C_3–C_7)$cycloalkyl$(C_1–C_4)$alkyl group; an ω-$(C_1–C_4)$dialkylamino$(C_2–C_4)$alkyl group;
or $R_8$ and $R_9$, together with the nitrogen atom to which they are attached, constitute a heterocyclic radical chosen from pyrrolidinyl, piperidyl, morpholin-4-yl, thiomorpholin-4-yl, piperazin-1-yl, 4-methylpiperazin-1-yl, 4-methylpiperid-1-yl, 2-methylpiperid-1-yl, 4,4-dimethylpiperid-1-yl, 4,4-difluoropiperid-1-yl, 4-trifluoromethylpiperid-1-yl, 4-methoxypiperid-1-yl, 3,4-dihydropiperid-1-yl, azepin-1-yl and cyclohexyl-spiro-4-piperid-1-yl;
$R_{10}$ represents a halogen atom; a $(C_1–C_4)$alkyl group; a hydroxyl group; a $(C_1–C_6)$alkoxy group; $R_{10}$ can also represent a group —$CH_2NR_{11}R_{12}$ when $R_5$ represents a group —$CH_2NR_{11}R_{12}$, the said groups then being identical;
$R_{11}$ and $R_{12}$ each independently represent hydrogen; a $(C_1–C_6)$alkyl group; a $(C_2–C_4)$alkenyl group; a $(C_3–C_7)$cycloalkyl group; a $(C_3–C_7)$cycloalkyl$(C_1–C_4)$ alkyl group; an ω-hydroxy($C_2$–$C_4$)alkylene group; an ω-methoxy($C_2$–$C_4$)alkylene group; an ω-trifluoromethyl($C_2$–$C_4$)alkylene group; an ω-halo($C_2$–$C_4$)alkylene group;

or $R_{11}$ and $R_{12}$, together with the nitrogen atom to which they are attached, constitute a monocylic or bicyclic heterocyclic radical chosen from azetidinyl, pyrrolidinyl, morpholin-4-yl, thiomorpholin-4-yl, piperid-1-yl, piperazin-1-yl, 1,2,3,6-tetrahydropyrid-1-yl, 2,3,4,5-tetrahydropyridinium, decahydroquinolyl, decahydroisoquinolyl, tetrahydroisoquinolyl, octahydro-1H-isoindolyl, ($C_4$–$C_6$)cycloalkyl-spiro-piperidyl, 3-azabicyclo[3.1.0]hexyl and 7-azabicyclo[2.2.1]heptan-7-yl, which is unsubstituted or substituted one or more times with a halogen atom or a ($C_1$–$C_4$)alkyl, hydroxyl, ($C_1$–$C_4$)alkoxy, trifluoromethyl or difluoromethylene group;

$R_{13}$ represents a phenyl, thiazol-2-yl or pyridyl group;

and also the salts thereof with mineral or organic acids, in the form of racemic mixtures or of pure enantiomers, are novel and form part of the invention.

The affinity of the compounds according to the invention for the bradykinin $B_1$ receptors was measured on MRC5 cell membrane suspensions using a technique similar to the one described by K. H. Schneck et al., in Eur. J. Pharmacol., 1994, 266, 277–282. In this test, the affinity of [des-Arg$^9$]bradykinin is between $10^{-6}$M and $10^{-7}$M, that of [des-Arg$^{10}$]kallidin is $2\times10^{-9}$M; and the compounds of the invention show affinity ranging up to $10^{-9}$M.

The affinity is expressed in terms of $IC_{50}$, the $IC_{50}$ being the concentration that inhibits 50% of the specific binding of the [des-Arg$^{10}$]kallidin-tritiated ligand to the MRC5 cell receptors.

The affinity of the compounds according to the invention for the bradykinin $B_2$ receptors was measured on MRC5 cell membrane suspensions according to a technique similar to the one described by D. G. Sawutz et al., in Eur. J. Pharmacol., 1992, 227, 309–315. In this test, the affinity of the bradykinin, expressed in terms of $IC_{50}$, is in the region of $10^{-9}$ M, whereas the compounds of the invention show no affinity for the bradykinin $B_2$ receptors at a concentration of $10^{-6}$ M.

The antagonistic effect of the compounds according to the invention was measured in vitro by inhibition of the contraction of rabbit thoracic aorta induced by the administration of [des-Arg$^9$]bradykinin, after a preincubation of the tissue for 20 hours in Krebs buffer saturated with $CO_2/O_2$ mixture, according to an adaptation of the technique described by L. Levesque et al. Br. J. Pharmacol., 1993, 109, 1254–1262.

The antagonistic effect of the compounds according to the invention was also measured on the release of [$^3$H]inositol phosphate by MRC5 fibroblasts in culture: after incorporation of [$^3$H]myoinositol for 48 hours, according to the technique described by F. Oury Donat et al., J. Neurochem., 1994, 62, (4), 1399–1407. The antagonistic effect is expressed as the percentage of inhibition of the release of [$^3$H]inositol phosphate induced by [des-Arg$^{10}$]kallidin at $10^{-8}$ M, on MRC5 fibroblasts preincubated for 4 hours in the presence of $IL_1\beta$ at 0.5 μg/ml.

The intestinal absorption of the compounds according to the invention was studied in vitro on the model of CACO-2 cell monolayer, according to an adaptation of the technique described by T. Lindmark et al., J. Pharmacol. Exp. Therap., 1995, 275 (2), 958–964.

Moreover, several compounds according to the invention were studied in vivo on animal models.

The antinociceptive effect was checked on a model of neuropathic pain in rats after administration of a compound according to the invention at a dose of 30 mg/kg orally (according to the protocol described in Pain, 2000, 86, 265–271).

It has been observed that a compound according to the invention, at a dose of from 1 to 30 mg/kg orally, inhibits the late phase of nociception induced with formalin in mice (Pain, 1987, 203–114); this is the sign of an action on inflammatory pain.

A model of thermal hyperalgia induced by UV irradiation in rats (Brit. Med. J., 1993, 110, 1441–1444) demonstrated the anti-hyperalgic effects of a compound according to the invention at a dose of from 1 to 3 mg/kg orally.

The compounds according to the invention may be useful for treating or preventing many pathologies, in particular inflammation pathologies, persistent or chronic inflammatory diseases (Drug News and Perspectives, 1994, 10 (7), 603–611), neurogenic inflammation, pain (Brit. J. Pharmacol., 1993, 110, 193–198), chronic pains, neuropathies, septic shock, burns (Pain, 1993, 53, 191–197), wounds, diseases of the respiratory pathways, asthma, systemic inflammatory response syndrome, oedema (Brit. J. Pharmacol., 1995, 114, 1005–1013), cerebral oedema, angiogenesis (Brit. J. Pharmacol., 1993, 109, 14–17), type I infectious diabetes (Abst. 14th Intern. Symp. on Kinins, C49, Denver Colo., 10–15 Sep. 1995), diabetic vasculopathy, ventricular hypertrophy, pulmonary fibrosis and systemic progressive sclerosis.

Mention may be made, for example, of:
inflammation, osteal pain, muscular pain, articular pain, facial pain, fibromyalgia, hyperalgia, pain associated with cancer, perioperative pain, menstrual pain, headaches, dental pain, gynaecological pain, migraines;

hyperactivity of the respiratory pathways in asthma, atopic or non-atopic asthma, allergic or non-allergic asthma, bronchitis, pneumoconiosis, chronic obstructive diseases of the respiratory pathways, pleurisy, chronic obstructive pulmonary diseases, rhinitis of viral or allergic origin;

post-capillary resistance, diabetes, diabetic vasculopathy, diabetic symptoms associated with insulitis (for example: hyperglycaemia, diuresis, proteinuria);

septic shock;

Alzheimer's disease, cranial trauma;

arthritis, rheumatoid arthritis, inflammatory diseases of the joints, atherosclerosis, multiple sclerosis;

diseases of the digestive system, diseases of the urinary system, cystitis, pancreatitis, nephritis, enterocolitis, ulcerative colitis, irritable bowel syndrome, Crohn's disease, liver diseases;

pathologies of the ocular system, uveitis, retinitis, glaucoma;

skin diseases such as atopic diseases, eczema, psoriasis, dermatitis, itching;

hair loss.

Moreover, the compounds of the invention are useful for their antiproliferative effect on cancer cells; their action on neurodegenerative diseases, myelin degeneration, degenerative diseases of viral origin; their cardioprotective effect.

Furthermore, the compounds of the invention are useful as myorelaxants, relaxants of smooth muscles, of spasms of the gastrointestinal tract and the uterus.

More generally, the compounds according to the invention may be useful for treating or preventing any pathology in which bradykinin plays a fundamental role, which are denoted hereinbelow as bradykinin-dependent pathologies.

The compounds of the present invention are especially active principles of pharmaceutical compositions, the toxicity of which is compatible with their use as medicinal products.

The compounds of formula (I) above may be used at daily doses of from 0.01 to 100 mg per kilo of body weight of the mammal to be treated, preferably at daily doses of from 0.1 to 50 mg/kg. In man, the dose may preferably range from 0.5 to 4000 mg per day and more particularly from 2.5 to 1000 mg depending on the age of the individual to be treated or the type of treatment: prophylactic or curative.

For their use as medicinal products, the compounds of formula (I) are generally administered in dosage units. The said dosage units are preferably formulated in pharmaceutical compositions in which the active principle is mixed with a pharmaceutical excipient.

Thus, according to another of its aspects, the present invention relates to pharmaceutical compositions containing, as active principle, a compound of formula (I) or a pharmaceutically acceptable salt and/or solvate or hydrate thereof.

In the pharmaceutical compositions of the present invention for oral, sublingual, inhaled, subcutaneous, intramuscular, intravenous, transdermal, local or rectal administration, the active principles may be administered in unit administration forms, as a mixture with standard pharmaceutical supports, to animals and to man. The appropriate unit administration forms comprise oral forms such as tablets, gel capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

When a solid composition in the form of tablets is prepared, the active principle, micronized or non-micronized, is mixed with a pharmaceutical vehicle which may be composed of diluents such as, for example, lactose, microcrystalline cellulose, starch and formulation adjuvants, for instance binders (polyvinylpyrrolidone, hydroxypropylmethylcellulose, etc.), glidants, for instance silica, and lubricants, for instance magnesium stearate, stearic acid, glyceryl tribehenate or sodium stearylfumarate.

Wetting agents or surfactants such as sodium lauryl sulphate may be added to the formulation.

The tablets may be prepared by various techniques: direct tabletting, dry granulation, wet granulation or hot-melt granulation.

The tablets may be uncoated or sugar-coated (for example with sucrose) or coated with various polymers or other suitable materials.

The tablets may have a flash, delayed or sustained release by preparing polymer matrices or by using specific polymers in film coating.

A preparation as a gel capsule is obtained by simple mixing of the active principle with dry pharmaceutical vehicles (simple mixing or dry, wet or hot-melt granulation) or liquid or semi-solid pharmaceutical vehicles.

The gel capsules may be soft or hard, and film-coated or otherwise, so as to have a flash, sustained or delayed activity (for example via an enteric form).

A preparation in the form of a syrup or elixir may contain the active principle together with a sweetener, preferably a calorie-free sweetener, methylparaben and propylparaben as antiseptic, and also a flavouring and a suitable dye.

The water-dispersible powders or granules may contain the active principle as a mixture with dispersants, wetting agents or suspending agents, for instance polyvinylpyrrolidone, and also with sweeteners or flavour enhancers.

For rectal administration, use is made of suppositories which are prepared with binders that melt at the rectal temperature, for example cocoa butter or polyethylene glycols.

Aqueous suspensions, isotonic saline solutions or sterile injectable solutions containing pharmacologically acceptable dispersants and/or solubilizing agents, for example propylene glycol or butylene glycol, are used for parenteral, intranasal or intraocular administration.

Thus, to prepare an aqueous solution for intravenous injection, a cosolvent such as, for example, an alcohol such as ethanol or a glycol such as polyethylene glycol or propylene glycol, and a hydrophilic surfactant such as Tween® 80, may be used. To prepare an oily solution for intramuscular injection, the active principle may be dissolved with a triglyceride or a glycerol ester.

Creams, ointments, gels or eye drops may be used for local administration.

Patches in multilayer or reservoir form in which the active principle may be in an alcoholic solution may be used for transdermal administration.

For administration by inhalation, an aerosol containing, for example, sorbitan trioleate or oleic acid and also trichlorofluoromethane, dichlorofluoromethane, dichlorotetrafluoroethane or any other biologically compatible propellent gas is used; a system containing the active principle alone or combined with an excipient, in powder form, may also be used.

The active principle may also be in complex form with a cyclodextrin, for example $\alpha$, $\beta$ or $\gamma$-cyclodextrin, 2-hydroxypropyl-$\beta$-cyclodextrin or methyl-$\beta$-cyclodextrin.

The active principle may also be formulated in the form of microcapsules or microspheres, optionally with one or more supports or additives.

Among the sustained-release forms that are useful in the case of chronic treatment, implants may be used. These may be prepared in the form of an oily suspension or in the form of a suspension of microspheres in an isotonic medium.

In each dosage unit, the active principle of formula (I) is present in amounts that are adapted to the daily doses envisaged. In general, each dosage unit is suitably adjusted according to the dosage and the intended type of administration, for example tablets, gel capsules and the like, sachets, ampules, syrups and the like, or drops, such that such a dosage unit contains from 0.5 to 1000 mg of active principle and preferably from 2.5 to 250 mg needing to be administered one to four times a day.

The compositions of the present invention may contain, along with the compounds of formula (I) above or a pharmaceutically acceptable salt and/or solvate or hydrate thereof, other active principles which may be useful in the treatment of the complaints or diseases mentioned above. For example, a pharmaceutical composition according to the present invention may contain a bradykinin $B_2$ receptor antagonist combined with a compound according to the present invention.

According to another of its aspects, the present invention relates to the use of the compounds of formula (I), or a pharmaceutically acceptable salt and/or solvate or hydrate thereof, for the preparation of medicinal products intended for treating any pathology in which bradykinin and $B_1$ receptors are involved.

According to another of its aspects, the present invention relates to the use of the compounds of formula (I), or a pharmaceutically acceptable salt and/or solvate or hydrate thereof, for the preparation of medicinal products intended for treating inflammation pathologies and persistent or chronic inflammatory diseases.

In the Preparations and the Examples, the following abbreviations are used:
ether: diethyl ether
iso ether: diisopropyl ether
DCM: dichloromethane
DMF: N,N-dimethylformamide
DMSO: dimethyl sulphoxide
EtOAc: ethyl acetate
THF: tetrahydrofuran
AcOH: acetic acid
TFA: trifluoroacetic acid
TEA: triethylamine
DIPEA: diisopropylethylamine
DMAP: 4-dimethylaminopyridine
DCE: dichloroethane
DCC: 1,3-dicyclohexylcarbodiimide
DCU: dicyclohexylurea
TBTU: O-(1H-benzotriazol-1-yl)-N,N,N',N'-tetramethyluronium tetrafluoroborate
Boc: tert-butoxycarbonyl
(Boc)$_2$O: di-tert-butyl dicarbonate
Penicillin amidase sold by Sigma
Alcalase sold by Novo
Sephadex® LH 20: sold by Pharmacia
BOP: benzotriazol-1-yloxytris(dimethylamino) phosphonium hexafluorophosphate
TBTU: benzotriazol-1-yl-N,N,N',N'-tetramethyluronium tetrafluoroborate
KHSO$_4$/K$_2$SO$_4$ buffer: solution of 16.66 g of KHSO$_4$ and 32.32 g of K$_2$SO$_4$ in 1 liter of water
Hydrochloric ether: saturated solution of HCl gas in diethyl ether
m.p.: melting point
RT: room temperature Except where otherwise mentioned, the proton nuclear magnetic resonance (NMR) spectra are recorded at 200 MHz in DMSO-d$_6$ optionally containing TFA, and the reference is placed on the DMSO which is at 2.50 ppm from tetramethylsilane. The chemical shifts δ are indicated in ppm.

s: singlet; bs: broad singlet; ds: doubled singlet; d: doublet; bd: broad doublet; dd: doubled doublet: t: triplet; q: quartet; qt: quintet; mt: multiplet; unres.: unresolved peak; sept.: septet.

When only the NMR indication appears in the present description, this means that the NMR spectrum recorded under the above conditions is in accordance with the expected structure.

The mass spectra indicate the value MH$^+$.

PREPARATIONS

Preparation 1.1

3-(Naphthalene-2-sulphonylamino)-3-phenylpropionic acid

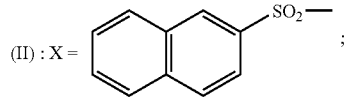

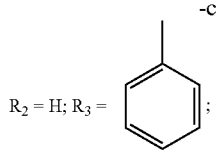

4.13 g of 3-amino-3-phenylpropionic acid are dissolved in a mixture of 100 ml of dioxane and 25 ml of 1N NaOH, 5.6 g of 2-naphthalenesulphonyl chloride are added portionwise while maintaining a pH of 10.5–10.8 by addition of 1N NaOH, and the mixture is stirred for 2 hours at RT. The reaction mixture is diluted by adding 400 ml of water, acidified to pH 2 by adding 2N HCl, and extracted with EtOAc, the organic phase is washed with KHSO$_4$/K$_2$SO$_4$ buffer solution and dried over Na$_2$SO$_4$, and the solvent is evaporated off under vacuum. 7.33 g of the expected product are obtained after triturating in heptane and drying under vacuum; m.p.=126–129° C.

NMR: δ (ppm): 2.55–2.70: mt: 2H; 4.70: t: 1H; 6.85–8.15: unres.: 12H.

Preparation 1.2

3-[Methyl(naphthalene-2-sulphonyl)amino]-3-phenylpropionic acid

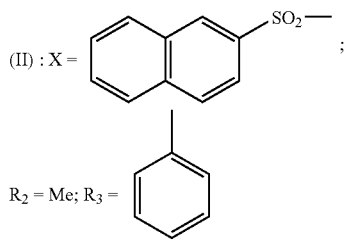

A) 3-(tert-Butoxycarbonylamino)-3-phenylpropionic acid 8.3 ml of triethylamine are added to a mixture of 8.3 g of 3-amino-3-phenylpropionic acid in 35 ml of water and 5 ml of dioxane, followed by addition, over 30 minutes, of a solution of 12.8 g of di-tert-butyl dicarbonate in 25 ml of dioxane, and the mixture is stirred overnight at RT. The reaction mixture is diluted with water, the aqueous phase is washed with ether and acidified to pH 2.5 by adding 2N HCl, and extracted with EtOAc, the organic phase is washed with water, with saturated NaCl solution and dried over Na$_2$SO$_4$, and the solvent is evaporated off under vacuum. 12.4 g of the expected product are obtained.

B) 3-(N-tert-Butoxycarbonylmethylamino)-3-phenylpropionic acid 0.27 g of 80% sodium hydride in oil is added portionwise to a mixture of 0.795 g of the compound obtained in the preceding step and 0.62 ml of methyl iodide in 10 ml of THF, and the mixture is stirred overnight at RT. The reaction mixture is diluted with EtOAc, water is added and the mixture is acidified to pH 2 by adding 1N HCl. After separation of the phases by settling, the organic phase is washed with water, with saturated NaCl solution and dried over Na$_2$SO$_4$, and the solvent is evaporated off under vacuum. 0.82 g of the expected product is obtained.

C) 3-(Methylamino)-3-phenylpropionyl trifluoroacetate

A mixture of 0.81 g of the compound obtained in the preceding step and 12 ml of TFA in 10 ml of DCM is stirred for 55 minutes at RT. The reaction mixture is concentrated under vacuum, the residue is taken up in DCM and the solvent is evaporated off under vacuum. The residue is dissolved in ether, heptane is added to the point of precipitation, the solvent is decanted off and the gum obtained is dried. 0.86 g of the expected product is obtained in the form of a foam.

D) 3-[Methyl(naphthalene-2-sulphonyl)amino]-3-phenylpropionic acid 5 ml of 1N NaOH are added to a mixture of 0.85 g of the compound obtained in the preceding step in 5 ml of dioxane, followed by portionwise addition of 0.698 g of 2-naphthalenesulphonyl chloride, while keeping the pH at 10–11 by adding 1N NaOH, and the mixture is stirred for 2 hours at RT. The reaction mixture is diluted with water, the aqueous phase is washed with ether and acidified to pH 2 by adding 1N HCl, and extracted with EtOAc, the organic phase is washed with water, with saturated NaCl solution and dried over $Na_2SO_4$, and the solvent is evaporated off under vacuum. 0.65 g of the expected product is obtained in the form of a wax.

Preparation 1.3

3-(3-Methylphenyl)-3-(naphthalene-2-sulphonylamino)propionic acid

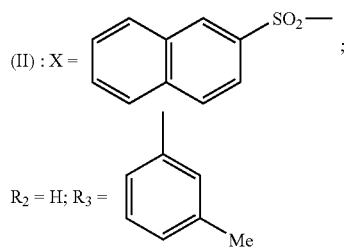

A) 3-Amino-3-(3-methylphenyl)propionic acid 11.8 ml of 3-methylbenzaldehyde are added to a mixture of 10.4 g of malonic acid and 15.4 g of ammonium acetate in 150 ml of 2-methoxyethanol, and the mixture is heated overnight at 80° C. After cooling to RT, the precipitate formed is filtered off under suction, washed with ether and dried. 6.8 g of the expected product are obtained.

NMR: δ (ppm): 2.25: s: 3H; 2.80 to 3.05: mt: 2H; 4,55: t: 1H; 7.10 to 7.30: unres.: 4H.

B) 3-(3-Methylphenyl)-3-(naphthalene-2-sulphonylamino)propionic acid 10 ml of 1N NaOH are added to a suspension of 1.79 g of the compound obtained in the preceding step in 25 ml of dioxane, followed by portionwise addition of 2.26 g of 2-naphthalenesulphonyl chloride, while keeping the pH at 10.5–12 by adding 1N NaOH, and the mixture is stirred for 2 hours at RT. The reaction mixture is diluted with water, the aqueous phase is washed with EtOAc and acidified to pH 1 by adding 6N HCl, and extracted with EtOAc, the organic phase is washed with saturated NaCl solution and dried over $Na_2SO_4$, and the solvent is evaporated off under vacuum. 3.37 g of the expected product are obtained after crystallization from heptane.

Preparation 1.4

3-(3,4-Dimethylphenyl)-3-(naphthalene-2-sulphonylamino)propionic acid

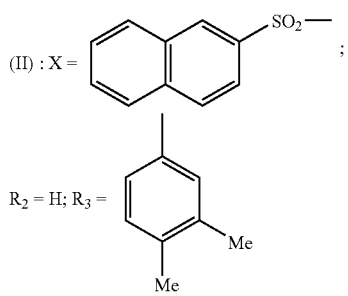

A) 3-Amino-3-(3,4-dimethylphenyl)propionic acid hydrochloride

A mixture of 5 g of 3,4-dimethylbenzaldehyde, 3.88 g of malonic acid and 5.74 g of ammonium acetate in 50 ml of EtOH is refluxed for 5 hours. After cooling to RT, the precipitate formed is filtered off by suction and washed with EtOH. The precipitate is taken up in a DCM/1N HCl mixture, the insoluble material is filtered off, the filtrate is decanted and the acidic aqueous phase is concentrated under vacuum up to the start of precipitation and cooled to 0° C., and the precipitate formed is filtered off by suction. The precipitate is taken up in a DCM/MeOH mixture (6/4; v/v) and dried over $Na_2SO_4$, and the solvents are evaporated off under vacuum. The residue is taken up in ether and the precipitate formed is filtered off by suction after trituration. 3.01 g of the expected product are obtained; m.p.=192° C. (dec.).

B) 3-(3,4-Dimethylphenyl)-3-(naphthalene-2-sulphonylamino)propionic acid

A solution of 1.98 g of 2-naphthalenesulphonyl chloride in 15 ml of dioxane is added dropwise to a mixture of 2 g of the compound obtained in the preceding step and 17.4 ml of 1N NaOH in 20 ml of dioxane, and the mixture is stirred overnight at RT. The reaction mixture is neutralized to pH 7 by adding 1N HCl and concentrated under vacuum. The residue is taken up in an EtOAc/saturated $NaHCO_3$ mixture, the precipitate formed is filtered off by suction and taken up in a DCM/1N HCl mixture, the organic phase is dried over $Na_2SO_4$ after separation of the phases by settling, and the solvent is evaporated off under vacuum. 1.66 g of the expected product are obtained; m.p.=122° C. (dec.).

Preparation 1.5

3-(3,5-Dimethoxyphenyl)-3-(naphthalene-2-sulphonylamino)propionic acid

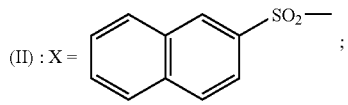

$R_2 = H; R_3 =$ 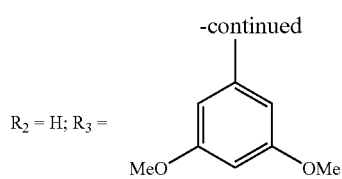

A) 3-Amino-3-(3,5-dimethoxyphenyl)propionic acid

A mixture of 5 g of 3,5-dimethoxybenzaldehyde, 3.13 g of malonic acid and 4.64 g of ammonium acetate in 50 ml of EtOH is refluxed for 5 hours. The reaction mixture is concentrated under vacuum, the residue is taken up in water, insoluble material is filtered off, the filtrate is washed with DCM and the aqueous phase is concentrated under vacuum. The residue is taken up in water and concentrated under vacuum again. The residue is taken up in EtOH and the solvent is evaporated off under vacuum. 2.96 g of the expected product are obtained.

B) 3-(3,5-Dimethoxyphenyl)-3-(naphthalene-2-sulphonylamino)propionic acid 1.01 g of 2-naphthalenesulphonyl chloride are added portionwise to a mixture of 1 g of the compound obtained in the preceding step and 4.5 ml of 1N NaOH in 15 ml of dioxane, and the mixture is stirred overnight at RT. The reaction mixture is diluted with water and washed with EtOAc, the aqueous phase is acidified to pH 1 by adding concentrated HCl, and extracted with ether, the organic phase is washed with 1N HCl and dried over $Na_2SO_4$, and the solvent is evaporated off under vacuum. 1.41 g of the expected product are obtained; m.p.=190° C.

Preparation 1.6

3-(3,4-Dimethoxyphenyl)-3-(naphthalene-2-sulphonylamino)propionic acid

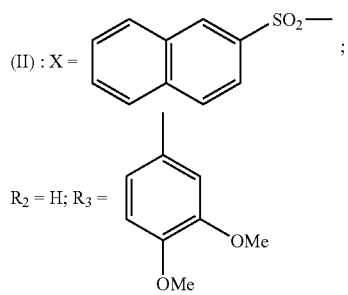

A) 3-Amino-3-(3,4-dimethoxyphenyl)propionic acid, hydrochloride

A mixture of 5 g of 3,4-dimethoxybenzaldehyde, 3.131 g of malonic acid and 4.64 g of ammonium acetate in 50 ml of EtOH is refluxed for 5 hours. After cooling to RT, the precipitate formed is filtered off by suction. The precipitate is taken up in water, acidified to pH 2 by adding 1N HCl, and the aqueous phase is washed with DCM and concentrated under vacuum. The residue is taken up in water and concentrated again under vacuum. The residue is taken up in EtOH and evaporated under vacuum. 2.99 g of the expected product are obtained.

B) 3-(3,4-Dimethoxyphenyl)-3-(naphthalene-2-sulphonylamino)propionic acid

This compound is prepared according to the procedure described in step B) of preparation 1.5, starting with 1 g of the compound obtained in the preceding step and 7.65 ml of 1N NaOH in 15 ml of dioxane. 1.33 g of the expected product are obtained.

Preparation 1.7

3-(Benzo[1,3]dioxol-5-yl)-3-(naphthalene-2-sulphonylamino)propionic acid

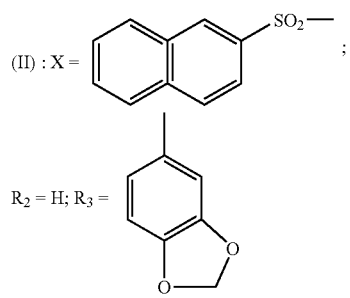

A) 3-Amino-3-(benzo[1,3]dioxol-5-yl)propionic acid

This compound is prepared according to the procedure described in Biorg. Med. Chem., 1994, 2 (9), 881.

B) 3-(Benzo[1,3]dioxol-5-yl)-3-(naphthalene-2-sulphonylamino)propionic acid

1N NaOH is added to a suspension of 2.16 g of the compound obtained in the preceding step in 40 ml of dioxane, until the pH=11.8, followed by portionwise addition of 2.33 g of 2-naphthalenesulphonyl chloride, and the mixture is stirred for 2 hours at RT while keeping the pH at 10.5–11.5 by adding 1N NaOH. The reaction mixture is diluted with an equal volume of water and washed with EtOAc, the aqueous phase is acidified to pH 1.5 by adding 6N HCl, and extracted with EtOAc, the organic phase is washed with $KHSO_4/K_2SO_4$ buffer, with saturated NaCl solution and dried over $Na_2SO_4$, and the solvent is evaporated off under vacuum. 3.9 g of the expected product are obtained after crystallization from heptane; m.p.=173–175° C.

NMR: δ (ppm): 2.45–2.60: mt: 2H; 4.65: q: 1H; 5.40–5.70: mt: 2H; 6.45–6.65: mt: 3H; 7.55–7.75: mt: 3H; 7.90–8.10: mt: 4H; 8.35: bd: 1H.

Preparation 1.8

3-(2,3-Dihydrobenzo[1,4]dioxin-6-yl)-3-(naphthalene-2-sulphonylamino)propionic acid

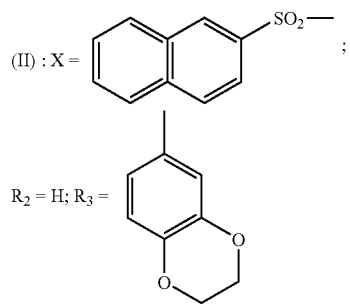

A) 3-Amino-3-(2,3-dihydrobenzo[1,4]dioxin-6-yl)propionic acid

A mixture of 5 g of 2,3-dihydrobenzo[1,4]dioxine-6-carbaldehyde, 3.17 g of malonic acid and 4.69 g of ammonium acetate in 50 ml of EtOH is refluxed for 5 hours. The reaction mixture is allowed to cool to RT and the precipitate formed is filtered off by suction and washed with EtOH and then with water. 1.965 g of the expected product are obtained after drying under vacuum.

B) 3-(2,3-Dihydrobenzo[1,4]dioxin-6-yl)-3-(naphthalene-2-sulphonylamino)propionic acid This compound is prepared according to the procedure described in step B of preparation 1.5, starting with 1 g of the compound obtained in the preceding step, 4.5 ml of 1N NaOH, 15 ml of dioxane and 1.02 g of 2-naphthalenesulphonyl chloride. 0.876 g of the expected product is obtained after crystallization from hexane.

Preparation 1.9

3-(2,3-Dihydrobenzo[1,4]dioxin-6-yl)-3-(5,6,7,8-tetrahydronaphthalene-2-sulphonylamino)propionic acid

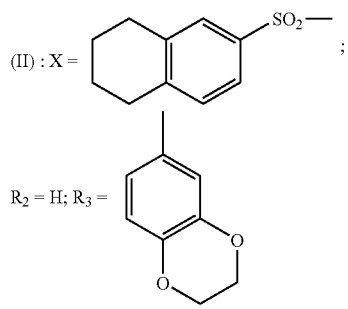

A solution of 0.570 g of 5,6,7,8-tetrahydronaphthalene-2-sulphonyl chloride in 15 ml of dioxane is added dropwise to a mixture of 0.5 g of the compound obtained in step A of preparation 1.8 and 4.5 ml of 1N NaOH in 20 ml of dioxane, and the mixture is stirred for 4 hours at RT. The reaction mixture is concentrated under vacuum, the residue is taken up in 1N NaOH and washed with DCM, the aqueous phase is acidified to pH 1 by adding concentrated HCl, and extracted with DCM, the organic phase is washed with saturated NaCl solution and dried over $Na_2SO_4$, and the solvent is evaporated off under vacuum. 0.5 g of the expected product is obtained.

Preparation 1.10

3-[(2,4-Dichloro-3-methylbenzenesulphonyl)phenylamino]propionic acid

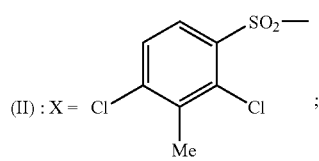

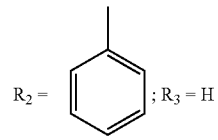

A) 2,4-Dichloro-3-methylbenzenesulphonyl chloride

This compound is prepared according to the procedure described in J. Am. Chem. Soc., 1940, 62, 511–512.

B) Methyl 3-(phenylamino)propionate

A mixture of 20 ml of aniline, 22 ml of methyl acrylate and 2 ml of acetic acid is refluxed for 8 hours. After concentrating the reaction mixture under vacuum, the resulting oil is distilled off under reduced pressure (b.p.=132° C. at 333.3 Pa and then b.p.=110° C. at 6.66 Pa). The product obtained is taken up in hexane and the precipitate formed is filtered off by suction. 25 g of the expected product are obtained.

C) Methyl 3-[(2,4-dichloro-3-methylbenzenesulphonyl)phenylamino]propionate

A mixture of 1.5 g of the compound obtained in step A, 1.03 g of the compound obtained in step B and 0.08 g of DMAP in 20 ml of pyridine is stirred for 1 hour at RT. The reaction mixture is concentrated under vacuum, the residue is extracted with EtOAc, the organic phase is washed with a buffer solution pH=2, with saturated NaCl solution and dried over $Na_2SO_4$, and the solvent is evaporated off under vacuum. 2.32 g of the expected product are obtained.

D) 3-[(2,4-Dichloro-3-methylbenzenesulphonyl)phenylamino]propionic acid 8.7 ml of 1N KOH are added to a solution of 2.32 g of the compound obtained in the preceding step in 10 ml of EtOH and 10 ml of dioxane, and the mixture is stirred overnight at RT. The reaction mixture is concentrated under vacuum, the residue is taken up in saturated $NaHCO_3$ solution, the aqueous phase is washed with ether, acidified to pH 1 by adding 1N HCl and extracted with DCM, the organic phase is washed with water and dried over $Na_2SO_4$, and the solvent is evaporated off under vacuum. 0.912 g of the expected product is obtained.

NMR: δ (ppm): 2.35: t: 2H; 2.5: s: 3H; 4.0: t: 2H; 7.15 to 7.4: unres.: 5H; 7.45 to 7.65: q: 2H; 12.2 to 12.5: bs: 1H.

Preparation 1.11

2,5-Dioxopyrrolidin-1-yl 3-(naphthalene-2-sulphonylamino)-3-phenylpropionate 1.13 g of 1,3-dicyclohexylcarbodiimide are added to a mixture of 1.78 g of the compound obtained in Preparation 1.1 and 0.578 g of N-hydroxysuccinimide in 15 ml of DMF, and the mixture is stirred overnight at RT. After filtering off by suction the 1,3-dicyclohexylurea formed, the filtrate is diluted with water and extracted with EtOAc, the organic phase is washed with saturated $NaHCO_3$ solution, with saturated NaCl solution and dried over $Na_2SO_4$, and the solvent is evaporated off under vacuum. 1.81 g of the expected product are obtained.

Preparation 1.12

3-Phenyl-3-(quinoline-2-sulphonylamino)propionic acid

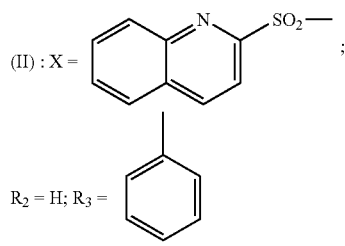

(II) : X = [quinoline-2-SO2—] ;

R2 = H; R3 = [phenyl]

This compound is prepared according to the procedure described in Preparation 3.13 of international patent application WO 97/25315.

Preparation 1.13

(R) 3-(N-Boc)Amino-3-(benzo[1.3]dioxol-5-yl)propionic acid

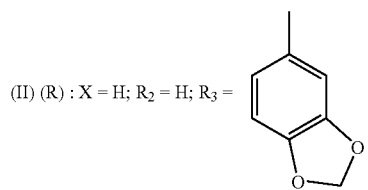

(II) (R) : X = H; R2 = H; R3 = [benzo[1,3]dioxol-5-yl]

A) (R) 3-(Phenylacetyl)amino-3-(benzo[1,3]dioxol-5-yl)propionic acid 20 g of 3-amino-3-(benzo[1,3]dioxol-5-yl)propionic acid hydrochloride are placed in 10 ml of acetone, 30 ml of water and 38 ml of TEA at −5° C. and 14 ml of phenylacetyl chloride in 20 ml of acetone are added dropwise, followed by stirring for 2 hours at −5° C. The acetone is concentrated. The aqueous phase is washed with Et₂O and the insoluble material is removed by filtration. The phases are separated again by settling and the aqueous phase is washed with Et₂O and then acidified with 1N HCl to pH 2. The resulting phase is poured into DCM and a precipitate forms. The precipitate is filtered off by suction and rinsed with DCM. 24 g of the expected compound are obtained.

B) (R) 3-Amino-3-(benzo[1,3]dioxol-5-yl)propionic acid HCl 4 g of the compound from the preceding step are placed in 150 ml of water, 12.23 ml of 1N KOH are added and the mixture is stirred for 15 minutes at RT. The pH of the solution is approximately 11; AcOH is added and the pH is adjusted to 7.5±0.1. 250 μl of penicillin amidase are added and the mixture is stirred overnight at RT, while maintaining the pH at 7.5±0.1. The mixture is acidified to pH 2 by adding 1N HCl and then washed with EtOAc. The aqueous phase is heated to 65° C. with active vegetable charcoal for 5 minutes. The resulting mixture is filtered through Celite® and the aqueous phase is washed with Et₂O and then concentrated to dryness and evaporated. The residue is taken up in an MeOH/DCM mixture (6/4; v/v) and the insoluble material (mineral) is then removed and the organic phase is dried over sodium sulphate and concentrated. 1.75 g of expected compound are obtained.

NMR: δ (ppm): 2.7–3.1: mt: 2H; 4.4: unres.: 1H; 6.0: s: 2H; 6.9: q: 2H; 7.1: s: 1H.

C) (R) 3-(N-Boc)Amino-3-(benzo[1.3]dioxol-5-yl)propionic acid 1.30 g of the compound obtained in the preceding step are placed in 20 ml of dioxane and 20 ml of water; 1.8 ml of TEA and then 1.54 g of (Boc)₂O are added and the mixture is stirred overnight at RT. The reaction mixture is diluted with water, washed with Et₂O and then acidified to pH 2 by addition of KHSO₄/K₂SO₄. The resulting mixture is extracted with EtOAc and then washed with saturated NaCl solution. 0.850 g of the expected compound is obtained.

$\alpha_D^{25}$=+54° (c=0.5; MeOH)

By working according to the methods described above, the compounds of formula (II) described in Table III below are prepared:

TABLE III $$X-N(R_2)-CH(R_3)-CH_2-CO_2H \quad (II)$$

| Preparation | X | R2 | R3 | m.p. ° C. |
|---|---|---|---|---|
| 1.14 | 5-dimethylamino-naphthalene-1-SO2— | H | [phenyl] | |

TABLE III-continued $$X-N(R_2)-CH(R_3)-CH_2-CO_2H \quad (II)$$

| Preparation | X | R₂ | R₃ | m.p. ° C. |
|---|---|---|---|---|
| 1.15 | naphthalen-2-yl-SO₂— | H | 3-phenoxyphenyl | |
| 1.16 | naphthalen-2-yl-SO₂— | H | 4-chlorophenyl | |
| 1.17 | 2,4-dichloro-3-methylphenyl-SO₂— | H | benzo[1,3]dioxol-5-yl (methyl-substituted) | 174° C. |
| 1.18 | naphthalen-2-yl-SO₂— | H | 3-methylfuran-3-yl | 139–142° C. |
| 1.19 | benzothiazol-2-yl-SO₂— | H | phenyl | 148° C. |
| 1.20 | pentamethylphenyl-SO₂— | methyl | phenyl | 120° C. |
| 1.21 | pentamethylphenyl-SO₂— | H | phenyl | 185° C. |

TABLE III-continued $$X-N(R_2)-CH(R_3)-CH_2-CO_2H \quad (II)$$

| Preparation | X | R₂ | R₃ | m.p. ° C. |
|---|---|---|---|---|
| 1.22 | 2,4-dichloro-3-methylphenyl-SO₂— | 3-methylphenyl | H | 159° C. |
| 1.23 | naphthalen-2-yl-SO₂— | 3-(benzyloxy)phenyl | H | 68° C. |
| 1.24 | 2,4,6-trichlorophenyl-SO₂— | 3-phenoxyphenyl | H | oil |
| 1.25TFA | naphthalen-2-yl-SO₂— | pyridin-3-yl | H | 137° C. |
| 1.26TFA | 2,4-dichloro-3-methylphenyl-SO₂— | pyridin-3-yl | H | 184° C. |
| 1.27TFA | 2,4-dichloro-3-methylphenyl-SO₂— | pyridin-4-yl | H | 163° C. |

TABLE III-continued $$X-N(R_2)-CH(R_3)-CH_2-CO_2H \quad \text{(II)}$$

| Preparation | X | R$_2$ | R$_3$ | m.p. ° C. |
|---|---|---|---|---|
| 1.28 | 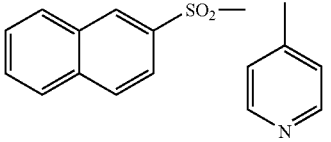 | 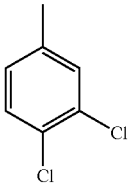 | H | 180° C. |
| 1.29TFA | 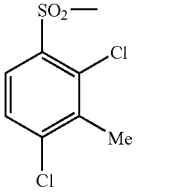 | 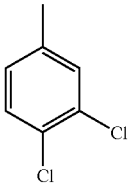 | H | 154° C. |
| 1.30 | 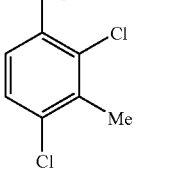 | 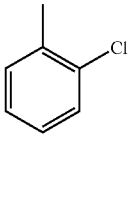 | H | 160° C. |
| 1.31 | 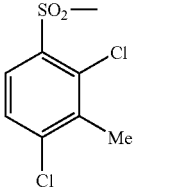 | 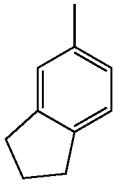 | H | 193° C. |

Preparation 1.14

NMR: 2.2 ppm: mt: 2H; 2.8 ppm: s: 6H; 4.5 ppm: t: 1H; 6.9 ppm: mt: 6H; 7.2 ppm: d: 1H; 7.4 ppm: t: 1H; 7.55 ppm: t: 1H; 7.9 ppm: d: 1H; 8.3 ppm: t: 1H.

Preparation 1.15

NMR; 2.55 ppm: mt: 2H; 4.65 ppm: mt: 1H; 6.4–8.0 ppm: mt: 15H; 8.1 ppm: s: 1H; 8.4 ppm: d: 1H.

Preparation 1.16

NMR; 2.5–2.7 ppm: mt: 2H; 4.7 ppm: q: 1H; 7.0–8.1 ppm: mt: 11H; 8.5 ppm: d: 1H.

Preparation 1.17

NMR (DMSO+TFA): 2.4 ppm: t: 2H; 2.55 ppm: s: 3H; 4.0 ppm: t: 2H; 6.05 ppm: s: 2H; 6.6 ppm: dd: 1H; 6.8 ppm: mt: 2H; 7.55 ppm: d: 1H; 7.65 ppm: d: 1H.

Preparation 1.18

NMR (DMSO+TFA): 2.40–2.65 ppm: mt: 2H; 4.60–4.75 ppm: t: 1H; 6.20 ppm: s: 1H; 7.10–8.40 ppm: unres.: 9H.

Preparation 1.25

NMR (250 MHz): 2.35–2.45 ppm: t: 2H; 3.80–3.90 ppm: t: 2H; 7.30–8.60 ppm: mt: 11H.

Preparation 1.26

NMR (250 MHz): 2.35–2.45 ppm: t: 2H; 2.50 ppm: s: 3H; 3.95–4.05 ppm: t: 2H; 7.35–8.50 ppm: mt: 6H.

Preparation 1.27

NMR (250 MHz): 2.40 ppm: s: 3H; 2.50–2.60 ppm: t: 2H; 4.15–4.25 ppm: t: 2H; 7.55–8.65 ppm: mt: 6H.

Preparation 1.28

NMR: 2.55–2.75 ppm: t: 2H; 4.15–4.45 ppm: t: 2H; 7.55–8.75 ppm: mt: 11H.

Preparation 1.29

NMR (DMSO+TFA): 2.4 ppm: t: 2H; 2.5 ppm: mt: 5H; 4.0 ppm: t: 2H; 7.25 ppm: dd: 1H; 7.7 ppm: mt: 4H.

Preparation 1.30

NMR: 2.4 ppm: t: 2H; 2.5 ppm: mt: 5H; 4.0 ppm: unres.: 2H; 7.3–7.6 ppm: mt: 6H.

Preparation 1.31

NMR (DMSO+TFA): 1.9 ppm: quint: 2H; 2.25 ppm: t: 2H; 2.4 ppm: mt: 4H; 2.85 ppm: t: 4H; 3.85 ppm: t: 2H; 6.8: dd: 1H; 7.0 ppm: unres.: 2H; 7.5 ppm: q: 2H.

Preparation 1.32

(II) : X = 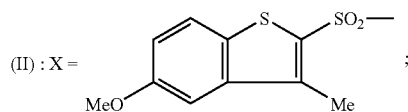 ;

$R_2 = H; R_3 =$ 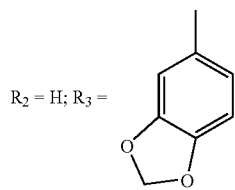

A) S-(4-Methoxy)phenyl ethanethioate 15 g of 4-methoxybenzenethiol are dissolved in 20 ml of water containing 4.3 g of NaOH and the mixture is stirred for 20 minutes at RT. 8.5 ml of 1-chloroacetone are added dropwise and the mixture is stirred for 1 hour at RT. The reaction mixture is extracted with ether (twice), dried and evaporated to give 20 g of the expected compound.

B) 5-Methoxy-3-methylbenzothiophene 10 g of the compound from the preceding step and 20 ml of polyphosphoric acid are mixed together in 400 ml of chlorobenzene, and the mixture is stirred for 1 hour at RT and then heated at 120° C. for 18 hours. The reaction mixture is allowed to cool and the phases are then separated by settling. The residual oil is taken up in DCM (twice) and the phases are then separated again by settling.

The supernatant phases are combined and then evaporated. The residue is taken up in DCM and then washed with water, followed by NaHCO$_3$ solution. After evaporating off the solvent, the residue is chromatographed on silica, eluting with a hexane/EtOAc mixture (98/2; v/v) to give 5.2 g of the expected compound.

C) Lithium (5-methoxy-3-methyl-1-benzothiophen-2-yl) sulphinate 1.69 g of the compound from the preceding step are dissolved in 10 ml of THF and the mixture is cooled to −20° C. 6.6 ml of butyllithium (1.8M in hexane) are added over 15 minutes, followed by slow addition of SO$_2$ in an amount sufficient to saturate the medium. After stirring for 20 minutes at −20° C., the mixture is allowed to warm to RT. 50 ml of Et$_2$O are added and the resulting mixture is then filtered by suction and dried to give 2.4 g of the expected compound.

D) 5-Methoxy-3-methyl-1-benzothiophene-2-sulphonyl chloride 2.4 g of the compound from the preceding step are suspended in 20 ml of CH$_2$Cl$_2$. The mixture is cooled to 5° C., followed by portionwise addition of 1.26 g of N-chlorosuccinimide, and the resulting mixture is stirred for one hour at 5° C. The reaction mixture is washed with water and the water is re-extracted with CH$_2$Cl$_2$. The organic phases are combined, washed with NaCl solution, dried and evaporated to give 1.8 g of the expected compound.

NMR: 2.50 ppm: s: 3H; 3.85 ppm: s: 3H; 7.0–7.80 ppm: mt: 3H.

E) The process is then performed according to the usual methods to obtain the expected compound.

Preparation 1.33

(II) : X = 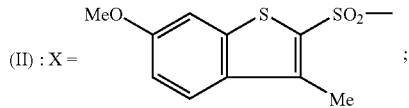 ;

$R_2 = H; R_3 =$ 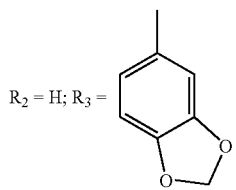

A) 6-Methoxy-3-methyl-1-benzothiophene-2-sulphonyl chloride

This compound is prepared according to the process described in the above preparation.

NMR: 2.50 ppm: s: 3H; 3.85 ppm: s: 3H; 7.0–7.70 ppm: mt: 3H.

B)

The process is then performed according to the usual methods to obtain the expected compound.

Other compounds of formula (II) prepared according to the methods known from the literature or described above were prepared in racemic form or in the form of pure isomers.

TABLE IV
$$X-NH-\underset{\underset{R_3}{|}}{CH}-CH_2CO_2H \quad (II)$$
| Preparation (isomer) | X | R₃ | m.p. ° C. or NMR |
|---|---|---|---|
| 1.34 | Boc | 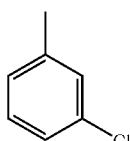 | 114° C. |
| 1.35 | 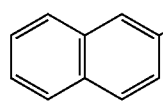 | 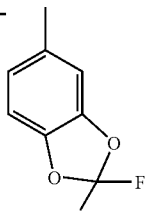 | 159° C. |
| 1.36 | 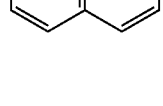 | 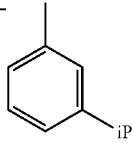 | NMR |
| 1.37 | H 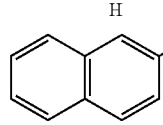 | 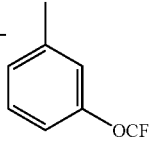 | 248° C. 145° C. |
| 1.38 (R) | Boc | 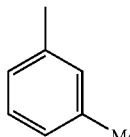 | 120° C. |
| 1.39 | H Boc | 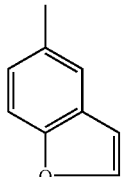 | NMR 167° C. |
| 1.40 (R) | H | 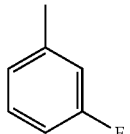 | NMR |
| 1.41 | H Boc | 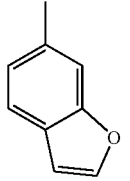 | 242° C. 190° C. |

TABLE IV-continued $$X-NH-\underset{R_3}{CH}-CH_2CO_2H \quad (II)$$

| Preparation (isomer) | X | R₃ | m.p. °C. or NMR |
|---|---|---|---|
| 1.42 | H<br>Boc | 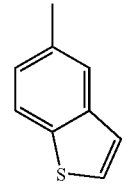 | 260° C.<br>198° C. |
| 1.43 | H<br>Boc | 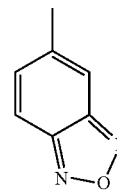 | 228° C.<br>NMR |
| 1.44 | H<br>Boc | 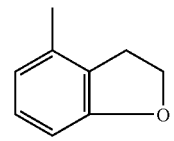 | 204° C.<br>125° C. |
| 1.45<br>(a) | H<br>Boc | 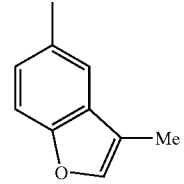 | NMR<br>NMR |

(a) This compound is prepared from 1-benzofurancarbonitrile described in European patent application 540 041.

Preparation 2.1

2-Amino-3-(4-cyanophenyl)-1-(pyrrolidin-1-yl)propan-1-one trifluoroacetate

7.5 g of BOP are added to a mixture of 4.06 g of 2-(tert-butoxycarbonylamino)-3-(4-cyanophenyl)propionic acid and 1.15 ml of pyrrolidine in 20 ml of DMF, and the mixture is stirred for 2 hours at RT, while keeping the pH at 7 by adding N-ethylmorpholine. The reaction mixture is concentrated under vacuum and the residue is chromatographed on silica gel, eluting with a chloroform/MeOH mixture (95/5; v/v). The product obtained is taken up in 20 ml of TFA in 20 ml of DCM, and the reaction mixture is stirred for 30 minutes at RT and concentrated under vacuum. The residue is taken up in ether and the precipitate formed is filtered off by suction. 3.95 g of the expected product are obtained after drying.

Preparation 2.2

2-Amino-3-[4-(tert-butylaminomethyl)phenyl]-1-(pyrrolidin-1-yl)propan-1-one bis(trifluoroacetate)

(III), 2TFA : Y = —CO—N⟨pyrrolidine⟩ ;
Z = R₅ = —CH₂—NR₁₁R₁₂ = —CH₂—NH-tBu

A) Ethyl 2-(benzhydrylideneamino)-3-(4-bromomethylphenyl)propionate

This compound is prepared according to the procedure described in Tetrahedron: Asymmetry, 1992, 3 (5), 637–650.

B) Ethyl 2-(benzhydrylideneamino)-3-[4-(tert-butylaminomethyl)phenyl]propionate 0.76 g of K₂CO₃ is added to a solution of 0.58 ml of tert-butylamine in 8 ml of DMF, and the mixture is stirred for 20 minutes at RT. A solution of 2.15 g of the compound obtained in the preceding step in 3 ml of DMF is then added and the mixture is stirred for 3 hours 30 minutes at RT. The reaction mixture is extracted with EtOAc, the organic phase is washed with water and with saturated NaCl solution and dried over Na$_2$SO$_4$, and the solvent is evaporated off under vacuum. 2.67 g of the expected product are obtained in the form of an oil.

C) Ethyl 2-amino-3-[4-(tert-butylaminomethyl)phenyl]propionate

A mixture of 2.66 g of the compound obtained in the preceding step and 30 ml of aqueous 1N HCl solution in 30 ml of ether is stirred overnight at RT. After separation of the phases by settling, EtOAc is added to the acidic aqueous phase and the mixture is basified to pH 11 by adding 10N NaOH. After separation of the phases by settling, the organic phase is washed with water and with saturated NaCl solution and dried over Na$_2$SO$_4$, and the solvent is evaporated off under vacuum. 0.88 g of the expected product is obtained in the form of an oil.

D) Ethyl 2-(tert-butoxycarbonylamino)-3-[4-(tert-butylaminomethyl)phenyl]propionate 0.7 g of di-tert-butyl dicarbonate is added portionwise to a solution of 0.88 g of the compound obtained in the preceding step in 12 ml of dioxane, and the mixture is stirred for 1 hour 30 minutes at RT. The reaction mixture is extracted with EtOAc, the organic phase is washed with water and with saturated NaCl solution and dried over Na$_2$SO$_4$, and the solvent is evaporated off under vacuum. 1.34 g of the expected product are obtained in the form of an oil.

E) 2-(tert-Butoxycarbonylamino)-3-[4-(tert-butylaminomethyl)phenyl]propionic acid.

A mixture of 1.33 g of the compound obtained in the preceding step and 0.75 ml of 8.3N KOH in 8 ml of MeOH is stirred for 2 hours at RT. A chloroform/water mixture is added to the reaction mixture and the resulting mixture is acidified to pH 4 by adding 10N HCl. After separation of the phases by settling, the organic phase is washed with water and with saturated NaCl solution and dried over Na$_2$SO$_4$, and the solvent is evaporated off under vacuum to give a first crop of 0.54 g of the expected product. The aqueous phases and the washing liquors are concentrated under vacuum, the residue is taken up in 2-propanol, the insoluble material is filtered off and the filtrate is concentrated under vacuum to give a second crop of 0.51 g of the expected product.

F) 2-(tert-Butoxycarbonylamino)-3-[4-(tert-butylaminomethyl)phenyl]-1-(pyrrolidin-1-yl)propan-1-one.

0.6 ml of DIPEA is added to a mixture of 1.03 g of the compound obtained in the preceding step in 15 ml of DMF, followed by addition of 0.28 ml of pyrrolidine and 1.46 g of BOP, and the mixture is stirred for 4 hours at RT, while maintaining the pH at 6 by adding DIPEA. The reaction mixture is extracted with EtOAc, the organic phase is washed with water, with 0.2N NaOH, with water and with saturated NaCl solution and dried over Na$_2$SO$_4$, and the solvent is evaporated off under vacuum. 1.3 g of the expected product are obtained in the form of an oil.

G) 2-Amino-3-[4-(tert-butylaminomethyl)phenyl]-1-(pyrrolidin-1-yl)propan-1-one bis(trifluoroacetate).

A mixture of 1.29 g of the compound obtained in the preceding step and 17 ml of TFA in 15 ml of DCM is stirred for 50 minutes at RT. After concentrating the reaction mixture under vacuum, the residue is taken up in DCM and the solvent is evaporated off under vacuum. The residue is taken up in ether and the solvent is then decanted off. 1.5 g of the expected product are obtained in the form of a foam after drying, and this product is used without further purification in Example 2.

Preparation 2.3

2-Amino-3-[4-(N-propyl-N-methylaminomethyl)phenyl]-1-(pyrrolidin-1-yl)propan-1-one dihydrochloride

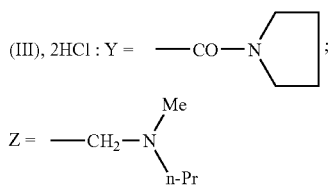

This compound is prepared according to Scheme 9.

A) 2-(tert-Butoxycarbonylamino)-3-(4-cyanophenyl)-1-(pyrrolidin-1-yl)propan-1-one 7.5 g of BOP are added to a mixture of 4.06 g of 2-(tert-butoxycarbonylamino)-3-(4-cyanophenyl)propionic acid and 1.15 ml of pyrrolidine in 20 ml of DMF, and the mixture is stirred for 2 hours at RT, while maintaining the pH at 7 by adding N-ethylmorpholine. The reaction mixture is concentrated under vacuum and the residue is chromatographed on silica gel, eluting with a chloroform/MeOH mixture (95/5; v/v). 3.8 g of the expected product are obtained.

B) 2-(tert-Butoxycarbonylamino)-3-(4-formylphenyl)-1-(pyrrolidin-1-yl)propan-1-one A solution of 2 g of the compound obtained in the preceding step in 150 ml of a pyridine/AcOH/H$_2$O mixture (2/1/1; v/v/v) is cooled to 0° C., 10.57 g of sodium hypophosphite hydrate are added under an argon atmosphere, followed by addition of 1.8 g of Raney® nickel in water, and the mixture is stirred for 10 minutes at RT. The reaction mixture is heated at 50° C. for 3 hours. After cooling to RT, the mixture is filtered through Celite®, washed with EtOH and then with DCM, and the filtrate is concentrated under vacuum. The residue is extracted with EtOAc, the organic phase is washed with water, with 5% KHSO$_4$ solution, with saturated NaCl solution, with saturated NaHCO$_3$ solution and with saturated NaCl solution and dried over Na$_2$SO$_4$, and the solvent is evaporated off under vacuum. The residue is chromatographed on silica gel, eluting with EtOAc. 1.7 g of the expected product are obtained; m.p.=134° C.

C) 2-(tert-Butoxycarbonylamino)-3-[4-(N-propyl-N-methylamino methyl)phenyl]-1-(pyrrolidin-1-yl)propan-1-one 0.42 ml of AcOH and then 0.707 g of sodium triacetoxyborohydride are added to a mixture of 0.77 g of the compound obtained in the preceding step and 0.34 ml of N-methylpropylamine in 10 ml of 1,2-dichloroethane, and the mixture is stirred overnight at RT. The reaction mixture is diluted with DCM, the organic phase is washed with saturated NaHCO$_3$ solution and with saturated NaCl solution and dried over Na$_2$SO$_4$, and the solvent is evaporated off under vacuum. 0.9 g of the expected product is obtained.

D) 2-Amino-3-[4-(N-propyl-N-methylaminomethyl)phenyl]-1-(pyrrolidin-1-yl)propan-1-one dihydrochloride 5 ml of 10N HCl are added to a mixture of 0.88 g of the compound obtained in the preceding step in 10 ml of MeOH and 5 ml of dioxane, and the mixture is stirred for 4 hours at RT. EtOH is added and the reaction mixture is concentrated under vacuum. The residue is taken up in ether and the precipitate formed is filtered by suction after trituration. 0.83 g of the expected product is obtained; m.p.=140° C. (dec.).

Preparation 2.4

2-Amino-3-[4-[N,N-bis(2-hydroxyethyl)aminomethyl]phenyl]-1-(pyrrolidin-1-yl)propan-1-one bis(trifluoroacetate)

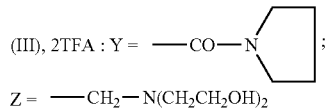

A) Ethyl 2-(benzhydrylideneamino)-3-[4-[N,N-bis(2-hydroxyethyl)aminomethyl]phenyl]propionate This compound is prepared according to the procedure described in step B of preparation 2.2, starting with 0.925 g of diethanolamine in 15 ml of DMF, 1.21 g of $K_2CO_3$ and 3.6 g of the compound obtained in step A) of preparation 2.2 in 20 ml of DMF. 4.23 g of the expected product are obtained in the form of an oil.

B) Ethyl 2-amino-3-[4-[N,N-bis(2-hydroxyethyl)aminomethyl]phenyl]propionate

This compound is prepared according to the procedure described in step C) of preparation 2.2, starting with 4.22 g of the compound obtained in the preceding step and 70 ml of 1N HCl in 70 ml of ether. 1.87 g of the expected product is obtained in the form of a wax.

C) Ethyl 2-(tert-butoxycarbonylamino)-3-[4-[N,N-bis(2-hydroxyethyl)aminomethyl]phenyl]propionate This compound is prepared according to the procedure described in step D of preparation 2.2, starting with 1.87 g of the compound obtained in the preceding step in 20 ml of dioxane and 1.4 g of di-tert-butyl dicarbonate. 2.15 g of the expected product are obtained.

D) 2-(tert-Butoxycarbonylamino)-3-[4-[N,N-bis(2-hydroxyethyl)aminomethyl]-phenyl]propionic acid A mixture of 2.13 g of the compound obtained in the preceding step and 1.3 ml of 8.3N KOH in 15 ml of MeOH is stirred for 3 hours at RT. Next, a further 0.3 ml of 8.3N KOH are added and the mixture is stirred for one hour at RT. An EtOAc/$H_2O$ mixture is added to the reaction mixture and the resulting mixture is acidified to pH 3.7 by adding 1N HCl. After separation of the phases by settling, the organic phase is washed with water and with saturated NaCl solution, and dried over $Na_2SO_4$, and the solvent is evaporated off under vacuum to give a first crop of the expected product. The aqueous phase is concentrated under vacuum, the residue is taken up in an MeOH/2-propanol mixture (1/1; v/v), the insoluble material is filtered off and the filtrate is concentrated under vacuum to give a second crop. 1.66 g of the expected product are obtained in the form of a white solid.

E) 2-(tert-Butoxycarbonylamino)-3-[4-[N,N-bis(2-hydroxyethyl)aminomethyl]-phenyl]-1-(pyrrolidin-1-yl)propan-1-one.

This compound is prepared according to the procedure described in step F of preparation 2.2, starting with 0.95 g of the compound obtained in the preceding step in 12 ml of DMF, 0.6 ml of DIPEA, 0.24 ml of pyrrolidine and 1.44 g of BOP. The expected product is obtained in the form of a wax, which is used without further purification in the following step.

F) 2-Amino-3-[4-[N,N-bis(2-hydroxyethyl)aminomethyl]phenyl] 1-(pyrrolidin-1-yl)propan-1-one bis(trifluoroacetate).

This compound is prepared according to the procedure described in step G) of preparation 2.2, starting with the compound obtained in the preceding step and 18 ml of TFA in 15 ml of DCM. The expected product is obtained, and is used without further purification in Example 4.

Preparation 2.5

1,2-Bis[4-(diethylaminomethyl)phenyl]ethylamine tris(trifluoroacetate)

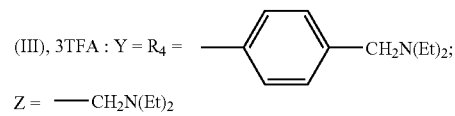

A) Methyl 4-(azidomethyl)benzoate 8.13 g of sodium azide are added over 5 minutes to a solution of 5.73 g of methyl 4-(bromomethyl)benzoate in 30 ml of DMSO and the mixture is stirred for 3 hours 30 minutes at RT. The reaction mixture is extracted with ether, the organic phase is washed with water and with saturated NaCl solution and dried over $Na_2SO_4$, and the solvent is evaporated off under vacuum. 4.72 g of the expected product are obtained in the form of a colourless oil.

B) Methyl 4-(aminomethyl)benzoate hydrochloride

A solution of 4.71 g of the compound obtained in the preceding step in 30 ml of THF is cooled to 4° C., 6.57 g of triphenylphosphine are added portionwise over 30 minutes and the mixture is stirred for 6 hours while allowing the temperature to return to RT. Next, 0.68 ml of water is added and the mixture is stirred for 16 hours at RT. The reaction mixture is extracted with EtOAc, the organic phase is washed with water and with saturated NaCl solution and dried over $Na_2SO_4$, and the solvents are evaporated off under vacuum. The residue is taken up in ether, the insoluble material is filtered off, the filtrate is concentrated under vacuum and the residue is chromatographed on silica gel, eluting with a chloroform/MeOH/$NH_4OH$ mixture (90/10/0.2; v/v/v). The product obtained is taken up in MeOH, 10N HCl is added to pH 1 and the mixture is concentrated under vacuum. 4.25 g of the expected product are obtained.

C) Methyl 4-(benzhydrylideneaminomethyl)benzoate

A mixture of 3.03 g of the compound obtained in the preceding step, 2.07 ml of triethylamine and 2.51 ml of benzophenoneimine in 50 ml of DCM is stirred overnight at RT. The reaction mixture is extracted with DCM, the organic phase is washed with water and with saturated NaCl solution and dried over $Na_2SO_4$, and the solvent is evaporated off under vacuum. 5.33 g of the expected product are obtained in the form of an oil.

D) Methyl 4-[1-amino-2-(4-methoxycarbonylphenyl)ethyl]benzoate

A solution of 5.32 g of the compound obtained in the preceding step in 40 ml of THF is cooled to −50° C., 10.3 ml of a 1.6 M solution of n-butyllithium in hexane are added over 35 minutes and the mixture is stirred for 30 minutes at between −50° C. and −30° C. The reaction mixture is cooled again to −50° C., a solution of 3.78 g of methyl 4-(bromomethyl)benzoate in 25 ml of THF is added over 30 minutes and the mixture is stirred for 4 hours after the temperature has returned to RT. Next, 50 ml of 1N HCl are added and the reaction mixture is stirred for 16 hours at RT. The phases of the reaction mixture are allowed to separate by settling, the acidic phase is washed with ether, the acidic aqueous phase is basified to pH 10 by adding 10N NaOH and extracted with EtOAc, the organic phase is washed with water and with saturated NaCl solution and dried over Na$_2$SO$_4$, and the solvent is evaporated off under vacuum. 3.88 g of the expected product are obtained in the form of a pasty white solid.

E) Methyl 4-[1-(tert-butoxycarbonylamino)-2-(4-methoxycarbonylphenyl)-ethyl]benzoate.

2.94 g of di-tert-butyl dicarbonate are added over 10 minutes to a solution of 3.88 g of the compound obtained in the preceding step in 30 ml of dioxane, and the mixture is stirred for 3 hours at RT. The reaction mixture is extracted with EtOAc, the organic phase is washed with water, with a KHSO$_4$/K$_2$SO$_4$ buffer solution, with water and with saturated NaCl solution and dried over Na$_2$SO$_4$, and the solvent is evaporated off under vacuum. 2.3 g of the expected product are obtained after crystallization from ether.

F) N-tert-Butoxycarbonyl-1,2-bis[4-(hydroxymethyl) phenyl]ethylamine.

A solution of 1.24 g of the compound obtained in the preceding step in 15 ml of THF is added over 40 minutes to a suspension of 0.456 g of lithium aluminium hydride in 25 ml of THF, and the mixture is stirred for 2 hours at RT. An EtOAc/ice mixture is then added and the reaction mixture is extracted with EtOAc, the organic phase is washed with water and with saturated NaCl solution and dried over Na$_2$SO$_4$, and the solvent is evaporated off under vacuum. 0.95 g of the expected product is obtained in the form of a white solid.

G) 4-[2-(tert-Butoxycarbonylamino)-2-(4-methanesulphonyloxymethylphenyl)-ethyl]benzyl methanesulphonate.

A solution of the compound obtained in the preceding step in 20 ml of DCM and 3 ml of THF is cooled to 4° C., 0.82 ml of triethylamine is added, followed by addition of a solution of 0.45 ml of methanesulphonyl chloride in 1 ml of DCM over 10 minutes, and the mixture is stirred for 3 hours 30 minutes at RT. The reaction mixture is extracted with DCM, the organic phase is washed with water and with saturated NaCl solution and dried over Na$_2$SO$_4$, and the solvent is evaporated off under vacuum. 1.21 g of the expected product are obtained.

H) N-(tert-Butoxycarbonyl)-1,2-bis [4-(diethylaminomethyl)phenyl]ethylamine.

A mixture of 1.2 g of the compound obtained in the preceding step and 1.05 ml of diethylamine in 20 ml of EtOH is heated at 60° C. for 4 hours. After cooling to RT, the reaction mixture is extracted with EtOAc, the organic phase is washed with water, with saturated NaHCO$_3$ solution, with water and with saturated NaCl solution and dried over Na$_2$SO$_4$, and the solvent is evaporated off under vacuum. The residue is chromatographed on silica gel, eluting with a chloroform/MeOH/NH$_4$OH mixture (85/15/0.2; v/v/v). 0.51 g of the expected product is obtained.

I) 1,2-bis[4-(Diethylaminomethyl)phenyl]ethylamine tris (trifluoroacetate).

A mixture of 0.5 g of the compound obtained in the preceding step and 12 ml of TFA in 10 ml of DCM is stirred for 45 minutes at RT. The reaction mixture is concentrated under vacuum and the residue is taken up in DCM and concentrated again under vacuum. 0.82 g of the expected product is obtained in the form of an oil.

Preparation 2.6

2-Amino-3-[4-(piperid-1-ylmethyl)phenyl]-1-(pyrrolidin-1-yl)propan-1-one dihydrochloride

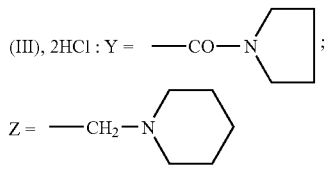

A) 2-(tert-Butoxycarbonylamino)-3-[4-(piperid-1-ylmethyl)phenyl]-1-(pyrrolidin-1-yl)propan-1-one This compound is prepared according to the procedure described in step C) of preparation 2.3, starting with 0.84 g of the compound obtained in step B) of preparation 2.3, 0.263 ml of piperidine, 10 ml of 1,2-dichloroethane, 0.452 ml of AcOH and 0.771 g of sodium triacetoxyborohydride. The reaction mixture is diluted with DCM, the organic phase is washed with saturated NaHCO$_3$ solution and with saturated NaCl solution and dried over Na$_2$SO$_4$, and the solvent is evaporated off under vacuum. The product obtained is taken up in ether, the insoluble material is filtered off and the filtrate is concentrated under vacuum. 0.975 g of the expected product is obtained in the form of an oil.

B) 2-Amino-3-[4-(piperid-1-ylmethyl)phenyl]-1-(pyrrolidin-1-yl)propan-1-one dihydrochloride This compound is prepared according to the procedure described in step D) of preparation 2.3, starting with 0.97 g of the compound obtained in the preceding step, 10 ml of MeOH, 5 ml of dioxane and 5 ml of 10N HCl. 0.91 g of the expected product is obtained; m.p.=170° C. (dec.)

NMR: 1.2–2.0 ppm: unres.: 10H; 2.4–3.4 ppm: unres.: 10H; 4.2 ppm: bs: 3H; 7.2 ppm: d: 2H; 7.6 ppm: d: 2H; 8.4 ppm: s: 3H; 11.2 ppm: s: 1H.

Preparation 2.7

2-Amino-3-[4-(diethylaminomethyl)phenyl]-1-(pyrrolidin-1-yl)propan-1-one dihydrochloride

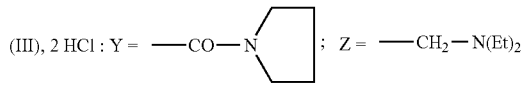

For its preparation steps D, E and F, this compound is obtained according to Scheme 10.

A) Ethyl 2-(benzhydrylideneamino)-3-[4-(diethylaminomethyl)phenyl]propionate

A mixture of 1 g of the compound obtained in step A) of preparation 2.2, 0.235 ml of diethylamine and 0.307 g of K$_2$CO$_3$ in 10 ml of DMF is stirred for 2 hours at RT. The reaction mixture is extracted with EtOAc, the organic phase is washed with water, with saturated NaHCO$_3$ solution and with saturated NaCl solution and dried over Na$_2$SO$_4$, and the solvent is evaporated off under vacuum. 0.927 g of the expected product is obtained in the form of an oil.

B) Ethyl 2-amino-3-[4-(diethylaminomethyl)phenyl]propionate

A mixture of 0.927 g of the compound obtained in the preceding step and 20 ml of 1N HCl in 30 ml of ether is stirred for 2 hours at RT. After separation of the phases by settling, the acidic aqueous phase is washed with ether, the aqueous phase is basified to pH 11 by adding solid NaHCO₃ and is extracted with DCM, the organic phase is washed with saturated NaCl solution and dried over Na₂SO₄, and the solvent is evaporated off under vacuum. 0.395 g of the expected product is obtained.

C) Ethyl 2-(tert-butoxycarbonylamino)-3-[4-(diethylaminomethyl)phenyl]propionate 1.72 g of di-tert-butyl dicarbonate are added to a solution of 2 g of the compound obtained in the preceding step in 20 ml of DCM, followed by addition of 1.1 ml of triethylamine, and the mixture is stirred for 2 hours at RT. The reaction mixture is concentrated under vacuum, the residue is extracted with EtOAc, the organic phase is washed with water and with saturated NaCl solution and dried over Na₂SO₄, and the solvent is evaporated off under vacuum. 2.6 g of the expected product are obtained; m.p.=56° C.

D) 2-(tert-Butoxycarbonylamino)-3-[4-(diethylaminomethyl)phenyl]propionic acid 10.1 ml of 1N KOH are added to a solution of 2.55 g of the compound obtained in the preceding step in 60 ml of EtOH and 20 ml of dioxane, and the mixture is heated for 1 hour at 60° C. After cooling to RT, 10 ml of 1N HCl are added and the reaction mixture is concentrated under vacuum. The residue is azeotroped by adding an EtOH/toluene mixture and is then concentrated under vacuum. The residue is taken up in a DCM/MeOH mixture (9/1; v/v), the insoluble material is filtered off and the filtrate is concentrated under vacuum. 2.4 g of the expected product are obtained.

E) 2-(tert-Butoxycarbonylamino)-3-[4-(diethylaminomethyl)phenyl]-1-(pyrrolidin-1-yl)propan-1-one 0.61 ml of triethylamine and then 2.12 g of BOP are added to a mixture of 1.53 g of the compound obtained in the preceding step and 0.365 ml of pyrrolidine in 10 ml of DMF, and the mixture is stirred for 2 hours at RT. The reaction mixture is poured into water and extracted with EtOAc, the organic phase is washed with water, with saturated NaHCO₃ solution and with saturated NaCl solution and dried over Na₂SO₄, and the solvent is evaporated off under vacuum. 1.5 g of the expected product are obtained.

F) 2-Amino-3-[4-(diethylaminomethyl)phenyl]-1-(pyrrolidin-1-yl)propan-1-one dihydrochloride 6 ml of concentrated HCl are added to a solution of 1.5 g of the compound obtained in the preceding step in 20 ml of dioxane and 10 ml of MeOH, and the mixture is stirred overnight at RT. The reaction mixture is concentrated under vacuum and the residue is taken up in EtOH and concentrated again under vacuum. The residue is taken up in ether and the solvent is decantered off after trituration. 1.37 g of the expected product are obtained in the form of a gum.

Preparation 2.8

2-Amino-3-[4-(diethylaminomethyl)phenyl]-N-isopropyl-N-methylpropionamide bis(trifluoroacetate)

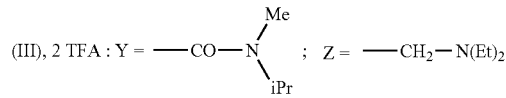

(III), 2 TFA : Y = —CO—N(Me)(iPr) ; Z = —CH₂—N(Et)₂

A) 2-(tert-Butoxycarbonylamino)-3-[4-(diethylaminomethyl)phenyl]-N-isopropyl-N-methylpropionamide 0.279 ml of triethylamine is added to a mixture of 0.7 g of the compound obtained in step D) of preparation 2.7 and 0.208 ml of N-methylisopropylamine in 10 ml of DMF, followed by addition of 0.973 g of BOP, and the mixture is stirred for 2 hours at RT. The reaction mixture is poured into water and extracted with EtOAc, the organic phase is washed with water, with saturated NaHCO₃ solution and with saturated NaCl solution and dried over Na₂SO₄, and the solvent is evaporated off under vacuum. 0.65 g of the expected product is obtained.

B) 2-amino-3-[4-(diethylaminomethyl)phenyl]-N-isopropyl-N-methylpropionamide bis(trifluoroacetate)

5 ml of TFA are added to a solution of 0.63 g of the compound obtained in the preceding step in 5 ml of DCM, and the mixture is stirred for 2 hours at RT. The reaction mixture is concentrated under vacuum, the residue is taken up in iso ether and the solvent is decantered off after trituration. The expected product is obtained after drying under vacuum.

Preparation 2.9

2-amino-3-[4-(diethylaminomethyl)phenyl]-N,N-diisopropylpropionamide dihydrochloride (III), 2HCl: Y=—CO—N(iPr)₂; Z=—CH₂—N(Et)₂

A) 2-(tert-Butoxycarbonylamino)-3-(4-cyanophenyl)-N,N-diisopropylpropionamide

A mixture of 1 g of 2-(tert-butoxycarbonylamino)-3-(4-cyanophenyl)propionic acid and 0.540 g of diisopropylamine in 10 ml of DCM is cooled to 0° C., 0.960 ml of triethylamine is added, followed by addition of 1.76 g of bromotripyrrolidinophosphonium hexafluorophosphate, and the mixture is stirred for 2 hours and allowed to warm to RT. The reaction mixture is concentrated under vacuum, the residue is extracted with EtOAc, the organic phase is washed with water, with 5% KHSO₄ solution, with water, with saturated NaHCO₃ solution and with saturated NaCl solution and dried over Na₂SO₄, and the solvent is evaporated off under vacuum. The residue is chromatographed on silica gel, eluting with a heptane/EtOAc mixture (80/20; v/v). 0.4 g of the expected product is obtained; m.p.=172° C.

B) 2-(tert-Butoxycarbonylamino)-3-(4-formylphenyl)-N,N-diisopropylpropionamide

This compound is prepared according to the procedure described in step B of preparation 2.3, starting with 0.380 g of the compound obtained in the preceding step, 25 ml of a pyridine/AcOH/H₂O mixture (2/1/1; v/v/v), 1,8 g of sodium hypophosphite hydrate and 0.31 g of Raney® nickel. 0.35 g of the expected product is obtained without performing chromatography; m.p.=152° C.

C) 2-(tert-Butoxycarbonylamino)-3-[4-(diethylaminomethyl)phenyl)-N,N-diisopropylpropionamide This compound is prepared according to the procedure described in step C of preparation 2.3, starting with 0.333 g of the compound obtained in the preceding step, 0.135 ml of diethylamine, 10 ml of 1,2-dichloroethane, 0.08 ml of AcOH and 0.281 g of sodium triacetoxyborohydride. 0.4 g of the expected product is obtained.

D) 2-Amino-3-[4-(diethylaminomethyl)phenyl]-N,N-diisopropylpropionamide dihydrochloride 5 ml of concentrated HCl are added to a mixture of 0.4 g of the compound obtained in the preceding step in 10 ml of MeOH and 5 ml of dioxane, and the mixture is stirred overnight at RT. The reaction mixture is concentrated under vacuum and the residue is taken up in EtOH and evaporated under vacuum. 0.37 g of the expected product is obtained.

Preparation 2.10

2-[4-(Diethylaminomethyl)phenyl]-1-(pyrid-3-yl)ethylamine tris(trifluoroacetate)

(III), 3TFA : Y = 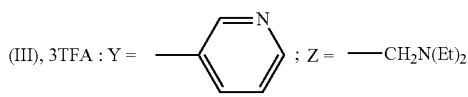 ; Z = —CH₂N(Et)₂

A) Benzhydrylidenepyrid-3-ylmethylamine 1.7 ml of 3-(aminomethyl)pyridine are added to a solution of 2.8 ml of benzophenoneimine in 50 ml of DCM, and the mixture is stirred overnight at RT. A further 0.28 ml of benzophenoneimine is added and the mixture is stirred for 2 hours at RT. The reaction mixture is concentrated under vacuum, the residue is extracted with ether, the organic phase is washed with water and with saturated NaCl solution and dried over Na₂SO₄, and the solvent is evaporated off under vacuum. 4.56 g of the expected product are obtained.

B) Methyl 4-[2-amino-2-(pyrid-3-yl)ethyl]benzoate

A solution of 3 g of the compound obtained in the preceding step in 30 ml of THF is cooled to −78° C., under an argon atmosphere, 8.2 ml of a 1.5 M solution of lithium diisopropylamide in cyclohexane are added and the mixture is stirred for 30 minutes while allowing the temperature to rise to −20° C. The mixture is cooled again to −78° C., a solution of 2.82 g of methyl 4-(bromomethyl)benzoate in 10 ml of THF is added dropwise and the mixture is stirred for 2 hours while allowing the temperature to rise to RT. The reaction mixture is cooled to 0° C., 25 ml of 1N HCl are added slowly, followed by addition of concentrated HCl solution to pH 2–3, and the mixture is stirred overnight at RT. An ether/water mixture (1/1; v/v) is added to the reaction mixture and, after separation of the phases by settling, the organic phase is extracted with 1N HCl solution, the combined aqueous phases are basified to pH 8 by adding concentrated NaOH and extracted with DCM, the organic phase is washed with saturated NaCl solution and dried over Na₂SO₄, and the solvent is evaporated off under vacuum. 2 g of the expected product are obtained.

C) Methyl 4-[2-(tert-butoxycarbonylamino)-2-(pyrid-3-yl)ethyl]benzoate 1.83 g of di-tert-butyl dicarbonate are added to a solution of 1.95 g of the compound obtained in the preceding step in 20 ml of DCM, followed by addition of 1.16 ml of triethylamine, and the mixture is stirred for 2 hours at RT. The reaction mixture is concentrated under vacuum, the residue is extracted with EtOAc, the organic phase is washed with water and with saturated NaCl solution and dried over Na₂SO₄, and the solvent is evaporated off under vacuum. The residue is chromatographed on silica gel, eluting with a heptane/EtOAc mixture of from (60/40; v/v) to (40/60; v/v). 1.3 g of the expected product are obtained.

D) N-tert-Butoxycarbonyl-2-(4-hydroxymethylphenyl)-1-(pyrid-3-yl)ethylamine

A solution of 1.13 g of the compound obtained in the preceding step in 30 ml of THF is cooled to −78° C., under an argon atmosphere, 7.2 ml of a 1M solution of diisobutylaluminium hydride in toluene are added dropwise and the mixture is stirred for 2 hours while allowing the temperature to rise to 0° C. The reaction mixture is cooled to −40° C., a further 7.2 ml of a 1M solution of diisobutylaluminium hydride in toluene are added and the mixture is stirred for 2 hours while allowing the temperature to rise to 0° C. 40 ml of saturated NH₄Cl solution are added, the mixture is extracted with EtOAc, the organic phase is washed with water and with saturated NaCl solution and dried over Na₂SO₄, and the solvent is evaporated off under vacuum. The residue is chromatographed on silica gel, eluting with a DCM/EtOAc mixture (40/60; v/v). 0.62 g of the expected product is obtained after crystallization from ether; m.p.=130° C.

E) N-(tert-butoxycarbonyl)-2-[4-(diethylaminomethyl)phenyl]-1-(pyrid-3-yl)ethylamine.

A solution of 0.61 g of the compound obtained in the preceding step in 20 ml of DCM is cooled to 0° C., 0.311 ml of triethylamine is added, followed by addition of 0.16 ml of methanesulphonyl chloride, and the mixture is stirred for 30 minutes at 0° C. Next, 0.58 ml of diethylamine is added and the mixture is stirred for 3 hours at RT. The reaction mixture is poured into water and extracted with DCM, the organic phase is washed with water and with saturated NaCl solution and dried over Na₂SO₄, and the solvent is evaporated off under vacuum. 0.45 g of the expected product is obtained.

F) 2-[4-(Diethylaminomethyl)phenyl]-1-(pyrid-3-yl)ethylamine tris(trifluoroacetate).

A mixture of 0.45 g of the compound obtained in the preceding step and 10 ml of TFA in 10 ml of DCM is stirred for 15 minutes at RT. The reaction mixture is concentrated under vacuum, the residue is taken up in ether, the solvent is decantered off and the expected crude product is used without further purification.

Preparation 2.11

Ethyl 2-amino-3-[4-(N-ethyl-N-methylaminomethyl)phenyl]propionate.

(III) : Y = —CO₂Et; Z = —CH₂—N<sup>Me</sup><sub>Et</sub>

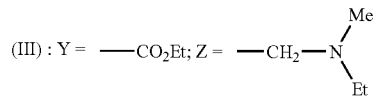

A) Ethyl 2-(benzhydrylideneamino)-3-[4-(N-ethyl-N-methylaminomethyl)phenyl]propionate A mixture of 1 g of the compound obtained in step A of Preparation 2.2 and 0.29 ml of N-methylethylamine in 10 ml of DMF is cooled to 0° C., 0.307 g of K₂CO₃ is added and the mixture is stirred for 4 hours at 0° C. The reaction mixture is poured into saturated NaCl solution and extracted with EtOAc, the organic phase is washed with saturated NaCl solution and dried over Na₂SO₄, and the solvent is evaporated off under vacuum. The expected product is obtained and is used without further purification.

B) Ethyl 2-amino-3-[4-(N-ethyl-N-methylaminomethyl)phenyl]propionate

A mixture of the compound obtained in the preceding step and 15 ml of 1N HCl in 15 ml of ether is stirred overnight at RT. After separation of the phases by settling, the aqueous phase is basified to pH 11 by adding Na₂CO₃ and is extracted with DCM, the organic phase is washed with saturated NaCl solution and dried over Na₂SO₄, and the solvent is evaporated off under vacuum. 0.43 g of the expected product is obtained, and is used without further purification in EXAMPLE 13.

Preparation 2.12

Ethyl 2-amino-3-[4-(dipropylaminomethyl)phenyl]propionate (III): Y=—CO$_2$Et; Z=—CH$_2$N(nPr)$_2$ A) Ethyl 2-(benzhydrylideneamino)-3-[4-(dipropylaminomethyl)phenyl]propionate This compound is prepared according to the procedure described in step A of Preparation 2.11, starting with 1 g of the compound obtained in step A of Preparation 2.2, 0.335 ml of dipropylamine and 0.307 g of K$_2$CO$_3$ in 10 ml of DMF. The expected product is obtained, and is used without further purification.

B) Ethyl 2-amino-3-[4-(dipropylaminomethyl)phenyl]propionate

This compound is prepared according to the procedure described in step B of Preparation 2.11, starting with the compound obtained in the preceding step and 15 ml of 1N HCl in 15 ml of ether. The expected product is obtained and is used without further purification.

Preparation 2.13

Ethyl 2-amino-3-[4-(diisopropylaminomethyl)phenyl]propionate (III): Y=—CO$_2$Et; Z=—CH$_2$N(iPr)$_2$ A) Ethyl 2-(benzhydrylideneamino)-3-[4-(diisopropylaminemethyl)phenyl]propionate This compound is prepared according to the procedure described in step A of Preparation 2.11, starting with 1 g of the compound obtained in step A of Preparation 2.2, 0.320 ml of diisopropylamine and 0.307 g of K$_2$CO$_3$ in 10 ml of DMF. The expected product is obtained and is used without further purification.

B) Ethyl 2-amino-3-[4-(diisopropylaminomethyl)phenyl]propionate

This compound is prepared according to the procedure described in step B of Preparation 2.11, starting with the compound obtained in the preceding step and 30 ml of 1N HCl in 30 ml of ether. 0.5 g of the expected product is obtained.

Preparation 2.14

2-Amino-3-[4-(tert-butylmethylaminomethyl)phenyl]-N-isopropyl-N-methylpropionamide bis(trifluoroacetate), (R) isomer

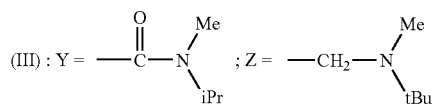

This compound is prepared according to the procedure described in Preparation 2.3, using 2-(tert-butoxycarbonylamino)-3-[4-(tert-butylmethylaminomethyl)phenyl]propionic acid, (R) isomer, as starting material.

NMR: 0.8–1.2 ppm: mt: 6H; 1.4 ppm: s: 9H; 2.5 ppm: d: 6H; 3.0 ppm: unres.: 2H; 3.9 ppm: mt: 1H; 4.5 ppm: mt: 2H; 7.3–7.5 ppm: mt: 4H.

Preparation 2.15

2-Amino-3-[4-(piperid-1-ylmethyl)phenyl]-N-isopropyl-N-methylpropionamide dihydrochloride

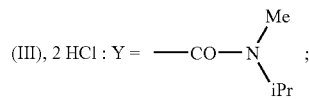

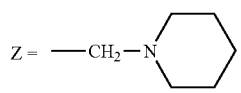

A) 2-(tert-Butoxycarbonylamino)-3-(4-cyanophenyl)-N-isopropyl-N-methylpropionamide This compound is prepared according to the procedure described in Preparation 1.6 of International patent application WO 97/25315.

B) 2-(tert-Butoxycarbonylamino)-3-(4-formylphenyl)-N-isopropyl-N-methylpropionamide A solution of 9 g of the compound obtained in the preceding step in 600 ml of a pyridine/AcOH/H$_2$O mixture (2/1/1; v/v/v) is cooled to 0° C., 47 g of sodium hypophosphite hydrate are added under an argon atmosphere, followed by addition of 8 g of Raney® nickel in water, and the mixture is stirred for 10 minutes at RT. The reaction mixture is heated at 55° C. for 3 hours. After cooling to RT, the mixture is filtered through Celite®, washed with EtOH and then with DCM, and the filtrate is concentrated under vacuum. The residue is extracted with EtOAc, the organic phase is washed with water, with 5% KHSO$_4$ solution, with saturated NaCl solution, with saturated NaHCO$_3$ solution and with saturated NaCl solution and dried over Na$_2$SO$_4$, and the solvent is evaporated off under vacuum. 7.6 g of the expected product are obtained after crystallization from an iso ether/pentane mixture; m.p.=122° C.

C) 2-(tert-Butoxycarbonylamino)-3-[4-(piperid-1-ylmethyl)phenyl]-N-isopropyl-N-methylpropionamide 0.18 ml of AcOH is added to a mixture of 0.55 g of the compound obtained in the preceding step and 0.172 ml of piperidine in 10 ml of 1,2-dichloroethane, followed by addition of 0.5 g of sodium triacetoxyborohydride, and the mixture is stirred overnight at RT. The reaction mixture is diluted with DCM, the organic phase is washed with saturated NaHCO$_3$ solution and with saturated NaCl solution and dried over Na$_2$SO$_4$, and the solvent is evaporated off under vacuum. 0.65 g of the expected product is obtained.

D) 2-Amino-3-[4-(piperid-1-ylmethyl)phenyl]-N-isopropyl-N-methylpropionamide dihydrochloride 3.5 ml of 10N HCl are added to a mixture of 0.65 g of the compound obtained in the preceding step in 10 ml of MeOH and 5 ml of dioxane, and the mixture is stirred overnight at RT. The reaction mixture is concentrated under vacuum, the residue is taken up in EtOH and the solvent is evaporated off under vacuum. The residue is taken up in ether and the precipitate formed is filtered off by suction, after trituration. 0.64 g of the expected product is obtained; m.p.=165° C. (dec).

Preparation 2.16

2-Amino-3-[4-(N-cyclopentyl-N-methylaminomethyl)phenyl]-N-isopropyl-N-methylpropionamide bis(trifluoroacetate)

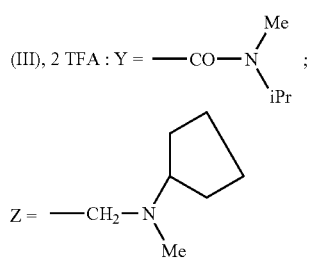

A) 2-(tert-Butoxycarbonylamino)-3-[4-(N-cyclopentyl-N-methylaminomethyl)phenyl]-N-isopropyl-N-methylpropionamide 0.164 ml of AcOH is added to a mixture of 0.5 g of the compound obtained in step B of Preparation 2.15 and 0.214 g of N-methylcyclopentylamine in 10 ml of 1,2-dichloroethane, followed by addition of 0.456 g of sodium triacetoxyborohydride, and the mixture is stirred overnight at RT. The reaction mixture is diluted with DCM, the organic phase is washed with saturated NaHCO$_3$ solution and the solvent is evaporated off under vacuum. The residue is taken up in EtOAc and extracted with pH 4 buffer, the acidic aqueous phase is washed with EtOAc, basified by addition of saturated NaHCO$_3$ solution and extracted with DCM, the organic phase is washed with saturated NaCl solution and dried over Na$_2$SO$_4$, and the solvent is evaporated off under vacuum. 0.31 g of the expected product is obtained.

B) 2-Amino-3-[4-(N-cyclopentyl-N-methylaminomethyl)phenyl]-N-isopropyl-N-methylpropionamide bis(trifluoroacetate)

A mixture of 0.309 g of the compound obtained in the preceding step and 10 ml of TFA in 10 ml of DCM is stirred for 2 hours at RT. The reaction mixture is concentrated under vacuum. The product obtained is used without further purification in Example 36.

Preparation 2.17

2-Amino-3-[4-(4-hydroxypiperid-1-ylmethyl)phenyl]-N-isopropyl-N-methylpropionamide bis(trifluoroacetate).

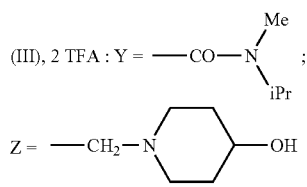

A) 2-(tert-Butoxycarbonylamino)-3-[4-(4-hydroxypiperid-1-ylmethyl)phenyl]-N-isopropyl-N-methylpropionamide 0.164 ml of AcOH is added to a mixture of 0.5 g of the compound obtained in step B of Preparation 2.15 and 0.146 g of 4-hydroxypiperidine in 10 ml of 1,2-dichloroethane, followed by addition of 0.456 g of sodium triacetoxyborohydride, and the mixture is stirred for 24 hours at RT. The reaction mixture is diluted with DCM, the organic phase is washed with saturated NaHCO$_3$ solution and with saturated NaCl solution and dried over Na$_2$SO$_4$, and the solvent is evaporated off under vacuum. 0.622 g of the expected product is obtained.

B) 2-Amino-3-[4-(4-hydroxypiperid-1-ylmethyl)phenyl]-N-isopropyl-N-methylpropionamide bis(trifluoroacetate)

A mixture of 0.622 g of the compound obtained in the preceding step and 10 ml of TFA in 10 ml of DCM is stirred for 1 hour at RT. The reaction mixture is concentrated under vacuum. The expected product is obtained, and is used without further purification.

Preparation 2.18

(R) 1-[2-Amino-3-(4-cyanophenyl)propionyl]pyrrolidine trifluoroacetate

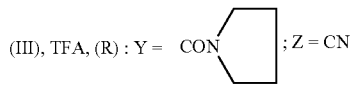

A) Ethyl 2-(N-Boc)amino-3-(4-cyanophenyl)propionate 26 g of Boc$_2$O dissolved in 100 ml of DCM are added gradually to a solution of 25.5 g of ethyl 2-amino-3-(4-cyanophenyl)propionate hydrochloride and 13.9 ml of Et$_3$N in 400 ml of DCM. After stirring for 6 hours at RT, the reaction medium is washed with a KHSO$_4$/K$_2$SO$_4$ solution, with saturated NaHCO$_3$ solution and with saturated NaCl solution. After drying over Na$_2$SO$_4$ and evaporation of the DCM, the residue is triturated in heptane to give 29 g of a white powder.

B) Ethyl (R) 2-(N-Boc)amino-3-(4-cyanophenyl)propionate

A mixture of 24 g of the product obtained in the preceding step and 8.4 g of NaHCO$_3$ in 900 ml of EtOAc and 500 ml of H$_2$O is treated with 2 ml of Alcalase® for 24 hours at RT. The 2 phases are separated by settling; the EtOAc phase is washed again with 100 ml of a 10% NaHCO$_3$ solution, which is combined to the first aqueous phase, and the aqueous phase is washed again with 100 ml of EtOAc, which are combined with the first EtOAc phase. The EtOAc phase thus obtained is dried over Na$_2$SO$_4$ and then evaporated to dryness; 12.45 g of compound B are obtained.

$\alpha_D^{25}$=+8.8° (c=1; MeOH)

C) (R) 2-(N-Boc)amino-3-(4-cyanophenyl)propionic acid 43 ml of a 1N NaOH solution are added to 12.18 g of compound B dissolved in 180 ml of MeOH, and the mixture is stirred for 1 hour at RT. Next, 43 ml of 1N HCl solution are added and 150 ml of methanol are evaporated off, the residue is then taken up in EtOAc and washed with water and then with saturated NaCl solution. 11 g of the expected compound are obtained, after crystallization from an Et$_2$O/heptane mixture.

$\alpha_D^{25}$=+−9.5° (c=1; MeOH)

D) N-hydroxysuccinimide (R) 2-(N-Boc)amino-3-(4-cyanophenyl)propionate 4.2 g of NSuOH are added to 10 g of the acid obtained above dissolved in 10 ml of dioxane, followed by addition over 20 minutes of 8.62 g of DCC dissolved in 30 ml of dioxane. After stirring overnight at RT, the DCU formed is filtered off and washed with dioxane. The filtrate is evaporated to dryness and the residue is triturated in ether to give a solid, which is filtered off and dried. 12.09 g of the expected compound are obtained.

$\alpha_D^{25} = +27.1°$ (c=1; MeOH)

E) (R) 1-[2-(N-Boc)amino-3-(4-cyanophenyl)propionyl]pyrrolidine.

2.6 ml of pyrrolidine dissolved in 20 ml of acetonitrile are added over 10 minutes to 11.6 g of the compound obtained in the above step dissolved in 150 ml of acetonitrile plus 20 ml of DMF. After stirring overnight at RT, a small amount of insoluble material is removed and the filtrate is concentrated under vacuum. The residue is taken up in EtOAc and washed with $KHSO_4/K_2SO_4$ solution, with saturated $NaHCO_3$ solution and with saturated NaCl solution; after drying over $Na_2SO_4$, the EtOAc is evaporated off under vacuum and the residue is triturated in ether to give 9.3 g of the expected compound in the form of a white solid.

$\alpha_D^{25} = -29.2°$ (c=1; MeOH)

F) (R) 1-[2-Amino-3-(4-cyanophenyl)propionyl]pyrrolidine trifluoroacetate.

8.7 g of the product obtained in the preceding step are stirred for 35 minutes in a mixture of 50 ml of DCM and 50 ml of TFA. After evaporation to dryness, the residue is taken up in isopropanol and re-evaporated to dryness, to give 8.67 g of the expected compound in solid form.

$\alpha_D^{25} = -46°$ (c=1; MeOH)

Preparation 2.19

(R) 2-amino-3-(4-diisopropylaminomethylphenyl)-N-isopropyl-N-methylpropionamide trifluoroacetate

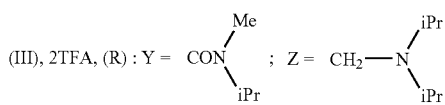

A) (R) 2-(N-Boc)amino-3-(4-cyanophenyl)-N-isopropyl-N-methylpropionamide 2 g of the acid obtained in Preparation 2.18, step C are placed in 20 ml of DCM in the presence of 750 µl of isopropylmethylamine, 1.26 ml of DIPEA and 3.2 g of BOP, and the mixture is then stirred for 4 hours at RT. The reaction mixture is concentrated to dryness and is then extracted with EtOAc, followed by washing successively with water, with pH 2 buffer solution, with saturated $NaHCO_3$ solution and with saturated NaCl solution. 2.40 g of the expected compound are obtained.

B) (R) 2-(N-Boc)amino-3-(4-formylphenyl)-N-isopropyl-N-methylpropionamide 2.4 g of the compound from the preceding step are placed in 130 ml of solvent consisting of a pyridine/AcOH/water mixture (2/1/1; v/v/v); 2.45 g of Raney nickel and 12.12 g of $NaH_2PO_2$ are added and the mixture is heated at 55° C. for 3 hours. The reaction mixture is filtered through Celite and the filtrate is concentrated. The residue is extracted with EtOAc and then washed successively with water, with pH 2 buffer solution, with saturated $NaHCO_3$ solution and with saturated NaCl solution. After concentration and drying, the residue is chromatographed on silica gel, eluting with a DCM/MeOH mixture (100/1; v/v). 1.60 g of the expected compound are obtained.

C) (R) 2-(N-Boc)amino-3-(4-diisopropylaminomethyl)-N-isopropyl-N-methylpropionamide A mixture containing 0.5 g of the compound obtained in the preceding step, 402 µl of diisopropylamine and 608 mg of $NaBH(OAc)_3$ in 20 ml of DCE is stirred for 24 hours at RT. The reaction mixture is concentrated to dryness, the residue is taken up in a water/EtOAc mixture and is then extracted with DCM and washed with saturated NaCl solution. 0.296 g of the expected compound is obtained.

D) (R) 2-Amino-3-(4-diisopropylaminomethylphenyl)-N-isopropyl-N-methylpropionamide trifluoroacetate 296 mg of the compound from the preceding step are placed in 5 ml of TFA and 10 ml of DCM, and the mixture is stirred for 3 hours at RT. The reaction mixture is concentrated to dryness, the residue is triturated in pentane, the solvent is decanted off and the oil formed is then recovered. The compound obtained is used in crude form in Example 39.

By working according to the methods described above, the compounds of formula (III) described in Table V below are prepared:

TABLE V (III)' = (III) or (XXXVII)

THN—CH—Y'
  |
  CH₂
  |
  (phenyl ring)
  |
  Z

| Preparation | T | Y' | Z | NMR or m.p. ° C. |
|---|---|---|---|---|
| 2.20 | H | $CO_2H$ | 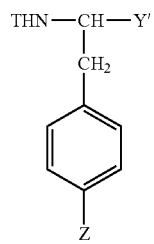 —CH₂—N(  )N—CH₃ | NMR |

TABLE V-continued $$(III)' = (III) \text{ or } (XXXVII)$$

THN—CH—Y'
|
CH₂
|
[phenyl ring]
|
Z

| Preparation | T | Y' | Z | NMR or m.p. °C. |
|---|---|---|---|---|
| 2.21 2HCl | H | —C(=O)—N(pyrrolidine) | —CH₂—N(Me)(tBu) | NMR |
| 2.22 | Boc | phenyl | —CH₂—N(Et)(Et) | 68–70° C. NMR |
| 2.23 2HCl | H | —C(=O)—N(Me)(iPr) | —CH₂—N(4-phenylpiperidine) | 170° C. |
| 2.24 | Boc | —C(=O)—N(Me)(iPr) | —CH₂—N(spiro[5.5]) | NMR |
| 2.25 | Boc | phenyl | —CH₂—N(Me)(tBu) | 102° C. NMR |
| 2.26 | Boc | —C(=O)—N(Et)(Et) | —CH₂—N(Et)(Et) | 85° C. |
| 2.27 | Boc | —C(=O)—N(morpholine) | —CH₂—N(Et)(Et) | 75° C. |
| 2.28 2HCl | H | 4-pyridyl | —CN | 267° C. |
| 2.29 | H | 2-furyl | —CN | 62° C. NMR |
| 2.30 2HCl | H | —C(=O)—N(Me)(iPr) | —CH₂—N(tBu)((CH₂)₂OH) | |

TABLE V-continued (III)' = (III) or (XXXVII)

THN—CH—Y'
      |
      CH₂
      |
      C₆H₄-Z (para)

| Preparation | T | Y' | Z | NMR or m.p. ° C. |
|---|---|---|---|---|
| 2.31 | Boc | —C(O)—NH—CH₂-(5-pyridyl-2-NH₂) | —CH₂—N(Et)(Et) | NMR |
| 2.32 | Boc | 1-methyl-benzimidazol-2-yl | —CH₂—N(Et)(Et) | 128–130° C. NMR |
| 2.33 | Boc | —C(O)—NH—(CH₂)₃—N(Me)(Me) | —CH₂—N(Et)(Et) | NMR |
| 2.34 | Boc | —C(O)—N(4-methylpiperazin-1-yl) | —CH₂—N(Et)(Et) | NMR |
| 2.35 2HCl | H | —C(O)—N(Me)(iPr) | —CH₂—N(iPr)(iPr) | 166° C. |
| 2.36 | Boc | —CH₂—N(3-azaspiro[5.5]undecane)—CH₂—N(Me)(tBu) | | 66–68° C. NMR |
| 2.37 | Boc | 2-methyl-1H-benzimidazol-yl | —CH₂—N(Et)(Et) | 99–102° C. NMR |
| 2.38 | Boc | phenyl | —CH₂—N(Me)(cyclopentyl) | NMR |
| 2.39 | H | 3-pyridyl | —CN | 92° C. |

TABLE V-continued

| | THN—CH—Y'<br>      \|<br>     CH₂—(C₆H₄)—Z | | (III)' = (III) or (XXXVII) |
|---|---|---|---|
| Preparation | T | Y' | Z | NMR or m.p. °C. |

| Preparation | T | Y' | Z | NMR or m.p. °C. |
|---|---|---|---|---|
| 2.40 | H | (6-methyl-1,3-benzodioxol-5-yl) | —CN | |

Preparation 2.20

NMR (DMSO+TFA): 2.8 ppm: s: 3H; 3.1 ppm: mt: 2H; 3.5 ppm: unres.: 8H; 4.2 ppm: t: 1H; 4.4 ppm: s: 2H; 7.35 ppm: d: 2H; 7.6 ppm: d: 2H.

Preparation 2.21

NMR: 1.25 ppm: s: 9H; 1.40–1.65 ppm: unres.: 4H; 2.40–4.60 ppm: mt: 10H; 7.10–7.60 ppm: mt: 4H.

Preparation 2.22

NMR: 0.85–1.00 ppm: t: 6H; 1.20 ppm: s: 9H; 2.30–4.30 ppm: unres.: 8H; 4.70 ppm: q: 1H; 7.10–7.75 ppm: unres.: 10H.

Preparation 2.24

NMR (DMSO+TFA): 1.0 ppm: mt: 6H; 1.2 ppm: s: 9H; 1.8 ppm: unres.: 14H; 2.6 ppm: d: 3H; 3.0 ppm: unres.: 6H; 4.1–4.7 ppm: unres.: 4H; 7.3 ppm: q: 4H.

Preparation 2.25

NMR: 1.0 ppm: s: 9H; 1.2 ppm: s: 9H; 1.9 ppm: s: 3H; 2.8 ppm: d: 2H; 3.4 ppm: s: 2H; 4.6 ppm: mt: 1H; 7.0–7.3 ppm: mt: 9H; 7.4 ppm: d: 1H.

Preparation 2.29

NMR: 2.9 ppm: mt: 2H; 4.0 ppm: t: 1H; 6.1 ppm: d: 1H; 6.3 ppm: d: 1H; 7.3 ppm: d: 2H; 7.5 ppm: s: 1H; 7.6 ppm: d: 2H.

Preparation 2.31

NMR: 0.85 ppm: t: 6H; 1.20 ppm: s: 9H; 2.40–4.30 ppm: unres.: 11H; 6.90–8.05 ppm: unres.: 9H.

Preparation 2.32

NMR: 0.90 ppm: t: 6H; 1.20 ppm: s: 9H; 2.40 ppm: q: 4H; 3.20–3.70 ppm: mt: 7H; 5.10 ppm: q: 1H; 7.10–7.70 ppm: mt: 9H.

Preparation 2.33

NMR (DMSO+TFA): 1.15 ppm: t: 6H; 1.20 ppm: s: 9H; 1.60–1.80 ppm: mt: 2H; 2.70–4.40 ppm: unres.: 19H; 7.25–7.45 ppm: mt: 4H.

Preparation 2.34

NMR (DMSO+TFA): 1.10 ppm: t: 6H; 1.20 ppm: s: 9H; 2.60–4.60 ppm: unres.: 20H; 7.20–7.45 ppm: mt: 4H.

Preparation 2.36

NMR: 1.00 ppm: s: 9H; 1.15 ppm: s: 9H; 2.70–4.60 ppm: unres.: 8H; 7.00–8.40 ppm: unres.: 9H.

Preparation 2.37

NMR: 0.90 ppm: t: 6H; 1.20 ppm: s: 9H; 2.35 ppm: q: 4H; 2.80–3.40 ppm: unres.: 4H; 4.80–5.00 ppm: mt: 1H; 7.00–7.50 ppm: unres.: 9H; 12.1 ppm: bs: 1H.

Preparation 2.38

NMR: 1.2 ppm: s: 9H; 1.2–1.8 ppm: unres.: 8H; 1.9 ppm: s: 3H; 2.6 ppm: mt: 1H; 2.8 ppm: d: 2H; 3.3 ppm: s: 2H; 4.6 ppm: mt: 11H; 7.0–7.2 ppm: mt: 9H; 7.4 ppm: d: 1H.

Preparation 2.41

(R) 2-Amino-3-(4-((2,6-dimethyl-1-piperidyl)methyl)phenyl-N-isopropyl-N-methylpropanamide, 2TFA

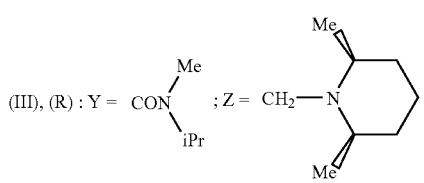

A)

A mixture containing 500 mg of the compound described in Preparation 2.19, step B, 390 μl of (cis)-2,6-dimethylpiperidine and 608 mg of NaBH(OAc)$_3$ is stirred for 48 hours at RT. The mixture is concentrated to dryness and then diluted with 30 ml of EtOAc and extracted with a pH 4 buffer solution. The aqueous phase is extracted with DCM and then washed with saturated NaHCO$_3$ solution and with saturated NaCl solution. 411 mg of the expected compound are obtained.

B)

411 mg of the compound obtained in the preceding step and 10 ml of TFA in 10 ml of DCM are stirred for 4 hours at RT. The mixture is concentrated to dryness and then triturated in a pentane/ether mixture. After decantation and drying, 0.480 g of the expected compound is obtained in the form of an oil.

Preparation 2.42

(R) 2-N-Boc)amino-3-(4-((3,3-dimethyl-1-piperidyl)methylphenyl)-N-isopropyl-N-methylpropanamide

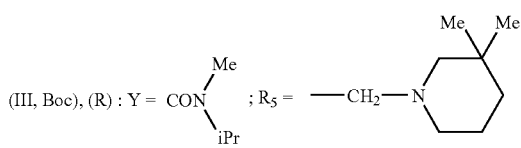

497 mg of the compound described in Preparation 2.19, step B are placed in 10 ml of DCE and 165 μl of AcOH and 455 mg of NaBH(OAc)$_3$ are added. After stirring overnight at RT, the reaction medium is concentrated and then taken up in Et2O/H$_2$O and extracted with a pH 4 buffer. The aqueous phases are basified to pH 8 with caustic soda and then extracted with DCM and washed with saturated NaCl solution. 0.168 g of the expected compound is obtained.

Preparation 2.43

(R) 2-(N,Boc)amino-3-(4-((4,4-difluoro-1-piperidyl)methyl)phenyl-N-isopropyl-N-methylpropanamide

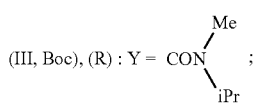

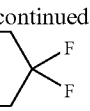

This compound is prepared as described in Preparation 2.41, starting with the compound of Preparation 2.19, step B and 4,4-difluoropiperidine.

Preparation 2.44

2-(R)-2-(N-Boc)amino-3-(4-((2,6-dimethyl-1-piperidyl)methyl)phenyl)propanoic acid

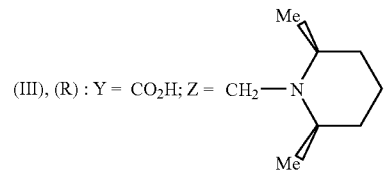

This compound is prepared by following Schemes 9 and 10.

A) Ethyl 2-(R)-2-(N-Boc)amino-3-(4-formylphenyl)propanoate 4 g of the compound from Preparation 2.18, step B are placed in 300 ml of a pyridine/AcOH/H$_2$O mixture (2/1/1; v/v/v) under argon. This mixture is treated with 5 g of Raney nickel and 30 g of NaH$_2$PO$_2$.H$_2$O for 6 hours at 55° C. The reaction mixture is filtered through Celite® and then concentrated. The residue is taken up in EtOAc, washed with H$_2$O, with 5% KHSO$_4$, with H$_2$O, with saturated NaHCO$_3$ solution and with saturated NaCl solution and then dried and concentrated. 3.91 g of the expected product are obtained in the form of an oil.

NMR: 1.2: t: 3H; 1.4: s: 9H; 2.9–3.2: mt: 2H; 4.0–4.4: mt: 3H; 7.4: d: 1H; 7.55: d: 2H; 7.9: d: 2H; 10.0: s: 1H.

B) Ethyl 2-(R)-2-(N-Boc)amino-3-(4-((2,6-dimethyl-1-piperidyl)methyl)phenyl-propanoate 3.9 g of the compound obtained in step B are placed in 30 ml of dichloroethane and the solution is treated with 6.7 g of NaHB(OAc)$_3$ and 4 ml of (cis)-2,6-dimethylpiperidine for 24 hours at RT. The reaction mixture is concentrated and the residue is taken up in ether and then extracted with 5% KHSO$_4$ and then with water. The aqueous phases are basified to pH 8 by adding NaHCO$_3$ and extracted with DCM, and the organic phase is dried and concentrated to give 3 g of the expected product in the form of an oil.

NMR: 0.9: d: 6H; 1.0: t: 3H; 1.05–1.8: mt: 15H; 2.3: unres.: 2H; 2.6–2.9: mt: 2H; 3.6: s: 2H; 2.9–4.1: mt: 3H; 7.0–7.2: mt: 5H.

C) (R)-2-(N-Boc)amino-3-(4-((2,6-dimethyl-1-piperidyl)methyl)phenyl)propanoic acid 3 g of the compound obtained in the preceding step are placed in 20 ml of MeOH and 20 ml of dioxane, followed by dropwise addition of 7.5 ml of 1N NaOH, and the mixture is stirred for 1 hour at RT. 7.5 ml of 1N HCl are added and the mixture is then concentrated to dryness. An azeotropic distillation is carried with absolute EtOH and toluene. The mixture is taken up in DCM, dried and filtered to give 2.7 g of the expected compound in the form of a dry foam.

NMR: 0.9: d: 6H; 1.0–1.4: mt: 15H; 2.4: unres.: 2H; 2.6–3.0: mt: 2H; 3.65: s: 2H; 4.0: unres.: 1H; 7.0: d: 1H; 7.2: d: 2H.

Preparation 2.45

2-(R)-2-(N-Boc)amino-3-(4-(((2-fluoroethyl)(ethyl)amino)methyl)phenyl)-N-isopropyl-N-methylpropanamide

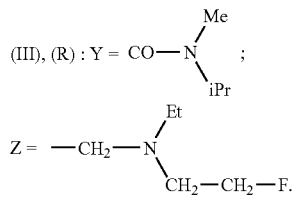

This compound is prepared according to Scheme 9a (step b) of the above description.

A) 2-(R)-2-(N-Boc)amino-3-(4-(((ethylamino)methyl)phenyl)-N-isopropyl-N-methyl)propanamide 520 mg of 2-(R)-2-(N-Boc)-3-(4-formylphenyl)-N-isopropyl-N-methylpropanamide are placed in 20 ml of DCE and treated with 3 ml of ethaneamine and 633 mg of NaHB(OAc)$_3$ plus 1 ml of AcOH, overnight at RT. The reaction mixture is concentrated and then taken up in a water/ether mixture. The aqueous phase is basified to pH 8 with NaHCO$_3$ and then extracted with DCM. 350 mg of the expected compound are obtained in the form of an oil. The NMR spectrum is in accordance with the structure of the compound.

B) 310 mg of the compound from the preceding step are dissolved in DMF (10 ml) and treated with 2-fluoro-1-iodoethane (143 mg) in the presence of K$_2$CO$_3$ (114 mg) for 48 hours at RT. The reaction is concentrated and the residue is taken up in EtOAc and extracted with H$_2$O and then with 5% KHSO$_4$. The aqueous phase is basified to pH 8 with NaHCO$_3$ and then extracted with CH$_2$Cl$_2$. 115 mg of the expected product are obtained in the form of an oil.
NMR

Preparation 2.46

2-(R)-2-(N-Boc)amino-3-(4-(((cyclopropyl)(isopropyl)amino)methyl)phenyl)-N-isopropyl-N-methyl)propanamide

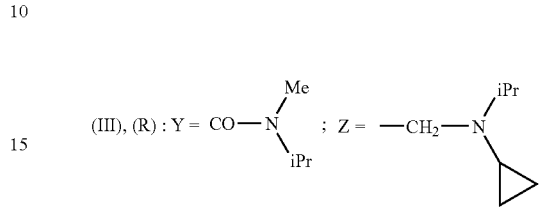

This compound is prepared according to Scheme 9a (step c).

A) 2-(R)-2-(N-Boc)amino-3-(4-((cyclopropylamino)methyl)phenyl)-N-isopropyl-N-methyl)propanamide This compound is obtained by reacting cyclopropylamine with 2-(R)-2-(N-Boc)-3-(4-formylphenyl)-N-isopropyl-N-methylpropanamide according to the procedure described in step A of the above preparation.

B) 2-(R)-2-(N-Boc)amino-3-(4-(((cyclopropyl)(isopropyl)amino)methyl)phenyl)-N-isopropyl-N-methyl)propanamide 220 mg of the compound from the preceding step and 125 µl of acetone are placed in 10 ml of DCE and treated with 180 mg of NaHB(OAc)$_3$ for 24 hours at RT. The reaction mixture is concentrated and is then taken up in ether and extracted with 5% KHSO$_4$ solution and then with H$_2$O. The aqueous phases are basified to pH 8 with NaHCO$_3$ and then extracted with DCM and dried. 105 mg of the expected compound are obtained in the form of an oil.

By working according to the preparations described above, the intermediate compounds described in the table below are prepared. (The reaction process used for the preparation is indicated in the right-hand column.)

TABLE VI

| Preparations (stereochemistry) | CONR$_8$R$_9$ | —CH$_2$NR$_{11}$R$_{12}$ | m.p. ° C. or NMR | Process |
|---|---|---|---|---|
| 2.47 (R) | CON(Me)(iPr) | 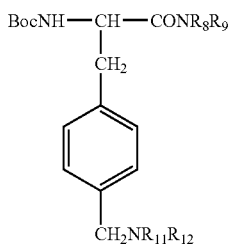 | NMR | a |

TABLE VI-continued $$\text{BocNH-CH(CH}_2\text{-C}_6\text{H}_4\text{-CH}_2\text{NR}_{11}\text{R}_{12}\text{)-CONR}_8\text{R}_9$$

| Preparations (stereochemistry) | CONR₈R₉ | —CH₂NR₁₁R₁₂ | m.p. ° C. or NMR | Process |
|---|---|---|---|---|
| 2.48 | CON(Me)(iPr) | CH₂N(cyclopropyl)(cyclobutyl) | NMR | a |
| 2.49 | CON(Me)(iPr) | CH₂N(Me)(iBu) | NMR | a |
| 2.50 | CON(Me)(iPr) | CH₂N(4-fluoropiperidinyl) | NMR | a |
| 2.51 | CON(Me)(iPr) | CH₂N(1,2,3,6-tetrahydropyridinyl) | NMR | a |
| 2.52 (R) | CON(Me)(iPr) | CH₂—N(4-phenylpiperidinyl) | NMR | a |
| 2.53 | CON(Me)(iPr) | CH₂N(Me)(CH₂—CF₃) | NMR | c |
| 2.54 (R) | CON(Me)(iPr) | CH₂N(iPr)(cyclopropyl) | crude product used | c |
| 2.55 (R) | CON(Me)(iPr) | CH₂N(4-(difluoromethylene)piperidinyl) | NMR | a |
| 2.56 | CON(Me)(tBu) | CH₂N(Et)(Et) | crude product used | a |
| 2.57 | CON(Me)(iPr) | CH₂N(Me)(nBu) | NMR | a |

TABLE VI-continued

| Preparations (stereochemistry) | CONR$_8$R$_9$ | —CH$_2$NR$_{11}$R$_{12}$ | m.p. ° C. or NMR | Process |
|---|---|---|---|---|
| 2.58 | CON(Et)(iPr) | CH$_2$N(iPr)(iPr) | NMR | d |
| 2.59 | CON(Me)(iPr) | CH$_2$N(Et)(cyclopentyl) | NMR | a |
| 2.60 | CON(Me)(iPr) | CH$_2$N(nPr)(CH$_2$-cyclopropyl) | NMR | a |
| 2.61 | CON(Me)(iPr) | CH$_2$N(Et)(nPr) | NMR | a |
| 2.62 | CON(Me)(iPr) | CH$_2$N(4-methylpiperidinyl) | NMR | a |
| 2.63 | CON(Me)(iPr) | CH$_2$N(CH$_2$CH=CH$_2$)$_2$ | NMR | a |
| 2.64 | CON(Me)(iPr) | CH$_2$N(Me)(CH$_2$-tBu) | NMR | a |
| 2.65 (R) | CON(Me)(iPr) | CH$_2$N(2,5-dimethylpyrrolidinyl) | NMR | a |
| 2.66 (R) | CON(Me)(cyclopentyl) | CH$_2$N(3,3-dimethylpiperidinyl) | NMR | d |

TABLE VI-continued

BocNH—CH—CONR$_8$R$_9$ with CH$_2$-(p-phenylene)-CH$_2$NR$_{11}$R$_{12}$

| Preparations (stereochemistry) | CONR$_8$R$_9$ | —CH$_2$NR$_{11}$R$_{12}$ | m.p. ° C. or NMR | Process |
|---|---|---|---|---|
| 2.67 | CON(Me)(iPr) | CH$_2$N(iPr)(cyclohexyl) | NMR | a |
| 2.68 | CON(Me)(iPr) | CH$_2$N(iBu)(cyclopentyl) | NMR | c |
| 2.69 (R) | CON(Me)(cyclopentyl) | CH$_2$N(2,6-dimethylpiperidyl) | NMR | a |
| 2.70 (R) | CON(Me)(iPr) | CH$_2$N(4-methylpiperidyl) | NMR | a |
| 2.71 | CON(Me)(iPr) | CH$_2$N(Et)(tBu) | NMR | a |
| 2.72 (R) | CON(Me)(cyclopentyl) | CH$_2$N(iPr)(iPr) | NMR | a |
| 2.73 | CON(Et)(cyclopentyl) | CH$_2$N(iPr)(iPr) | NMR | d |
| 2.74 (R) | CON(Me)(iPr) | CH$_2$N(Et)(cyclopentyl) | NMR | d |
| 2.75 (R) | CON(Me)(cyclopentyl) | CH$_2$N(Me)(cyclopentyl) | NMR | d |

TABLE VI-continued

BocNH—CH—CONR$_8$R$_9$ with CH$_2$ linked to para-substituted phenyl bearing CH$_2$NR$_{11}$R$_{12}$

| Preparations (stereochemistry) | CONR$_8$R$_9$ | —CH$_2$NR$_{11}$R$_{12}$ | m.p. ° C. or NMR | Process |
|---|---|---|---|---|
| 2.76 | CON(Me)(iPr) | CH$_2$N-piperidine-4-Et | NMR | a |
| 2.77 (R) | CON(Me)(iPr) | CH$_2$N-(2-Me)piperidine | NMR | a |
| 2.78 | CON(Me)(iPr) | CH$_2$N-decahydroquinoline | NMR | a |
| 2.79 | CON(Me)(tBu) | CH$_2$N-piperidine-4-Me | NMR | a |
| 2.80 | CON(Me)(iPr) | CH$_2$N-piperidine-4-OMe | NMR | a |
| 2.81 (R) | CON(Me)(iPr) | CH$_2$N-piperidine-4-CF$_3$ | NMR | a |
| 2.82 | CON(Me)(iPr) | CH$_2$N-piperidine-4,4-diMe | 103° C. | a |
| 2.83 (R) | CON(Me)(iPr) | CH$_2$N(tBu)(CH$_2$—CH$_2$—OMe) | NMR | a |
| 2.84 | CON(Me)(iPr) | CH$_2$N(Et)(iBu) | NMR | a |
| 2.85 | CON(Me)(iPr) | CH$_2$N-(3,5-diMe)piperidine | NMR | a |

TABLE VI-continued

BocNH—CH—CONR$_8$R$_9$
         |
        CH$_2$
         |
      (C$_6$H$_4$)
         |
      CH$_2$NR$_{11}$R$_{12}$

| Preparations (stereochemistry) | CONR$_8$R$_9$ | —CH$_2$NR$_{11}$R$_{12}$ | m.p. ° C. or NMR | Process |
|---|---|---|---|---|
| 2.86 (R) | CON(Me)(iPr) | CH$_2$N(Et)(tBu) | NMR | a |
| 2.87 | CON-(4,4-dimethylpiperidine) | CH$_2$N-(2,6-dimethylpiperidine) | crude product | d |
| 2.88 | CON-(2,5-dimethylpyrrolidine) | CH$_2$N-(2,6-dimethylpiperidine) | 130° C. | d |
| 2.89 (R) | CON(Me)(iPr) | CH$_2$N-(4-ethylpiperidine) | NMR | a |
| 2.90 (R) | CON(Me)(iPr) | CH$_2$N-(trans-decahydroisoquinoline) | NMR | a |
| 2.91 (R) | CON(Me)(iPr) | CH$_2$N-(cis-decahydroisoquinoline) | crude product used | a |
| 2.92 (R) | CON-(pyrrolidine) | CH$_2$N-(2,6-dimethylpiperidine) | NMR | d |
| 2.93 (R) | CON-(piperidine) | CH$_2$N-(2,6-dimethylpiperidine) | NMR | d |

TABLE VI-continued

BocNH—CH—CONR$_8$R$_9$
           |
          CH$_2$
           |
       [C$_6$H$_4$]
           |
       CH$_2$NR$_{11}$R$_{12}$

| Preparations (stereochemistry) | CONR$_8$R$_9$ | —CH$_2$NR$_{11}$R$_{12}$ | m.p. ° C. or NMR | Process |
|---|---|---|---|---|
| 2.94 (R) | CON(2-Me-piperidine) | CH$_2$N(2,6-diMe-piperidine) | NMR | d |
| 2.95 (R) | CON(azepane) | CH$_2$N(2,6-diMe-piperidine) | NMR | d |
| 2.96 (R) | CON(Me)(iPr) | CH$_2$N(2,5-diMe-pyrrolidine) | NMR | d |
| 2.97 (R) | CON(Me)(iPr) | CH$_2$N(3-azabicyclo) | NMR | a |
| 2.98 (R) | CON(4-Me-piperidine) | CH$_2$N(2,6-diMe-piperidine) | NMR | d |
| 2.99 (R) | CON(1,2,3,6-tetrahydropyridine) | CH$_2$N(2,6-diMe-piperidine) | NMR | d |
| 2.100 (R) | CON(2,5-diMe-pyrrolidine) | CH$_2$N(2,6-diMe-piperidine) | 152° C. | d |

TABLE VI-continued
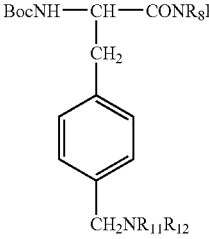
| Preparations (stereochemistry) | CONR₈R₉ | —CH₂NR₁₁R₁₂ | m.p. ° C. or NMR | Process |
|---|---|---|---|---|
| 2.101 (R) | 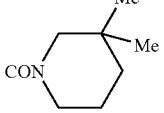 | 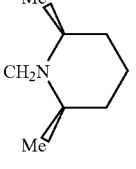 | NMR | d |
| 2.102 (R) |  | 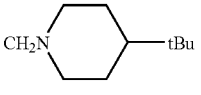 | NMR | a |
| 2.103 (R) |  | 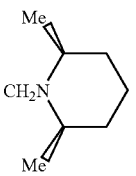 | NMR | d |
| 2.104 (R) | 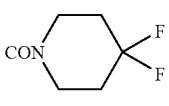 | 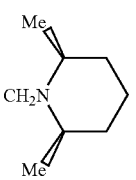 | 120° C. | a |
| 2.105 (R) | 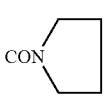 | 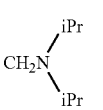 | NMR | a |
| 2.106 |  | 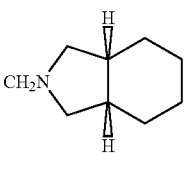 | NMR | a |
| 2.107 (R) |  | 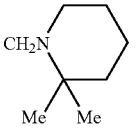 | NMR | a |
| 2.108 |  | 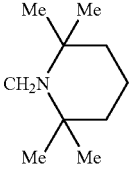 | NMR | a |

TABLE VI-continued $$BocNH-CH(CH_2-C_6H_4-CH_2NR_{11}R_{12})-CONR_8R_9$$

| Preparations (stereochemistry) | CONR$_8$R$_9$ | —CH$_2$NR$_{11}$R$_{12}$ | m.p. ° C. or NMR | Process |
|---|---|---|---|---|
| 2.109 (R) | CON(Me)(iPr) | CH$_2$N-(1,2,3,4-tetrahydroisoquinolin-2-yl) | NMR | a |
| 2.110 (R) | CON(Me)(iPr) | CH$_2$N(piperidin-1-yl)-4-iPr | NMR | a |
| 2.111 (R) | CON(Me)(iPr) | CH$_2$N(azabicyclic) | NMR | a |
| 2.112 (R) | CON(piperidin-1-yl)-4-OMe | CH$_2$N(2,6-dimethylpiperidin-1-yl) | NMR | a | a This compound is prepared from a compound (III) in which Z = CN and Y = CONR$_8$R$_9$, using the process described in Scheme 9 to obtain Z = CH$_2$NR$_{11}$R$_{12}$.
b This compound is prepared from a compound (III) in which Z = CN and Y = CONR$_8$R$_9$, using the process described in Scheme 9a (step b) to obtain Z = CH$_2$NR$_{11}$R$_{12}$.
c This compound is prepared from a compound (III) in which Z = CN and Y = CONR$_8$R$_9$, using the process described in Scheme 9a (step c) to obtain Z = CH$_2$NR$_{11}$R$_{12}$.
d This compound is prepared from a compound (XXXVI) in which Y = CO$_2$R', using the process described in Scheme 10 to obtain compound (III) with Y = CONR$_8$R$_9$.

Preparation 2.113

(R)2-(N-Boc)amino-3-(4-(3,6-dihydro)-1(2H)-pyridylmethyl)phenyl)-1-(1,3-thiazol-2-yl)-1-propanone

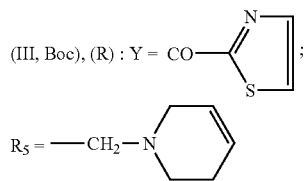

(III, Boc), (R) : Y = CO-(1,3-thiazol-2-yl);

R$_5$ = —CH$_2$—N(3,6-dihydro-2H-pyridyl)

A) 2-(N-Boc)amino-3-(4-cyanophenyl)-N-methoxy-N-methylpropanamide 2 g of (N-Boc)-4-cyanophenylalanine, 2.32 g of TBTU, 2.40 ml of DIPEA and 806 mg of N,O-dimethylhydroxylamine hydrochloride are mixed together in 30 ml of DCM. After stirring for 24 hours at RT, the reaction mixture is concentrated to dryness and the residue is then extracted with EtOAc. The organic phase is washed with a pH 2 buffer solution, a saturated NaHCO$_3$ solution and then a saturated NaCl solution. The expected compound crystallizes from a mixture of isopropyl ether and pentane (1.89 g).

B) 4-(2-(N-Boc)amino-3-oxo-3-(1,3-thiazol-2-yl)propyl)benzonitrile

A solution of 1,3-thiazole in 50 ml of THF at −78° C. is prepared, to which are added dropwise 9.57 ml of 2.5 M butyllithium in hexane and then the compound from the preceding step dissolved in 25 ml of THF. After stirring for 1 hour at −78° C., 50 ml of pH 2 buffer solution are added and the mixture is stirred for a further 1 hour at RT. The reaction medium is extracted with EtOAc and the organic phase is then washed with a pH 2 buffer and then with saturated NaCl solution. The mixture is evaporated to dryness and the residue is then chromatographed on silica, eluting with a heptane/acetone mixture (8/2; v/v) to give 1.65 g of the expected compound.

C) 4-(2-(N-Boc)amino-3-oxo-3-(1,3-thiazol-2-yl)propyl)benzaldehyde 1.65 g of the compound from the preceding step, 3 g of Raney nickel and 14 g of NaH$_2$PO$_2$.H$_2$O are placed in 100 ml of a pyridine/acetic acid/water mixture (2/1/1; v/v/v) and the mixture is heated at 55° C. for 3 hours. The nickel is removed by decantation and the medium is then concentrated. The reaction medium is extracted with EtOAc and the organic phase is then washed with a pH 2 buffer, a saturated NaHCO$_3$ solution and saturated NaCl solution. The resulting solution is evaporated to dryness and the residue is then chromatographed on silica, eluting with a heptane/AcOEt mixture (6/4; v/v) to give 400 mg of the expected compound.

D) (R)-2-(N-Boc)amino-3-(4-(3,6-dihydro)-1(2H)-pyridylmethyl)phenyl)-1-(1,3-thiazol-2-yl)-1-propanone 400 mg of the compound from the preceding step, 105 µl of 1,2,3,6-tetrahydropyridine and 3.65 mg of NaBH(OAc)$_3$ are placed in 20 ml of DCE and the mixture is stirred overnight at RT. The reaction mixture is concentrated to dryness and the residue is then taken up in a pH 2 buffer and washed with ether. The acidic phase is extracted with DCM and then washed with saturated NaHCO$_3$ solution. 0.283 g of the expected compound is obtained.

Preparation 2.114

2-(N-Boc)amino-N-isopropyl-N-methyl-3-(4-(1-piperidylmethyl)phenyl)propanethioamide

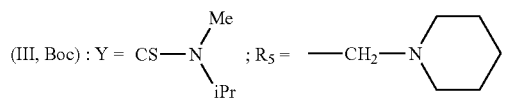

1.33 g of the compound from Preparation 2.15, step C are placed in 40 ml of anhydrous toluene and the solution is treated with 1.29 g of Lawesson's reagent at 80° C., under argon, for 4 hours. The reaction medium is concentrated and then chromatographed on silica, eluting with a DCM/MeOH/NH$_4$OH mixture (100/4/0.3; v/v/v) to give 0.185 g of the expected compound.

Preparation 3.1

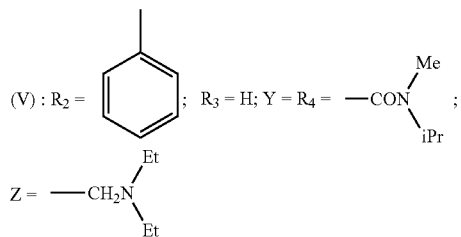

A) 3-Phenylaminopropionic acid, TFA 2 g of tert-butyl 3-phenylaminopropionate are placed in 30 ml of TFA and 20 ml of CH$_2$Cl$_2$, the mixture is stirred for 4 hours at RT and then concentrated to dryness.

B)

The compound obtained in the preceding step is mixed, at 0° C., in 30 ml of DCM, with 3.80 g of 2-amino-3-(4-((diethylamino)methyl)phenyl)-N-isopropyl-N-methylpropanamide and 5.02 ml of TEA, 4 g of BOP are added and the mixture is then stirred for 4 hours at RT and concentrated to dryness. The residue is extracted with ether and washed with water, with saturated NaHCO$_3$ solution and then with saturated NaCl solution. The resulting solution is dried over sodium sulphate and then chromatographed on silica, eluting with DCM/MeOH (95/5; v/v)+3 ml of NH$_4$OH per liter of eluent. 1.924 g of the expected compound are obtained.

NMR (DMSO+TFA): 0.8–1.2 ppm: mt: 12H; 2.3–3.0 ppm: mt: 11H; 3.3 ppm: unres.: 2H; 4.0 ppm: mt: 1H; 4.2 ppm: s: 2H; 4.4 ppm: mt: 1H; 7.0–7.4 ppm: mt: 9H.

Preparation 3.2

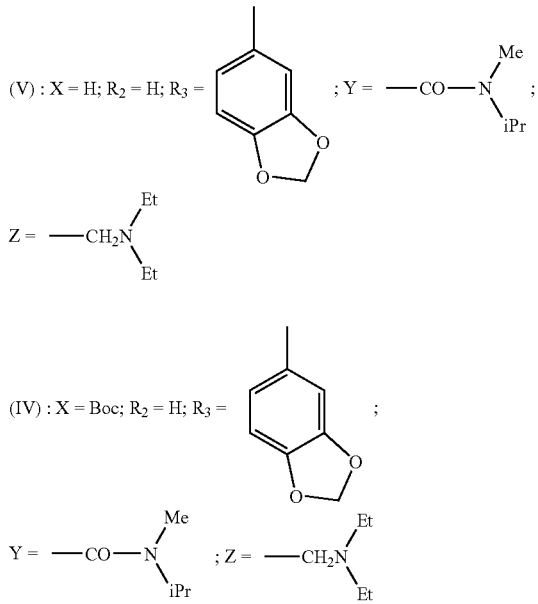

1.11 g of 3-(N-Boc)amino-3-(benzo[1,3]dioxol-5-yl)propionic acid, 1.508 g of 2-amino-3-(4-(diethylaminoethyl)phenyl)-1-(pyrrolidin-1-yl)propan-1-one (Preparation 2.8), 1.60 g of BOP and 1.50 ml of TEA are placed in 20 ml of DCM and stirred for 2 hours at RT. After concentrating to dryness, the residue is taken up in EtOAc and washed with water, with saturated NaHCO$_3$ solution and then with saturated NaCl solution. The resulting solution is dried over sodium sulphate and concentrated. The residue is triturated in pentane and the precipitate formed is filtered off by suction. The product is chromatographed on silica, eluting with a DCM/MeOH mixture (95/5; v/v)+4 ml of NH$_4$OH per liter of eluent. 1.402 g of the expected compound are obtained.

B)

1.4 g of the compound from the preceding step are placed in 15 ml of TFA and 20 ml of DCM and stirred for 2 hours at RT. The reaction mixture is concentrated to dryness and then taken up in DCM and washed with 1N NaOH solution. The solution is dried over sodium sulphate and concentrated. The oil obtained is crystallized in a refrigerator.

NMR: 0.8–1.1 ppm: mt: 12H; 2.2–2.6 ppm: mt: 9H; 2.8 ppm: mt: 2H; 3.5 ppm: s: 2H; 4.1 ppm: t: 1H; 4.5–5.0 ppm: mt: 2H; 6.0 ppm: s: 2H; 6.8–7.3 ppm: mt: 7H; 8.5 ppm: mt: 1H.

By working as described in Preparations 1, 2 and 3 above, the compounds of formula (IV), (V) or (VII) collated below are prepared:

TABLE VII (IV) or (V) or (VII) or (IX)

$$X'N(R_2)-CH(R_3)-CH_2-C(=O)-NH-CH(Y')-CH_2-C_6H_4-Z'$$

| Preparations | X' | R₂ | R₃ | Y' | Z' |
|---|---|---|---|---|---|
| 3.3 2HCl | H | H | phenyl | —C(=O)—N(pyrrolidine) | —CH₂—N(Et)₂ |
| 3.4 | 2,4-dichloro-3-methylphenyl-SO₂— | H | benzo[1,3]dioxol-5-yl | 4-pyridyl | CHO |
| 3.5 | 2,4-dichloro-3-methylphenyl-SO₂— | H | phenyl | 2-furyl | CHO |
| 3.6 | naphthalen-2-yl-SO₂— | H | benzo[1,3]dioxol-5-yl | CO₂H | —CH₂—N(Et)₂ |
| 3.7 | 2,4-dichloro-3-methylphenyl-SO₂— | H | phenyl | 3-pyridyl | CHO |

Preparation 3.3

NMR (DMSO+TFA): 1.2 ppm: mt: 6H; 1.6 ppm: unres.: 4H; 2.4–3.2 ppm: mt: 12H; 4.2 ppm: s: 2H; 4.5 ppm: mt: 2H; 7.0–7.5 ppm: mt: 9H.

Preparation 3.4

NMR: 2.2 ppm: t: 2H; 2.4 ppm: s: 3H; 2.8–3.1: mt: 2H; 3.7 ppm: t: 2H; 5.0 ppm: unres.: 1H; 5.9 ppm: s: 2H; 6.4: dd: 1H; 6.6 ppm: d: 1H; 6.7 ppm: d: 1H; 7.1–7.5 ppm: mt: 6H; 7.7 ppm: d: 2H; 8.4 ppm: mt: 3H; 9.9 ppm: s: 1H.

Preparation 3.5

NMR: 2.2 ppm: t: 2H; 2.4 ppm: s: 3H; 2.8–3.1 ppm: mt: 2H; 3.8 ppm: t: 2H; 5.0 ppm: mt: 1H; 6.1: d: 1H; 6.3 ppm: mt: 1H; 7.0–7.6 ppm: mt: 10H; 7.7 ppm: d: 2H; 8.3 ppm: d: 1H; 9.9 ppm: s: 1H.

NMR: 2.2 ppm: t: 2H; 2.4 ppm: s: 3H; 2.7–3.1 ppm: mt: 2H; 3.8 ppm: t: 2H; 5.0 ppm: mt: 1H; 7.0–7.8 ppm: mt: 13H; 8.3–8.5 ppm: mt: 3H; 9.9 ppm: s: 1H.

Preparation 3.8

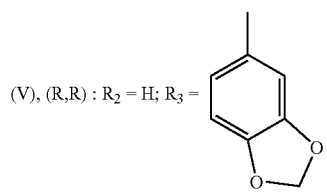

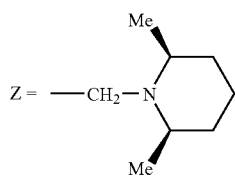

A)

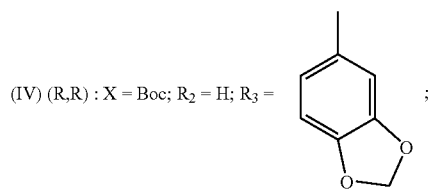

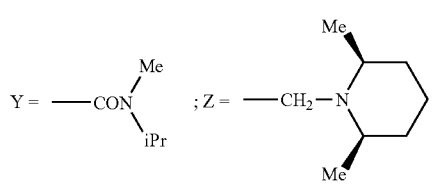

A mixture containing 480 mg of the compound from Preparation 2.41, 259 mg of the compound from Preparation 1.13, 370 mg of BOP and 440 µl of DIPEA in 10 ml of DCM is stirred at RT for 3 hours. The medium is concentrated to dryness and is then taken up in EtOAc, washed with water and extracted with pH 2 buffer, and the aqueous phase is then basified to pH 8 with saturated $NaHCO_3$ solution. This mixture is extracted with DCM and then washed with saturated NaCl solution to give 0.437 g of the expected compound.

NMR: 0.5 to 1.6 ppm: unres.: 27H; 2.2 to 3.6 ppm: unres.: 10H; 3.8 to 5 ppm: unres.: 4H; 5.9 ppm: d: 2H; 6.6 to 7.3 ppm: unres.: 8H; 8.1 ppm: t: 1H.

B) 437 mg of the compound obtained in the preceding step and 10 ml of TFA in 20 ml of DCM are stirred for 4 hours at RT. The mixture is concentrated to dryness and then crystallized from ethyl ether/pentane mixture. The residue is taken up in a DCM/saturated $NaHCO_3$ solution mixture; the organic phase is dried and concentrated to dryness under vacuum to give 343 mg of the expected compound.

Preparation 3.9

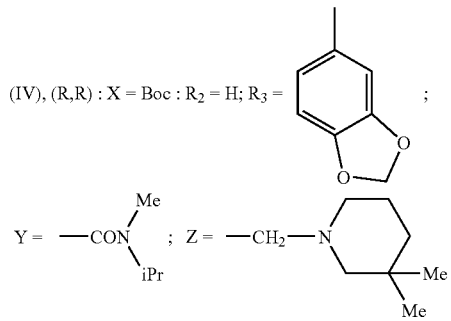

163 mg of the compound obtained in Preparation 2.42 are placed in 5 ml of DCM with 3 ml of TFA and are stirred for 1 hour at RT. The medium is concentrated and then triturated in $iPr_2O$ and decanted to recover the oil formed. The oil formed is taken up in 10 ml of DCM, 115 mg of the compound from Preparation 1.13 and 170 mg of BOP are then added and the mixture is maintained at pH 7 by addition of DIPEA. After the usual work-up, 0.225 g of the expected compound is obtained, which is used in crude form in the following step.

Preparation 3.10

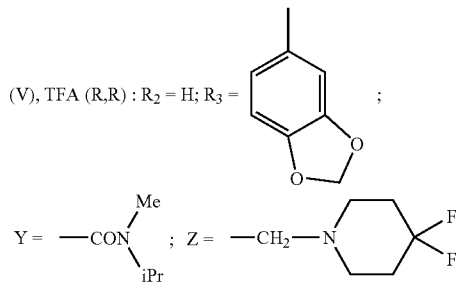

This compound is prepared according to the methods described above, starting with the compound from Preparation 2.43 and the compound from Preparation 1.13.

EXAMPLE 1

N-[1-(4-Aminomethylbenzyl)-2-oxo-2-(pyrrolidin-1-yl)ethyl]-3-(naphthalene-2-sulphonylamino)-3-phenylpropionamide hydrochloride

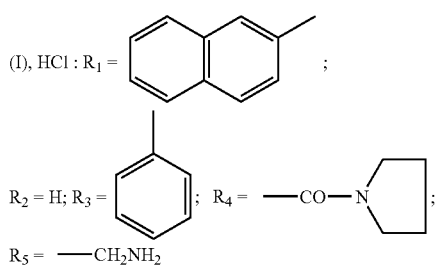

A) N-[1-(4-Cyanobenzyl)-2-oxo-2-(pyrrolidin-1-yl)ethyl]-3-(naphthalene-2-sulphonylamino)-3-phenylpropionamide 0.25 ml of triethylamine is added to a mixture of 0.715 g of the compound from Preparation 2.1 in 15 ml of acetonitrile, followed by addition of 0.71 g of the compound from Preparation 1.1 and 0.45 g of DCC, and the mixture is stirred for 5 hours at RT. The reaction mixture is concentrated under vacuum, the residue is taken up in acetone, the DCU is filtered off and the filtrate is concentrated under vacuum. The residue is triturated in ether and the solvent is then decanted off (several times). 0.61 g of the expected product is obtained after drying under vacuum over $P_2O_5$; m.p.=195–200° C.

NMR: δ (ppm): 1.40–170: unres.: 4H; 2.30–3.40: unres.: 8H; 4.40–4.60: unres.: and 4.60–4.70: unres.: 2H; 6.75–8.15: unres.: 16H.

B) N-[1-(4-Aminomethylbenzyl)-2-oxo-2-(pyrrolidin-1-yl)ethyl]-3-(naphthalene-2-sulphonylamino)-3-phenylpropionamide hydrochloride.

1 g of the compound obtained in the preceding step is dissolved in 4.5 ml of concentrated aqueous ammonia, 20 ml of MeOH, 5 ml of dioxane and 20 ml of toluene, 0.9 g of Raney® nickel is added and the mixture is hydrogenated at 50° C. under a pressure of 50 bar for 7 hours. The catalyst is filtered off through Celite® and washed with MeOH/chloroform solution, and the filtrate is concentrated under vacuum. The residue is taken up in ether and the precipitate formed is filtered off by suction. The product obtained is taken up in hydrochloric ether and the precipitate formed is filtered off by suction and dried. 0.85 g of the expected product is obtained.

$MH^+$=585

EXAMPLE 2

N-[1-[4-(tert-Butylaminomethyl)benzyl]-2-oxo-2-(pyrrolidin-1-yl)ethyl]-3-(naphthalene-2-sulphonylamino)-3-phenylpropionamide hydrochloride

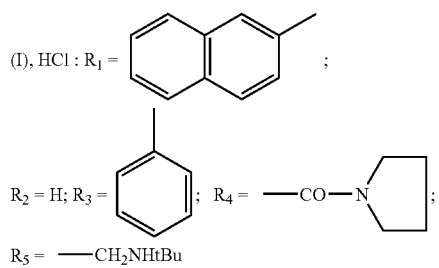

1.46 ml of DIPEA are added to a mixture of 1.06 g of the compound obtained in Preparation 1.1 in 15 ml of DMF, followed by addition of 1.49 g of the compound obtained in Preparation 2.2 and 1.38 g of BOP, and the mixture is stirred for 2 hours 30 minutes at RT, while maintaining the pH at 6 by adding DIPEA. The reaction mixture is extracted with EtOAc, the organic phase is washed with water, with 0.2N NaOH, with water and with saturated NaCl solution and dried over $Na_2SO_4$, and the solvent is evaporated off under vacuum. The residue is chromatographed on silica gel, eluting with a chloroform/MeOH/$NH_4OH$ mixture (85/15/0.2; v/v/v). The product obtained is dissolved in 10 ml of MeOH, 0.2 ml of 10N HCl is added and the mixture is concentrated under vacuum. The residue is chromatographed on Sephadex® LH20, eluting with a DCM/MeOH mixture (60/40; v/v). 0.66 g of the expected product is obtained.

NMR: δ (ppm): 1.3: s: 9H; 1.5–1.9: unres.: 4H; 2.3–3.4: unres.: 8H; 3.95: d: 2H; 4.4–4.9: unres.: 2H; 6.8–8.6: unres.: 18H.

EXAMPLE 3

N-[1-[4-(N-Propyl-N-methylaminomethyl)benzyl]-2-oxo-2-(pyrrolidin-1-yl)ethyl]-3-(naphthalene-2-sulphonylamino)-3-phenylpropionamide

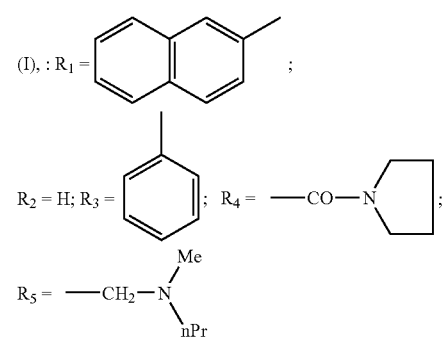

0.458 ml of triethylamine is added to a mixture of 0.39 g of the compound obtained in Preparation 1.1 and 0.41 g of the compound obtained in Preparation 2.3 in 10 ml of DCM, followed by addition of 0.533 g of BOP, and the mixture is stirred for 4 hours at RT. The reaction mixture is concentrated under vacuum, the residue is extracted with EtOAc, the organic phase is washed with water, with saturated NaCl solution, with saturated $NaHCO_3$ solution and with saturated NaCl solution and dried over $Na_2SO_4$, and the solvent is evaporated off under vacuum. 0.3 g of the expected product is obtained after crystallization from ether.

NMR: δ (ppm): 0.75 t: 3H; 1.2–1.7: unres.: 6H; 2.0: s: 3H; 2.15: t: 2H; 2.25–3.5: unres.: 10H; 4.1 to 4.8: unres.: 2H; 6.7 to 8.5: unres.: 18H.

EXAMPLE 4

N-[1-[4-[N,N-bis(2-hydroxyethyl)aminomethyl]benzyl]-2-oxo-2-(pyrrolidin-1-yl)ethyl]-3-(naphthalene-2-sulphonylamino)-3-phenylpropionamide

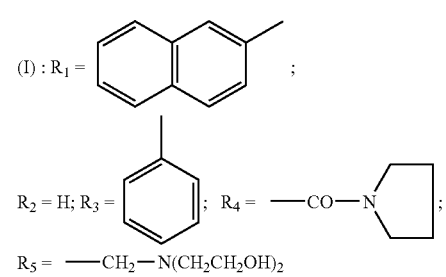

1.3 ml of DIPEA are added to a mixture of the compound obtained in Preparation 2.4 in 15 ml of DMF, followed by addition of 0.96 g of the compound obtained in Preparation 1.1 and 1.33 g of BOP, and the mixture is stirred for 2 hours at RT, while maintaining the pH at 6 by adding DIPEA. The reaction mixture is extracted with EtOAc, the organic phase is washed with water, with 0.5N NaOH, with water and with saturated NaCl solution and dried over Na₂SO₄, and the solvent is evaporated off under vacuum. The residue is chromatographed on silica gel, eluting with a DCM/MeOH/NH₄OH mixture (90/10/0.2; v/v/v). The product obtained is chromatographed on Sephadex® LH 20, eluting with a DCM/MeOH mixture (60/40; v/v). 0.44 g of the expected product is obtained.

NMR: δ (ppm): 1.3 to 1.7: unres.: 4H; 2.2 to 3.6: unres.: 18H; 4.2 to 4.8: unres.: 4H; 6.8 to 8.4: m: 18H.

EXAMPLE 5

N-[1,2-bis[4-(diethylaminomethyl)phenyl]ethyl]-3-(naphthalene-2-sulphonylamino)-3-phenylpropionamide

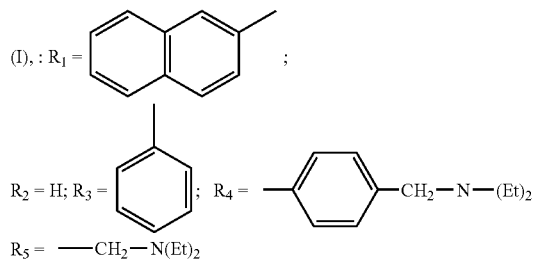

0.8 ml of DIPEA is added to a mixture of 0.82 g of the compound obtained in Preparation 2.5 in 10 ml of DMF, followed by addition of 0.39 g of the compound obtained in Preparation 1.1 and 0.53 g of the BOP, and the mixture is stirred for 1 hour 30 minutes at RT, while maintaining the pH at 6 by adding DIPEA. The reaction mixture is extracted with EtOAc, the organic phase is washed with water, with 0.1N NaOH, with water and with saturated NaCl solution and dried over Na₂SO₄, and the solvent is evaporated off under vacuum. The residue is chromatographed on Sephadex® LH 20, eluting with a DCM/MeOH mixture (60/40; v/v). 0.32 g of the expected product is obtained.

NMR: δ (ppm): 0.85: t: 12H; 2.1 to 3.6: unres.: 16H; 4.4 to 4.9: unres.: 2H; 6.6 to 8.4: unres.: 22H.

EXAMPLE 6

N-[1-[4-(diethylaminomethyl)benzyl]-2-oxo-2-(pyrrolidin-1-yl)ethyl]-3-[methyl-(naphthalene-2-sulphonyl)amino]-3-phenylpropionamide

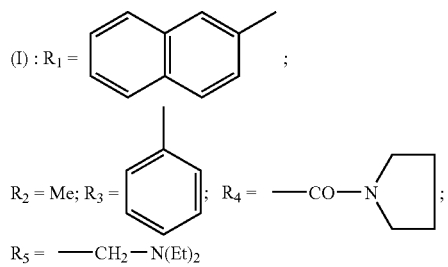

1 ml of DIPEA is added to a mixture of 0.72 g of the compound obtained in Preparation 2.7 in 6 ml of DMF, followed by addition of 0.51 g of the compound obtained in Preparation 1.2 and 0.67 g of BOP, and the mixture is stirred for 3 hours at RT while maintaining the pH at 6 by adding DIPEA. The reaction mixture is extracted with EtOAc, the organic phase is washed with water, with 0.5N NaOH, with water and with saturated NaCl solution and dried over Na₂SO₄, and the solvent is evaporated off under vacuum. The residue is chromatographed on silica gel, eluting with a DCM/MeOH/NH₄OH mixture (90/10/0.2; v/v/v). 0.27 g of the expected product is obtained.

NMR: δ (ppm): 0.95: t: 6H; 1.35 to 1.8: unres.: 4H; 2.1 to 3.6: unres.: 12H; 4.0 to 4.6: unres.: 3H; 5.55: mt: 1H; 6.8 to 8.6: unres.: 17H.

EXAMPLE 7

N-[2-[4-(Diethylaminomethyl)phenyl]-1-(N-isopropyl-N-methylcarbamoyl)ethyl]-3-(3,4-dimethylphenyl)-3-(naphthalene-2-sulphonylamino)propionamide hydrochloride

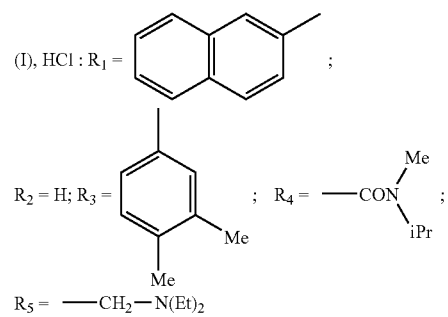

0.312 ml of triethylamine is added to a mixture of 0.288 g of the compound obtained in Preparation 1.4 and 0.4 g of the compound obtained in Preparation 2.8 in 15 ml of DCM and 3 ml of DMF, followed by addition of 0.332 g of BOP, and the mixture is stirred for 2 hours at RT. The reaction mixture is diluted with DCM and the organic phase is washed with 1N NaOH and with water and concentrated under vacuum. The residue is extracted with EtOAc, the organic phase is washed with water, with saturated NaHCO₃ solution and with saturated NaCl solution and dried over Na₂SO₄, and the solvent is evaporated off under vacuum. The residue is dissolved in acetonitrile, acidified to pH 1 by adding hydrochloric ether and diluted with ether, and the precipitate formed is filtered off by suction. 0.263 g of the expected product is obtained.

NMR: δ (ppm): 0.6–1.3: unres.: 12H; 1.6–1.8: unres.: 6H; 2.3–3.2: unres.: 11H; 3.7–4.9: unres.: 5H; 6.4–8.4: unres.: 16H.

EXAMPLE 8

N-[2-[4-(Diethylaminomethyl)phenyl]-1-(N-isopropyl-N-methylcarbamoyl)ethyl]-3-(benzo[1,3]dioxol-5-yl)-3-(naphthalene-2-sulphonylamino)propionamide hydrochloride

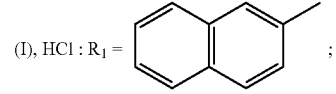

-continued

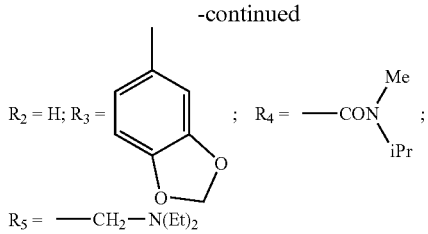

0.996 ml of triethylamine and 1.16 g of BOP are added to a mixture of 0.95 g of the compound obtained in Preparation 1.7 and 1.27 g of the compound obtained in Preparation 2.8 in 10 ml of DCM, and the mixture is stirred for 3 hours at RT. The reaction mixture is concentrated under vacuum, the residue is extracted with EtOAc, the organic phase is washed with water, with saturated $NaHCO_3$ solution and with saturated NaCl solution and dried over $Na_2SO_4$, and the solvent is evaporated off under vacuum. The residue is chromatographed on silica gel, eluting with a DCM/MeOH mixture (93/7; v/v). The product obtained is dissolved in EtOAc, acidified to pH 1 by adding hydrochloric ether and concentrated under vacuum. 0.78 g of the expected product is obtained after crystallization from an EtOAc/iso ether mixture.

NMR: δ (ppm). 0.6 to 1.4: unres.: 12H; 2.2 to 3.2: unres.: 1H; 3.7 to 5.0: unres.: 5H; 5.2 to 5.8: unres.: 2H; 6.2 to 8.5: unres.: 16H; 10.4: s: 1H.

EXAMPLE 9

N-[1-[4-(Diethylaminomethyl)benzyl]-2-oxo-2-(pyrrolidin-1-yl)ethyl]-3-(2,3-dihydrobenzo[1,4]dioxin-6-yl)-3-(naphthalene-2-sulphonylamino)propionamide hydrochloride

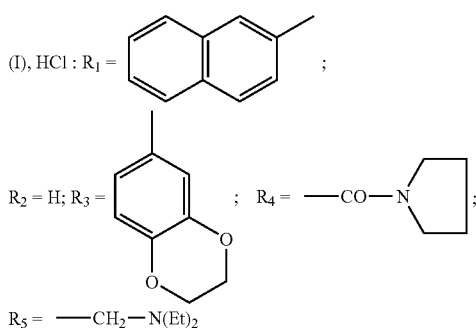

0.497 ml of triethylamine and 0.529 g of BOP are added to a mixture of 0.494 g of the compound obtained in Preparation 1.8 and 0.450 g of the compound obtained in Preparation 2.7 in 10 ml of DCM, and the mixture is stirred for 2 hours at RT. The reaction mixture is concentrated under vacuum, the residue is extracted with DCM, the organic phase is washed with water, with 1N NaOH and with water and dried over $Na_2SO_4$, and the solvent is evaporated off under vacuum. The product obtained is dissolved in a 2-propanol/acetonitrile mixture, acidified to pH 1 by adding hydrochloric ether and diluted with ether, and the precipitate formed is filtered off by suction. 0.280 g of the expected product is obtained.

NMR: δ (ppm): 1.2: mt: 6H; 1.4 to 1.8: unres.: 12H; 3.6 to 5.0: unres.: 8H; 6.1 to 8.4: unres.: 16H; 10.5: s: 1H.

EXAMPLE 10

N-[2-[4-(Diethylaminomethyl)phenyl]-1-(N-isopropyl-N-methylcarbamoyl)ethyl]-3-(2,3-dihydrobenzo[1,4]dioxin-6-yl)-3-(5,6,7,8-tetrahydronaphthalene-2-sulphonylamino)propionamide hydrochloride

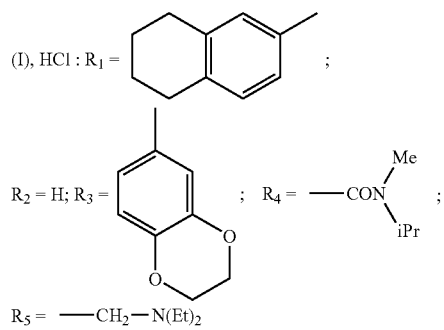

0.312 ml of triethylamine is added to a mixture of 0.312 g of the compound obtained in Preparation 1.9 and 0.4 g of the compound obtained in Preparation 2.8 in 15 ml of DCM and 3 ml of DMF, followed by addition of 0.332 g of BOP, and the mixture is stirred for 2 hours at RT. The reaction mixture is concentrated under vacuum, the residue is extracted with EtOAc, the organic phase is washed with a pH 4 buffer solution, with water and with saturated $NaHCO_3$ solution and dried over $Na_2SO_4$, and the solvent is evaporated off under vacuum. The product obtained is dissolved in EtOAc, acidified to pH 1 by adding hydrochloric ether and diluted with ether, and the precipitate formed is filtered off by suction. 0.24 g of the expected product is obtained.

NMR: δ (ppm): 0.6–1.0: unres.: 6H; 1.05–1.35: unres.: 6H; 1.4 to 1.8: unres.: 4H; 2.2 to 3.1: unres.: 15H; 3.9–5.0: unres.: 9H; 6.2 to 8.4: unres.: 12H.

EXAMPLE 11

N-[1-[4-(Diethylaminomethyl)benzyl]-2-oxo-2-(pyrrolidin-1-yl)ethyl]-3-[(2,4-dichloro-3-methylbenzenesulphonyl)phenylamino]propionamide hexafluorophosphate

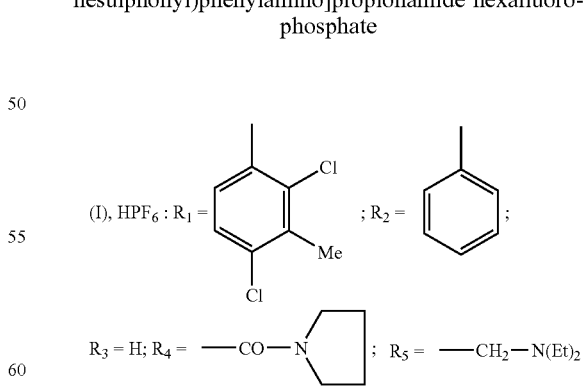

This compound is prepared according to the procedure described in Example 3, starting with 0.46 g of the compound obtained in Preparation 2.7 and 0.475 g of the compound obtained in Preparation 1.10 in 10 ml of DCM and 0.511 ml of triethylamine, followed by 0.595 g of BOP.

0.35 g of the expected product is obtained after crystallization from ether; m.p.=204–208° C.

NMR: δ (ppm): 1.05: t: 6H; 1.4 to 1.8: unres.: 4H; 2.2: t: 2H; 2.4: s: 3H; 2.5 to 3.5: unres.: 10H; 3.6 to 4.6: unres.: 5H; 6.8 to 7.7: unres.: 11H; 8.3: d: 1H; 10.4: bs: 1H.

EXAMPLE 12

N-[2-[4-(Diethylaminomethyl)phenyl]-1-(pyrid-3-yl)ethyl]-3-[(2,4-dichloro-3-methylbenzenesulphonyl)phenylamino]propionamide dihydrochloride

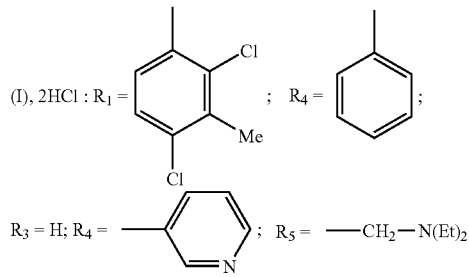

This compound is prepared according to the procedure described in Example 8, starting with the crude compound obtained in Preparation 2.10, 0.454 g of the compound obtained in Preparation 1.10 in 20 ml of DCM, 0.326 ml of triethylamine and 0.518 g of BOP. The product obtained is chromatographed on silica gel, eluting with a DCM/MeOH/2% NH$_4$OH mixture (95/5/0.5; v/v/v). The product obtained is dissolved in EtOAc, acidified to pH 1 by adding hydrochloric ether and concentrated under vacuum. 0.5 g of the expected product is obtained after crystallization from an EtOAc/iso ether mixture; m.p.=155° C. (decomposition).

NMR: δ (ppm): 1.1: t: 6H; 2.2: mt: 2H; 2.4: s: 3H; 2.7 to 3.2: unres.: 6H; 3.8: t: 2H; 4.1: bd: 2H; 5.1: q: 1H; 6.8 to 9.0: unres.: 16H; 10.8: s: 1H.

EXAMPLE 13

N-[1-[4-(N-ethyl-N-methylaminomethyl)benzyl]-2-oxo-2-(pyrrolidin-1-yl)ethyl]-3-(naphthalene-2-sulphonylamino)-3-phenylpropionamide

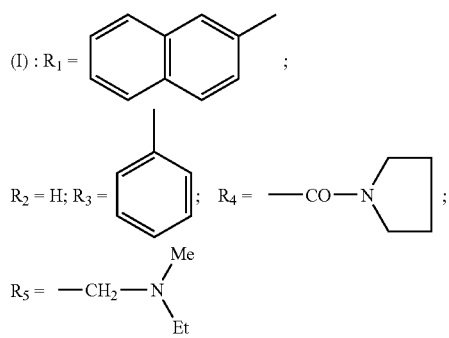

A) Ethyl 3-[4-(N-ethyl-N-methylaminomethyl)phenyl]-2-[3-(naphthalene-2-sulphonylamino)-3-phenylpropionylamino]propionate 0.791 g of BOP and 0.226 ml of triethylamine are added to a mixture of 0.578 g of the compound obtained in Preparation 1.1 and 0.430 g of the compound obtained in Preparation 2.11 in 10 ml of DCM, and the mixture is stirred for 3 hours at RT. The reaction mixture is concentrated under vacuum, the residue is extracted with EtOAc, the organic phase is washed with water, with saturated NaHCO$_3$ solution and with saturated NaCl solution and dried over Na$_2$SO$_4$, and the solvent is evaporated off under vacuum. The residue is chromatographed on silica gel, eluting with a DCM/MeOH mixture (100/4; v/v). 0.5 g of the expected product is obtained.

B) 3-[4-(N-Ethyl-N-methylaminomethyl)phenyl]-2-[3-(naphthalene-2-sulphonylamino)-3-phenylpropionylamino]propionic acid.

1.7 ml of 1N KOH are added to a mixture of 0.5 g of the compound obtained in the preceding step in 10 ml of EtOH and 10 ml of dioxane, and the mixture is heated at 60° C. for 4 hours. After cooling to RT, 1.7 ml of 1N HCl are added and the mixture is concentrated under vacuum. The residue is taken up in EtOH and concentrated again under vacuum. The expected product is obtained, and is used without further purification.

C) N-[1-[4-(N-Ethyl-N-methylaminomethyl)benzyl]-2-oxo-2-(pyrrolidin-1-yl)ethyl]-3-(naphthalene-2-sulphonylamino)-3-phenylpropionamide 0.403 g of BOP and 0.115 ml of triethylamine are added to a mixture of the compound obtained in the preceding step and 0.07 ml of pyrrolidine in 10 ml of DMF, and the mixture is stirred for 2 hours at RT. The reaction mixture is poured into water and extracted with EtOAc, the organic phase is washed with water, with saturated NaHCO$_3$ solution and with saturated NaCl solution and dried over Na$_2$SO$_4$, and the solvent is evaporated off under vacuum. 0.4 g of the expected product is obtained after crystallization from iso ether.

NMR: δ (ppm): 1.1: t: 3H; 1.3 to 1.85: unres.: 4H; 2.1: s: 3H; 2.2 to 3.5: unres.: 12H; 4.2 to 5.0: unres.: 2H; 6.8 to 8.6: unres.: 18H.

EXAMPLE 14

N-[1-[4-(Diethylaminomethyl)benzyl]-2-oxo-2-(pyrrolidin-1-yl)ethyl]-3-(naphthalene-2-sulphonylamino)-3-phenylpropionamide

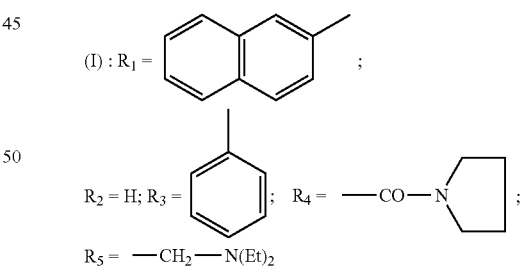

A) Ethyl 3-[4-(diethylaminomethyl)phenyl]-2-[3-(naphthalene-2-sulphonylamino)-3-phenylpropionylamino]propionate A mixture of 0.599 g of the compound obtained in Preparation 1.11, 0.368 g of the compound obtained in step B of Preparation 2.7 and 0.184 ml of triethylamine in 10 ml of DMF is stirred for 4 hours at RT. After concentrating the reaction mixture under vacuum, the residue is taken up in EtOAc, the organic phase is washed with water and with saturated NaHCO$_3$ solution and dried over Na$_2$SO$_4$, and the solvent is evaporated off under vacuum. 0.715 g of the expected product is obtained.

B) 3-[4-(Diethylaminomethyl)phenyl]-2-[3-(naphthalene-2-sulphonylamino)-3-phenylpropionylamino]propionic acid.

1.75 ml of 1N KOH are added to a mixture of 0.715 g of the compound obtained in the preceding step in 10 ml of EtOH and 10 ml of dioxane, and the mixture is heated overnight at 60° C. 1.75 ml of 1N HCl are added and the mixture is concentrated under vacuum. The expected product is obtained, and is used without further purification.

C) N-[1-[4-(Diethylaminomethyl)benzyl]-2-oxo-2-(pyrrolidin-1-yl)ethyl]-3-(naphthalene-2-sulphonylamino)-3-phenylpropionamide 0.161 ml of triethylamine and 0.515 g of BOP are added to a mixture of the compound obtained in the preceding step and 0.098 ml of pyrrolidine in 10 ml of DMF, and the mixture is stirred for 2 hours at RT. The reaction mixture is poured into water and extracted with EtOAc, the organic phase is washed with saturated $NaHCO_3$ solution and with saturated NaCl solution and dried over $Na_2SO_4$, and the solvent is evaporated off under vacuum. 0.618 g of the expected product is obtained.

NMR: δ (ppm): 0.8 to 1.0: t: 6H; 1.3 to 1.7: unres.: 4H; 2.2 to 3.5: unres.: 14H; 4.1 to 4.8: unres.: 2H; 6.7 to 8.4: unres.: 18H.

EXAMPLE 15

N-[2-[4-(Diethylaminomethyl)phenyl]-1-(N-ethyl-N-isopropylcarbamoyl)ethyl]-3-(benzo[1,3]dioxol-5-yl)-3-(naphthalene-2-sulphonylamino)propionamide hydrochloride

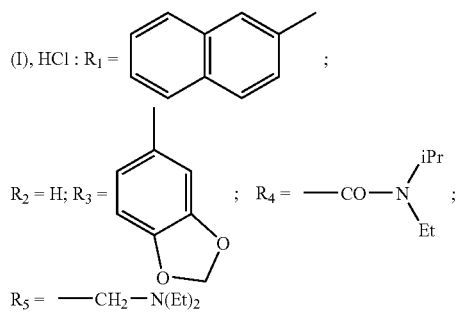

A) Ethyl 3-[4-(diethylaminomethyl)phenyl]-2-[3-(naphthalene-2-sulphonylamino)-3-(benzo[1,3]dioxol-5-yl)propionylamino]propionate 0.652 g of BOP and 0.205 ml of triethylamine are added to a mixture of 0.589 g of the compound obtained in Preparation 1.7 and 0.410 g of the compound obtained in step B of Preparation 2.7 in 10 ml of DMF, and the mixture is stirred for 2 hours at RT. The reaction mixture is poured into an EtOAc/saturated $NaHCO_3$ mixture, the organic phase is washed with water and with saturated NaCl solution and dried over $Na_2SO_4$, and the solvent is evaporated off under vacuum. 0.839 g of the expected product is obtained.

B) 3-[4-(Diethylaminometbyl)phenyl]-2-[3-(naphthalene-2-sulphonylamino)-3-(benzo[1,3]dioxol-5-yl)propionylamino]propionic acid.

1.9 ml of 1N KOH are added to a mixture of 0.83 g of the compound obtained in the preceding step in 7 ml of MeOH, 7 ml of EtOH and 7 ml of dioxane, and the mixture is stirred for 4 hours at RT. 1.9 ml of 1N HCl are added and the mixture is concentrated under vacuum. The residue is taken up in an EtOH/MeOH mixture (50/50; v/v), concentrated under vacuum, taken up in toluene and concentrated under vacuum again. 1.204 g of the expected product are obtained.

C) N-[2-[4-(Diethylaminomethyl)phenyl]-1-(N-ethyl-N-isopropylcarbamoyl)-ethyl]-3-(benzo[1,3]dioxol-5-yl)-3-(naphthalene-2-sulphonylamino)propionamide hydrochloride 0.46 g of bromotripyrrolidinophosphonium hexafluorophosphate and 0.33 ml of DIPEA are added to a mixture of 0.6 g of the compound obtained in the preceding step and 0.126 ml of N-ethylisopropylamine in 15 ml of DCM, and the mixture is stirred for 24 hours at RT. The reaction mixture is concentrated under vacuum, the residue is extracted with EtOAc, the organic phase is washed with water, with saturated $NaHCO_3$ solution and with saturated NaCl solution, the organic phase is extracted with a pH 4 buffer solution, the aqueous phase is basified by adding saturated $NaHCO_3$ solution and extracted with DCM, the organic phase is washed with saturated $NaHCO_3$ solution and dried over $Na_2SO_4$, and the solvent is evaporated off under vacuum. The residue is chromatographed on silica gel, eluting with a DCM/MeOH mixture (95/5; v/v). The product obtained is dissolved in EtOAc, acidified to pH 1 by adding hydrochloric ether and diluted with ether, and the precipitate formed is filtered off by suction. 0.058 g of the expected product is obtained.

NMR: δ (ppm): 0.6–1.4: unres.: 15H; 2.2–3.3: unres.: 10H; 3.7–4.9: unres.: 5H; 5.3–5.8: unres.: 2H; 6.3–8.5: unres.: 16H; 10.5: s: 1H.

EXAMPLE 16

N-[1-[4-(Diethylaminomethyl)benzyl]-2-oxo-2-(pyrrolidin-1-yl)ethyl]-3-phenyl-3-(quinoline-2-sulphonylamino)propionamide dihydrochloride

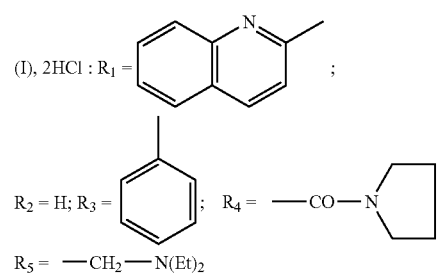

A) Ethyl 3-[4-(diethylaminomethyl)phenyl]-2-[3-phenyl-3-(quinoline-2-sulphonylamino)propionylamino]propionate 0.467 g of BOP is added to a mixture of 0.376 g of the compound obtained in Preparation 1.12 and 0.421 g of the compound obtained in step B of Preparation 2.7 in 10 ml of DMF, followed by addition of 0.147 ml of triethylamine, and the mixture is stirred for 2 hours at RT. The reaction mixture is poured into an $NaHCO_3$ solution and extracted with EtOAc, the extracts are washed with saturated $NaHCO_3$ solution and extracted with 1N HCl, the acidic aqueous phase is basified by adding solid $NaHCO_3$ and extracted with EtOAc, the organic phase is washed with water and dried over $Na_2SO_4$, and the solvent is evaporated off under vacuum. 0.455 g of the expected product is obtained.

B) 3-[4-(Diethylaminomethyl)phenyl]-2-[3-phenyl-3-(quinoline-2-sulphonylamino)propionylamino]propionic acid 1.63 ml of 1N NaOH are added to a mixture of 0.455 g of the compound obtained in the preceding step in 20 ml of EtOH and 5 ml of dioxane, and the mixture is then stirred overnight at RT. 1.63 ml of 1N HCl are added and the mixture is concentrated under vacuum. The residue is taken up in toluene and concentrated again under vacuum. The expected product is obtained, and is used without further purification.

C) N-[1-[4-(Diethylaminomethyl)benzyl]-2-oxo-2-(pyrrolidin-1-yl)ethyl]-3-phenyl-3-(quinoline-2-sulphonylamino)propionamide dihydrochloride 0.103 ml of triethylamine is added to a mixture of the compound obtained in the preceding step and 0.063 ml of pyrrolidine in 10 ml of DMF, followed by addition of 0.327 g of BOP, and the mixture is stirred for 2 hours at RT. The reaction mixture is poured into an EtOAc/saturated NaHCO₃ mixture, the organic phase is washed with saturated NaCl solution and dried over Na₂SO₄, and the solvent is evaporated off under vacuum. The residue is chromatographed on silica gel, eluting with a DCM/MeOH mixture (95/5; v/v) and then with a DCM/MeOH/NTH₄OH mixture (90/10/0.4; v/v/v). The product obtained is dissolved in EtOAc, acidified to pH 1 by adding hydrochloric ether and diluted with ether, and the precipitate formed is filtered off by suction. 0.086 g of the expected product is obtained.

NMR: δ (ppm): 1.0 to 1.9: unres.: 10H; 2.45 to 3.55: unres.: 12H; 4.0 to 5.0: unres.: 4H; 6.8 to 8.9: unres.: 17H; 10.1: s: 1H.

EXAMPLE 17

N-[1-[4-(Ethylaminomethyl)benzyl]-2-oxo-2-(pyrrolidin-1-yl)ethyl]-3-(naphthalene-2-sulphonylamino)-3-phenylpropionamide hydrochloride

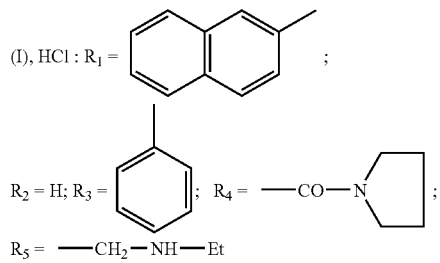

A) N-[1-[4-Formylbenzyl)-2-oxo-2-(pyrrolidin-1-yl)ethyl]-3-(naphthalene-2-sulphonylamino)-3-phenylpropionamide 3 g of aluminium/nickel alloy are added to a mixture of 3 g of the compound obtained in step A of Example 1 and 40 ml of 75% formic acid, and the mixture is refluxed for 2 hours. The insoluble material is filtered off by suction while hot and washed with MeOH, and the filtrate is concentrated under vacuum. The residue is taken up in chloroform, the insoluble material is filtered off by suction and washed with an MeOH/chloroform mixture, and the filtrate is concentrated under vacuum. The residue is taken up in chloroform and filtered, the filtrate is washed with saturated NaHCO₃ solution and with saturated NaCl solution and dried over Na₂SO₄, and the solvent is evaporated off under vacuum. 2.4 g of the expected product are obtained.

B) N-[1-[4-(Ethylaminomethyl)benzyl]-2-oxo-2-(pyrrolidin-1-yl)ethyl]-3-(naphthalene-2-sulphonylamino)-3-phenylpropionamide hydrochloride AcOH is added, to pH 5, to a mixture of 0.5 g of the compound obtained in the preceding step, 0.057 g of sodium cyanoborohydride, 0.077 g of ethylamine hydrochloride and 0.119 ml of triethylamine in 15 ml of MeOH, and the mixture is stirred for 2 hours at RT. The mixture is concentrated under vacuum, the residue is extracted with DCM, the organic phase is washed with saturated NaHCO₃ solution, with KHSO₄/K₂SO₄ buffer solution, with saturated NaHCO₃ solution and dried over Na₂SO₄, and the solvent is evaporated off under vacuum. The residue is chromatographed on silica gel, eluting with a DCM/MeOH mixture (90/10; v/v) and then a DCM/MeOH/NH₄OH mixture (90/10/0.4; v/v/v). The product obtained is dissolved in EtOAc, acidified to pH 1 by adding hydrochloric ether and diluted with ether, and the precipitate formed is filtered off by suction. 0.112 g of the expected product is obtained after crystallization from an MeOH/ether mixture.

NMR: δ (ppm): 1.0 to 1.9: unres.: 7H; 2.3 to 3.4: unres.: 10H; 4.0: s: 2H; 4.25 to 4.8: unres.: 2H; 6.6 to 8.2: unres.: 14H.

EXAMPLE 18

N-[1-[4-(Dimethylaminomethyl)benzyl]-2-oxo-2-(pyrrolidin-1-yl)ethyl]-3-(naphthalene-2-sulphonylamino)-3-phenylpropionamide

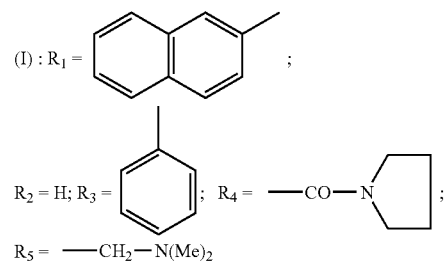

1 ml of AcOH and 0.129 g of dimethylamine hydrochloride are added to a solution of 0.830 g of the compound obtained in step A of Example 17 in 10 ml of DCM, followed by portionwise addition of 0.456 g of sodium triacetoxyborohydride, and the mixture is stirred for 18 hours at RT. The reaction mixture is diluted with DCM, the organic phase is washed with saturated NaCl solution and dried over Na₂SO₄, and the solvent is evaporated off under vacuum. The residue is chromatographed on silica gel, eluting with a chloroform/MeOH mixture (95/5; v/v). 0.52 g of the expected product is obtained.

MH⁺=613

EXAMPLE 19

N-[1-[4-(Azetidin-1-ylmethyl)benzyl]-2-oxo-2-(pyrrolidin-1-yl)ethyl]-3-(naphthalene-2-sulphonylamino)-3-phenylpropionamide hydrochloride

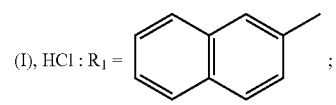

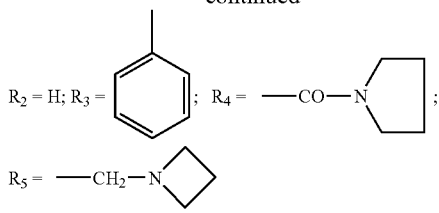

A mixture of 0.489 g of the compound obtained in step A of Example 17 and 0.086 g of azetidine hydrochloride and 116 µl of TEA in 15 ml of MeOH is stirred for 1 hour at RT. Next, 0.072 ml of AcOH is added, the mixture is stirred for 15 minutes at RT, 0.079 g of sodium cyanoborohydride is added and the mixture is stirred for 2 hours at RT. The reaction mixture is concentrated under vacuum, the residue is extracted with DCM, the organic phase is washed with saturated NaHCO$_3$ solution and dried over Na$_2$SO$_4$, and the solvent is evaporated off under vacuum. The residue is chromatographed on silica gel, eluting with a DCM/MeOH mixture (95/5; v/v) and then a DCM/MeOH/NH$_4$OH mixture (95/5/0.5; v/v/v). The product obtained is dissolved in EtOAc, acidified to pH 1 by adding hydrochloric ether and diluted with ether, and the precipitate formed is filtered off by suction. 0.115 g of the expected product is obtained.

NMR: δ (ppm): 1.4–1.8: unres.: 4H; 2.1 to 3.25: unres.: 10H; 3.6–4.8: unres.: 8H; 6.8–8.5: unres.: 18H; 10.85: s: 1H.

EXAMPLE 20

N-[1-[4-(dibutylaminomethyl)benzyl]-2-oxo-2-(pyrrolidin-1-yl)ethyl]-3-naphthalene-2-sulphonylamino)-3-phenylpropionamide

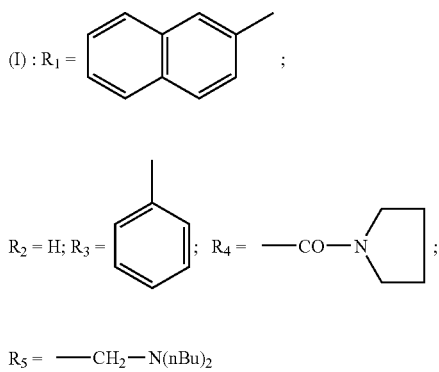

A) N-[1-[4-(Hydroxymethyl)benzyl]-2-oxo-2-(pyrrolidin-1-yl)ethyl]-3-(naphthalene-2-sulphonylamino)-3-phenylpropionamide 0.57 g of sodium nitrite is added to a mixture of 3.5 g of the compound obtained in Example 1 in 100 ml of water and 20 ml of dioxane, and the mixture is heated at 110° C. for 2 hours. The reaction mixture is concentrated under vacuum, the residue is extracted with EtOAc, the organic phase is washed with water and dried over Na$_2$SO$_4$, and the solvent is evaporated off under vacuum. The residue is taken up in ether and the precipitate formed is filtered off by suction. 2.78 g of the expected product are obtained.

B) N-[1-[4-(Chloromethyl)benzyl]-2-oxo-2-(pyrrolidin-1-yl)ethyl]-3-(naphthalene-2-sulphonylamino)-3-phenyl-propionamide and N-[1-[4-(methylsulphonyloxymethyl)benzyl]-2-oxo-2-(pyrrolidin-1-yl)ethyl]-3-(naphthalene-2-sulphonylamino)-3-phenylpropionamide 0.3 ml of triethylamine is added to a solution of 1 g of the compound obtained in the preceding step in 10 ml of DCM, followed by addition of 0.167 ml of methanesulphonyl chloride, and the mixture is stirred for 30 minutes at RT. A further 0.3 ml of triethylamine is added, followed by addition of 0.167 ml of methanesulphonyl chloride and the reaction mixture is stirred for 30 minutes and concentrated under vacuum. The residue is extracted with EtOAc, the organic phase is washed with water and dried over Na$_2$SO$_4$, and the solvent is evaporated off under vacuum. 0.68 g of the mixture of expected products is obtained.

C) N-[1-[4-(dibutylaminomethyl)benzyl]-2-oxo-2-(pyrrolidin-1-yl)ethyl]-3-naphthalene-2-sulphonylamino)-3-phenylpropionamide 0.045 g of 80% sodium hydride in oil is added to a solution of 0.245 g of dibutylamine in 5 ml of THF, and the mixture is stirred for 30 minutes at RT. 1 g of the compound obtained in the preceding step is then added and the mixture is stirred for 18 hours at RT. The reaction mixture is concentrated under vacuum, the residue is extracted with DCM, the organic phase is washed with water and dried over Na$_2$SO$_4$, and the solvent is evaporated off under vacuum. The residue is chromatographed on silica gel, eluting with a chloroform/MeOH mixture (95/5; v/v). 0.2 g of the expected product is obtained.

MH$^+$=698

EXAMPLE 21

N-[1-[4-(Butylaminomethyl)benzyl]-2-oxo-2-(pyrrolidin-1-yl)ethyl]-3-(naphthalene-2-sulphonylamino)-3-phenylpropionamide hydrochloride

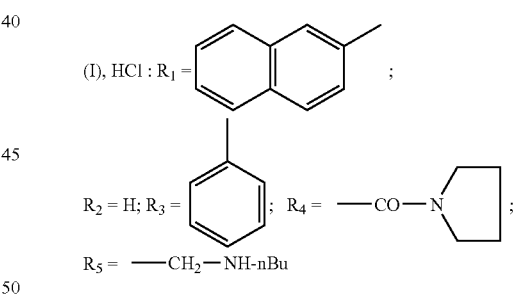

A) N-[1-[4-(N-Benzyl-N-butylaminomethyl)benzyl]-2-oxo-2-(pyrrolidin-1-yl)ethyl]-3-(naphthalene-2-sulphonylamino)-3-phenylpropionamide hydrochloride 0.073 g of 80% sodium hydride in oil is added to a solution of 0.397 g of N-butylbenzylamine in 5 ml of THF, and the mixture is stirred for 30 minutes at RT. 1.5 g of the compound obtained in step B of Example 20 are then added and the mixture is stirred for 18 hours at RT. The insoluble material is filtered off by suction and washed with THF, and the filtrate is concentrated under vacuum. The residue is extracted with DCM, the organic phase is washed with 0.1N HCl and with saturated NaCl solution and dried over Na$_2$SO$_4$, and the solvent is evaporated off under vacuum. The residue is chromatographed on silica gel, eluting with a chloroform/MeOH mixture (96/4; v/v). 0.265 g of the expected product is obtained.

B) N-[1-[4-(Butylaminomethyl)benzyl]-2-oxo-2-(pyrrolidin-1-yl)ethyl]-3-(naphthalene-2-sulphonylamino)-3-phenylpropionamide hydrochloride 0.6 ml of 1N HCl is added to a solution of 0.47 g of the compound obtained in the preceding step in 5 ml of MeOH, followed by addition of 0.5 g of 10% palladium-on-charcoal, and the mixture is hydrogenated at RT under a pressure of 13 332 Pa for 18 hours. The catalyst is filtered off through Celite® and washed with an MeOH/chloroform mixture, and the filtrate is concentrated under vacuum. The residue is chromatographed on silica gel, eluting with a chloroform/MeOH mixture (95/5; v/v). 0.12 g of the expected product is obtained.

$MH^+$=641

By working according to the procedures described in the preceding Examples, the compounds according to the invention collated in Table VIII below are prepared.

TABLE VIII (I)

| Examples | $R_3$ | $R_4$ | $R_5$ | Salt mass or NMR |
|---|---|---|---|---|
| 22 (a) | 3-F-phenyl (methyl) | —CO—N(pyrrolidine) | —CH$_2$—N(piperidine) | NMR |
| 23 (b) | 3-Me-phenyl (methyl) | —CO—N(pyrrolidine) | —CH$_2$—N(Et)$_2$ | HCl NMR |
| 24 (c) | 3,5-di-OMe-phenyl (methyl) | —CO—N(pyrrolidine) | —CH$_2$—N(Et)$_2$ | NMR |
| 25 (d) | 3,4-di-OMe-phenyl (methyl) | —CO—N(pyrrolidine) | —CH$_2$—N(Et)$_2$ | NMR |
| 26 (e) | 2,3-dihydrobenzo[1,4]dioxin-6-yl (methyl) | —CO—N(Me)(iPr) | —CH$_2$—N(Et)$_2$ | NMR |

TABLE VIII-continued
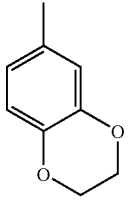
(I)
| Examples | R₃ | R₄ | R₅ | Salt mass or NMR |
|---|---|---|---|---|
| 27 (f) | 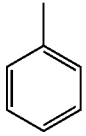 | —CO—N(iPr)₂ | —CH₂—N(Et)₂ | HCl NMR |
| 28 (g) | 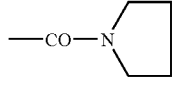 | —CO—N⟨pyrrolidine⟩ | —CH₂N(n-Pr)₂ | HCl NMR |
| 29 (h) | 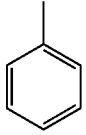 | —CO—N⟨pyrrolidine⟩ | —CH₂—N(iPr)₂ | HCl NMR |
| 30 (i) | 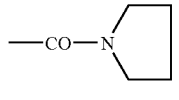 | —CO—N(Me)(cyclopentyl) | —CH₂—N(Et)₂ | HCl NMR |
| 31 (j) | 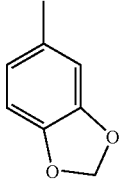 | —CO—N⟨pyrrolidine⟩ | —CH₂N(Et)₂ | HCl NMR |
| 32 (k) | 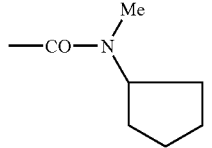 | —CO—N⟨pyrrolidine⟩ | —CH₂NH—CH₂CH₂OH | Mass |

TABLE VIII-continued (I)

[Structure: naphthalene-SO$_2$-NH-CH(R$_3$)-CH$_2$-C(=O)-NH-CH(R$_4$)-CH$_2$-C$_6$H$_4$-R$_5$]

| Examples | R$_3$ | R$_4$ | R$_5$ | Salt mass or NMR |
|---|---|---|---|---|
| 33 (l) | phenyl | —CO—N(pyrrolidine) | —CH$_2$—N(pyrrolidine) | Mass |
| 34 (m) | benzo[1,3]dioxol-5-yl | —CO—N(Me)(iPr) | —CH$_2$—N(piperidine) | NMR |
| 35 (n) | benzo[1,3]dioxol-5-yl | —CO—N(Me)(iPr) | —CH$_2$—N(Me)(cyclopentyl) | NMR |
| 36 (o) | benzo[1,3]dioxol-5-yl | —CO—N(Me)(iPr) | —CH$_2$—N(4-hydroxypiperidine) | NMR |

Mass or proton NMR spectra at 200 MHz in DMSO-d$_6$ of the compounds of the Examples of Table I.

EXAMPLE 22

δ (ppm): 1.2–1.9: unres.: 10H; 2.5–3.4: unres.: 12H; 4.2: s: 2H; 4.45: t: 1H; 4.7: t: 1H; 6.8–8.3: unres.: 16H.

EXAMPLE 23

δ (ppm): 1.2: t: 6H; 1.4–1.75: unres.: 4H; 1.8: s: 3H; 2.2–3.2: unres.: 12H; 4.0–4.8: unres.: 4H; 6.5–8.4: unres.: 17H; 10.4: s: 1H.

EXAMPLE 24

δ (ppm): 0.9: t: 6H; 1.3–1.6: unres.: 4H; 2.2–3.5: unres.: 20H; 4.2–4.7: unres.: 2H; 5.85: t: 1H; 6.15: d: 2H; 6.8–8.3: unres.: 13H.

EXAMPLE 25

δ (ppm): 1.0: t: 6H; 1.4–1.8: unres.: 4H; 2.3–3.7: unres.: 20H; 4.3–4.8: unres.: 2H; 6.4–8.4: unres.: 16H.

EXAMPLE 26

δ (ppm): 0.5–1.0: unres.: 12H; 2.2–2.9: unres.: 11H; 3.35–5.0: unres.: 9H; 6.2–8.4: unres.: 16H.

EXAMPLE 27

δ (ppm): 0.5–1.4: unres.: 18H; 2.2–3.1: unres.: 8H; 3.15–4.8: unres.: 10H; 6.2–8.3: unres.: 16H; 10.35: s: 1H.

EXAMPLE 28

δ (ppm): 0.6–0–9: mt: 6H; 1.3–1.9: mt: 8H; 2.2–3.65: mt: 12H; 4.0–4.9: unres.: 4H; 6.7–8.5: unres.: 18H; 10.5: bs: 1H.

EXAMPLE 29

δ (ppm): 1.0–1.8: unres.: 16H; 2.2–3.7: unres.: 10H; 4.0–4.8: unres.: 4H; 6.7–8.5: unres.: 18H; 9.2: bs: 1H.

EXAMPLE 30

δ (ppm): 1.3–1.8: unres.: 4H; 2.2–3.8: unres.: 8H; 3.9–5.0: unres.: 6H; 6.6–8.8: unres.: 22H; 11.35: mt: 1H.

EXAMPLE 31

δ (ppm): 1.0–1.3: mt: 6H; 1.4–1.8: unres.: 4H; 2.2–3.2: unres.: 12H; 4.0–4.7: unres.: 4H; 5.2–5.7: unres.: 2H; 6.2–8.4: unres.: 16H; 10.2: bs: 1H.

EXAMPLE 32

MH$^+$=629

EXAMPLE 33

MH$^+$=639

EXAMPLE 34

δ (ppm): 0.5–1.0: unres.: 6H; 1.25–1.65: unres.: 6H; 2.1–3.0: unres.: 11H; 3.2–4.9: unres.: 5H; 5.2–5.8: unres.: 2H; 6.2–8.4: unres.: 16H.

EXAMPLE 35

δ (ppm): 0.4–0.9: unres.: 6H; 1.15–2.1: unres.: 11H; 2.15–2.9: unres.: 8H; 3.2–4.8: unres.: 5H; 5.2–5.7: mt: 2H; 6.2–8.3: unres. 16H.

EXAMPLE 36

δ (ppm): 0.4–0.8: unres.: 6H; 1.05–2.65: unres.: 4H; 2.7–2.9: unres.: 11H; 3.2–4.8: unres.: 7H; 5.2–5.65: unres.: 2H; 6.2–8.3: unres.: 16H.

(a) This compound is prepared according to the procedure described in Example 3, starting with the compound obtained in Preparation 1.1 and the compound obtained in Preparation 2.6.

(b) This compound is prepared according to the procedure described in Example 3, starting with the compound obtained in Preparation 1.3 and the compound obtained in Preparation 2.7. The crude product obtained is dissolved in EtOAc and acidified to pH 1 by adding hydrochloric ether, diluted with ether, and the precipitate formed is filtered off by suction.

(c) This compound is prepared according to the procedure described in Example 3, starting with the compound obtained in Preparation 1.5 and the compound obtained in Preparation 2.7.

(d) This compound is prepared according to the procedure described in Example 3, starting with the compound obtained in Preparation 1.6 and the compound obtained in Preparation 2.7.

(e) This compound is prepared according to the procedure described in Example 7, starting with the compound obtained in Preparation 1.8 and the compound obtained in Preparation 2.8, without preparing the hydrochloride.

(f) This compound is prepared according to the procedure described in Example 8, starting with the compound obtained in Preparation 1.8 and the compound obtained in Preparation 2.9.

(g) This compound is prepared according to the procedure described in Example 13, step A, starting with the compound obtained in Preparation 1.1 and the compound obtained in Preparation 2.12, followed by saponification with 1N KOH according to step B and coupling with pyrrolidine according to step C. At the end of step C, formation of the hydrochloride in EtOAc by addition of hydrochloric ether.

(h) This compound is prepared according to the procedure described in Example 13, step A, starting with the compound obtained in Preparation 1.1 and the compound obtained in Preparation 2.13, followed by saponification with 1N KOH according to step B and coupling with pyrrolidine according to step C. Formation of the hydrochloride according to (g) above.

(i) This compound is prepared according to the procedure described in step C of Example 13, starting with the compound obtained in step B of Example 15 and N-methylcyclopentylamine. The product obtained is chromatographed on silica gel, eluting with a DCM/MeOH/NH$_4$OH mixture (95/5/0.4; v/v/v) and the hydrochloride is then formed in EtOAc/hydrochloric ether.

(j) This compound is prepared according to the procedure described in step C of Example 13, starting with the compound obtained in step B of Example 15 and pyrrolidine. The product obtained is chromatographed on silica gel, eluting with a DCM/MeOH/NH$_4$OH mixture (95/5/0.4; v/v/v) and the hydrochloride is then formed in EtOAc/hydrochloric ether and crystallized from MeOH/ether.

(k) This compound is prepared according to the procedure described in Example 17, starting with the compound obtained in step A of Example 18 and 2-aminoethanol.

(l) This compound is prepared according to the procedure described in Example 18, starting with the compound obtained in step A of Example 17 and pyrrolidine.

(m) This compound is prepared according to the procedure described in Example 8, starting with the compound obtained in Preparation 1.7 and the compound obtained in Preparation 2.15, without performing chromatography or salification.

(n) This compound is prepared according to the procedure described in Example 8, starting with the compound obtained in Preparation 1.7 and the compound obtained in Preparation 2.16, without performing chromatography or salification.

(o) This compound is prepared according to the procedure described in Example 8, starting with the compound obtained in Preparation 1.7 and the compound obtained in Preparation 2.17, without performing chromatography or salification.

EXAMPLE 37

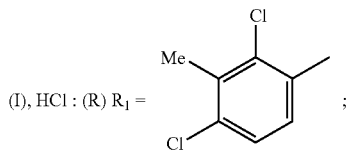

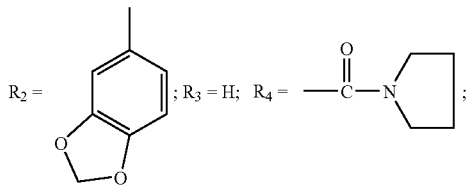

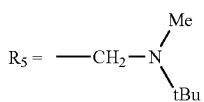

A) (R) N-[1-(4-Cyanobenzyl)-2-oxo-2-(pyrrolidin-1-yl) ethyl]-3-[N-(benzo[1,3]dioxol-5-yl)amino]propionamide.

This compound is obtained by the action of the compound from Preparation 1.17 on the compound from Preparation 2.18.

B) (R) N-[1-(4-formylbenzyl)-2-oxo-2-(pyrrolidin-1-yl) ethyl]-3-[N-(benzo[1,3]dioxol-5-yl)amino]propionamide.

550 mg of the compound from the preceding step are placed in 16 ml of a pyridine/acetic acid/water mixture (2/1/1) at 0° C., and 1.3 g of $NaH_2PO_2.H_2O$ and 260 mg of Raney nickel are added. The reaction medium is heated for 2 hours at 55° C. and then filtered through Celite® and rinsed with an EtOH/DCM mixture (1/1), and the filtrate is concentrated. The residue is extracted with EtOAc and then washed successively with water (twice), with saturated $NaHCO_3$ solution, with water, with 5% $KHSO_4$ solution and with saturated NaCl solution. The expected product is obtained, and is used without further purification in the following step.

126

C) The product obtained in the preceding step is placed in 10 ml of dichloromethane and is treated with 160 µl of methyl-tert-butylamine and 264 mg of $NaHB(OAc)_3$. After stirring for 24 hours at RT, the medium is diluted with DCM and then washed successively with water (twice), with saturated $NaHCO_3$ solution and with saturated NaCl solution. The hydrochloride is prepared by adding $Et_2O$ saturated with HCl gas to a solution of the compound in $EtOAc/Et_2O$ (1/1; v/v). 0.36 g of the expected compound is obtained, which crystallizes from an $EtOAc/Et_2O$ mixture; m.p.=166° C.

$\alpha_D^{25} = -7.8$ (c=1; MeOH).

NMR: 1.4–2.05 ppm: unres.: 13H; 2.2–4.8 ppm: unres.: 16H; 6.15 ppm: s: 2H; 6.65–7.8 ppm: unres.: 9H; 8.5 ppm: d: 1H; 9.95 ppm: bs: 1H.

EXAMPLE 38

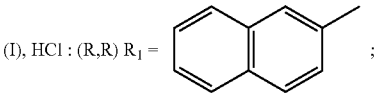

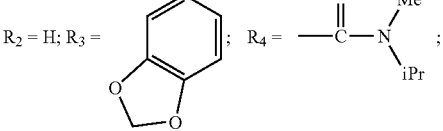

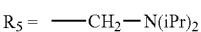

A) (R,R)-2-((3-(N-Boc)amino-3-(benzo[1,3]dioxol-5-yl) propanoyl)amino)-3-(4-(diisopropylaminomethyl)phenyl)-N-isopropyl-N-methylpropionamide.

237 mg of the compound obtained in Preparation 1.13 and the compound obtained in Preparation 2.19 are mixed with 303 mg of BOP and 360 µl of DIPEA in 10 ml of DCM. After stirring for 3 hours at RT, the mixture is concentrated to dryness. The residue is extracted with EtOAc and then washed successively with water, with saturated $NaHCO_3$ solution and with saturated NaCl solution. 420 mg of the expected compound are obtained.

B) (R,R)-2-((3-Amino-3-(benzo[1,3]dioxol-5-yl)propanoyl) amino)-3-(4-(diisopropylaminomethyl)phenyl)-N-isopropyl-N-methylpropionamide, 2TFA.

420 mg of the compound from the preceding step are placed in 15 ml of TFA and 20 ml of DCM. After stirring for 2 hours at RT, the mixture is concentrated to dryness. 0.504 g of the expected compound is obtained, which crystallizes from $Et_2O$.

C) (R,R)-2-((3-Naphthalene-2-sulphonylamino-3-(benzo[1, 3]dioxol-5-yl)propanoyl)amino)-3-(4-(diisopropylaminomethyl)phenyl)-N-isopropyl-N-methylpropionamide.

500 mg of the compound from the preceding step are mixed with 153 mg of 2-naphthalenesulphonyl chloride and 354 µl of DIPEA in 5 ml of DCM, and the mixture is stirred for 2 hours at RT. The reaction mixture is concentrated to dryness and then washed with water, followed by saturated $NaHCO_3$ solution. The hydrochloride is prepared by addition of $Et_2O$ saturated with HCl to a solution of the compound of EtOAc. 0.280 g of the expected compound is obtained.

NMR: 0.6–1.6 ppm: unres.: 18H; 2.2–3.1 ppm: unres.: 7H; 3.4–5.8 ppm: unres.: 9H; 6.3–8.6 ppm: unres.: 16H; 9.1 ppm: bs: 1H.

$\alpha_D^{25} = +55.2°$ (c=1; MeOH).

By working as in the above examples, the compounds according to the invention of formula (I) described in Table IX are prepared.

TABLE IX
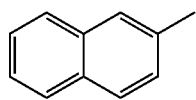
| Example | R₁ | R₂ | R₃ | R₄ | R₅ |
|---|---|---|---|---|---|
| 39 c2HCl | 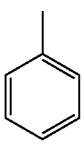 | H | 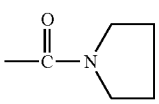 | 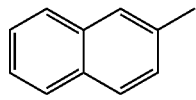 | 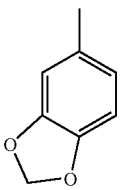 |
| 40 HCl | 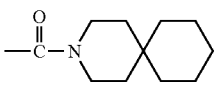 | H | 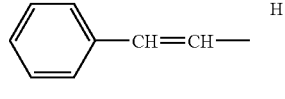 | 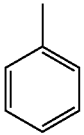 | 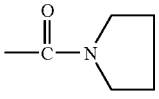 |
| 41 HCl | 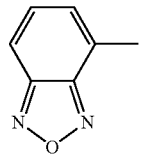 | H | 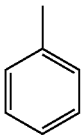 | 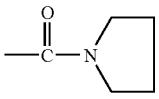 | 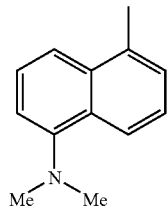 |
| 42 HCl | 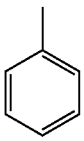 | H | 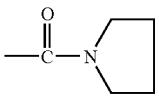 | 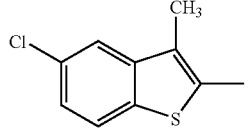 | 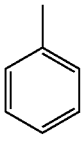 |
| 43 2HCl | 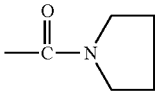 | H | | | |
| 44 HCl | 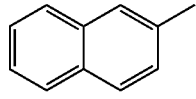 | H | | | |
| 45 | 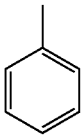 | H | 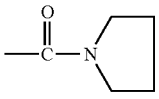 | | |

TABLE IX-continued
(I)
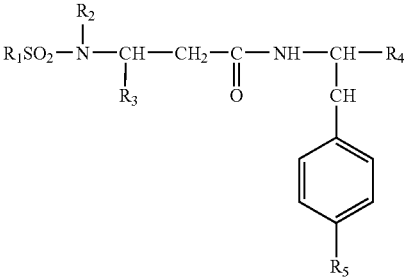
| Example | R₁ | R₂ | R₃ | R₄ | R₅ |
|---|---|---|---|---|---|
| 46 | 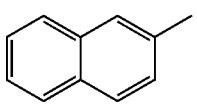 | H | 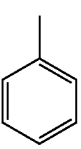 | 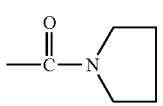 | 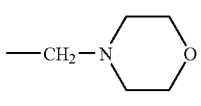 |
| 47 HCl | 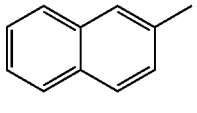 | H | 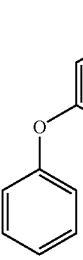 | 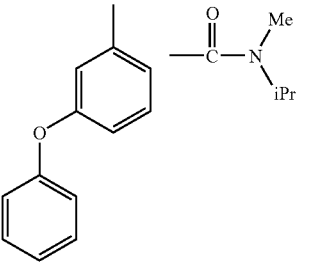 | 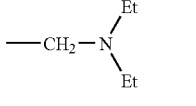 |
| 48 | 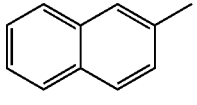 | H | 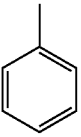 | 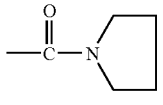 | 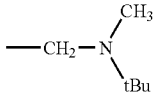 |
| 49 | 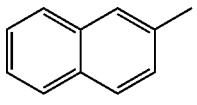 | H | 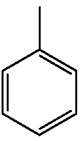 | 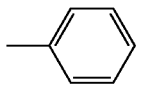 | 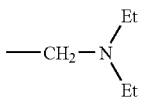 |
| 50 HCl | 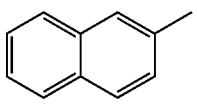 | H | 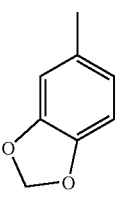 | 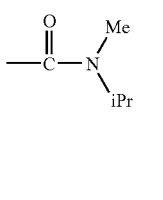 | 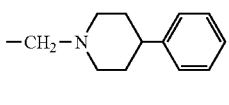 |
| 51 HCl | 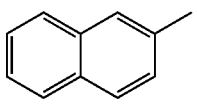 | H | 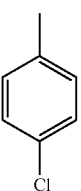 | 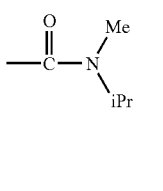 | 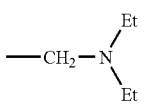 |

TABLE IX-continued (I)

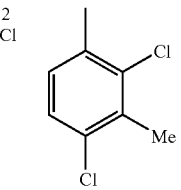

| Example | R₁ | R₂ | R₃ | R₄ | R₅ |
|---|---|---|---|---|---|
| 52 HCl | 2,4-dichloro-3-methylphenyl | phenyl | H | phenyl | —CH$_2$—N(Et)(Et) |
| 53 | 2-methylnaphthyl | H | | 5-methyl-benzo[1,3]dioxole | —C(O)—N(Me)(iPr) | —CH$_2$—N(3-azaspiro[5.5]undecane) |
| 54 HCl | 2,4-dichloro-3-methylphenyl | phenyl | H | phenyl | —CH$_2$—N(Me)(tBu) |
| 55 HCl | 2,4-dichloro-3-methylphenyl | 5-methyl-benzo[1,3]dioxole | H | phenyl | —CH$_2$—N(Et)(Et) |
| 56 HCl | 2,4-dichloro-3-methylphenyl | 5-methyl-benzo[1,3]dioxole | H | 5-methyl-benzo[1,3]dioxole | —C(O)—N(Me)(iPr) | —CH$_2$—N(Et)(Et) |
| 57 | 2-methylnaphthyl | H | | 5-methyl-benzo[1,3]dioxole | phenyl | —CH$_2$—N(Me)(tBu) |

Note: Due to the complexity of the structures, the table above approximates the substituent descriptions. The actual image contains drawn chemical structures for each R group.

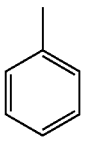
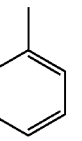
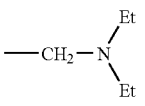
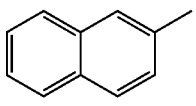
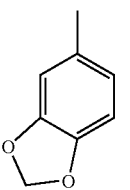
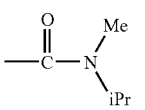
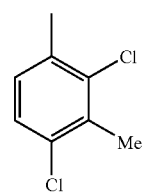
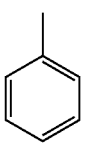
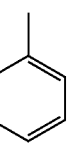
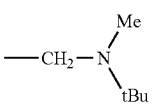
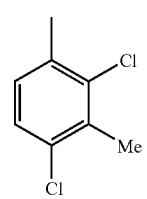
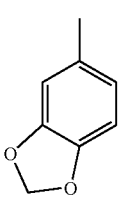
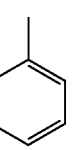
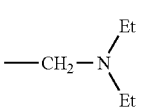
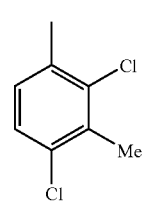
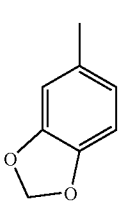
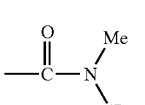
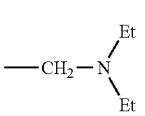
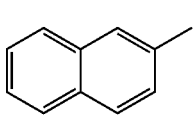
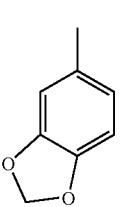
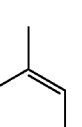
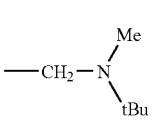

TABLE IX-continued (I)

| Example | R₁ | R₂ | R₃ | R₄ | R₅ |
|---|---|---|---|---|---|
| 58 | 2-naphthyl | H | phenyl | −C(O)−N(Et)(Et) | −CH₂−N(Et)(Et) |
| 59 | 2-naphthyl | H | phenyl | −C(O)−morpholinyl | −CH₂−N(Et)(Et) |
| 60 2HCl | 2,6-dichloro-3-methylphenyl | H | 5-benzo[1,3]dioxolyl | 4-pyridyl | −CH₂−N(Et)(Et) |
| 61 HCl | 2,6-dichloro-3-methylphenyl | H | phenyl | 2-furyl | −CH₂−N(Et)(Et) |
| 62 HCl | 2-naphthyl | H | 3-furyl | −C(O)−N(Me)(iPr) | −CH₂−N(Et)(Et) |
| 63 | 2-benzothiazolyl | H | phenyl | −C(O)−N(Et)(Et) | −CH₂−N(Et)(Et) |
| 64 | 2-naphthyl | H | 5-benzo[1,3]dioxolyl | −C(O)−N(Me)(iPr) | −CH₂−N(tBu)((CH₂)₂−OH) |

TABLE IX-continued (I)

$$R_1SO_2-N(R_2)-CH(R_3)-CH_2-C(O)-NH-CH(R_4)-CH_2-C_6H_4-R_5$$

| Example | $R_1$ | $R_2$ | $R_3$ | $R_4$ | $R_5$ |
|---|---|---|---|---|---|
| 65 | 2-naphthyl | H | benzo[1,3]dioxol-5-yl | —C(O)—NH—CH$_2$—(6-amino-pyridin-3-yl) | —CH$_2$—N(Et)$_2$ |
| 66 | pentamethylphenyl | phenyl | H | —C(O)—N(pyrrolidinyl) | —CH$_2$—N(Et)$_2$ |
| 67 | pentamethylphenyl | H | phenyl | —C(O)—N(pyrrolidinyl) | —CH$_2$—N(Et)$_2$ |
| 68 HCl | 2,3-dichloro-6-methylphenyl (with 2-Me) | H | 3-methylphenyl | —C(O)—N(Me)(iPr) | —CH$_2$—N(Et)$_2$ |
| 69 HCl | 2,3-dichloro-6-methylphenyl | H | phenyl | —C(O)—N(Me)(iPr) | —CH$_2$—N(Et)$_2$ |

TABLE IX-continued (I)

| Example | R₁ | R₂ | R₃ | R₄ | R₅ |
|---|---|---|---|---|---|
| 70 | 2-naphthyl-methyl | H | 3-(benzyloxy)phenyl-methyl | —C(O)—N-pyrrolidinyl | —CH₂—N(Et)₂ |
| 71 2HCl | 2,6-dichloro-3-methylphenyl-methyl | phenyl-methyl | H | 2-imidazolyl | —CH₂—N(Et)₂ |
| 72 HCl | 2,6-dichloro-3-methylphenyl-methyl | benzo[1,3]dioxol-5-yl-methyl | H | —C(O)—N-pyrrolidinyl | —CH₂—N-piperidinyl |
| 73 | 2-naphthyl-methyl | H | benzo[1,3]dioxol-5-yl-methyl | —C(O)—NH(CH₂)₃N(Me)₂ | —CH₂—N(Et)₂ |
| 74 | 2-naphthyl-methyl | H | benzo[1,3]dioxol-5-yl-methyl | —C(O)—N(4-methylpiperazinyl) | —CH₂—N(Et)₂ |

TABLE IX-continued $$R_1SO_2-\underset{R_3}{\underset{|}{N}}-\overset{R_2}{\underset{|}{CH}}-CH_2-\overset{}{\underset{O}{C}}-NH-CH-R_4 \quad (I)$$
(with CH-phenyl-R5 substituent)

| Example | R₁ | R₂ | R₃ | R₄ | R₅ |
|---------|----|----|----|----|----|
| 75 HCl | 2,3-dichloro-4-methylphenyl | phenyl | H | 2-methylbenzothiazole | —CH₂—N(Et)₂ |
| 76 | 2,4,6-trichloro-3-methylphenyl | 3-(benzyloxy)phenyl | H | pyrrolidinyl carbonyl | —CH₂—N(Et)₂ |
| 77 HCl | 2-naphthyl | H | methyl-benzodioxole | —C(O)—N(Me)(iPr) | —CH₂—N(iPr)₂ |
| 78 2HCl | 2-naphthyl | H | methyl-benzodioxole | 4-pyridyl | —CH₂—N(Me)(tBu) |
| 79 2HCl | 2-naphthyl | 3-pyridyl | H | —C(O)—N(Me)(iPr) | —CH₂—N(Et)₂ |
| 80 2HCl | 2,3-dichloro-4-methylphenyl | 3-pyridyl | H | —C(O)—N(Me)(iPr) | —CH₂—N(Et)₂ |

TABLE IX-continued $$R_1SO_2-N(R_2)-CH(R_3)-CH_2-C(O)-NH-CH(R_4)-CH_2-C_6H_4-R_5 \quad (I)$$

| Example | R₁ | R₂ | R₃ | R₄ | R₅ |
|---|---|---|---|---|---|
| 81 HCl | 2-naphthyl | H | 5-(1,3-benzodioxolyl) | —C(O)—N(Me)(cyclobutyl) | —CH₂—N(Et)₂ |
| 82 2HCl | 2,6-dichloro-3-methylphenyl | 4-pyridyl | H | —C(O)—N(Me)(iPr) | —CH₂—N(Et)₂ |
| 83 HCl | 2,6-dichloro-3-methylphenyl | H | 5-(1,3-benzodioxolyl) | phenyl | —CH₂—N(Me)(tBu) |
| 84 2HCl | 2-naphthyl | 4-pyridyl | H | —C(O)—N(Me)(iPr) | —CH₂—N(Et)₂ |
| 85 HCl | 2-naphthyl | H | 5-(1,3-benzodioxolyl) | 2-(1H-benzimidazolyl) | —CH₂—N(Et)₂ |
| 86 HCl | 2,6-dichloro-3-methylphenyl | phenyl | H | phenyl | —CH₂—N(Me)(cyclopentyl) |

TABLE IX-continued
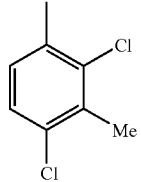
(I)
| Example | R₁ | R₂ | R₃ | R₄ | R₅ |
|---------|-----|-----|-----|-----|-----|
| 87 HCl | 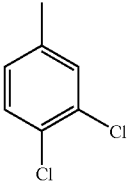 | 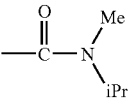 | H | 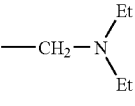 | 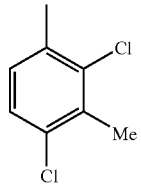 |
| 88 HCl | 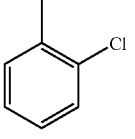 | 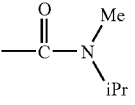 | H | 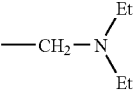 | 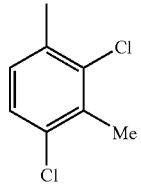 |
| 89 | 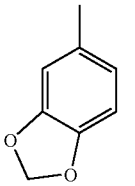 | 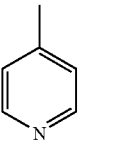 | H | 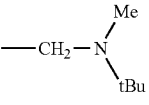 | 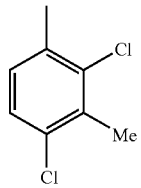 |
| 90 2HCl | 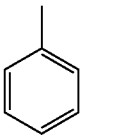 | 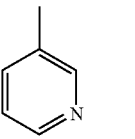 | H | 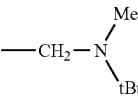 | 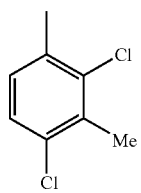 |
| 91 HCl | 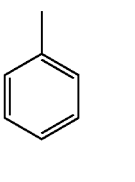 | 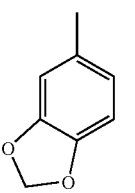 | H | 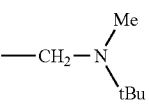 | 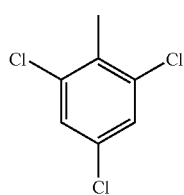 |
| 92 | 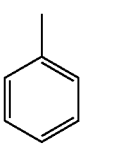 | 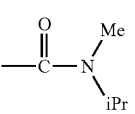 | H | 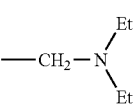 | |

TABLE IX-continued
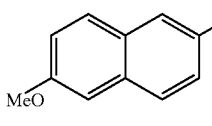
(I)
| Example | R₁ | R₂ | R₃ | R₄ | R₅ |
|---|---|---|---|---|---|
| 93 | 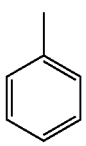 | 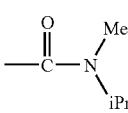 | H | 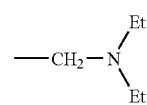 | 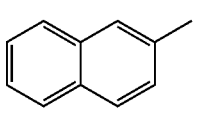 |
| 94 | 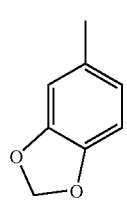 | H | 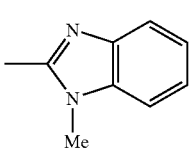 | 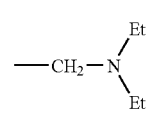 | 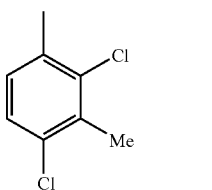 |
| 95 | 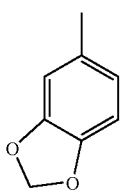 | H | 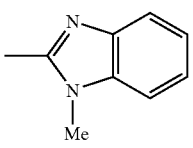 | 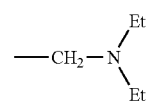 | 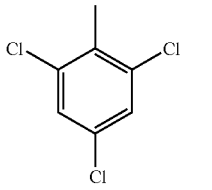 |
| 96 HCl | 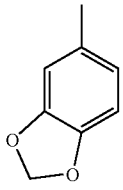 | H | 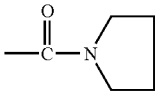 | 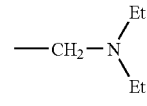 | 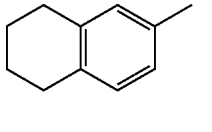 |
| 97 HCl | 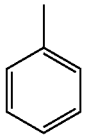 | 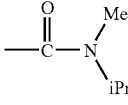 | H | 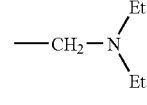 | 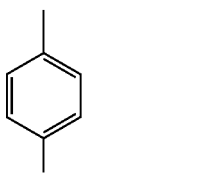 |
| 98 HCl | 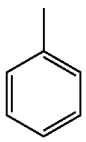 | 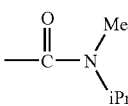 | H | 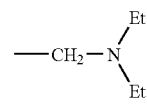 | —CH₂—N(Et)(Et) |

TABLE IX-continued (I)

| Example | R₁ | R₂ | R₃ | R₄ | R₅ |
|---|---|---|---|---|---|
| 99 HCl | 2,3-dichloro-6-methylphenyl | 5-methyl-indan-yl | H | phenyl | —CH₂—N(Me)(tBu) |
| 100 HCl | 6-methoxy-naphth-2-yl | 5-methyl-benzo[1,3]dioxol-yl | H | —C(O)—N(pyrrolidinyl) | —CH₂—N(Et)(Et) |
| 101 HCl | naphth-2-yl (methyl) | 7-methyl-2,3-dihydro-benzo[1,4]dioxin-yl | H | —C(O)—N(Me)(iPr) | —CH₂—N(iPr)(iPr) |
| 102 HCl R isomer | 2,3-dichloro-6-methylphenyl | 5-methyl-benzo[1,3]dioxol-yl | H | —C(O)—N(Me)(iPr) | —CH₂—N(Me)(tBu) |
| 103 HCl | 2,3-dichloro-6-methylphenyl | 5-methyl-benzo[1,3]dioxol-yl | H | —C(O)—N(Me)(iPr) | —CH₂—N(Me)(iPr) |
| 104 HCl R,R isomer | 6-methyl-naphth-2-yl | 5-methyl-benzo[1,3]dioxol-yl | H | —C(O)—N(Me)(iPr) | —CH₂—N(Me)(tBu) |

TABLE IX-continued
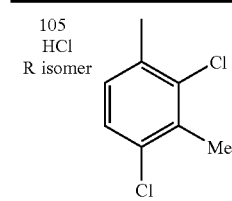
(I)
| Example | R₁ | R₂ | R₃ | R₄ | R₅ |
|---|---|---|---|---|---|
| 105 HCl R isomer | 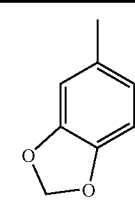 | 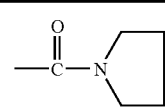 | H | 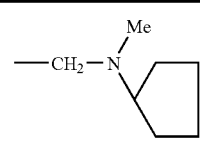 | 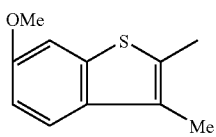 |
| 106 | 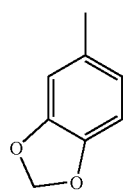 | 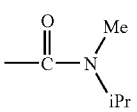 | H | 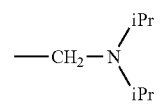 | 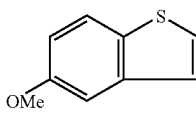 |
| 107 | 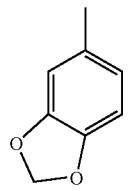 | 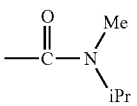 | H | 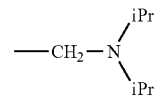 | 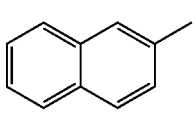 |
| 108 HCl R,R Isomer | 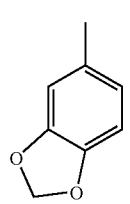 | 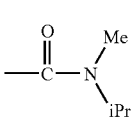 | H | 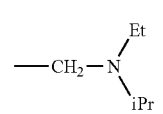 | 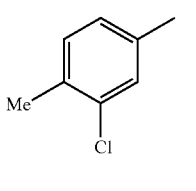 |
| 109 HCl R,R Isomer | 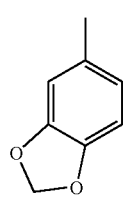 | 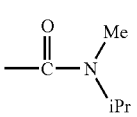 | H | 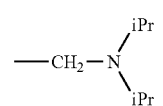 | |

EXAMPLE 39

NMR: 1.3–1.8 ppm: unres.: 4H; 2.2–3.6 ppm: unres.: 21H; 4.2–4.8 ppm: unres.: 2H; 6.8–8.4 ppm: unres.: 18H; 10.2 ppm: bs: 1H.

EXAMPLE 41

NMR: 1.1–1.8 ppm: unres.: 10H; 2.4–3.4 ppm: unres.: 12H; 4.2 ppm: bs: 2H; 4.4–4.8 ppm: unres.: 2H; 6.5–8.5 ppm: unres.: 18H; 10.3 ppm: bs: 1H.

EXAMPLE 42

NMR: 1.2–2 ppm: unres.: 10H; 2.4–3.3 ppm: unres.: 12H; 4.2–4.9 ppm: unres.: 4H; 6.9–9.1 ppm: unres.: 14H; 10.2 ppm: bs: 1H.

EXAMPLE 43

NMR: 1–1.8 ppm: unres.: 10H; 2.2–3.5 ppm: unres.: 18H; 4–5 ppm: unres.: 4H; 6.6–8.7 ppm: unres.: 17H; 10.7 ppm: bs: 1H.

EXAMPLE 44

NMR; 1.2 ppm: mt: 6H; 1.4–1.8 ppm: unres.: 4H; 2.2–3.3 ppm: unres.: 15H; 4.1–4.9 ppm: wires.: 4H; 6.8–8.1 ppm: wires.: 12H; 8.35 ppm: d: 1H; 8.9 ppm: d: 1H; 10.25 ppm: bs: 1H.

EXAMPLE 47

NMR: 0.5–1.3 ppm: unres.: 12H; 2.1–3.1 ppm: unres.: 11H; 3.6–5 ppm: unres.: 5H; 6.2–8.5 ppm: unres.: 22H; 10.1 ppm: bs: 1H.

EXAMPLE 48

NMR: 1 ppm: s: 9H; 1.2–1.7 ppm: unres.: 4H; 1.9 ppm: s: 3H; 2.2–3.5 ppm: unres.: 10H; 4.1–4.75 ppm: unres.: 2H; 6.7–8.4 ppm: unres.: 18H.

EXAMPLE 49

NMR: 0.95 ppm: t: 6H; 2.1–3.6 ppm: unres.: 10H; 4.4–5.1 ppm: unres.: 2H; 6.6–8.6 ppm: unres.: 23H.

EXAMPLE 50

NMR: 1.3–1 ppm: unres.: 6H; 1.7–3.5 ppm: unres.: 16H; 4–5 ppm: unres.: 5H; 5.2–5.7 ppm: unres.: 2H; 6.2–8.4 ppm: unres.: 21H; 10.7 ppm: bs: 1H.

EXAMPLE 51

NMR: 0.4–1.3 ppm: unres.: 12H; 2.1–3.1 ppm: unres.: 11H; 3.6–4.8 ppm: unres.: 5H; 6.6–8.5 ppm: unres.: 17H; 10 ppm: bs: 1H.

EXAMPLE 52

NMR: 1.15 ppm: t: 6H; 2.2 ppm: t: 2H; 2.5 ppm: s: 3H; 2.7–3.1 ppm: unres.: 6H; 3.8 ppm: t: 2H; 4.15 ppm: d: 2H; 4.9 ppm: q: 1H; 6.9–7.7 ppm: unres.: 16H; 8.5 ppm: d: 1H; 10.5 ppm: bs: 1H.

EXAMPLE 53

NMR: 0.4–1.5 ppm: unres.: 20H; 2–2.85 ppm: unres.: 11H; 3.3–4.8 ppm: unres.: 5H; 5.2–5.7 ppm: 2s: 2H; 6.2–8.3 ppm: unres.: 16H.

EXAMPLE 54

NMR: 1.4 ppm: s: 9H; 2–2.6 ppm: unres.: 8H; 2.9 ppm: d: 2H; 3.6–4.6 ppm: unres.: 4H; 4.9 ppm: q: 1H; 6.9–7.7 ppm: unres.: 16H; 8.5 ppm: d: 1H; 9.9 ppm: bs: 1H.

EXAMPLE 55

NMR: 1.15 ppm: t: 6H; 2.4 ppm: s: 3H; 2.8–3.1 ppm: unres.: 6H; 3.75 ppm: t: 2H; 4.15 ppm: d: 2H; 4.9 ppm: q: 1H; 5.95 ppm: s: 2H; 6.4–7.7 ppm: unres.: 14H; 8.4 ppm: d: 1H; 10.1 ppm: bs: 1H.

EXAMPLE 56

NMR: 0.7–1.3 ppm: unres.: 12H; 2.2 ppm: t: 2H; 2.3–3.1 ppm: unres.: 12H; 3.6–5 ppm: unres.: 6H; 6 ppm: s: 2H; 6.4–7.7 ppm: unres.: 9H; 8.3 ppm: dd: 1H; 10.2 ppm: bs: 1H.

EXAMPLE 57

NMR: 1.05 ppm: ds: 9H; 1.85 ppm: ds: 3H; 2.1–3.4 ppm: unres.: 6H; 4.3–4.9 ppm: unres.: 2H; 5.2–5.8 ppm: 2ds: 2H; 6.1–8.4 ppm: unres.: 21H.

EXAMPLE 60

NMR: 1.25 ppm: t: 6H; 2.3 ppm: mt: 2H; 2.5 ppm: s: 3H; 3 ppm: mt: 6H; 3.85 ppm: t: 2H; 4.25 ppm: d: 2H; 5.25 ppm: q: 1H; 6.1 ppm: s: 2H; 6.4–9.2 ppm: unres.: 14H; 10.7 ppm: bs: 1H.

EXAMPLE 61

NMR: 1.2 ppm: t: 6H; 2.3 ppm: mt: 2H; 2.5 ppm: s: 3H; 2.7–3.3 ppm: unres.: 6H; 3.9 ppm: t: 2H; 4.2 ppm: d: 2H; 5.1 ppm: q: 1H; 6.1–7.8 ppm: unres.: 14H; 8.45 ppm: d: 1H; 10.6 ppm: bs: 1H.

EXAMPLE 62

NMR: 0.5–1.4 ppm: unres.: 12H; 2–5 ppm: unres.: 16H; 5.95–8.5 ppm: unres.: 16H.

EXAMPLE 64

NMR: 0.6–1.3 ppm: unres.: 15H; 2.2–3.25 ppm: unres.: 9H; 3.4–5 ppm: unres.: 8H; 5.3–5.8 ppm: unres.: 2H; 6.3–8.5 ppm: unres.: 16H.

EXAMPLE 65

NMR: 0.85 ppm: td: 6H; 2.1–2.9 ppm: unres.: 8H; 3.2–4.7 ppm: unres.: 6H; 5.2–5.8 ppm: unres.: 3H; 6.1–8.3 ppm: unres.: 19H.

EXAMPLE 68

NMR: 0.6–1.3 ppm: unres.: 12H; 2–3.1 ppm: unres.: 17H; 3.6–5 ppm: unres.: 6H; 6.7–7.7 ppm: unres.: 10H; 8.3 ppm: dd: 1H; 9.9 ppm: bs: 1H.

EXAMPLE 69

NMR: 0.65–1.3 ppm: unres.: 12H; 2.15 ppm: t: 2H; 2.25 ppm: s: 3H; 2.3–3.1 ppm: unres.: 9H; 3.7–5 ppm: unres.: 6H; 7–7.7 ppm: unres.: 11H; 8.4 ppm: dd: 1H; 9.9 ppm: bs: 1H.

EXAMPLE 71

NMR: 1.2 ppm: t: 6H; 2.1–2.6 ppm: unres.: 5H; 2.8–3.5 ppm: unres.: 6H; 3.9 ppm: t: 2H; 4.2 ppm: bd: 2H; 5.2 ppm: q: 1H; 7–7.8 ppm: unres.: 13H; 8.9 ppm: d: 1H; 10.4 ppm: bs: 1H; 14.4 ppm: bs: 2H.

EXAMPLE 72

NMR: 1–1.9 ppm: unres.: 10H; 2.2 ppm: t: 2H; 2.5 ppm: s: 3H; 2.6–3.5 ppm: unres.: 10H; 3.75 ppm: t: 2H; 4.15 ppm: d: 2H; 4.5 ppm: q: 1H; 6 ppm: s: 2H; 6.3–7.7 ppm: unres.: 9H; 8.3 ppm: d: 1H; 10.2 ppm: s: 1H.

EXAMPLE 73

NMR: 0.9 ppm: mt: 6H; 1.3 ppm: mt: 2H; 1.9–2.2 ppm: unres.: 5H; 2.25–3.6 ppm: unres.: 12H; 4.2 ppm: mt: 1H; 4.55 ppm: mt: 1H; 5.2–5.7 ppm: unres.: 2H; 6.2–8.4 ppm: unres.: 17H.

EXAMPLE 74

NMR: 0.9 ppm: mt: 6H; 1.3–3.5 ppm: unres.: 19H; 4.3–4.8 ppm: unres.: 2H; 5.2–5.7 ppm: unres.: 2H; 6.2–8.4 ppm: unres.: 16H.

EXAMPLE 77

NMR: 0.5–1.4 ppm: unres.: 18H; 2.1–3 ppm: unres.: 8H; 3.3–4.8 ppm: unres.: 7H; 5.2–5.65 ppm: unres.: 2H; 6.2–8.4 ppm: unres.: 16H; 9.15 ppm: s: 1H.

EXAMPLE 78

NMR: 1.4 ppm: s: 9H; 2.2–2.75 ppm: unres.: 5H; 2.9 ppm: t: 2H; 3.8 ppm: mt: 1H; 4.5 ppm: mt: 2H; 5 ppm: mt: 1H; 5.1–5.7 ppm: 2ds: 2H; 6.2–9.1 ppm: unres.: 20H; 9.6 ppm: s: 1H.

EXAMPLE 79

NMR: 0.7–1.3 ppm: unres.: 12H; 2.1–3.1 ppm: unres.: 11H; 3.7–5 ppm: unres.: 6H; 7.1–8.2 ppm: unres.: 16H; 10.85 ppm: s: 1H.

EXAMPLE 80

NMR: 0.7–1.4 ppm: unres.: 12H; 2.2–3.2 ppm: unres.: 14H; 3.7–5 ppm: unres.: 6H; 7–8.8 ppm: unres.: 11H; 10.8 ppm: s: 1H.

EXAMPLE 82

NMR: 0.7–1.5 ppm: unres.: 12H; 2.4–3.3 ppm: unres.: 14H; 4–5.1 ppm: unres.: 6H; 7.2–9 ppm: unres.: 11H; 10.8 ppm: s: 1H.

EXAMPLE 83

NMR: 1.4 ppm: s: 9H; 2–3 ppm: unres.: 10H; 3.6–4.6 ppm: unres.: 4H; 4.9 ppm: mt: 1H; 5.95 ppm: s: 2H; 6.3–7.7 ppm: unres.: 14H; 8.4 ppm: d: 1H; 9.65 ppm: bs: 1H.

EXAMPLE 84

NMR: 0.6–1.4 ppm: unres.: 12H; 2.4–3.2 ppm: unres.: 11H; 3.8–5.1 ppm: unres.: 6H; 7–8.9 ppm: unres.: 15H; 10.9 ppm: bs: 2H.

EXAMPLE 85

NMR: 1 ppm: t: 6H; 2.3–3.7 ppm: unres.: 10H; 4.7 ppm: mt: 1H; 5 ppm: mt: 1H; 5.1–5.8 ppm: 2ds: 2H; 6.2–8.8 ppm: unres.: 20H; 12.15 ppm: sd: 1H.

EXAMPLE 86

NMR: 1.2–2.55 ppm: unres.: 16H; 2.85 ppm: mt: 2H; 3.1–4.4 ppm: unres.: 5H; 4.9 ppm: mt: 1H; 6.8–7.6 ppm: unres.: 16H; 8.4 ppm: d: 1H; 10.6 ppm: bs: 1H.

EXAMPLE 87

NMR: 0.6–1.3 ppm: unres.: 12H; 2.2 ppm: t: 2H; 2.35–3.1 ppm: unres.: 12H; 3.7–5 ppm: unres.: 6H; 6.9–7.8 ppm: unres.: 9H; 8.3 ppm: dd: 1H; 10.1 ppm: bs: 1H.

EXAMPLE 88

NMR: 0.7–1.3 ppm: unres.: 12H; 2.3 ppm: t: 2H; 2.4–3.1 ppm: unres.: 12H; 3.5–5 ppm: unres.: 6H; 7–7.7 ppm: unres.: 10H; 8.4 ppm: dd: 1H; 10 ppm: bs: 1H.

EXAMPLE 89

NMR: 1.05 ppm: s: 9H; 1.85 ppm: s: 3H; 2.2 ppm: t: 2H; 2.6 ppm: s: 3H; 2.8 ppm: mt: 2H; 3.4 ppm: s: 2H; 3.7 ppm: s: 2H; 4.9 ppm: mt: 1H; 5.95 ppm: s: 2H; 6.3–8.6 ppm: unres.: 14H.

EXAMPLE 90

NMR: 1.5 ppm: s: 9H; 2.2–2.6 ppm: unres.: 8H; 3 ppm: unres.: 2H; 3.8–4.6 ppm: 2 unres.: 4H; 5.2 ppm: unres.: 1H; 7–9.2 ppm: unres.: 17H; 10 ppm: bs: 1H.

EXAMPLE 91

NMR: 1.5 ppm: s: 9H; 2.3 ppm: t: 2H; 2.4–2.6 ppm: unres.: 6H; 3 ppm: bd: 2H; 3.8–4.1 ppm: unres.: 3H; 4.4–5 ppm: unres.: 2H; 6 ppm: s: 2H; 6.6–7.8 ppm: unres.: 14H; 8.5 ppm: d: 1H; 10.4 ppm: bs: 1H.

EXAMPLE 94

NMR: 0.9 ppm: t: 6H; 2.1–3.7 ppm: unres.: 14H; 4.50 ppm: mt: 1H; 5–5.7 ppm: unres.: 3H; 6–8.6 ppm: unres.: 20H.

EXAMPLE 95

NMR: 0.95 ppm: t: 6H; 2.1–2.7 ppm: unres.: 9H; 3–4 ppm: unres.: 9H; 5.4 ppm: q: 1H; 6.05 ppm: s: 2H; 6.4–7.8 ppm: unres.: 13H; 8.7 ppm: d: 1H.

EXAMPLE 99

NMR: 1.5 ppm: s: 9H; 1.9–2.55 ppm: unres.: 10H; 2.6–3.1 ppm: unres.: 6H: 3.75–4.8 ppm: unres.: 4H; 5.05 ppm: mt: 1H; 6.7–7.8 ppm: unres.: 14H; 8.55 ppm: d: 1H; 9.4 ppm: bs: 1H.

EXAMPLE 101

NMR: 0.5–1.4 ppm: unres.: 18H; 2.1–3 ppm: unres.: 7H; 3.3–4.9 ppm: unres.: 11H; 6.1–8.4 ppm: unres.: 16H; 9.1 ppm: bs: 1H.

EXAMPLE 102

NMR: 0.8–1.2 ppm: unres.: 6H; 1.5 ppm: s: 9H; 2.2–3.1 ppm: unres.: 13H; 3.7–5.1 ppm: unres.: 6H: 6.1 ppm: s: 1H; 6.5–7.8 ppm: unres.: 9H; 8.3–8.6 ppm: unres.: 1H; 9.5 ppm: bs: 1H.

EXAMPLE 103

NMR: 0.8–1.5 ppm: unres.: 12H; 2.35 ppm: t: 2H; 2.5 ppm: s: 6H; 2.6–3.1 ppm: unres.: 5H; 3.45 ppm: mt: 1H; 3.8–5.1 ppm: unres.: 6H; 6.15 ppm: s: 2H; 6.5–7.8 ppm: unres.: 9H; 8.3–8.6 ppm: unres.: 1H; 10.5 ppm: bs: 1H.

EXAMPLE 104

NMR: 0.7 ppm: mt: 6H; 1.4 ppm: s: 9H; 2.2–3 ppm: unres.: 10H; 3.8 ppm: mt: 1H; 4.3–4.9 ppm: unres.: 4H; 5.2–5.7 ppm: 2s: 2H; 6.2–8.4 ppm: unres.: 16H; 9.5 ppm: s: 1H.

EXAMPLE 105

NMR: 1.4–2.4 ppm: unres.: 14H; 2.5 ppm: s: 6H; 2.65 to 5 ppm: unres.: 12H; 6.1 ppm: s: 2H; 6.5–7.8 ppm: unres.: 9H; 8.45 ppm: d: 1H; 10.8 ppm: bs: 1H.

EXAMPLE 106

MH$^+$: 765

EXAMPLE 107

MH$^+$: 765

EXAMPLE 108

NMR: 0.6 to 1.4 ppm: unres.: 15H; 2.1 to 3.5 ppm: unres.: 11H; 3.6 to 4.9 ppm: unres.: 5H; 5.2 to 5.7 ppm: 2s: 2H; 6.2 to 6.5 ppm: unres.: 3H; 7 to 8.4 ppm: unres.: 13H; 9.8 ppm: bs: 1H.

EXAMPLE 109

NMR: 0.5 to 1.5 ppm: unres.: 18H; 2.1 to 3 ppm: unres.: 10H; 3.4 to 4.9 ppm: unres.: 7H; 5.75 to 5.80 ppm: 2s: 2H; 6.2 to 6.65 ppm: unres.: 3H; 7 to 7.6 ppm: unres.: 7H; 8.1 to 8.4 ppm: unres.: 2H; 8.8 ppm: bs: 1H.

EXAMPLE 110

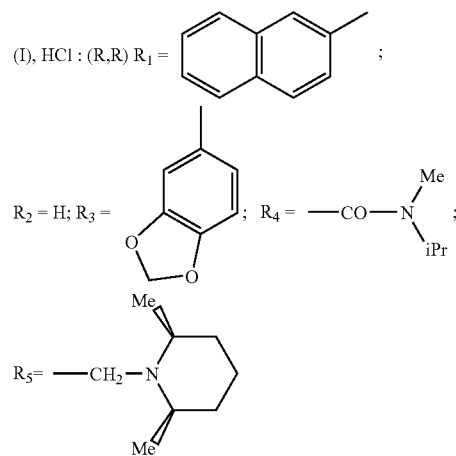

A mixture containing 250 mg of the compound from Preparation 3.8, 74 mg of 2-naphthalenesulphonyl chloride and 171 µl of DIPEA in 10 ml of DCM is stirred overnight at RT. The medium is concentrated to dryness and is then taken up in EtOAc and washed with water and with saturated NaHCO$_3$ solution. The resulting solution is extracted with a pH 2 buffer and then basified to pH 8 with saturated NaHCO$_3$ solution. This mixture is extracted with DCM and then washed with saturated NaCl solution. The resulting mixture is taken up in an EtOAc/Et$_2$O mixture and the hydrochloride is prepared by addition of hydrochloric ether. 140 mg of the expected compound are obtained.

NMR: 0.7 to 2.1 ppm: unres.: 18H; 2.3 to 3.2 ppm: unres.: 9H; 3.3 ppm: mt: 1H; 3.8 to 5 ppm: unres.: 4H; 5.4 to 5.8 ppm: 2s: 2H; 6.4 to 6.8 ppm: unres.: 3H; 7.1 to 8.2 ppm: unres.: 11H; 8.2 to 8.5 ppm: mt: 2H; 9.4 to 10.3 ppm: 2 bs: 1H.

$\alpha_D^{25}$=+50° (c=1; MeOH)

MH$^+$: 727

EXAMPLE 111

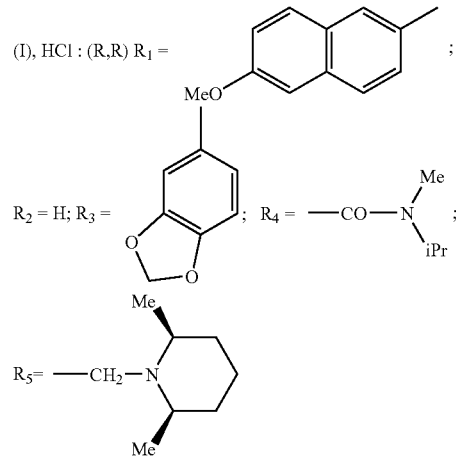

This compound is prepared by working according to the example described above, starting with the compound from Preparation 3.8 and 6-methoxynaphthalene-2-sulphonyl chloride obtained according to J. Med. Chem., 1999, 42, 3557–3571.

NMR: 0.6 to 2 ppm: unres.: 18H; 2.2 to 3.6 ppm: unres.: 10H; 3.8 to 5 ppm: unres.: 7H; 5.4 to 5.8 ppm: 2s: 2H; 6.3 to 6.6 ppm: unres.: 3H; 7.1 to 8.1 ppm: unres.: 10H; 8.1 to 8.5 ppm: unres.: 2H; 9.4 to 10.2 ppm: 2bs: 1H.

$\alpha_D^{25} = +32°$ (c=1; MeOH)

MH$^+$: 757

EXAMPLE 111a

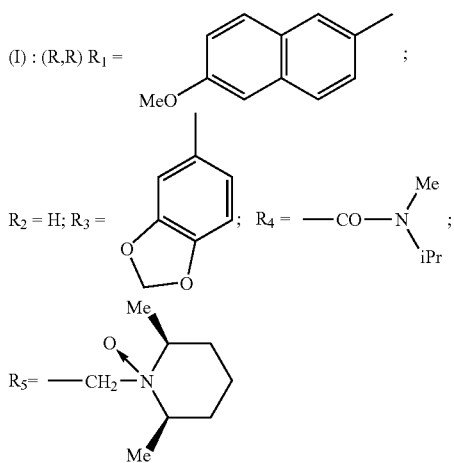

152 mg of the compound of Example 111 are placed in a mixture of 50 ml of DCM and 20 ml of saturated NaHCO$_3$ solution. The organic phase obtained is dried and then concentrated to give the compound in the form of a base. The medium is taken up in 5 ml of DCM and treated with 75 mg of 60% meta-chloroperbenzoic acid for 1 hour at RT. The reaction mixture is extracted with DCM and the organic phase is then washed with saturated NaCl solution. 0.14 g of the expected compound is obtained, which crystallizes from methyl tert-butyl ether.

MH+: 773

NMR: 0.6 to 1.8 ppm: unres.: 18H; 2.2 to 3.4 ppm: unres.: 10H; 3.8 ppm: s: 3H; 4.3 to 4.9 ppm: unres.: 4H ; 5.4 to 5.6 ppm: d: 2H; 6.3 ppm: mt: 3H; 7.1 to 7.8 ppm: unres.: 10H.

EXAMPLE 112

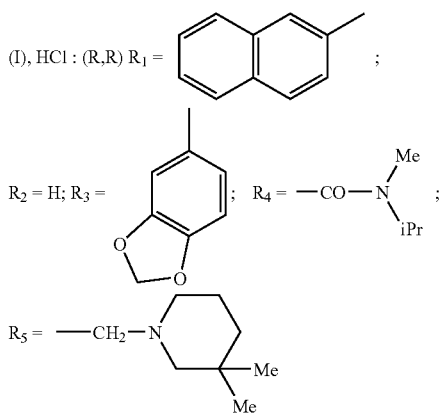

225 mg of the product obtained in Preparation 3.9 are placed in 3 ml of TFA and 10 ml of DCM, and the mixture is stirred for 30 minutes at RT. The medium is concentrated and then triturated in iPr$_2$O. The oil formed is decanted off. The oil formed is taken up in 5 ml of DCM and treated with 100 μl of TEA and then 82 mg of 2-naphthalenesulphonyl chloride, while maintaining the pH at 7 by adding TEA. The medium is stirred overnight at RT and is then concentrated. It is extracted with EtOAc and washed with water (3 times) and with saturated NaCl solution. The hydrochloride is prepared, which crystallizes from an EtOAc/Et$_2$O mixture.

NMR: 0.5 to 2 ppm: unres.: 16H; 2.2 to 3 ppm: unres.: 11H; 3.2 to 4.8 ppm: unres.: 5H; 5.3 and 5.6 ppm: 2s: 2H; 6.3 to 6.6 ppm: unres.: 3H; 7 to 7.3 ppm: unres.: 2H; 7.4 to 7.8 ppm: unres.: 6H; 7.9 to 8.1 ppm: unres.: 5H; 8.3 ppm: mt: 1H.

$\alpha_D^{25} = +42.1°$ (c=1; MeOH)

MH$^+$: 727

EXAMPLE 113

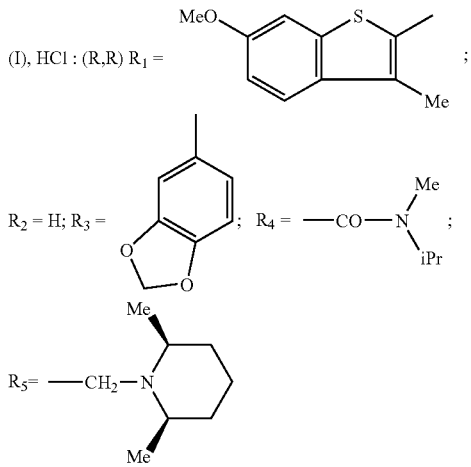

This compound is prepared according to the examples described above, starting with the compound from Preparation 3.8 and the compound from Preparation 1.33, step A.

MH$^+$: 777

EXAMPLE 114

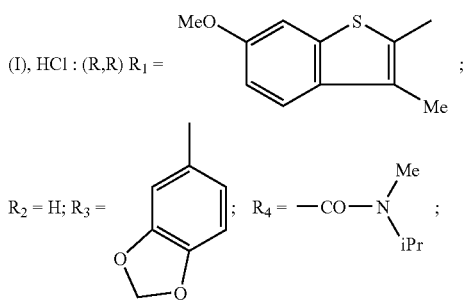

-continued

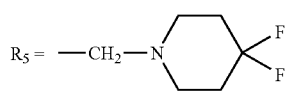

This compound is prepared according to the examples described above, starting with the compound from Preparation 3.10 and the sulphonyl chloride described in Preparation 1.33, step A.

$MH^+$: 785

Other compounds of formula (I) according to the invention were prepared by using the methods described above and identified by their mass spectrum and their NMR spectrum. They are described in the following 2 Tables:

TABLE X

| Examples | $R_1$ | $R_3$ | $R_4$ | $\begin{array}{c} R_{11} \\ N \\ R_{12} \end{array}$ | Salt |
|---|---|---|---|---|---|
| 115 | 2-naphthyl | 3,4-methylenedioxyphenyl (5-position methyl) | –C(O)–N(Me)(iPr) | –N(Me)(iPr) | — |
| 116 (R, R) | 2-naphthyl | phenyl (methyl) | –C(O)–N(Me)(iPr) | –N(iPr)(iPr) | HCl |
| 117 | 2-naphthyl | 3,4-methylenedioxyphenyl (5-position methyl) | –C(O)–N(Me)(iPr) | N(cyclopropyl)(cyclobutyl) | HCl |
| 118 | 2-naphthyl | 3,4-methylenedioxyphenyl (5-position methyl) | –C(O)–N(Me)(iPr) | –N(Me)(iBu) | HCl |

TABLE X-continued

| Examples | R₁ | R₃ | R₄ | $\begin{array}{c}R_{11}\\N\\R_{12}\end{array}$ | Salt |
|---|---|---|---|---|---|
| 119 (R, R) | 2-naphthyl | benzo[1,3]dioxol-5-yl | -C(O)-N(Me)(iPr) | -N(Me)(cyclopentyl) | HCl |
| 120 | 2-naphthyl | benzo[1,3]dioxol-5-yl | -C(O)-N(Me)(iPr) | 4-fluoropiperidin-1-yl | HCl |
| 121 | 2-naphthyl | benzo[1,3]dioxol-5-yl | -C(O)-N(Me)(iPr) | 3,6-dihydro-2H-pyridin-1-yl | HCl |
| 122 (R, R) | 5-chloro-2,3-dimethylbenzo[b]thiophen-6-yl | benzo[1,3]dioxol-5-yl | -C(O)-N(Me)(iPr) | -N(iPr)(iPr) with Me | HCl |
| 123 (R, R) | 5-chloro-2,3-dimethylbenzo[b]thiophen-6-yl | benzo[1,3]dioxol-5-yl | -C(O)-N(Me)(iPr) | 4-phenylpiperidin-1-yl | HCl |
| 124 (R, R) | 3,4-dichlorophenyl | benzo[1,3]dioxol-5-yl | -C(O)-N(Me)(iPr) | -N(iPr)(iPr) | HCl |

TABLE X-continued (I)

R₁—SO₂—NH—CH(R₃)—CH₂—C(=O)—NH—CH(R₄)—[4-(CH₂-N(R₁₁)(R₁₂))-phenyl-CH₂-]

| Examples | R₁ | R₃ | R₄ | N(R₁₁)(R₁₂) | Salt |
|---|---|---|---|---|---|
| 125 (R, R) | naphthalen-2-yl | benzo[1,3]dioxol-5-yl | –C(=O)–N(Me)(iPr) | 4-phenylpiperidin-1-yl (N-Me) | HCl |
| 126 | naphthalen-2-yl | benzo[1,3]dioxol-5-yl | –C(=O)–N(Me)(iPr) | –N(Me)(CH₂CF₃) | — |
| 127 | naphthalen-2-yl | thiophen-3-yl | –C(=O)–N(pyrrolidinyl) | –N(Et)(Et) | HCl |
| 128 | naphthalen-2-yl | benzo[1,3]dioxol-5-yl | –C(=O)–N(Me)(iPr) | 4,4-difluoropiperidin-1-yl | — |
| 129 | naphthalen-2-yl | thiophen-3-yl | –C(=O)–N(Me)(iPr) | –N(Et)(Et) | HCl |
| 130 | 6-methoxynaphthalen-2-yl | benzo[1,3]dioxol-5-yl | –C(=O)–N(Me)(iPr) | –N(iPr)(iPr) | HCl |

TABLE X-continued (I) R₁—SO₂—NH—CH(R₃)—CH₂—C(O)—NH—CH(R₄)—CH₂—[C₆H₄]—CH₂—N(R₁₁)(R₁₂)

| Examples | R₁ | R₃ | R₄ | N(R₁₁)(R₁₂) | Salt |
|---|---|---|---|---|---|
| 131 | 2,4-dichloro-3-methylphenyl | benzo[1,3]dioxol-5-yl | C(O)N(Me)(iPr) | N(Me)(iPr) | HCl |
| 132 | naphthalen-2-yl | 3-methylphenyl | C(O)N(Me)(iPr) | N(Et)(Et) | HCl |
| 133 | 2,3-dimethylbenzothiophen-? | benzo[1,3]dioxol-5-yl | C(O)N(Me)(iPr) | N(iPr)(iPr) | HCl |
| 134 (R, R) | naphthalen-2-yl | 2,3-dihydrobenzo[1,4]dioxin-6-yl | C(O)N(Me)(iPr) | N(iPr)(iPr) | HCl |
| 135 (R, R) | naphthalen-2-yl | benzo[1,3]dioxol-5-yl | C(O)N(Me)(iPr) | N(iPr)(cyclopropylmethyl) | HCl |
| 136 | naphthalen-2-yl | benzo[1,3]dioxol-5-yl | C(O)N(Me)(iPr) | N(iPr)(iBu) | HCl |

TABLE X-continued

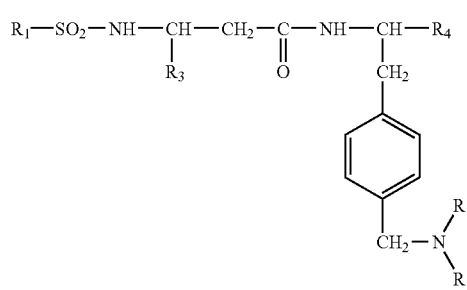

| Examples | R₁ | R₃ | R₄ | NR₁₁R₁₂ | Salt |
|---|---|---|---|---|---|
| 137 | 2-naphthyl | 3-chlorophenyl-methyl | -C(O)-N(Me)(iPr) | -N(Et)(Et) | HCl |
| 138 | 2-naphthyl | (2,2-difluoro-benzo[1,3]dioxol-5-yl)methyl | -C(O)-N(Me)(iPr) | -N(iPr)(iPr) | HCl |
| 139 | 2-naphthyl | 3-(trifluoromethyl)phenyl-methyl | -C(O)-N(Me)(iPr) | -N(Me)(cyclopentyl) | HCl |
| 140 | 2-naphthyl | 4-methyl-thiophen-3-yl | -C(O)-N(Me)(iPr) | -N(Me)(cyclopentyl) | HCl |
| 141 (R,R) | 2,5-dichloro-4-methylphenyl | benzo[1,3]dioxol-5-yl-methyl | -C(O)-N(Me)(iPr) | -N(iPr)(iPr) | HCl |
| 142 (R,R) | 5-chloro-2,3-dimethyl-benzothiophen-6-yl | benzo[1,3]dioxol-5-yl-methyl | -C(O)-N(Me)(iPr) | -N(Me)(cyclopentyl) | HCl |

TABLE X-continued $$R_1-SO_2-NH-\underset{R_3}{CH}-CH_2-\underset{O}{C}-NH-CH-R_4 \quad (I)$$

(with CH₂–(p-phenylene)–CH₂–NR₁₁R₁₂ substituent on the CH–R₄ carbon)

| Examples | R₁ | R₃ | R₄ | NR₁₁R₁₂ | Salt |
|---|---|---|---|---|---|
| 143 | 2-naphthyl | 3-methylthiophen-... (thiophene) | –C(O)–N(Me)(iPr) | N(iPr)(iPr) | HCl |
| 144 (R, R) | 2-naphthyl | benzo[1,3]dioxol-5-yl | –C(O)–N(Me)(iPr) | 4-(difluoromethylene)-1-methylpiperidin-1-yl | HCl |
| 145 | 2-naphthyl | benzo[1,3]dioxol-5-yl | –C(O)–N(Me)(iPr) | 3,5-dimethyl-1-methylpiperidin-1-yl | HCl |
| 146 | 2-naphthyl | benzo[1,3]dioxol-5-yl | –C(O)–N(iBu)(Me) | N(iPr)(iPr) | HCl |
| 147 | 2-naphthyl | benzo[1,3]dioxol-5-yl | –C(O)–N(cyclopentyl)(Me) | N(iPr)(iPr) | HCl |
| 148 (R, R) | 2-naphthyl | benzo[1,3]dioxol-5-yl | –C(O)–N(Me)(iPr) | N(Et)(CH₂CH₂F) | HCl |

TABLE X-continued (I) R₁—SO₂—NH—CH(R₃)—CH₂—C(O)—NH—CH(R₄)—... with 4-(CH₂—NR₁₁R₁₂)phenyl-CH₂ group

| Examples | R₁ | R₃ | R₄ | NR₁₁R₁₂ | Salt |
|---|---|---|---|---|---|
| 149 | 2-naphthyl | benzo[1,3]dioxol-5-yl | —C(O)—N(Me)(tBu) | —N(Et)(Et) | — |
| 150 | 2-naphthyl | benzo[1,3]dioxol-5-yl | —C(O)—N(Me)(iPr) | —N(nBu)(Me) | HCl |
| 151 | 2-naphthyl | thiophen-3-yl | —C(O)—N(Me)(iPr) | —N(nBu)(Me) | HCl |
| 152 | 2-naphthyl | benzo[1,3]dioxol-5-yl | —C(O)—N(Et)(iPr) | —N(iPr)(iPr) | HCl |
| 153 | 2-naphthyl | benzo[1,3]dioxol-5-yl | —C(O)—N(Me)(iPr) | —N(Et)(cyclopentyl) | HCl |
| 154 | 2-naphthyl | benzo[1,3]dioxol-5-yl | —C(O)—N(Me)(iPr) | —N(nPr)(CH₂-cyclopropyl) | HCl |

TABLE X-continued

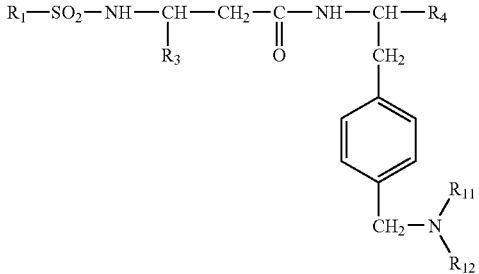

(I)

| Examples | R₁ | R₃ | R₄ | NR₁₁R₁₂ | Salt |
|---|---|---|---|---|---|
| 155 | 2-naphthyl | 3,4-methylenedioxyphenyl | -C(O)-N(Me)(iPr) | -N(nPr)(Et) | HCl |
| 156 | 2-naphthyl | 3,4-methylenedioxyphenyl | -C(O)-N(Me)(iPr) | 4-Me-piperidin-1-yl | |
| 157 | 2-naphthyl | 3-iPr-phenyl | -C(O)-N(Me)(iPr) | -N(iPr)(iPr) | HCl |
| 158 | 2-naphthyl | 3,4-methylenedioxyphenyl | -C(O)-N(Me)(iPr) | -N(CH₂-CH=CH₂)₂ | HCl |
| 159 | 2-naphthyl | 3-CF₃-phenyl | -C(O)-N(Me)(iPr) | -N(iPr)(iPr) | HCl |
| 160 | 2-naphthyl | 3,4-methylenedioxyphenyl | -C(O)-N(Me)(iPr) | -N(Me)(CH₂-tBu) | HCl |

TABLE X-continued
| Examples | R₁ | R₃ | R₄ | NR₁₁R₁₂ | Salt |
|---|---|---|---|---|---|
| 161 (R, R) | 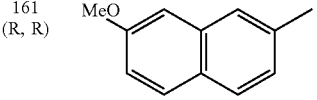 | 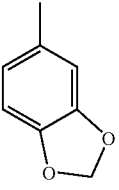 | 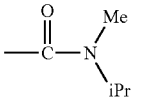 |  | HCl |
| 162 (R, R) | 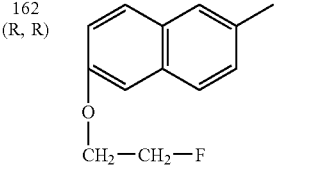 | 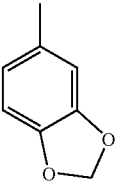 | 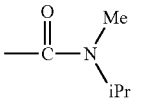 |  | HCl |
| 163 (R, R) | 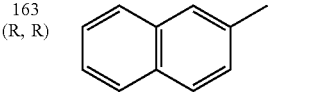 | 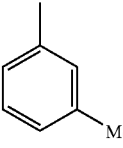 | 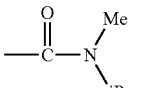 |  | HCl |
| 164 (R, R) | 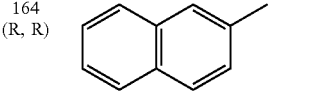 | 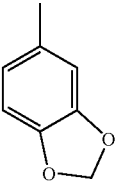 | 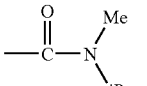 | 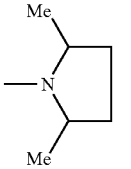 | HCl |
| 165 (R, R) a) | 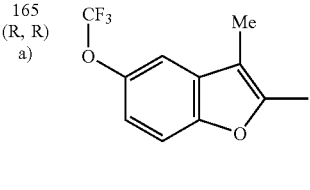 | 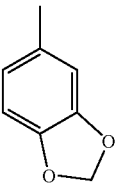 | 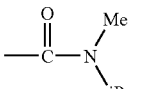 |  | HCl |
| 166 (R, R) | 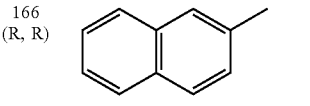 | 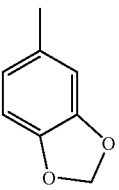 | 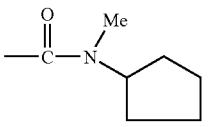 | 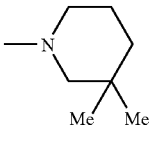 | HCl |

TABLE X-continued (I)

| Examples | R₁ | R₃ | R₄ | NR₁₁R₁₂ | Salt |
|---|---|---|---|---|---|
| 167 | 2-naphthyl | methylenedioxyphenyl | -C(O)-N(Me)(iPr) | -N(iPr)(cyclohexyl) | HCl |
| 168 | 2-naphthyl | methylenedioxyphenyl | -C(O)-N(Me)(iPr) | -N(CH₂-iPr)(cyclopentyl) | HCl |
| 169 (R, R) | 2-naphthyl | methylenedioxyphenyl | -C(O)-N(Me)(cyclopentyl) | 2,6-dimethylpiperidinyl | HCl |
| 170 (R, R) | 6-MeO-2,3-dimethylbenzothiophene | methylenedioxyphenyl | -C(O)-N(Me)(cyclopentyl) | 3,3-dimethylpiperidinyl | HCl |
| 171 (R, R) a) | 5-MeO-2,3-dimethylbenzofuran | methylenedioxyphenyl | -C(O)-N(Me)(iPr) | -N(iPr)(iPr) | HCl |
| 172 (R, R) | 2-naphthyl | methylenedioxyphenyl | -C(O)-N(Me)(iPr) | 4-methylpiperidinyl | HCl |

TABLE X-continued (I) $R_1-SO_2-NH-CH(R_3)-CH_2-C(O)-NH-CH(R_4)-CH_2-[C_6H_4]-CH_2-N(R_{11})(R_{12})$

| Examples | R₁ | R₃ | R₄ | N(R₁₁)(R₁₂) | Salt |
|---|---|---|---|---|---|
| 173 (R, R) | 6-MeO-2,3-diMe-benzothiophen-5-yl | benzo[1,3]dioxol-5-yl | -C(O)-N(Me)(iPr) | 4-Me-piperidin-1-yl | HCl |
| 174 (R, R) | 3,4-diCl-phenyl | benzo[1,3]dioxol-5-yl | -C(O)-N(Me)(iPr) | 2,6-diMe-piperidin-1-yl | HCl |
| 175 | naphth-2-yl | benzo[1,3]dioxol-5-yl | -C(O)-N(Me)(iPr) | -N(Et)(tBu) | HCl |
| 176 (R, R) | 6-MeO-3-Me-benzothiophen-2-yl | benzo[1,3]dioxol-5-yl | -C(O)-N(Me)(cyclopentyl) | -N(iPr)(iPr) | HCl |
| 177 | naphth-2-yl | thiophen-3-yl | -C(O)-pyrrolidin-1-yl | -N(iPr)(iPr) | HCl |
| 178 (R, R) | 6-MeO-naphth-2-yl | benzo[1,3]dioxol-5-yl | -C(O)-N(Me)(cyclopentyl) | 3,3-diMe-piperidin-1-yl | HCl |

TABLE X-continued

![Structure (I): R1—SO2—NH—CH(R3)—CH2—C(=O)—NH—CH(R4)—CH2—C6H4—CH2—N(R11)(R12)]

| Examples | R$_1$ | R$_3$ | R$_4$ | N(R$_{11}$)(R$_{12}$) | Salt |
|---|---|---|---|---|---|
| 179 R, (R, S) | 2-naphthyl | 1,3-benzodioxol-5-yl | —C(=O)—N(Me)(tBu) | —N(Et)(Et) | HCl |
| 180 | 2-naphthyl | 2-thienyl | —C(=O)—N(Me)(iPr) | —N(iPr)(iPr) | HCl |
| 181 (R, R) | 6-MeO-2-naphthyl | 1,3-benzodioxol-5-yl | —C(=O)—N(Me)(iPr) | 3,3-dimethylpiperidin-1-yl | HCl |
| 182 | 2-naphthyl | 3-(OCF$_3$)-phenyl | —C(=O)—N(Me)(iPr) | —N(iPr)(iPr) | HCl |
| 183 | 2-naphthyl | 1,3-benzodioxol-5-yl | —C(=O)—N(Et)(cyclopentyl) | —N(iPr)(iPr) | HCl |
| 184 (R, R) | 6-OMe-3-Me-benzothiophen-2-yl | 1,3-benzodioxol-5-yl | —C(=O)—N(Me)(iPr) | —N(Et)(cyclopentyl) | HCl |

TABLE X-continued
(I)
| Examples | R₁ | R₃ | R₄ | NR₁₁R₁₂ | Salt |
|---|---|---|---|---|---|
| 185 (R, R) | 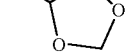 |  |  |  | HCl |
| 186 (R, R) | 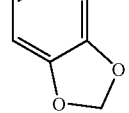 |  | 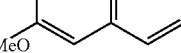 | | HCl |
| 187 (R, R) | 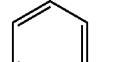 | 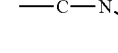 | 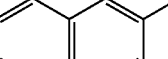 | | HCl |
| 188 | 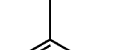 | 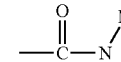 | 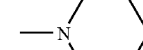 | 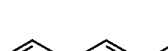 | HCl |
| 189 (R, R) | 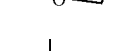 | 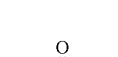 | 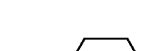 |  | HCl |
| 190 |  |  |  | | HCl |

TABLE X-continued $$R_1-SO_2-NH-\underset{R_3}{CH}-CH_2-\underset{O}{\overset{\|}{C}}-NH-\underset{\underset{\underset{\underset{\underset{R_{12}}{\overset{|}{N}}}{\overset{|}{N}}}{\overset{|}{CH_2}}}{\overset{|}{CH_2}}}{CH}-R_4 \qquad (I)$$

| Examples | R₁ | R₃ | R₄ | $N\begin{subarray}{l}R_{11}\\ R_{12}\end{subarray}$ | Salt |
|---|---|---|---|---|---|
| 191 (R, (R, S)) | 2-methylnaphthyl | methylenedioxyphenyl | C(O)N(Me)(tBu) | 4-methylpiperidinyl | HCl |
| 192 (R, R) | 4-methyl-5-chloro-benzofurazanyl | methylenedioxyphenyl | C(O)N(Me)(iPr) | N(iPr)₂ | HCl |
| 193 | 5-CF₃O-2-methyl-3-Me-benzothiophenyl | methylenedioxyphenyl | C(O)N(Me)(iPr) | N(iPr)₂ | HCl |
| 194 (R, R) | 5-MeO-2-methyl-3-Me-benzothiophenyl | methylenedioxyphenyl | C(O)N(Me)(iPr) | N(iPr)₂ | HCl |
| 195 | methylenedioxynaphthyl | methylenedioxyphenyl | C(O)N(Me)(iPr) | N(iPr)₂ | HCl |

TABLE X-continued

| Examples | R₁ | R₃ | R₄ | NR₁₁R₁₂ | Salt |
|---|---|---|---|---|---|
| 196 (R, R) | 6-MeO-2,3-dimethylbenzothiophene | benzodioxol-5-yl | C(O)N(Me)cyclopentyl | | HCl |
| 197 | 2-naphthyl | benzodioxol-5-yl | C(O)N(Me)iPr | 4-methoxy-1-methylpiperidine | HPF₆ |
| 198 (R, R) | 2-naphthyl | benzodioxol-5-yl | C(O)N(Me)iPr | 4-trifluoromethyl-1-methylpiperidine | HCl |
| 199 | 6-methoxy-2-naphthyl | benzodioxol-5-yl | C(O)N(Me)cyclopentyl | N(iPr)₂ | HCl |
| 200 (R, R) | 6-methoxy-2-naphthyl | benzodioxol-5-yl | C(O)N(Me)iPr | N(iPr)₂ | HCl |
| 201 | 2-naphthyl | benzodioxol-5-yl | C(O)N(Me)iPr | cis-octahydroisoindole | HCl |

TABLE X-continued $$R_1-SO_2-NH-CH-CH_2-C-NH-CH-R_4 \quad (I)$$

(with $R_3$ on the first CH, $O$ on the carbonyl, and $CH_2$-phenyl-$CH_2$-$NR_{11}R_{12}$ on the $R_4$-bearing carbon)

| Examples | R$_1$ | R$_3$ | R$_4$ | NR$_{11}$R$_{12}$ | Salt |
|---|---|---|---|---|---|
| 202 (R, R) | 2-naphthyl | 3,4-methylenedioxyphenyl (5-Me) | —C(O)—N(Me)(cyclopentyl) | —N(iPr)(iPr) | HCl |
| 203 | 6-MeO-2-naphthyl | 3,4-methylenedioxyphenyl (5-Me) | —C(O)—N(Me)(iPr) | 4,4-dimethylpiperidin-1-yl | HCl |
| 204 (R, R) | 6-MeO-2-naphthyl | phenyl | —C(O)—N(Me)(iPr) | 2,6-dimethylpiperidin-1-yl | HCl |
| 205 (R, R) | 6-MeO-2-naphthyl | 3,4-methylenedioxyphenyl (5-Me) | —C(O)—N(Me)(iPr) | —N(tBu)(CH$_2$CH$_2$OMe) | HCl |
| 206 | 2-naphthyl | 3,4-methylenedioxyphenyl (5-Me) | —C(O)—N(Me)(iPr) | —N(Et)(iBu) | HCl |
| 207 (R, R) | 5-chloro-4-methyl-2,1,3-benzoxadiazol-yl | 3,4-methylenedioxyphenyl (5-Me) | —C(O)—N(Me)(iPr) | 2,6-dimethylpiperidin-1-yl | HCl |

TABLE X-continued
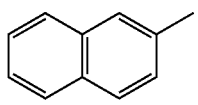
| Examples | R₁ | R₃ | R₄ | NR₁₁R₁₂ | Salt |
|---|---|---|---|---|---|
| 208 | 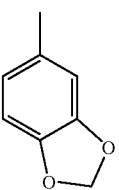 | 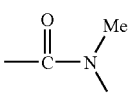 | 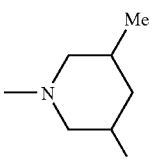 | 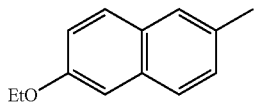 | HCl |
| 209 (R, R) | 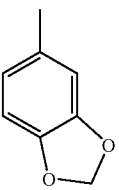 | 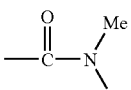 | 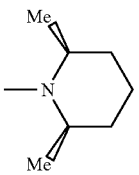 | 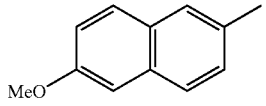 | HCl |
| 210 (R, R) | 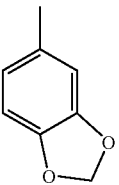 | 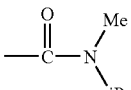 | 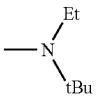 | 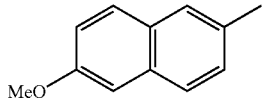 | — |
| 211 | 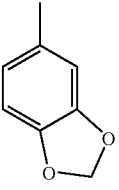 | 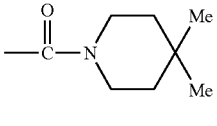 | 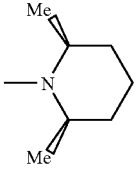 | 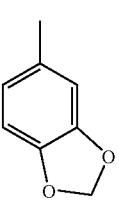 | HCl |
| 212 | 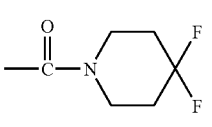 | | 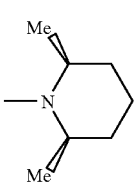 | | HCl |

TABLE X-continued (I) Structure: R₁—SO₂—NH—CH(R₃)—CH₂—C(=O)—NH—CH(R₄)—CH₂—[p-C₆H₄]—CH₂—N(R₁₁)(R₁₂)

| Examples | R₁ | R₃ | R₄ | N(R₁₁)(R₁₂) | Salt |
|---|---|---|---|---|---|
| 213 | 6-methoxy-2-naphthyl | 3,4-difluorophenyl | —C(=O)—N(Me)(iPr) | 2,6-dimethylpiperidin-1-yl | HCl |
| 214 (R, R) | 6-methoxy-2-naphthyl | 3-methylphenyl | —C(=O)—N(Me)(iPr) | 2,6-dimethylpiperidin-1-yl | HCl |
| 215 (R, R) | 2-methylthieno[3,2-c]pyridin-... | benzo[1,3]dioxol-5-yl | —C(=O)—N(Me)(iPr) | 2,6-dimethylpiperidin-1-yl | HCl |
| 216 (R, R) | 2,3-dimethylbenzo[b]thiophen-... | benzo[1,3]dioxol-5-yl | —C(=O)—N(Me)(iPr) | 2,6-dimethylpiperidin-1-yl | HCl |
| 217 (R, R) | 2-chloro-4-methylphenyl(Me) | benzo[1,3]dioxol-5-yl | —C(=O)—N(Me)(iPr) | 2,6-dimethylpiperidin-1-yl | HCl |
| 218 (R, R) | 6-methoxy-2-naphthyl | benzo[1,3]dioxol-5-yl | —C(=O)—N(Me)(iPr) | 4,4-difluoropiperidin-1-yl | HCl |

TABLE X-continued
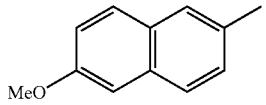
(I)
| Examples | R₁ | R₃ | R₄ | N(R₁₁)(R₁₂) | Salt |
|---|---|---|---|---|---|
| 219 | 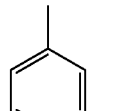 | 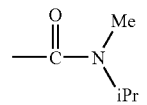 | 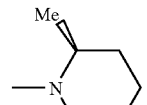 | 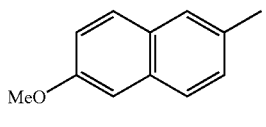 | HCl |
| 220 | 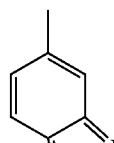 | 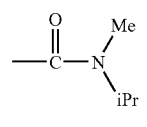 | 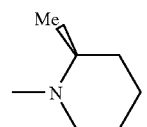 | 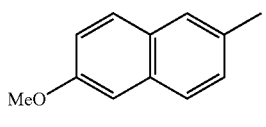 | HCl |
| 221 | 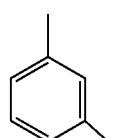 | 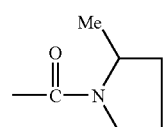 | 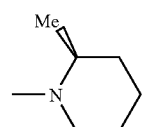 | 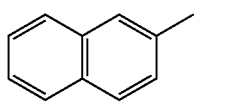 | HCl |
| 222 (R, R) | 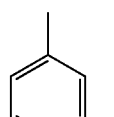 | 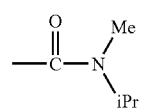 | 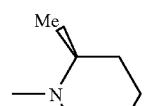 | 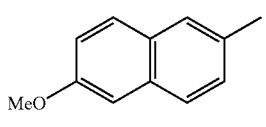 | HCl |
| 223 (R, R) | 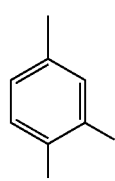 | 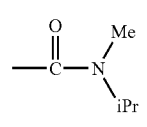 | 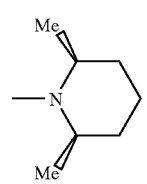 | 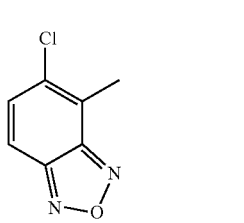 | HCl |
| 224 (R, R) | 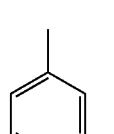 | 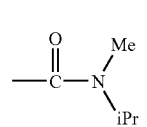 | 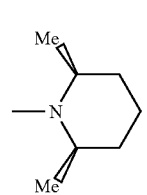 | | HCl |

TABLE X-continued
| Examples | R₁ | R₃ | R₄ | $\overset{R_{11}}{\underset{R_{12}}{N}}$ | Salt |
|---|---|---|---|---|---|
| 225 (R, R) | 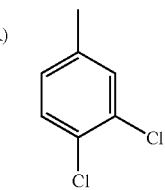 | 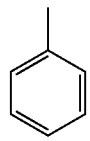 | 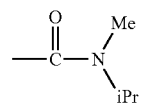 | 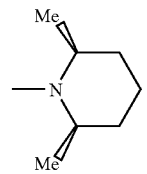 | HCl |
| 226 (R, R) | 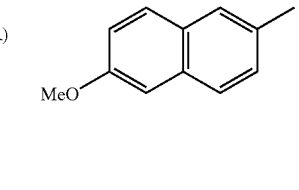 | 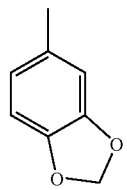 | 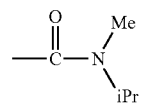 | 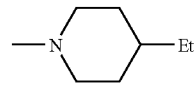 | HCl |
| 227 (R, R) | 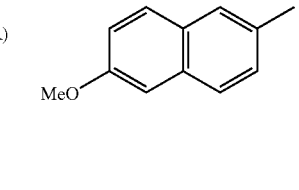 | 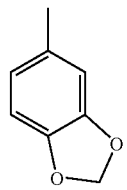 | 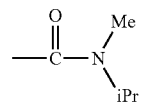 | 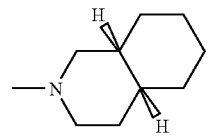 | HCl |
| 228 | 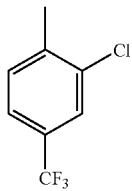 | 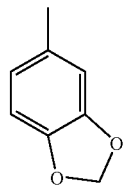 | 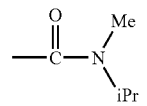 | 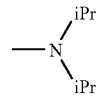 | HCl |
| 229 (R, R) | 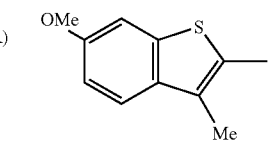 | 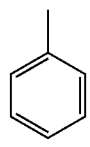 | 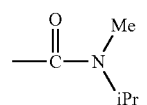 | 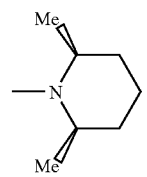 | HCl |
| 230 (R, R) | 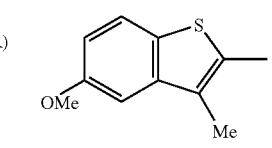 | 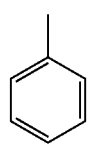 | 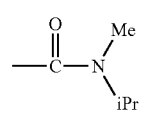 | 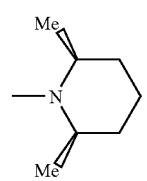 | HCl |

TABLE X-continued $$R_1-SO_2-NH-\underset{R_3}{CH}-CH_2-\underset{O}{C}-NH-CH-R_4 \quad (I)$$

(with CH$_2$-C$_6$H$_4$-CH$_2$-N(R$_{11}$)(R$_{12}$) substituent)

| Examples | R$_1$ | R$_3$ | R$_4$ | N(R$_{11}$)(R$_{12}$) | Salt |
|---|---|---|---|---|---|
| 231 (R, R) | 6-MeO-naphth-2-yl | benzo[1,3]dioxol-5-yl | C(O)N(Me)(iPr) | decahydroisoquinolin-2-yl | HCl |
| 232 (R, R) | 6-iPrO-naphth-2-yl | phenyl | C(O)N(Me)(iPr) | 2,6-dimethylpiperidin-1-yl | HCl |
| 233 (R, R) | naphth-1-yl | phenyl | C(O)N(Me)(iPr) | 2,6-dimethylpiperidin-1-yl | HCl |
| 234 — | naphth-2-yl | 3-fluorophenyl | C(O)N(Me)(iPr) | 2,6-dimethylpiperidin-1-yl | HCl |
| 235 — | naphth-2-yl | thiazol-2-yl | C(O)N(Me)(iPr) | N(iPr)(iPr) | HCl |
| 236 (R, R) | 6-EtO-naphth-2-yl | phenyl | C(O)N(Me)(iPr) | 2,6-dimethylpiperidin-1-yl | HCl |

TABLE X-continued
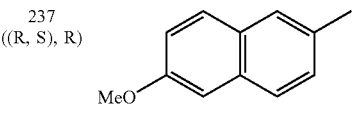
(I)
| Examples | R₁ | R₃ | R₄ | $\begin{array}{c}R_{11}\\ \diagdown N \diagup \\ R_{12}\end{array}$ | Salt |
|---|---|---|---|---|---|
| 237 ((R, S), R) | 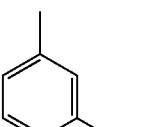 | 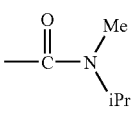 | 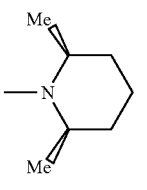 | 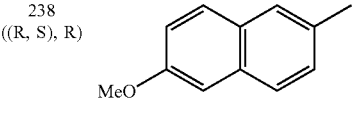 | HCl |
| 238 ((R, S), R) | 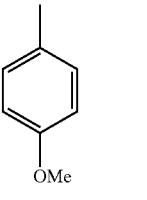 | 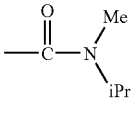 | 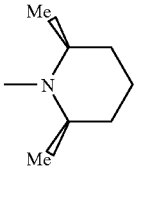 | 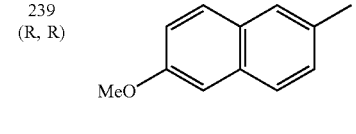 | HCl |
| 239 (R, R) | 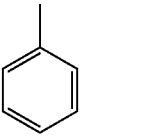 | 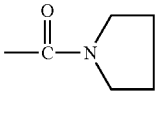 | 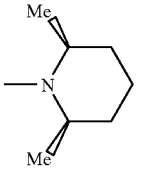 | 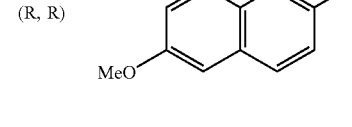 | HCl |
| 240 (R, R) | 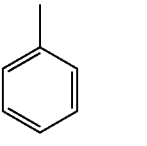 | 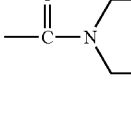 | 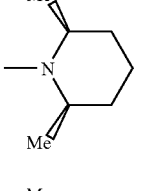 | 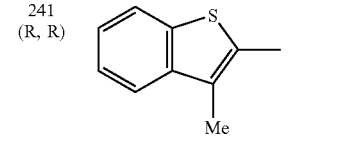 | HCl |
| 241 (R, R) | 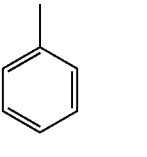 | 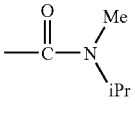 | 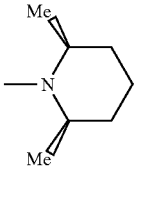 | 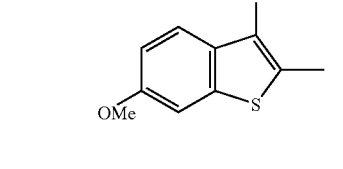 | HCl |
| 242 | 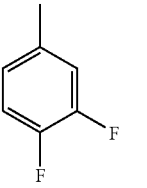 | 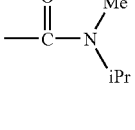 | 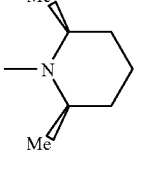 | | HCl |

TABLE X-continued $$R_1-SO_2-NH-\underset{R_3}{CH}-CH_2-\underset{O}{C}-NH-\underset{CH_2}{CH}-R_4 \quad (I)$$

(with 4-substituted phenyl bearing $CH_2-N(R_{11})(R_{12})$)

| Examples | R₁ | R₃ | R₄ | N(R₁₁)(R₁₂) | Salt |
|---|---|---|---|---|---|
| 243 | 6-methoxy-2,3-dimethylbenzo[b]thiophene | 3-F-phenyl | —C(O)—N(Me)(iPr) | 2,6-dimethylpiperidin-1-yl | HCl |
| 244 | 5-methoxy-2,3-dimethylbenzo[b]thiophene | 3-F-phenyl | —C(O)—N(Me)(iPr) | 2,6-dimethylpiperidin-1-yl | HCl |
| 245 (R, R) | 2-chloro-4-methylphenyl (Me) | phenyl | —C(O)—N(Me)(iPr) | 2,6-dimethylpiperidin-1-yl | HCl |
| 246 (R, R) | 5-methoxynaphthalen-1-yl | phenyl | —C(O)—N(Me)(iPr) | 2,6-dimethylpiperidin-1-yl | HCl |
| 247 (R, R) | 6-bromonaphthalen-2-yl | benzo[1,3]dioxol-5-yl | —C(O)—N(Me)(iPr) | N(iPr)(iPr) | HCl |
| 248 (R, R) | 6-methoxynaphthalen-2-yl | 4-Br-phenyl | —C(O)—N(Me)(iPr) | 2,6-dimethylpiperidin-1-yl | HCl |

TABLE X-continued $$R_1-SO_2-NH-\underset{R_3}{CH}-CH_2-\underset{O}{C}-NH-CH-R_4 \quad (I)$$

(with CH2-phenyl-CH2-N(R11)(R12) on the R4-bearing carbon)

| Examples | R₁ | R₃ | R₄ | N(R₁₁)(R₁₂) | Salt |
|---|---|---|---|---|---|
| 249 ((R), R, S) | 6-MeO-naphth-2-yl-methyl | phenyl | C(O)N(Me)(tBu) | 4-Me-piperidin-1-yl | HCl |
| 250 (R, R) | 2,3-diMe-benzofuran-... | phenyl | C(O)N(Me)(iPr) | 2,6-diMe-piperidin-1-yl | HCl |
| 251 (R, R) | 3-Cl-2-Me-benzothiophen-... | phenyl | C(O)N(Me)(iPr) | 2,6-diMe-piperidin-1-yl | HCl |
| 252 (R, R) | 6-MeO-naphth-2-yl-methyl | 4-Cl-phenyl | C(O)N(Me)(iPr) | 2,6-diMe-piperidin-1-yl | HCl |
| 253 (R, R) | 6-MeO-naphth-2-yl-methyl | phenyl | C(O)N(Et)(Et) | 2,6-diMe-piperidin-1-yl | HCl |
| 254 (R, R) | 4-Me-5-Cl-benzo[1,2,5]thiadiazol-... | phenyl | C(O)N(Me)(iPr) | 2,6-diMe-piperidin-1-yl | HCl |

TABLE X-continued
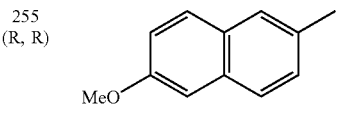
(I)
| Examples | R₁ | R₃ | R₄ | $\overset{R_{11}}{\underset{R_{12}}{N}}$ | Salt |
|---|---|---|---|---|---|
| 255 (R, R) | 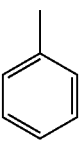 | 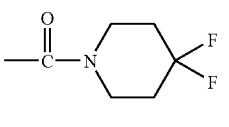 | 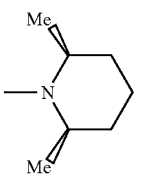 | 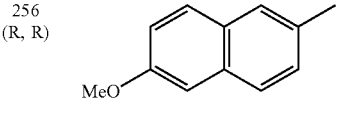 | HCl |
| 256 (R, R) | 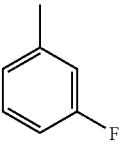 | 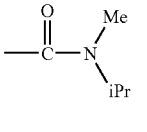 | 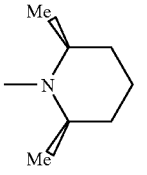 | 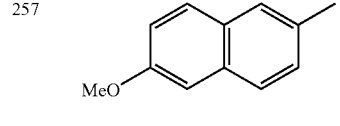 | HCl |
| 257 | 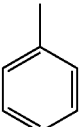 | 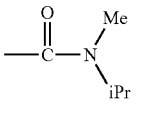 | 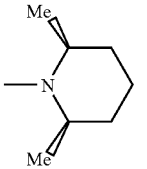 | 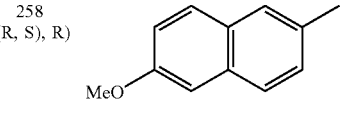 | HCl |
| 258 ((R, S), R) | 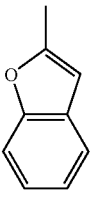 | 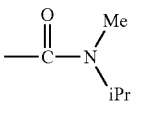 | 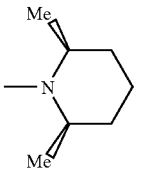 | 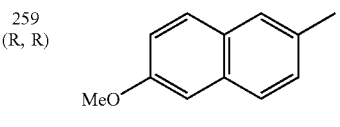 | HCl |
| 259 (R, R) | 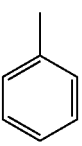 | 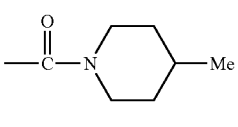 | 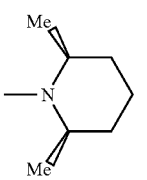 | 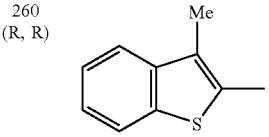 | HCl |
| 260 (R, R) | 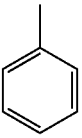 | 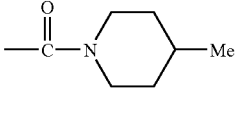 | 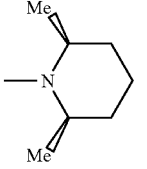 | | HCl |

TABLE X-continued (I) R₁—SO₂—NH—CH(R₃)—CH₂—C(O)—NH—CH(R₄)—CH₂—[C₆H₄]—CH₂—N(R₁₁)(R₁₂)

| Examples | R₁ | R₃ | R₄ | N(R₁₁)(R₁₂) | Salt |
|---|---|---|---|---|---|
| 261 (R, R) | 6-MeO-naphth-2-yl | phenyl | —C(O)—N(3,6-dihydro-2H-pyridin-1-yl) | 2,6-dimethylpiperidin-1-yl | HCl |
| 262 ((R, S), R) | 6-MeO-naphth-2-yl | benzofuran-5-yl | —C(O)—N(Me)(iPr) | 2,6-dimethylpiperidin-1-yl | HCl |
| 263 (R, R) | 6-MeO-naphth-2-yl | 3-F-phenyl | —C(O)—N(2,5-dimethylpyrrolidin-1-yl) | 2,6-dimethylpiperidin-1-yl | HCl |
| 264 | 6-MeO-naphth-2-yl | 3-iPr-phenyl | —C(O)—N(Me)(iPr) | 2,6-dimethylpiperidin-1-yl | HCl |
| 265 | 6-MeO-naphth-2-yl | 4-iPr-phenyl | —C(O)—N(Me)(iPr) | 2,6-dimethylpiperidin-1-yl | HCl |
| 266 (R, R) | 6-MeO-naphth-2-yl | benzo[1,3]dioxol-5-yl | —C(O)—N(3,3-dimethylpiperidin-1-yl) | 2,6-dimethylpiperidin-1-yl | HCl |

TABLE X-continued $$R_1-SO_2-NH-CH(R_3)-CH_2-C(O)-NH-CH(R_4)-CH_2-C_6H_4-CH_2-N(R_{11})(R_{12})$$ (I)

| Examples | R₁ | R₃ | R₄ | N(R₁₁)(R₁₂) | Salt |
|---|---|---|---|---|---|
| 267 (R, R) | 6-MeO-naphth-2-yl | benzo[1,3]dioxol-5-yl | —C(O)—N(Me)(iPr) | 4-tBu-1-methylpiperidinyl | HCl |
| 268 (R, R) | 2-Me-3-Me-benzo[b]thiophen-? | benzo[1,3]dioxol-5-yl | —C(O)—piperidin-1-yl | 2,6-diMe-piperidin-1-yl | HCl |
| 269 (R, R) | 6-MeO-naphth-2-yl | benzo[1,3]dioxol-5-yl | —C(O)—piperidin-1-yl | 2,6-diMe-piperidin-1-yl | HCl |
| 270 (R, R) | 6-MeO-naphth-2-yl | phenyl | —C(O)—(2-Me-piperidin-1-yl) | 2,6-diMe-piperidin-1-yl | HCl |
| 271 (R, R) | 6-MeO-naphth-2-yl | phenyl | —C(O)—azepan-1-yl | 2,6-diMe-piperidin-1-yl | HCl |
| 272 ((R, S), R) | 6-MeO-naphth-2-yl | benzo[1,3]dioxol-5-yl | —C(O)—N(Me)(iPr) | 2,6-diMe-piperidin-1-yl | HCl |

TABLE X-continued (I) structure: R₁—SO₂—NH—CH(R₃)—CH₂—C(=O)—NH—CH(R₄)—CH₂—[p-phenylene]—CH₂—N(R₁₁)(R₁₂)

| Examples | R₁ | R₃ | R₄ | N(R₁₁)(R₁₂) | Salt |
|---|---|---|---|---|---|
| 273 (R, R) | 6-MeO-naphth-2-yl | 4-Cl-phenyl | —C(=O)—N(piperidin-1-yl) | 2,6-dimethylpiperidin-1-yl | HCl |
| 274 (R, R) | 6-MeO-naphth-2-yl | phenyl | —C(=O)—N(Me)(iPr) | 2,5-dimethylpyrrolidin-1-yl | HCl |
| 275 (R, R) | 6-MeO-naphth-2-yl | phenyl | —C(=O)—N(Me)(iPr) | 2-azabicyclo[2.2.1] (N-linked) | HCl |
| 276 (R, R) | 6-MeO-naphth-2-yl | 3-F-phenyl | —C(=O)—N(piperidin-1-yl) | 2,6-dimethylpiperidin-1-yl | HCl |
| 277 | naphth-2-yl | benzo[1,3]dioxol-5-yl | —C(=O)—(thiazol-2-yl) | N-methyl-N-cyclopentyl | HCl |
| 278 (R, R) | 6-MeO-naphth-2-yl | 3-F-phenyl | —C(=O)—N(Me)(iPr) | 4-ethylpiperidin-1-yl | HCl |

TABLE X-continued (I)

| Examples | R₁ | R₃ | R₄ | $\underset{R_{12}}{\overset{R_{11}}{N}}$ | Salt |
|---|---|---|---|---|---|
| 279 (R, R) | MeO-naphthyl | 3-F-phenyl | -C(O)-N(Me)(iPr) | 4,4-dimethylpiperidin-1-yl | HCl |
| 280 (R, R) | MeO-naphthyl | 3-F-phenyl | -C(O)-N(Et)₂ | 2,6-dimethylpiperidin-1-yl | HCl |
| 281 (R, R) | MeO-naphthyl | 3-F-phenyl | -C(O)-N(Me)(iPr) | -C(O)-N(tBu)(Et) | HCl |
| 282 ((R, S), R) | MeO-naphthyl | benzofuran-6-yl | -C(O)-N(Me)(iPr) | 2,6-dimethylpiperidin-1-yl | HCl |
| 283 ((R, S), R) | MeO-naphthyl | 4-CF₃-phenyl | -C(O)-N(Me)(iPr) | 2,6-dimethylpiperidin-1-yl | HCl |
| 284 (R, R) | MeO-naphthyl | 4-Me-phenyl | -C(O)-N(Me)(iPr) | 2,6-dimethylpiperidin-1-yl | HCl |

TABLE X-continued

TABLE X-continued
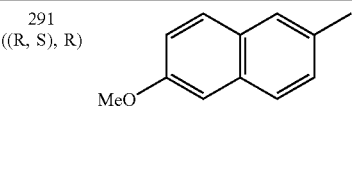
| Examples | R₁ | R₃ | R₄ | $\underset{R_{12}}{\overset{R_{11}}{N}}$ | Salt |
|---|---|---|---|---|---|
| 291 ((R, S), R) | 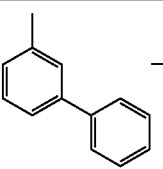 | 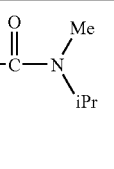 | 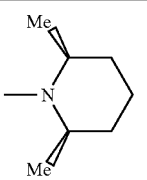 | 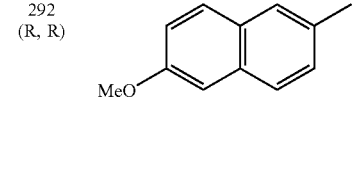 | HCl |
| 292 (R, R) | 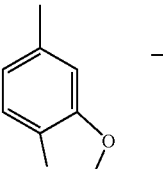 | 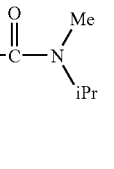 | 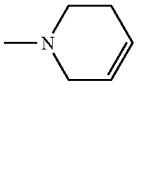 | 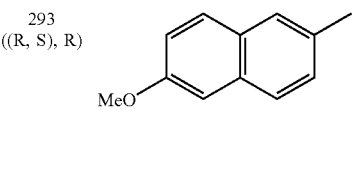 | HCl |
| 293 ((R, S), R) | 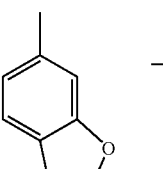 | 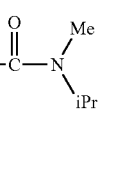 | 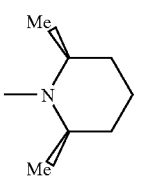 | 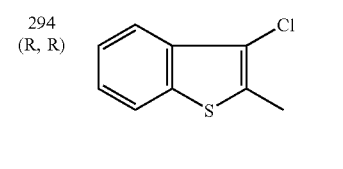 | HCl |
| 294 (R, R) | 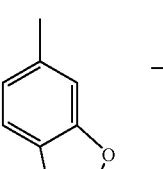 | 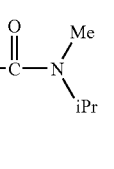 | 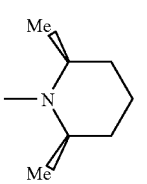 | 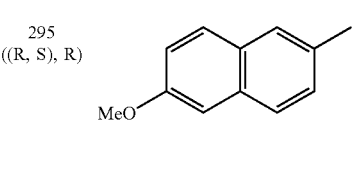 | HCl |
| 295 ((R, S), R) | 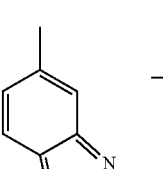 | 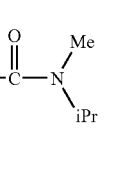 | 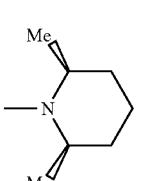 | 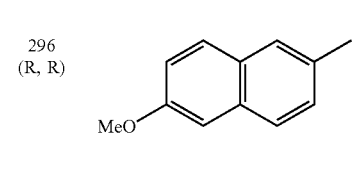 | HCl |
| 296 (R, R) | 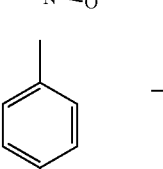 | 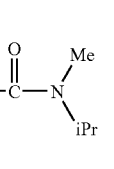 | 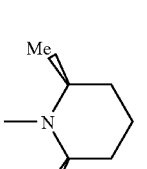 | | HCl |

TABLE X-continued

| Examples | R₁ | R₃ | R₄ | N(R₁₁)(R₁₂) | Salt |
|---|---|---|---|---|---|
| 297 (R, R) | 6-MeO-naphthalen-2-yl | 2,3-methylenedioxyphenyl (4-yl) | -C(O)-N(Me)(iPr) | 1,2,3,4-tetrahydroisoquinolin-2-yl | HCl |
| 298 ((R, S), R) | 6-MeO-naphthalen-2-yl | benzofuran-4-yl | -C(O)-N(Me)(iPr) | 2,6-dimethylpiperidin-1-yl | HCl |
| 299 (R, R) | 6-MeO-naphthalen-2-yl | 2,3-methylenedioxyphenyl (5-yl) | -C(O)-pyrrolidin-1-yl | 2,6-dimethylpiperidin-1-yl | HCl |
| 300 (R, R) | 2,3-dimethylbenzofuran-5-yl | 2,3-methylenedioxyphenyl (5-yl) | -C(O)-N(Me)(iPr) | 2,6-dimethylpiperidin-1-yl | HCl |
| 301 (R, R) | 6-MeO-naphthalen-2-yl | 2,3-methylenedioxyphenyl (5-yl) | -C(O)-N(Me)(iPr) | N(iPr)(cyclohexyl) | HCl |
| 302 (R, R) | 6-MeO-naphthalen-2-yl | 2,3-methylenedioxyphenyl (5-yl) | -C(O)-thiazol-2-yl | 3,6-dihydro-2H-pyridin-1-yl | HCl |

TABLE X-continued
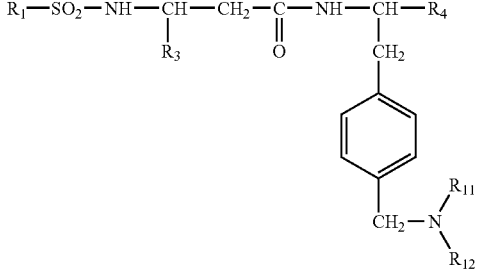
(I)
| Examples | R₁ | R₃ | R₄ | N R₁₁ R₁₂ | Salt |
|---|---|---|---|---|---|
| 303 | 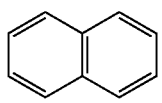 | 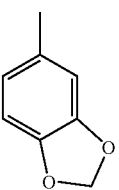 | 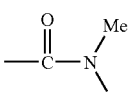 | 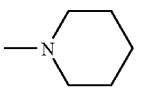 | HCl |
| 304 (S, R) | 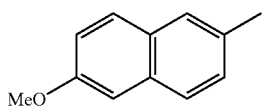 | 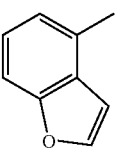 | 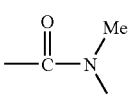 | 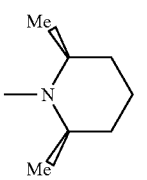 | (CF₃CO₂H) |
| 305 242142A (R, R) | 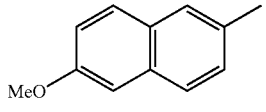 | 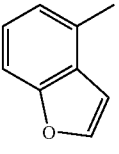 | 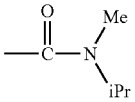 | 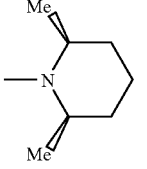 | (CF₃CO₂H) |
| 306 (R, R) | 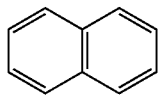 | 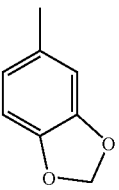 | 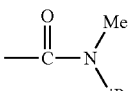 | 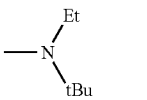 | HCl |
| 307 ((R, S), R) | 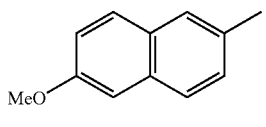 | 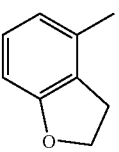 | 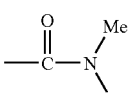 | 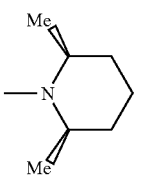 | HCl |
| 308 (S, R) | 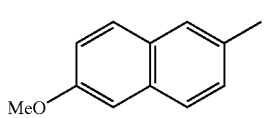 | 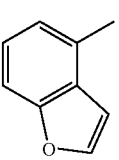 | 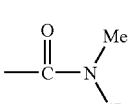 | 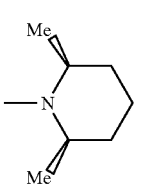 | (CF₃CO₂H) |

TABLE X-continued $$R_1-SO_2-NH-CH(R_3)-CH_2-C(O)-NH-CH(R_4)-CH_2-C_6H_4-CH_2-N(R_{11})(R_{12})$$ (I)

| Examples | R$_1$ | R$_3$ | R$_4$ | N(R$_{11}$)(R$_{12}$) | Salt |
|---|---|---|---|---|---|
| 309 (R, R) | 6-MeO-naphth-2-yl | 4-methylbenzofuran-? | C(O)N(Me)(iPr) | 2,6-dimethylpiperidin-1-yl | (CF$_3$CO$_2$H) |
| 310 (R, R) | 6-MeO-naphth-2-yl | benzo[1,3]dioxol-5-yl | C(O)N(Me)(iPr) | 4-isopropylpiperidin-1-yl | HCl |
| 311 ((R, S), R) | 6-MeO-naphth-2-yl | 3-methylbenzofuran-5-yl | C(O)N(Me)(iPr) | 2,6-dimethylpiperidin-1-yl | HCl |
| 312 (R, R) | 6-MeO-naphth-2-yl | 4-fluorophenyl | C(O)N(Me)(iPr) | 2,6-dimethylpiperidin-1-yl | HCl |
| 313 (S, S) | 6-MeO-naphth-2-yl | benzo[1,3]dioxol-5-yl | C(O)N(Me)(iPr) | 2,6-dimethylpiperidin-1-yl | HCl |
| 314 (R, R) | 6-MeO-naphth-2-yl | benzo[1,3]dioxol-5-yl | C(O)N(Me)(iPr) | 2-azabicyclo[2.2.1]heptan-2-yl | HCl | a) For these compounds, the intermediate sulphonyl chloride (VI) is obtained according to Preparation 1.32.

TABLE XI $$R_1-SO_2-N(R_2)-CH_2-CH_2-C(=O)-NH-CH(CH_2-C_6H_4-R_5)-R_4 \quad (I)$$

| Examples | $R_1$ | $R_2$ | $R_4$ | $R_5$ | Salt |
|---|---|---|---|---|---|
| 315 (R) | 2,3-dichloro-6-methylphenyl | 1,3-benzodioxol-5-yl | -C(=O)-N(pyrrolidine) | $CH_2-N(iPr)_2$ | HCl |
| 316 (R) | 5-chloro-3-methylbenzo[b]thiophen-2-yl | 1,3-benzodioxol-5-yl | -C(=O)-N(pyrrolidine) | $CH_2-N(Me)(tBu)$ | HCl |
| 317 | 2,3-dichloro-6-methylphenyl | 1,3-benzodioxol-5-yl | -C(=O)-N(Me)(iPr) | $CH_2-N(Me)(tBu)$ | HCl |
| 318 | 2-chloro-3-methyl-4-... | 1,3-benzodioxol-5-yl | -C(=O)-(thiazol-2-yl) | $CH_2-N(Me)(cyclopentyl)$ | HCl |

Moreover, several compounds according to the invention were prepared by a "parallel synthesis" method by reacting various sulphonyl halides of formula $R_1SO_2Hal$ with a compound of formula (V) in which Y represents $CONR_8R_9$ and Z represents $CH_2NR_{11}R_{12}$.

EXAMPLES 319 TO 335

A) A solution of 0.98 g of the compound from Preparation 3.2 is prepared in a mixture of 40 ml of $CH_3CN$ and 10 ml of DCM.

B) Tubes are prepared, each containing:
  1.014 ml of the solution prepared in A, i.e. 40 µmol;
  1.2 equivalents of sulphonyl chloride of formula $R_1SO_2Cl$, i.e. 48 µmol;
  1.5 equivalents of morpholinomethylpolystyrene resin at 3.64 mmol/g, i.e. 16.5 mg of resin.

C) The tubes are stirred for 24 hours at RT and are then each treated with 0.6 equivalent of tris(2-aminomethyl)amine resin, i.e. 6 mg.

Each tube is filtered and concentrated, and the medium is then taken up in DMSO to obtain a solution containing 1 µmol per liter of the expected compound. The nature of the compound formed and its purity are monitored by measuring the HPLC retention time (Rt in minutes) and the mass spectrum.

The solutions of the compounds according to the invention obtained are used without further modification to measure the affinity of the said compounds for the bradykinin $B_1$ receptors.

In the examples below, the sulphonyl chlorides $R_1SO_2Cl$ used are commercially available.

TABLE XII
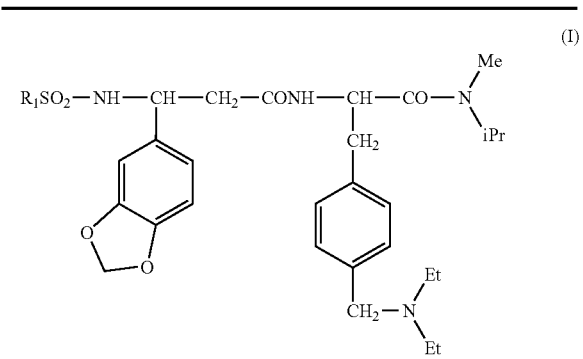
| Examples | R₁ | mass | Rt (minutes) |
|---|---|---|---|
| 319 | 2,3,5-trichlorophenyl | 738 | 4.19 |
| 320 | 2,3-dichlorophenyl | 704 | 4.02 |
| 321 | 3,4-dichlorophenyl | 704 | 4.13 |
| 322 | 2,3,4-trichlorophenyl | 738 | 4.2 |
| 323 | 2,4,5-trichlorophenyl | 738 | 4.25 |
| 324 | 2-chloro-4-trifluoromethylphenyl | 738 | 4.19 |
TABLE XII-continued
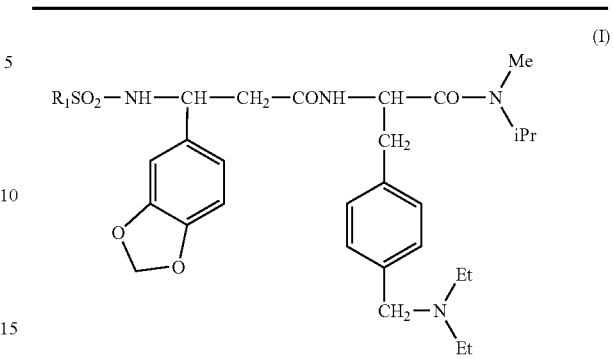
| Examples | R₁ | mass | Rt (minutes) |
|---|---|---|---|
| 325 | 1-naphthyl | 686 | 3.97 |
| 326 | 3,4-dimethoxyphenyl | 696 | 3.56 |
| 327 | 2,4-dimethoxyphenyl | 696 | 3.7 |
| 328 | benzofurazan-4-yl | 678 | 3.72 |
| 329 | 5-chloro-1,3,4-trimethylpyrazol-? | 688 | 3.41 |
| 330 | 2,3-dichloro-5-methylthiophen-? | 710 | 4.17 |
| 331 | 5-chloro-2,3-dimethylbenzothiophen-? | 740 | 4.31 |

TABLE XII-continued

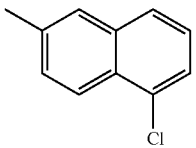

| Examples | R₁ | mass | Rt (minutes) |
|---|---|---|---|
| 332 | 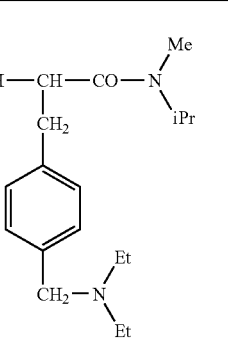 | 720 | 4.2 |
| 333 | 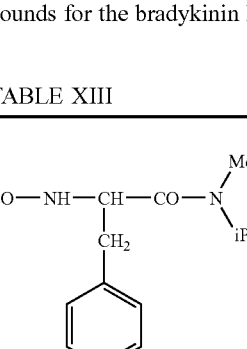 | 708 | 4.26 |
| 334 | 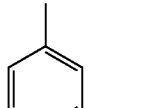 | 772 | 4.33 |
| 335 | 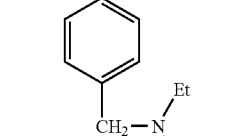 | 709 | 3.82 |

EXAMPLES 336 TO 338

A) A solution of 1.924 g of the compound from Preparation 3.1 is prepared in 100 ml of $CH_3CN$.

B) Tubes are prepared, each containing:
- 941 μl of the solution prepared in A, i.e. 40 μmol;
- 1.2 equivalents of sulphonyl chloride of formula $R_1SO_2Cl$, i.e. 48 μmol;
- 1.5 equivalents of morpholinomethylpolystyrene resin at 3.64 mmol/g, i.e. 16.5 mg of resin;
- 0.2 equivalent of DMAP/polystyrene resin, used as activator.

C) The tubes are stirred for 24 hours at RT and are then each treated with 0.6 equivalent of tris(2-aminoethyl)amine resin, i.e. 6 mg. Each tube is filtered and concentrated and then taken up in DMSO to obtain a solution containing 1 μmol per liter of the expected compound. The nature of the compound formed and its purity are monitored by measuring the HPLC retention time (Rt minutes) and the mass spectrum.

The solutions of the compounds according to the invention obtained are used in unmodified form to measure the affinity of the said compounds for the bradykinin $B_1$ receptors.

TABLE XIII

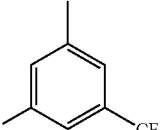

| Examples | R₁ | mass | Rt (minutes) |
|---|---|---|---|
| 336 |  | 660 | 4.49 |
| 337 | 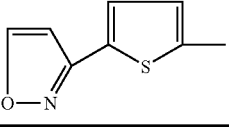 | 694 | 4.9 |
| 338 | 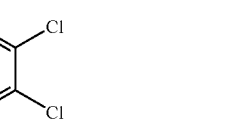 | 696 | 5.1 |

EXAMPLES 339 TO 353

Preparation (R,R)-2-(((3-amino-3-benzo[1,3]dioxol-5-yl)propanoyl)amino)-3-(4-(diisopropylaminomethyl)phenyl)-N-isopropyl-N-methylpropionamide

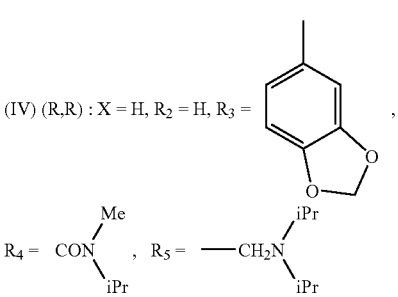

(IV) (R,R) : X = H, R₂ = H, R₃ = [structure], $R_4$ = CON(Me)(iPr), $R_5$ = —CH₂N(iPr)(iPr)

A) 8.6 g of the trifluoroacetate obtained in Example 38, step B are dissolved in DCM and washed with a saturated $NaHCO_3$ solution and then saturated NaCl. After drying and concentration, 5.43 g of the expected compound are obtained in the form of a dry foam.

B) A solution of 524.7 mg of the compound from Preparation A is prepared in 25 ml of CH₃CN.

C) Tubes are prepared, each containing:
- 1 ml of the solution prepared in B, i.e. 40 µmol;
- 1.2 equivalents of sulphonyl chloride of formula R₁SO₂Cl, i.e. 48 µmol;
- 1.5 equivalents of morpholinomethylpolystyrene resin at 3.64 µmol/g, i.e. 16.5 mg of resin:

D) The tubes are stirred overnight at RT and are then each treated with 0.6 equivalent of tris(2-aminomethyl)amine resin, i.e. 6 mg. Each tube is filtered and concentrated and then taken up in DMSO to obtain a solution containing 1 µmol per liter of the expected compound. The nature of the compound and its purity are monitored by measuring the HPLC retention time (Rt minutes) and the mass spectrum.

The solutions of the compounds according to the invention obtained are used without further modification to measure the affinity of the said compounds for the bradykinin B₁ receptors.

TABLE XIV

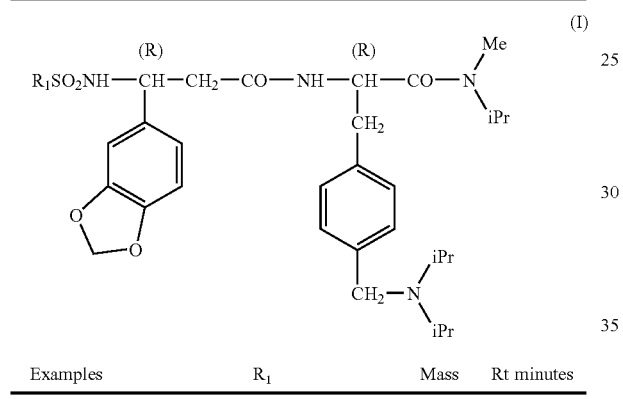

| Examples | R₁ | Mass | Rt minutes |
|---|---|---|---|
| 339 | (6-chloronaphthalen-2-yl) | 748 | 5.22 |
| 340 | (5-chlorothiophen-2-yl) | 704 | 4.79 |
| 341 | (3-chlorobenzothiophen-2-yl) | 754 | 5.08 |
| 342 | (4,7-dichloro-benzo[1,2,5]oxadiazol-...) | 740 | 4.78 |
| 343 | (2,4-dichloro-6-methylphenyl) | 746 | 5.17 |

TABLE XIV-continued

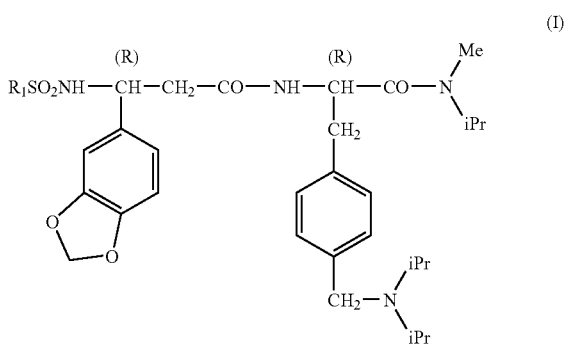

| Examples | R₁ | Mass | Rt minutes |
|---|---|---|---|
| 344 | (2,4,6-trimethylphenyl) | 706 | 5.06 |
| 345 | (4-chloro-2,5-dimethylphenyl) | 726 | 5.22 |
| 346 | (2,5-dichlorophenyl) | 732 | 4.94 |
| 347 | (3,4-difluorophenyl) | 700 | 4.73 |
| 348 | (3-chloro-4-fluorophenyl) | 716 | 4.9 |
| 349 | (3-chlorophenyl) | 698 | 4.77 |

TABLE XIV-continued (I)

R₁SO₂NH—CH(R)—CH₂—CO—NH—CH(R)—CO—N(Me)(iPr) with CH₂ substituent to 4-(CH₂—N(iPr)(iPr))phenyl and benzo[1,3]dioxol-5-yl

| Examples | R₁ | Mass | Rt minutes |
|---|---|---|---|
| 350 | 4-Cl-phenyl | 698 | 4.8 |
| 351 | 4-OMe-phenyl | 694 | 4.47 |
| 352 | 3-CF₃-phenyl | 732 | 4.96 |
| 353 | 4-Me-cyclohexyl | 678 | 4.64 |

EXAMPLES 354 TO 363

Preparation (R,R)-2-(((3-Amino-3-benzo[1,3]dioxol-5-yl)propanoyl)amino)-3-(4-(N-methyl-N-cyclopentylaminomethyl)phenyl)-N-isopropyl-N,N-disopropylpropionamide (IV) (R,R) : X = H, R₂ = H, R₃ = benzo[1,3]dioxol-5-yl,

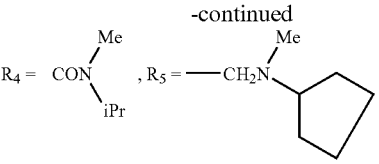

R₄ = CON(Me)(iPr), R₅ = —CH₂N(Me)(cyclopentyl)

This compound is prepared from the compounds obtained in Preparations 2.47 and 1.13: these 2 compounds are reacted after the necessary deprotection to give, after deprotection, the expected compound in the form of a bis(trifluoroacetate).

A) 210 mg of this bis(trifluoroacetate) are dissolved in DCM and washed with saturated NaHCO₃ solution and then with saturated NaCl. After drying and concentration, 141 mg of the expected compound are obtained in the form of an oil.

B) A solution of 141 mg of the compound from step A in 20 ml of CH₃CN is prepared.

C) Tubes are prepared, each containing:
- 1.48 ml of the solution prepared, i.e. 20 μmol;
- 1.2 equivalents of sulphonyl chloride of formula R₁SO₂Cl, i.e. 24 μmol;
- 1.5 equivalents of morpholinomethylpolystyrene resin at 3.64 μmol/g, i.e. 8.24 mg of resin.

D) The tubes are stirred overnight at RT and are then each treated with 0.6 equivalent of tris(2-aminomethyl)amine resin, i.e. 3 mg. Each tube is filtered, concentrated and then taken up in DMSO to give a solution containing 1 μmol per liter of the expected compound. The nature of the compound and its purity are monitored by measuring the HPLC retention time (Rt minutes) and the mass spectrum.

TABLE XV (I)

R₁SO₂—NH—CH(R)—CH₂—CO—NH—CH(R)—CO—N(Me)(iPr) with CH₂ substituent to 4-(CH₂—N(Me)(cyclopentyl))phenyl and benzo[1,3]dioxol-5-yl

| Examples | R₁ | Mass | Rt minutes |
|---|---|---|---|
| 354 | 3-Cl-4-Me-phenyl | 710 | 4.62 |
| 355 | 2,5-diCl-4-Me-phenyl | 744 | 4.87 |

TABLE XV-continued $$R_1SO_2-NH-\underset{(R)}{CH}-CH_2-CO-NH-\underset{(R)}{CH}-CO-N\underset{iPr}{\overset{Me}{}} \quad (I)$$

(with benzo[1,3]dioxol-5-yl on first CH, and 4-(CH₂-N(Me)-cyclopentyl)phenyl-CH₂ on second CH)

| Examples | R₁ | Mass | Rt minutes |
|---|---|---|---|
| 356 | 2,5-dichloro-3-methylthien-4-yl | 736 | 4.7 |
| 357 | 3-chloro-5-methyl-2-chlorothien-yl | 736 | 4.83 |
| 358 | 2,3-dimethylbenzofuran-yl | 702 | 4.51 |
| 359 | 2,3-dimethylbenzothiophen-yl | 732 | 4.73 |
| 360 | 2,3,5-trimethylbenzothiophen-yl | 746 | 4.92 |
| 361 | 5-fluoro-2,3-dimethylbenzothiophen-yl | 750 | 4.79 |
| 362 | 2,5-dimethylbenzothiophen-yl | 732 | 4.81 |
| 363 | 5-chloro-2,3-dimethylbenzofuran-yl | 750 | 4.95 |

The invention claimed is:

1. A compound of formula:

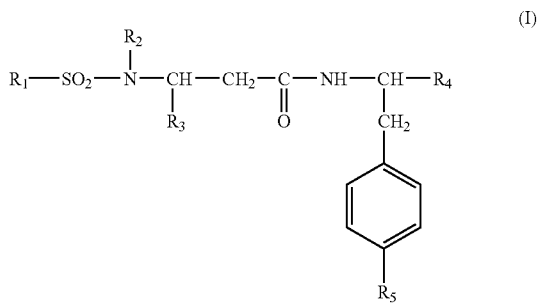

in which:

R₁ represents a phenylvinyl group; a phenyl group which is unsubstituted or substituted one or more times with R₆, which may be identical or different; a naphthyl group which is unsubstituted or substituted one or more times with R₆, which may be identical or different; a tetrahydronaphthyl group; a naphtho[2,3-d][1,3]dioxol-6-yl group; a heterocyclic radical chosen from quinolyl, isoquinolyl, 1-benzofur-2-yl, 2,1,3-benzoxadiazol-4-yl, 2,1,3-benzothiadiazol-4-yl, 1,3-benzothiazol-2-yl, 1-benzothiophen-2-yl, 1H-pyrazol-4-yl, thien-2-yl, 5-isoxazothien-2-yl, benzothien-2-yl, thieno[3,2-c]pyrid-2-yl; the said heterocyclic radicals being unsubstituted or substituted one or more times with R₆, which may be identical or different;

R₂ represents hydrogen or a (C₁–C₄)alkyl group and R₃ represents a phenyl group which is unsubstituted or substituted one or more times with R₇, which may be identical or different; a heterocyclic radical chosen from benzo[1,3]dioxol-5-yl, 2,1,3-benzothiadiazol-5-yl, 2,1,3-benzoxadiazol-5-yl, benzothiophen-5-yl, 2,3-dihydrobenzo[1,4]dioxin-6-yl, benzofuryl, dihydrobenzofuryl, 1,3-thiazol-2-yl, furyl and thienyl, the said heterocyclic radical being an substituted or substituted one or more times with a halogen atom or with a (C₁–C₄)alkyl group;

or alternatively R₂ represents a phenyl group which is unsubstituted or substituted one or more times with R₆, which may be identical or different; a heterocyclic radical chosen from benzo[1,3]diaxol-5-yl, pyridyl and indanyl, and R₃ represents hydrogen;

R₄ represents a group —CONR₈R₉; a group —CSNR₈R₉; a group —COR₁₃; a phenyl group which is unsubstituted or substituted one or more times with R₁₀; a heterocyclic radical chosen from pyridyl, imidazolyl, furyl, benzimidazolyl, benzothiazol-2-yl and benzo[1,3]dioxol-5-yl, the said radicals being unsubstituted or substituted with one or more methyl groups or halogen atoms;

R₅ represents a group —CH₂NR₁₁R₁₂ or —CH₂N(O)R₁₁R₁₂;

R₆ represents a halogen atom; a (C₁–C₄)alkyl group; a trifluoromethyl group; a (C₁–C₄)alkoxy group; a 2-fluoroethoxy group; a trifluoromethoxy, methylenedioxy or difluoromethylenedioxy group;

R₇ represents a halogen atom; a (C₁–C₄)alkyl group; a phenyl group; a trifluoromethyl group; a (C₁–C₄) alkoxy group; a benzyloxy group; a trifluoromethoxy group;

$R_8$ and $R_9$ each independently represent hydrogen; a $(C_1-C_4)$alkyl group; a $(C_3-C_7)$cycloalkyl group; a $(C_3-C_7)$cycloalkyl$(C_1-C_4)$alkyl group; an ω-$(C_1-C_4)$ dialkylamino$(C_2-C_4)$alkyl group;

or alternatively $R_8$ and $R_9$, together with the nitrogen atom to which they are attached, constitute a heterocyclic radical chosen from pyrrolidinyl, morpholin-4-yl, thiomorpholin-4-yl, azepin-1-yl, piperidyl which is unsubstituted or substituted with one or more halogen atoms or one or more $(C_1-C_4)$alkyl or $(C_1-C_4)$alkoxy or trifluoromethyl groups, 3,4-dihydropiperid-1-yl, cyclohexyl-spiro-4-piperid-1-yl, and piperazinyl which is unsubstituted or substituted with one or more $(C_1-C_4)$ alkyl groups;

$R_{10}$ represents a halogen atom; a $(C_1-C_4)$alkyl group; a hydroxy group; a $(C_1-C_6)$alkoxy group; $R_{10}$ can also represent a group —$CH_2NR_{11}R_{12}$ when $R_5$ represents a group —$CH_2NR_{11}R_{12}$, the said groups then being identical;

$R_{11}$ and $R_{12}$ each independently represent hydrogen; a $(C_1-C_6)$alkyl group; a $(C_2-C_4)$alkenyl group; a $(C_3-C_7)$cycloalkyl group; a $(C_3-C_7)$cycloalkyl$(C_1-C_4)$ alkyl group; an ω-hydroxy$(C_2-C_4)$alkylene group; an ω-methoxy$(C_2-C_4)$alkylene group; an ω-trifluoromethyl$(C_2-C_4)$alkylene group; an ω-halo$(C_2-C_4)$alkylene group, or alternatively $R_{11}$ and $R_{12}$, together with the nitrogen atom to which they are attached, constitute a monocyclic, bicyclic or heterocyclic radical chosen from azetidinyl, pyrrolidinyl, morpholin-4-yl, thiomorpholin-4-yl, piperid-1-yl, piperazin-1-yl, 1,2,3,6-tetrahydropyrid-1-yl, 2,3,4,5-tetrahydropyridinium, decahydroquinolyl, decahydroisoquinolyl, tetrahydroisoquinolyl, octahydro-1H-isoindolyl, $(C_4-C_6)$cycloalkyl-spiro-piperidyl, 3-azabicyclo[3.1.0]hexyl and 7-azabicyclo[2.2.1]heptan-7-yl, which may be unsubstituted or substituted one or more times with a halogen atom or a $(C_1-C_4)$alkyl, hydroxyl, $(C_1-C_4)$alkoxy, trifluoromethyl, difluoromethylene or phenyl group;

$R_{13}$ represents a phenyl, thiazol-2-yl or pyridyl group; or a salt thereof with a mineral or organic acid, or a solvate or hydrate of said compound or said salt.

2. The compound according to claim 1 of formula:

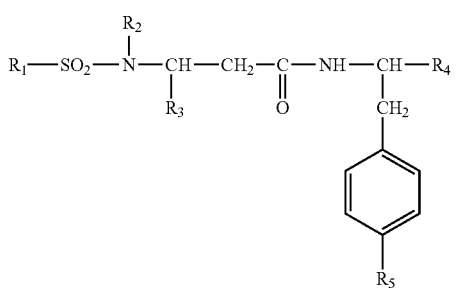

(I)

in which:

$R_1$ represents a phenylvinyl group; a phenyl group which is unsubstituted or substituted one or more times with $R_6$, which may be identical or different; a naphthyl group which is unsubstituted or substituted one or more times with $R_6$, which may be identical or different; a tetrahydronaphthyl group; a heterocyclic radical chosen from quinolyl, 1-benzofur-2-yl, 2,1,3-benzoxadiazol-4-yl, 2,1,3-benzothiadiazol-4-yl, 1,3-benzothiazol-2-yl, 1-benzothiophen-2-yl, 1H-pyrazol-4-yl, thien-2-yl, 5-isoxazolethien-2-yl, benzothien-2-yl, thieno[3,2-c]pyrid-2-yl; naphtho[2,3-d][1,3]dioxol-6-yl; the said heterocyclic radicals being unsubstituted or substituted one or more times with $R_6$, which may be identical or different;

$R_2$ represents hydrogen or a $(C_1-C_4)$alkyl group and $R_3$ represents a phenyl group which is unsubstituted or substituted one or more times with $R_7$, which may be identical or different; a heterocyclic radical chosen from benzo[1,3]dioxol-5-yl which is unsubstituted or substituted in the −2 position with two fluorine atoms; 2,1,3-benzothiadiazol-5-yl; 2,3-dihydrobenzo[1,4]dioxin-6-yl; 1,3-thiazol-2-yl; 1-benzofur-2-yl; 1-benzofur-5-yl; furyl; thien-2-yl; thien-3-yl;

or $R_2$ represents a phenyl group which is unsubstituted or substituted one or more times with $R_6$, which may be identical or different; a heterocyclic radical chosen from benzo[1,3]dioxol-5-yl; pyridyl; indanyl; and $R_3$ represents hydrogen;

$R_4$ represents a group —$CONR_8R_9$; a phenyl group which is unsubstituted or substituted one or more times with $R_{10}$; a heterocyclic radical chosen from pyridyl, imidazolyl, furyl, benzimidazolyl, benzothiazol-2-yl and benzo[1,3]dioxol-5-yl, the said radicals being unsubstituted or substituted with a methyl;

$R_5$ represents a group —$CH_2NR_{11}R_{12}$;

$R_6$ represents a halogen atom; a $(C_1-C_4)$alkyl group; a trifluoromethyl group; a $(C_1-C_4)$alkoxy group; a 2-fluoroethoxy group; a trifluoromethoxy, methylenedioxy or difluoromethylenedioxy group;

$R_7$ represents a halogen atom; a $(C_1-C_4)$alkyl group; a trifluoromethyl group; a $(C_1-C_4)$alkoxy group; a benzyloxy group; a trifluoromethoxy group;

$R_8$ and $R_9$ each independently represent hydrogen; a $(C_1-C_4)$alkyl group; a $(C_3-C_7)$cycloalkyl group; a $(C_3-C_7)$cycloalkyl$(C_1-C_4)$alkyl group; an ω-$(C_1-C_4)$ dialkylamino$(C_2-C_4)$alkyl group;

or $R_8$ and $R_9$, together with the nitrogen atom to which they are attached, constitute a heterocyclic radical chosen from pyrrolidinyl, piperidyl, morpholin-4-yl, thiomorpholin-4-yl, piperazin-1-yl, 4-methylpiperazin-1-yl, 4-methylpiperid-1-yl, 2-methylpiperid-1-yl, 4,4-dimethylpiperid-1-yl, 4,4-difluoropiperid-1-yl, 4-trifluoromethylpiperid-1-yl, 3,4-dihydropiperid-1-yl, azepin-1-yl and cyclohexyl-spiro-4-piperid-1-yl;

$R_{10}$ represents a halogen atom; a $(C_1-C_4)$alkyl group; a hydroxyl group; a $(C_1-C_6$alkoxy group; $R_{10}$ can also represent a group —$CH_2NR_{11}R_{12}$ when $R_5$ represents a group —$CH_2NR_{11}R_{12}$, the said groups then being identical;

$R_{11}$ and $R_{12}$ each independently represent hydrogen; a $(C_1-C_6)$alkyl group; a $(C_2-C_4$alkenyl group; a $(C_3-C_7)$ cycloalkyl group; a $(C_3-C_7)$cycloalkyl$(C_1-C_4)$alkyl group; an ω-hydroxy$(C_2-C_4)$alkylene group; an ω-methoxy$(C_2-C_4)$alkylene group; an ω-trifluoromethyl$(C_2-C_4)$alkylene group; an ω-halo$(C_2-C_4)$alkylene group;

or $R_{11}$ and $R_{12}$, together with the nitrogen atom to which they are attached, constitute a monocyclic, bicyclic or heterocyclic radical chosen from azetidinyl, pyrrolidinyl, morpholin-4-yl, thiomorpholin-4-yl, piperid-1-yl, piperazin-1-yl, 1,2,3,6-tetrahydropyrid-1-yl, decahydroquinolyl, decahydroisoquinolyl, octahydro-1H-isoindolyl, $(C_4-C_6)$cycloalkyl-spiro-piperidyl and 3-azabicyclo[3.1.0]hexyl, which may be unsubstituted or substituted one or more times with a halogen atom or a ($C_1$–$C_4$)alkyl, hydroxyl, ($C_1$–$C_4$)alkoxy, trifluoromethyl, difluoromethylene or phenyl group;
or a salt thereof with a mineral or organic acid, or a solvate or hydrate of said compound or said salt.

3. The compound of formula (I) according to claim 1 in which $R_1$ represents a 2,4-dichloro-3-methylphenyl, naphthyl, 6-methoxynaphth-2-yl, 3-methylbenzothiophen-2-yl, 3-methyl-5-chlorobenzothiophen-2-yl, 3-methyl-5-methoxybenzothiophen-2-yl, 3-methyl-6-methoxybenzothiophen-2-yl or 3-methyl-1-benzofur-2-yl group.

4. The compound of formula (I) according to claim 1 in which $R_2$ represents hydrogen and $R_3$ represents a benzo[1,3]dioxol-5-yl or phenyl group which is unsubstituted or substituted with a halogen.

5. The compound of formula (I) according to claim 1 in which $R_4$ represents a group —$CONR_8R_9$ and —$NR_8R_9$ represents a di($C_1$–$C_4$)alkylamino radical, a pyrrolidinyl or piperidyl group which is unsubstituted or substituted one or two times with a methyl or a halogen.

6. The compound of formula (I) according to claim 1 in which $R_5$ represents a group —$CH_2NR_{11}R_{12}$ in which —$NR_{11}R_{12}$ represents an ethylisobutylamino, ethylisopropylamino, ethyl-tert-butylamino, diisopropylamino, cyclopentylmethylamino or cyclopentylethylamino radical or a piperidyl radical which is unsubstituted or substituted one or more times with a methyl or a halogen.

7. The compound according to claim 1 of formula:

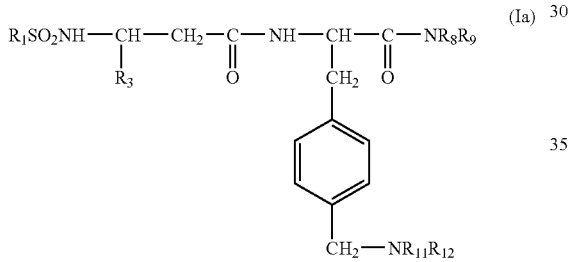

(Ia)

in which:
$R_1$ represents a 2,4-dichloro-3-methylphenyl, naphthyl, 6-methoxynaphth-2-yl, 3-methylbenzothiophen-2-yl, 3-methyl-5-chlorobenzothiophen-2-yl, 3-methyl-5-methoxybenzothiophen-2-yl, 3-methyl-6-methoxybenzothiophen-2-yl or 3-methyl-1-benzofur-2-yl group;
$R_3$ represents a benzo[1,3]dioxol-5-yl or phenyl group which is unsubstituted or substituted with a halogen;
$R_8$ and $R_9$, together with the nitrogen atom to which they are attached, constitute a di($C_1$–$C_4$)alkylamino, pyrrolidinyl or piperidyl radical which is unsubstituted or substituted one or two times with a methyl or a halogen;
$R_{11}$ and $R_{12}$, together with the nitrogen atom to which they are attached, constitute an ethylisobutylamino, ethylisopropylamino, ethyl-tert-butylamino, diisopropylamino, cyclopentylmethylamino or cyclopentylethylamino radical or a piperidyl radical which is unsubstituted or substituted one or more times with a methyl or a halogen;
or a salt thereof with a mineral or organic acid, or a solvate or hydrate of said compound or said salt.

8. The compound according to claim 1, chosen from:
(R,R) 2-((3-(1,3-benzodioxol-5-yl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide;

(R,R) 2-((3-(1,3-benzodioxol-5-yl)-3-((2-naphthylsulphonyl)amino)propanoyl)amino)-3-(4-((cyclopentyl(ethyl)amino)methyl)phenyl)-N-isopropyl-N-methylpropanamide;
(R,R) 3-(4-((2,6-cis-dimethyl-1-piperidyl)methyl)phenyl)-2-((3-(((6-methoxy-2-naphthyl)sulphonyl)amino)-3-phenylpropanoyl)amino)-N-isopropyl-N-methyl propanamide;
(R,R) 2-((3-(1,3-benzodioxol-5-yl)-3-(((6-methoxy-2-naphthyl)sulphonyl)amino)propanoyl)amino)-3-(4-((tert-butyl(ethyl)amino)methyl)phenyl)-N-isopropyl-N-methylpropanamide;
(R,R) 2-((3-(1,3-benzodioxol-5-yl)-3-(((3-methyl-1-benzothiophen-2-yl)sulphonyl)amino)propanoyl)amino)-3-(4-((2,6-cis-dimethyl-1-piperidyl)methyl)phenyl)-N-isopropyl-N-methylpropanamide;
(R,R) 3-(4-((2,6-cis-dimethyl-1-piperidyl)methyl)phenyl)-2-((3-(((5-methoxy-3-methyl-1-benzothiophen-2-yl)sulphonyl)amino)-3-phenylpropanoyl)amino)-N-isopropyl-N-methylpropanamide;
(R,R) N-(4-((2,6-cis-dimethyl-1-piperidyl)methyl)benzyl)-3-(((6-methoxy-2-naphthyl)sulphonyl)amino)-3-phenyl-N-(1-piperidylcarbonyl)propanamide;
(R,R) 2-((3-(4-chlorophenyl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide;
(R,R) 3-(4-((2,6-cis-dimethyl-1-piperidyl)methyl)phenyl)-2-(3-(((6-methoxy-2-naphthyl)sulphonyl)amino)-3-phenylpropanoyl)amino)-N,N-diethylpropanamide;
(R,R) 2-((3-(3-fluorophenyl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide;
(R,R) 2-((3-(1,3-benzodioxol-5-yl)-3-(((3-methyl-1-benzofur-2-yl)sulphonyl)amino)propanoyl)amino)-3-(4-((2,6-cis-dimethyl-1-piperidyl)methyl)phenyl)-N-isopropyl-N-methylpropanamide;
(R,R) 2-((3-(1,3-benzodioxol-5-yl)-3-((2-naphthylsulphonyl)amino)propanoyl)amino)-3-(3-((tert-butyl(ethyl)amino)methyl)phenyl)-N-isopropyl-N-methylpropanamide;
(R,R) 3-(4-(7-azabicyclo[2.2.1]hept-7-ylmethyl)phenyl)-2-((3-(1,3-benzodioxol-5-yl)-3-(((6-methoxynaphthyl)sulphonyl)amino)propanoyl)amino)-N-isopropyl-N-methyl propanamide;
or a salt thereof, or a solvate or hydrate of said compound or said salt.

9. A process for preparing a compound of formula (I) according to claim 1, or a salt thereof, or a solvate or hydrate of said compound or said salt, wherein:
an acid or a functional derivative of this acid of formula:

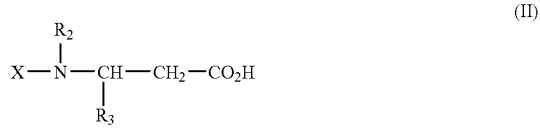

(II)

in which $R_2$ and $R_3$ are as defined for a compound of formula (I) in claim 1, X represents either hydrogen or a group $R_1SO_2$— in which $R_1$ is as defined for a compound of formula (I) in claim 1, or an N-protecting group, is reacted with a compound of formula:

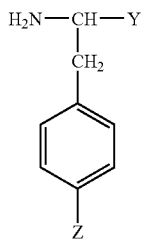
(III)

in which Y represents either $R_4$ as defined for a compound of formula (I) in claim 1, or a $(C_1-C_4)$alkoxycarbonyl, and Z represents either $R_5$ as defined for a compound of formula (I) in claim 1, or a —CN group, on the condition that, when Y represents $R_4$ which represents a phenyl substituted with a group —$CH_2NR_{11}R_{12}$, Z represents $R_5$ which represents a group —$CH_2NR_{11}R_{12}$, $R_{11}$ and $R_{12}$ being as defined for a compound of formula (I) in claim 1; and when $X=R_1SO_2$—, $Y=R_4$ and $Z=R_5$, the expected compound of formula (I) is obtained;

or when $X \neq R_1SO_2$ and/or $Y \neq R_4$ and/or $Z \neq R_5$, that is to say when at least one of the X, Y and Z groups represents, respectively, X=H or an N-protecting group, $Y=(C_1-C_4)$alkoxycarbonyl, Z=—CN, the compound thus obtained of formula:

$$X-\underset{R_3}{\underset{|}{N}}-CH-CH_2-CO-NH-CH-Y \quad \underset{\underset{Z}{\underset{|}{\bigcirc}}}{\overset{R_2}{\underset{|}{|}}} \quad (IV)$$

(with $CH_2$ — phenyl — Z pendant)

is subjected to one or more of the following steps:

when X represents an N-protecting group, this group is removed and the compound thus obtained of formula:

$$HN-\underset{R_3}{\underset{|}{CH}}-CH_2-CO-NH-CH-Y \quad \overset{R_2}{\underset{|}{|}} \quad (V)$$

(with $CH_2$ — phenyl — Z pendant)

is reacted with a sulphonyl halide of formula:

$$R_1SO_2\text{-Hal} \quad (VI)$$

in which Hal represents a halogen;

when Y represents a $(C_1-C_4)$alkoxycarbonyl, it is hydrolyzed and the acid thus obtained or a functional derivative of this acid of formula:

$$X-\underset{R_3}{\underset{|}{N}}-CH-CH_2-CO-NH-CH-CO_2H \quad \overset{R_2}{\underset{|}{|}} \quad (VII)$$

(with $CH_2$ — phenyl — Z pendant)

is reacted with a compound of formula:

$$HNR_8R_9 \quad (VIII);$$

in which $R_8$ and $R_9$ are as defined for a compound of formula (I) from claim 1;

when Z represents a —CN group, this group is converted into $R_5$.

10. A compound of formula:

$$X-NH-\underset{R_3}{\underset{|}{CH}}-CH_2-CO-CO_2H \quad (IIa)$$

in which:

X represents hydrogen or an N-protecting group;

$R_3$ represents a heterocyclic radical chosen from: (2,2-difluoro)benzo[1,3]dioxol-5-yl, 3-isopropylphenyl, 3-trifluoromethoxyphenyl, 2,1,3-benzoxadiazol-5-yl, benzothiophen-5-yl, 1-benzofur-6-yl, 1-benzofur-4-yl, 1-benzofur-3-methyl-5-yl, 2,3-dihydrobenzofur-4-yl;

or a salt thereof with a mineral or organic acid, in racemic form or in the form of a pure enantiomer.

11. A compound of formula:

$$R_1SO_2-NR_2-\underset{R_3}{\underset{|}{CH}}-CH_2-COOH \quad (IIb)$$

in which:

$R_1$ represents a phenylvinyl; a heterocycle chosen from 1-benzofur-2-yl, 2,1,3-benzoxadiazol-4-yl, 2,1,3-benzothiadiazol-4-yl, 1,3-benzothiazol-2-yl, 1-benzothiophen-2-yl, 1H-pyrazol-4-yl, thien-2-yl, 5-isoxazolthien-2-yl, benzothien-2-yl, thieno[3,2-c]pyrid-2-yl and naphtho[2,3-d][1,3]dioxol-6-yl; the said heterocycles being unsubstituted or substituted one or more times with $R_6$, which may be identical or different;

$R_2$ represents hydrogen or a $(C_1-C_4)$alkyl and $R_3$ represents a phenyl which is unsubstituted or substituted one or more times with $R_7$, which may be identical or different; a heterocyclic radical chosen from benzo[1,3]dioxol-5-yl which is unsubstituted or substituted in position –2 with two fluorine atoms; 2,1,3-benzothiodiazol-5-yl; 2,1,3-benzoxadiazol-5-yl; benzothiophen- 5-yl; 2,3-dihydrobenzo[1,4]dioxin-6-yl; 1-benzofur-2-yl; 1-benzofur-5-yl; 1-benzofur-6-yl; 1-benzofur-4-yl; 1-benzofur-3-methyl-5-yl; 2,3-dihydrobenzofur-4-yl; 1,3-thiazol-2-yl; furyl; thien-2-yl; thien-3-yl;

or $R_2$ represents a phenyl which is unsubstituted or substituted one or more times with $R_6$, which may be identical or different; a benzo[1,3]dioxol-5-yl; a pyridyl; an indanyl; and $R_3$ represents hydrogen;

$R_6$ represents a halogen atom; a $(C_1-C_4)$alkyl group; a trifluoromethyl group; a $(C_1-C_4)$alkoxy group; a 2-fluoroethoxy group; a trifluoromethoxy, methylenedioxy or difluoromethylenedioxy group;

$R_7$ represents a halogen atom; a $(C_1-C_4)$alkyl group; a phenyl group; a trifluoromethyl group; a $(C_1-C_4)$alkoxy group; a benzyloxy group; a trifluoromethoxy group;

or a salt thereof with a mineral or organic acid, in racemic form or in the form of a pure enantiomer.

12. A compound of formula:

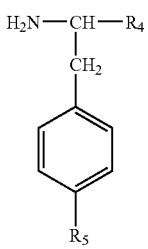

(III')

in which;

$R_4$ represents a group —$CONR_8R_9$; a group —$CSNR_8R_9$; a group —$COR_{13}$; a phenyl group which is unsubstituted or substituted one or more times with $R_{10}$; a heterocyclic radical chosen from pyridyl, imidazolyl, furyl, benzimidazolyl, benzothiazol-2-yl and benzo[1,3]dioxol-5-yl, the said radicals being unsubstituted or substituted with a methyl;

$R_5$ represents a group —$CH_2NR_{11}R_{12}$ or —$CH_2N(O)R_{11}R_{12}$;

$R_8$ and $R_9$ each independently represent hydrogen; a $(C_1-C_4)$alkyl group; a $(C_3-C_7)$cycloalkyl group; a $(C_3-C_7)$cycloalkyl$(C_1-C_4)$alkyl group; an ω-$(C_1-C_4)$dialkylamino$(C_2-C_4)$alkyl group;

or alternatively $R_8$ and $R_9$, together with the nitrogen atom to which they are attached, constitute a heterocyclic radical chosen from pyrrolidinyl, piperidyl, morpholin-4-yl, thiomorpholin-4-yl, piperazin-1-yl, 4-methylpiperazin-1-yl, 4-methylpiperid-1-yl, 2-methylpiperid-1-yl, 4,4-dimethylpiperid-1-yl, 4,4-difluoropiperid-1-yl, 4-trifluoromethylpiperid-1-yl, 4-methoxypiperid-1-yl, 3,4-dihydropiperid-1-yl, azepin-1-yl and cyclohexyl-spiro-4-piperid-1-yl;

$R_{10}$ represents a halogen atom; a $(C_1-C_4)$alkyl group; a hydroxy group; a $(C_1-C_6)$alkoxy group; $R_{10}$ can also represent a group —$CH_2NR_{11}R_{12}$ when $R_5$ represents a group —$CH_2NR_{11}R_{12}$, the said groups then being identical;

$R_{11}$ and $R_{12}$ each independently represent hydrogen; a $(C_1-C_6)$alkyl group; a $(C_2-C_4)$alkenyl group; a $(C_3-C_7)$cycloalkyl group; a $(C_3-C_7)$cycloalkyl$(C_1-C_4)$alkyl group; an ω-hydroxy$(C_2-C_4)$alkylene group; an ω-methoxy$(C_2-C_4)$alkylene group; an ω-trifluoromethyl$(C_2-C_4)$alkylene group; an ω-halo$(C_2-C_4)$alkylene group;

or alternatively $R_{11}$ and $R_{12}$, together with the nitrogen atom to which they are attached, constitute a monocyclic, bicyclic or heterocyclic radical chosen from azetidinyl, pyrrolidinyl, morpholin-4-yl, thiomorpholin-4-yl, piperid-1-yl, piperazin-1-yl, 1,2,3,6-tetrahydropyrid-1-yl, 2,3,4,5-tetrahydropyridinium, decahydroquinolyl, decahydroisoquinolyl, tetrahydroisoquinolyl, octahydro-1H-isoindolyl, $(C_4-C_6)$cycloalkyl-spiro-piperidyl, 3-azabicyclo[3.1.0]hexyl and 7-azabicyclo[2.2.1]heptan-7-yl, which may be unsubstituted or substituted one or more times with a halogen atom or a $(C_1-C_4)$alkyl, hydroxyl, $(C_1-C_4)$alkoxy, trifluoromethyl or difluoromethylene group;

$R_{13}$ represents a phenyl, thiazol-2-yl or pyridyl group;

or a salt thereof with a mineral or organic acid, in the form of a racemic mixture or of a pure enantiomer.

13. A pharmaceutical composition containing, as active principle, a compound according to claim 1 or a pharmaceutically acceptable salt thereof, or a solvate or hydrate of said compound or said salt.

14. A method for treating pain or inflammation which comprises administering to a patient in need of such treatment an effective amount of a compound according to claim 1.

15. The compound of formula (I) according to claim 2 in which $R_1$ represents a 2,4-dichloro-3-methylphenyl, naphthyl, 6-methoxynaphth-2-yl, 3-methylbenzothiophen-2-yl, 3-methyl-5-chlorobenzothiophen-2-yl, 3-methyl-5-methoxybenzothiophen-2-yl, 3-methyl-6-methoxybenzothiophen-2-yl or 3-methyl-1-benzofur-2-yl group.

16. The compound of formula (I) according to claim 2 in which $R_2$ represents hydrogen and $R_3$ represents a benzo[1,3]dioxol-5-yl or phenyl group which is unsubstituted or substituted with a halogen.

17. The compound of formula (I) according to claim 2 in which $R_4$ represents a group —$CONR_8R_9$ and —$NR_8R_9$ represents a di$(C_1-C_4)$alkylamino radical, a pyrrolidinyl or piperidyl group which is unsubstituted or substituted one or two times with a methyl or a halogen.

18. The compound of formula (I) according to claim 2 in which $R_5$ represents a group —$CH_2NR_{11}R_{12}$ in which —$NR_{11}R_{12}$ represents an ethylisobutylamino, ethylisopropylamino, ethyl-tert-butylamino, diisopropylamino, cyclopentylmethylamino or cyclopentylethylamino radical or a piperidyl radical which is unsubstituted or substituted one or more times with a methyl or a halogen.

19. The compound according to claim 2 of formula:

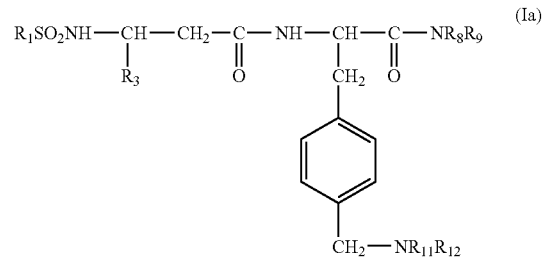

(Ia)

in which:

$R_1$ represents a 2,4-dichloro-3-methylphenyl, naphthyl, 6-methoxynaphth-2-yl, 3-methylbenzothiophen-2-yl, 3-methyl-5-chlorobenzothiophen-2-yl, 3-methyl-5-methoxybenzothiophen-2-yl, 3-methyl-6-methoxybenzothiophen-2-yl, or 3-methyl-1-benzofur-2-yl group;

$R_3$ represents a benzo[1,3]dioxol-5-yl or phenyl group which is unsubstituted or substituted with a halogen;

$R_8$ and $R_9$, together with the nitrogen atom to which they are attached, constitute a di($C_1$–$C_4$)alkylamino, pyrrolidinyl or piperidyl radical which is unsubstituted or substituted one or two times with a methyl or a halogen;

$R_{11}$ and $R_{12}$, together with the nitrogen atom to which they are attached, constitute an ethylisobutylamino, ethylisopropylamino, ethyl-tert-butylamino, diisopropylamino, cyclopentylmethylamino or cyclopentylethylamino radical or a piperidyl radical which is unsubstituted or substituted one or more times with a methyl or a halogen;

or a salt thereof with a mineral or organic acid, or a solvate or hydrate or said compound or said salt.

20. (R,R) 2-((3-(1,3-benzodioxol-5-yl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide or a salt, solvate or hydrate thereof, or a solvate or hydrate of said salt according to claim 8.

21. (R,R) 2-((3-(1,3-benzodioxol-5-yl)-3-(((6-methoxy-2-naphthyl)sulphonyl)-amino)propanoyl)amino)-3-(4-((2,6-cis-dimethyl-1-piperidyl)methyl)phenyl)-N-isopropyl-N-methylpropanamide hydrochloride according to claim 20.

22. A pharmaceutical composition containing, as active principle, a compound according to claim 2 or a pharmaceutically acceptable salt thereof, or a solvate or hydrate of said compound or said salt.

23. A pharmaceutical composition containing, as active principle, a compound according to claim 3 or a pharmaceutically acceptable salt thereof, or a solvate or hydrate of said compound or said salt.

24. A pharmaceutical composition containing, as active principle, a compound according to claim 4 or a pharmaceutically acceptable salt thereof, or a solvate or hydrate of said compound or said salt.

25. A pharmaceutical composition containing, as active principle, a compound according to claim 5 or a pharmaceutically acceptable salt and/or thereof, or a solvate or hydrate of said compound or said salt.

26. A pharmaceutical composition containing, as active principle, a compound according to claim 6 or a pharmaceutically acceptable salt thereof, or a solvate or hydrate of said compound or said salt.

27. A pharmaceutical composition containing, as active principle, a compound according to claim 7 or a pharmaceutically acceptable salt thereof, or a solvate or hydrate of said compound or said salt.

28. A pharmaceutical composition containing, as active principle, a compound according to claim 8 or a pharmaceutically acceptable salt thereof, or a solvate or hydrate of said compound or said salt.

29. A pharmaceutical composition containing, as active principle, a compound according to claim 15 or a pharmaceutically acceptable salt thereof, or a solvte or hydrate of said compound or said salt.

30. A pharmaceutical composition containing, as active principle, a compound according to claim 16 or a pharmaceutically acceptable salt thereof, or a solvate or hydrate of said compound or said salt.

31. A pharmaceutical composition containing, as active principle, a compound according to claim 17 or a pharmaceutically acceptable salt thereof, or a solvate or hydrate of said compound or said salt.

32. A pharmaceutical composition containing, as active principle, a compound according to claim 18 or a pharmaceutically acceptable salt thereof, or a solvate or hydrate of said compound or said salt.

33. A pharmaceutical composition containing, as active principle, a compound according to claim 19 or a pharmaceutically acceptable salt thereof, or a solvate or hydrate of said compound or said salt.

34. A pharmaceutical composition containing, as active principle, a compound according to claim 20 or a pharmaceutically acceptable salt thereof, or a solvate or hydrate of said compound or said salt.

35. A pharmaceutical composition containing, as active principle, a compound according to claim 21 or a pharmaceutically acceptable salt thereof, or a solvate or hydrate of said compound or said salt.

36. A method for treating pain or inflammation which comprises administering to a patient in need of such treatment an effective amount of a compound according to claim 2.

37. A method for treating pain or inflammation which comprises administering to a patient in need of such treatment an effective amount of a compound according to claim 3.

38. A method for treating pain or inflammation which comprises administering to a patient in need of such treatment an effective amount of a compound according to claim 4.

39. A method for treating pain or inflammation which comprises administering to a patient in need of such treatment an effective amount of a compound according to claim 5.

40. A method for treating pain or inflammation which comprises administering to a patient in need of such treatment an effective amount of a compound according to claim 6.

41. A method for treating pain or inflammation which comprises administering to a patient in need of such treatment an effective amount of a compound according to claim 7.

42. A method for treating pain or inflammation which comprises administering to a patient in need of such treatment an effective amount of a compound according to claim 8.

43. A method for treating pain or inflammation which comprises administering to a patient in need of such treatment am effective amount of a compound according to claim 15.

44. A method for treating pain or inflammation which comprises administering to a patient in need of such treatment an effective amount of a compound according to claim 16.

45. A method for treating pain or inflammation which comprises administering to a patient in need of such treatment an effective amount of a compound according to claim 17.

46. A method for treating pain or inflammation which comprises administering to a patient in need of such treatment an effective amount of a compound according to claim 18.

47. A method for treating pain or inflammation which comprises administering to a patient in need of such treatment an effective amount of a compound according to claim 19.

48. A method for treating pain or inflammation which comprises administering to a patient in need of such treatment an effective amount of a compound according to claim 20.

49. A method for treating pain or inflammation which comprises administering to a patient in need of such treatment an effective amount of a compound according to claim 21.

50. (R,R) 2-((3-(1,3-benzodioxol-5-yl)-3-(((6-methoxy-2-naphthyl)sulphonyl)amino)propanoyl)amino)-3-(4-((2,6-cis-dimethyl-1-piperidyl)methyl)phenyl)-N-isopropyl-N-methylpropanamide fumarate according to claim 20.

* * * * *

UNITED STATES PATENT AND TRADEMARK OFFICE
CERTIFICATE OF CORRECTION

PATENT NO. : 7,157,454 B2
APPLICATION NO. : 10/472674
DATED : January 2, 2007
INVENTOR(S) : Ferrari et al.

It is certified that error appears in the above-identified patent and that said Letters Patent is hereby corrected as shown below:

Column 19, lines 35 to 45: In Scheme 6, Formula (III), "$H_2N-CH-R_4$" should read -- $H_2N-CH-CO_2R'$ --.

Column 20, lines 60 to 65: Below the compound: 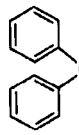 insert -- (XIX) --.

Column 35, line 16: "tetrahydrofaran" should read as -- tetrahydrofuran --.

Columns 45 to 47, Table III, Preparations 1.15, 1.16, 1.18, and 1.23:

"  " should read as --  --.

Column 75, Preparation 2.36: "  " should read as --  --.

Column 79, line 37: "2-N-Boc)" should read as -- 2-(N-Boc) --.

Column 101, Table VII, Preparation 3.6:

"  " should read as --  --.

Column 113, line 61: "aminometbyl" should read as -- aminomethyl --.

Columns 129 to 152: In Table IX, at each instance, the relevant portion Formula (I)

" 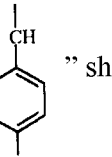 " should read as -- 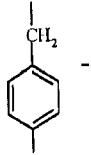 --.

Column 153, lines 28 to 29: "wires.: 4H; 6.8-8.1 ppm: wires" should read as -- unres.: 4H; 6.8-8.1 ppm: unres --.

Column 153, line 52: "NMR: 1.3-1" should read as -- NMR: 0.5-1 --.

UNITED STATES PATENT AND TRADEMARK OFFICE
CERTIFICATE OF CORRECTION

PATENT NO. : 7,157,454 B2  Page 2 of 3
APPLICATION NO. : 10/472674
DATED : January 2, 2007
INVENTOR(S) : Ferrari et al.

It is certified that error appears in the above-identified patent and that said Letters Patent is hereby corrected as shown below:

Column 190, Table X, Example 196: In the column labeled N-$R_{11}R_{12}$, insert

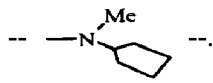 --.

Columns 225 to 226, Table X, Example 303: " 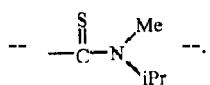 " should read as

-- (structure with S double bond, C-N with Me and iPr) --.

In Claim 1:  Column 240, line 29: "isoxazothien" should read as -- isoxazolthien --;
Column 240, line 41: "being an substituted" should read as -- being unsubstituted --;
Column 240, line 47: "diaxol" should read as -- dioxol --.

In Claim 2:  Column 242, line 48: "($C_1$-$C_6$alkoxy" should read as -- ($C_1$-$C_6$)alkoxy --;
Column 242, line 53: "($C_2$-$C_4$alkenyl" should read as -- ($C_2$-$C_4$)alkenyl --.

In Claim 11:

Column 246, lines 66 to 67: "2,1,3-benzothiodiazol-5-yl" should read as -- 2,1,3-benzothiadiazol-5-yl --.

In Claim 25:

Column 249, line 45: "and/or" should be deleted.

UNITED STATES PATENT AND TRADEMARK OFFICE
CERTIFICATE OF CORRECTION

PATENT NO.       : 7,157,454 B2
APPLICATION NO.  : 10/472674
DATED            : January 2, 2007
INVENTOR(S)      : Ferrari et al.

It is certified that error appears in the above-identified patent and that said Letters Patent is hereby corrected as shown below:

In Claim 29:

Column 249, line 62: "solvte" should read as -- solvate --.

Signed and Sealed this

Twenty-seventh Day of May, 2008

JON W. DUDAS
*Director of the United States Patent and Trademark Office*